US005286750A

United States Patent [19]

Mueller et al.

[11] Patent Number: 5,286,750

[45] Date of Patent: Feb. 15, 1994

[54] PHENYLACETIC ACID DERIVATIVES AND FUNGICIDES CONTAINING THEM

[75] Inventors: Bernd Mueller, Frankenthal; Hubert Sauter, Mannheim; Eberhard Ammermann, Ludwigshafen; Gisela Lorenz, Neustadt; Franz Roehl, Ludwigshafen, all of Fed. Rep. of Germany

[73] Assignee: BASF Aktiengesellschaft, Ludwigshafen, Fed. Rep. of Germany

[21] Appl. No.: 32,201

[22] Filed: Mar. 15, 1993

Related U.S. Application Data

[63] Continuation of Ser. No. 595,413, Oct. 11, 1990, abandoned.

[30] Foreign Application Priority Data

Oct. 11, 1989 [DE] Fed. Rep. of Germany ....... 3933891

[51] Int. Cl.[5] .................... A61K 31/22; A61K 31/38; C07C 67/02; C07D 239/02

[52] U.S. Cl. .................................... 514/546; 560/255; 544/318; 544/326; 544/333; 544/334; 544/335; 544/353; 544/354; 544/356; 546/153; 546/157; 546/174; 549/64; 549/80; 514/269; 514/256; 514/345; 514/351; 514/438; 514/444; 514/448

[58] Field of Search ......................... 560/255; 514/546

[56] References Cited

U.S. PATENT DOCUMENTS

| | | | |
|---|---|---|---|
| 4,331,664 | 5/1982 | Takaya et al. | 514/206 |
| 4,709,078 | 11/1987 | Schirmer et al. | 560/60 |
| 4,782,089 | 11/1990 | Walsh | 514/541 |
| 4,822,908 | 4/1989 | Karbach et al. | 560/60 |
| 4,829,085 | 5/1989 | Wenderoth et al. | 514/552 |
| 4,895,974 | 1/1990 | Crowley | 560/60 |
| 4,913,721 | 4/1990 | Clough et al. | 71/76 |
| 4,914,128 | 4/1990 | Schirmer et al. | 514/532 |
| 4,937,372 | 6/1990 | Wenderoth et al. | 560/55 |
| 4,994,495 | 2/1991 | Clough et al. | 514/574 |
| 4,997,973 | 3/1991 | Wenderoth et al. | 560/55 |
| 4,999,042 | 3/1991 | Anthony et al. | 504/235 |
| 5,008,438 | 4/1991 | Schuetz et al. | 560/55 |
| 5,021,581 | 6/1981 | Clough et al. | 546/309 |

FOREIGN PATENT DOCUMENTS

| | | |
|---|---|---|
| 3670 | 8/1979 | European Pat. Off. . |
| 0178826 | 4/1986 | European Pat. Off. . |
| 252406 | 1/1988 | European Pat. Off. . |
| 341845 | 11/1988 | European Pat. Off. . |
| 342459 | 11/1989 | European Pat. Off. . |
| 3317356 | 11/1983 | Fed. Rep. of Germany . |
| 3247669 | 6/1984 | Fed. Rep. of Germany . |
| 1026921 | 4/1966 | United Kingdom . |

OTHER PUBLICATIONS

Schauble et al., "Complex Metal Hydride Reduction . . ." *J. Org. Chem.* 39(6) (1974) 755–760.

Howard et al., "Use of Vinylogous Urethanes . . ." *J. Org. Chem.* 45(9) (1980) 1713–1715.

Jefford et al, "Intramolecular carbenoid reactions of pyrrole derivatives. A total synthesis of (+)-ipalbidine", *Helvetica Chimica Acta*, vol. 69, pp. 2048–2061 (1986).

Itoh et al, "Synthesis of aryl glyoxylate. I. The reaction of alkyl dichloro(alkoxy)acetates with aromatics in the presence of Lewis Acid", *Bulletin of the Chemical Society of Japan*, vol. 57, No. 3, pp. 810–814 (Mar. 3, 1984).

Reutrakul et al, "Decarboxylation of sodium glycidates: A convenient method for the synthesis of alpha-acetoxyketones, alpha-diketone, and alphaketoesters", *Chemistry Letters,*, No. 6, pp. 879–880 (Jun., 1982).

Chemical Abstracts, vol. 104, No. 21, Abstract No. 186092a, p. 603 (May 26, 1986).

*Primary Examiner*—John M. Ford
*Assistant Examiner*—Matthew V. Grumbling
*Attorney, Agent, or Firm*—Oblon, Spivak, McClelland, Maier & Neustadt

[57] ABSTRACT

Unsaturated phenylacetic acid derivatives of the general formula (Abstract continued on next page.)

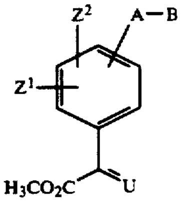

where U is $=O$, $=CH-OCH_3$, $=N-OCH_3$, $=N-NH-CH_3$, $=CH_2$, $=CH-CH_3$, $=CH-CH_2-CH_3$ or $=CH-S-CH_3$ and $Z^1$ and $Z^2$ are hydrogen, halogen, trifluoromethyl, cyanide, $NO_2$ or unsubstituted or substituted alkyl, alkenyl, aryl, alkynyl, alkoxy, aryloxy, arylalkoxy, acyloxy, hetaryl, $-CO_2R^1$, $-CONR^2R^3$, $COR^4$ or $NR^5R^6$, and $Z^1$ and $Z^2$ may also form a ring, A is meta or para and is $(CH_2)_n$, $CH=CH$, $O-(CH_2)_n$, $O-(CH_2)_n-CO$, $CH_2-O-CO-(CH_2)_n$, $CO-O-(CH_2)_n$, $O-CO-(CH_2)_n$, $O-(CH_2)_n-CO-O$, $O-(CH_2)_{n+2}-O$, $CH_2O-(CH_2)_n$, $CH_2-S-(CH_2)_n$, $CH_2-NR^7-(CH_2)_n$, $CH(CN)-O-CO-(CH_2)_n$, $CH=N-(CH_2)_n$ or $CH=N-O-(CH_2)_n$.

n is from 0 to 20,

B is substituted or unsubstituted and is hydrogen, alkyl, cycloalkyl, aryl or hetaryl, $R^1$ to $R^7$ are hydrogen or unsubstituted or substituted alkyl, cycloalkyl, alkenyl, alkynyl, aryl, hetaryl, aralkyl or cycloalkylalkyl, their acid addition products and base addition products, and fungicides and insecticides containing these compounds.

6 Claims, No Drawings

PHENYLACETIC ACID DERIVATIVES AND FUNGICIDES CONTAINING THEM

This application is continuation of application Ser. No. 07/595,413, filed on Oct. 11, 1990, now abandoned.

The present invention relates to phenylacetic acid derivatives having a fungicidal and insecticidal action, fungicides containing these compounds and methods for controlling fungi.

It is known that methyl acrylate derivatives or glyoxylic ester O-methyl oxime derivatives, for example methyl 2-(2-benzoyloxyphenyl)-3-methoxyacrylate (EP-178 826), 2-benzyloxyphenylglyoxylic acid methyl ester O-methyl oxime (DE-36 23 921) or 2-phenyloxymethylenephenylglyoxylic acid methyl ester O-methyl oxime (DE-36 23 921), can be used as fungicides. However, the fungicidal action of these compounds is unsatisfactory.

We have found that novel unsaturated phenylacetic acid derivatives of the formula I

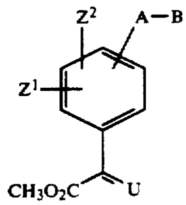
I where U is $=O$, $=CH-OCH_3$, $=N-OCH_3$, $=N-NH-CH_3$, $=CH_2$, $=CH-CH_3$, $=CH-CH_2-CH_3$, $=CH-S-CH_3$, $Z^1$ and $Z^2$ are identical or different and are each hydrogen, halogen, trifluoromethyl, cyanide, $NO_2$ or the unsubstituted or substituted radicals alkyl, alkenyl, aryl, alkynyl, alkoxy, aryloxy, arylalkoxy, acyloxy, hetaryl, $-CO_2R^1$, $-CONR^2R^3$, $-COR^4$ or $-NR^5R^6$ or $Z^1$ and $Z^2$ together form a ring which is fused with the phenyl radical of which they are substituents, A is meta or para to the substituted methyl acetate radical and is $(CH_2)_n$, $O-(CH_2)_n$, $O-(CH_2)_n-CO$, $CH{=}CH-(CH_2)_n$, $CH_2O-CO-(CH_2)_n$, $CO-O-(CH_2)_n$, $O-CO-(CH_2)_n$, $O-(CH_2)_n-CO-O$, $O-(CH_2)_{n+2}-O$, $CH_2-O-(CH_2)_n$, $CH_2-S-(CH_2)_n$, $CH_2-NR^7-(CH_2)_n$, $CH(CN)-O-CO-(CH_2)_n$, $CH{=}N-(CH_2)_n$ or $CH{=}N-O-(CH_2)_n$, n is from 0 to 20, B is hydrogen or the unsubstituted or substituted radicals alkyl, cycloalkyl, aryl or hetaryl, where the radial —A—B must not be hydrogen, and $R^1$ to $R^7$ are identical or different and are each hydrogen or the unsubstituted or substituted radials alkyl, cycloalkyl, alkenyl, alkynyl, aryl, hetaryl, aralkyl or cycloalkylalkyl, and their plant-tolerated acid addition products or base addition products, except for the compounds of the formulae

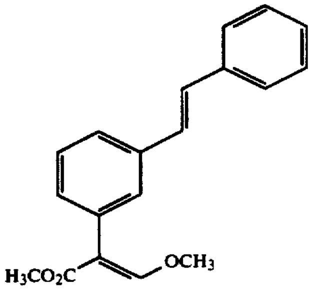
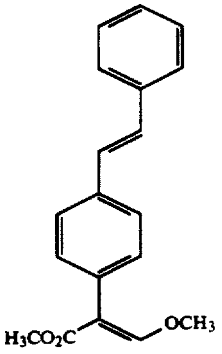
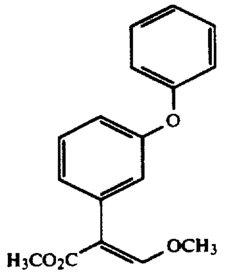
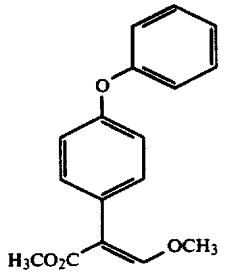
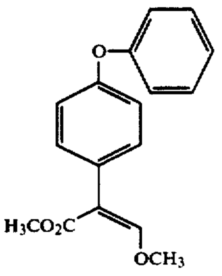
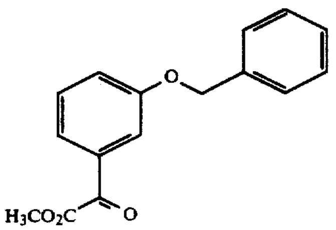
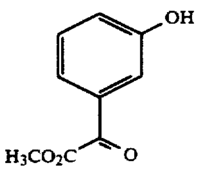
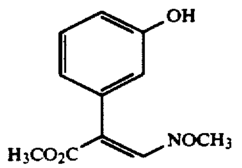
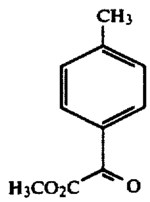
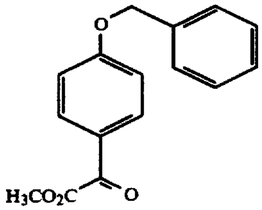
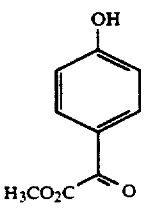
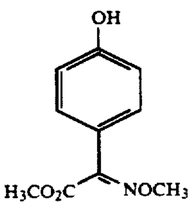

-continued

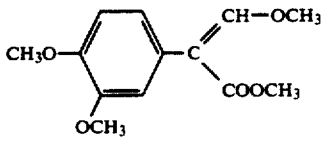

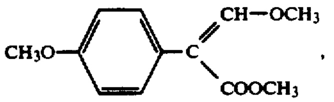

have high fungitoxic and insecticidal activity and are also very well tolerated by plants.

Acids for acid addition products are, for example, mineral acids, such as hydrochloric acid, hydrobromic acid, phosphoric acid, sulfuric acid or nitric acid, or carboxylic acids, such as formic acid, acetic acid, oxalic acid, malonic acid, lactic acid, malic acid, succinic acid, tartaric acid, citric acid, salicylic acid, p-toluenesulfonic acid or dodecylbenzenesulfonic acid, or proton-acidic compounds generally, for example saccharin.

Bases for base addition products are, for example, potassium hydroxide, sodium hydroxide, potassium carbonate, sodium carbonate and ammonium hydroxide.

In the preparation, the novel compounds of the formula I may be obtained as mixtures of stereoisomers (E/Z isomers, diastereomers, enantismers), which can be separated into the individual components in a conventional manner, for example by crystallization or chromatography. Both the individual isomers and mixtures thereof can be used as fungicides and form subjects of the invention.

$Z^1$ and $Z^2$ are each, for example, hydrogen, fluorine, chlorine, bromine, a straight-chain, cyclic or branched, saturated or unsaturated hydrocarbon radical of 1 to 6, in particular 1 to 4, carbon atoms, $C_1$–$C_4$-alkoxy, $C_2$–$C_6$-alkylcarbonyloxy, phenyl, phenoxy, benzyl, benzyloxy, thienyl, furyl, pyrryl, pyrazolyl, imidazolyl, oxazolyl, isoxazolyl, thiazolyl, pyridyl, pyridazinyl, pyrimidyl, pyrazinyl, quinolyl, isoquinolyl, indolyl, benzimidazolyl, quinazolyl, quinoxalyl, $COOR^1$, $CONR^2R^3$, $COR^4$ or $NR^5R^6$, or the stated hydrocarbon, aryl or hetaryl radicals may have from 1 to 3 identical or different substituents from the group consisting of fluorine, chlorine, bromine, iodine, $C_1$–$C_8$-alkyl, $C_1$–$C_8$-alkylthio, $C_1$–$C_8$-alkylsulfinyl, cyano, hydroxyl and nitro.

$Z^1$ and $Z^2$ are each, in particular, hydrogen, fluorine, chlorine, bromine, a straight-chain, cyclic or branched, saturated or unsaturated hydrocarbon radical of 1 to 6, in particular 1 to 4, carbon atoms, $C_1$–$C_4$-alkoxy, $C_2$–$C_6$-alkylcarbonyl, phenyl, phenoxy, benzyl or benzyloxy.

$Z^1$ and $Z^2$ are each preferably hydrogen.

A is meta or para to the substituted methyl acetate radical and is $(CH_2)_n$, $CH{=}CH{-}(CH_2)_n$, $O{-}(CH_2)_n$, $O{-}(CH_2)_n{-}CO$, $CH_2{-}O{-}CO{-}(CH_2)_n$, $CO{-}O{-}(CH_2)_n$, $O{-}CO{-}(CH_2)_n$, $O{-}(CH_2)$ n—$CO{-}O$, $O{-}(CH_2)_{n+2}{-}O$, $CH_2{-}O{-}(CH_2)_n$, $CH_2{-}S{-}(CH_2)_n$, $CH_2{-}NR^7{-}(CH_2)_n$, $CH(CN){-}O{-}CO{-}(CH_2){=}_n$, $CH{=}N{-}(CH_2)_n$ or $CH{=}N{-}O{-}(CH_2)_n$.

A is, in particular, $(CH_2)_n$, $CH{=}CH{-}(CH_2)_n$, $O{-}(CH_2)_n$, $CH_2{-}O{-}CO{-}(CH_2){=}_n$, $CH_2{-}O{-}(CH_2)_n$ or $CH_2{-}S{-}(CH_2)_n$.

n is, for example, from 0 to 20, in particular from 0 to 10, preferably 0, 1, 2, 3 or 4.

B is, for example, an unsaturated or saturated straight-chain or branched hydrocarbon radical of 1 to 6, in particular 1 to 4, carbon atoms, $C_3$–$C_6$-cycloalkyl, phenyl, phenoxy, thienyl, furyl, pyrryl, pyrazolyl, imidazolyl, oxazolyl, isoxazolyl, thiazolyl, pyridyl, pyridazinyl, pyrimidyl, pyrazinyl, quinolyl, isoquinolyl, indolyl, benzimidazolyl, quinazolyl or quinoxazolyl, where the stated cycloalkyl, alkyl, aryl or heteraryl radicals may have from 1 to 3 identical or different substituents from the group consisting of fluorine, chlorine, bromine, iodine, $C_1$–$C_8$-alkyl, $C_1$–$C_8$-alkylthio, $C_1$–$C_8$-alkylsulfinyl, cyano, hydroxyl and nitro.

B is preferably an unsaturated or saturated straight-chain or branched hydrocarbon radical of 1 to 6, in particular 1 to 4, carbon atoms, $C_3$–$C_6$-cycloalkyl, phenyl, phenoxy, pyridyl or benzoimidazolyl.

Preferred compounds are those in which the group AB is meta to the group

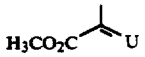

U is $=O$, $=CH{-}OCH_3$, $=N{-}OCH_3$, $=N{-}NHCH_3$, $=CH_2$, $=CH{-}CH_3$, $=CH{-}CH_3{-}CH_3$ or $-CH{-}SCH_3$, preferably $=O$, $=CH{-}OCH_3$, $=N{-}OCH_3$, $=CH{-}CH_3$ or $=CH{-}S{-}CH_3$, particularly preferably $=O$, $=CH{-}OCH_3$, $=N{-}OCH_3$ or $=CH{-}CH_3$.

If U gives rise to syn/anti isomers, the invention relates to all isomers, in particular the anti isomers.

$R^1$ to $R^7$ are each, for example, identical or different straight-chain or branched hydrocarbon radicals of 1 to 6, in particular 1 to 4, carbon atoms, cyclic hydrocarbon radicals of 3 to 6 carbon atoms, phenyl, benzyl, cyclohexylmethyl, thienyl, furyl, pyrryl, pyrazolyl, imidazolyl, oxazolyl, isoxazolyl, thiazolyl, pyridyl, pyridazinyl, pyrimidyl, pyrazinyl, quinolyl, isoquinolyl, indolyl, benzoimidazolyl, quinazolyl or quinoxalyl, where the stated alkyl, cycloalkyl, aryl or hetaryl radicals may have from 1 to 3 identical or different substituents from the group consisting of fluorine, chlorine, bromine, iodine, $C_1$–$C_8$-alkyl, $C_1$–$C_8$-alkylthio, $C_1$–$C_8$-alkylsulfinyl, cyano, hydroxyl and nitro.

The novel compounds can be prepared, for example, by the following processes:

The benzyl bromides 2 are obtained by known processes (EP 251 082) from the corresponding phenylacetic esters 1 (Scheme 1).

(Scheme 1)

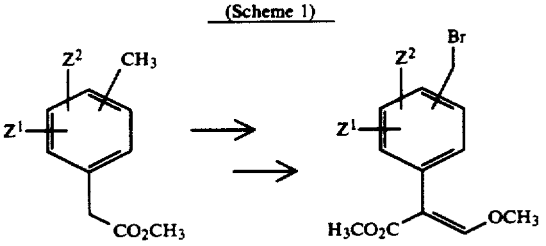

1 2

The ketoesters 5 are key intermediates and can be prepared by reacting the corresponding haloaromatics 3 with magnesium and then reacting the resulting Grignard compounds 4 with dimethyl oxalate (M. Rambaud et al., Synthesis 1988, 564), oxalic acid imidazolide methyl ester (EP 253 213) or oxalyl chloride methyl ester. The derivatives 6 can be synthesized (Scheme 2) from the ketoesters 5 by reaction with $CH_3ON^+H_3Cl^-$ or by a Wittig reaction with $(C_6H_5)_3P^+—CH_2—O—CH_3X^-$ or $(C_6H_5)_3P^+—CH_2—CH_3X^-$, where X is halogen.

Scheme 2

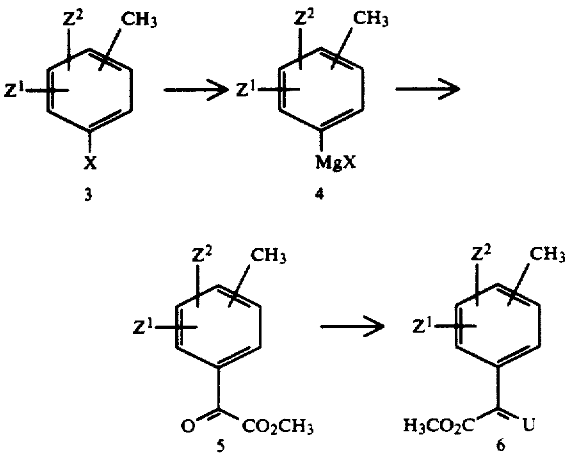

3 4 5 6

X: Halogen

U: $=CH—OCH_3$, $=N—OCH_3$ or $=CH—OCH_3$

Alternatively, the ketoesters 5 are obtainable from the corresponding aldehydes 7 (Scheme 3).

The aldehydes 7 are converted into the corresponding cyanohydrins 8 by reaction with HCN. The cyanohydrins 8 are converted by reaction with HCl and methanol into the imidoester hydrochlorides 9, which are then hydrolyzed to the mandelic esters 10. These mandelic esters 10 can then be oxidized with NaOCl/tetramethylpiperidin-N-oxyl (Tempo; P. Anelli et al., JOC 52 (1987), 2559) to the ketoesters 5 (Scheme 3).

Scheme 3

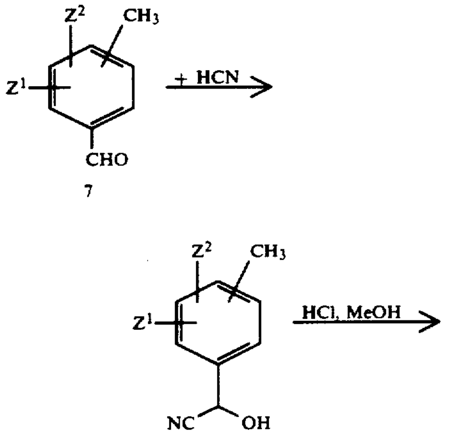

7 8

-continued

Scheme 3

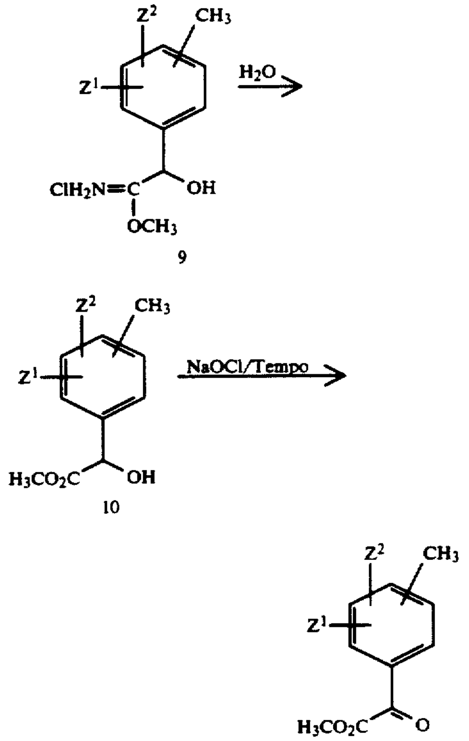

9 10 5

Either the ketoesters 5 can be brominated with NBS (N-bromosuccinimide) to give the ketoester bromides 11 (Scheme 4) or their keto functions can be reacted with $P^+(C_6H_5)_3—CH_2—O—CH_3{}^-Cl$ (EP 178 826), $CH_3—O—NH_3{}^-Cl$ (EP 253 213) or $H_2N—NHCH_3$ (OZ 39 772). The subsequent NBS bromination of these derivatives 12 then gives the benzyl bromides 13 (Scheme 4).

Scheme 4

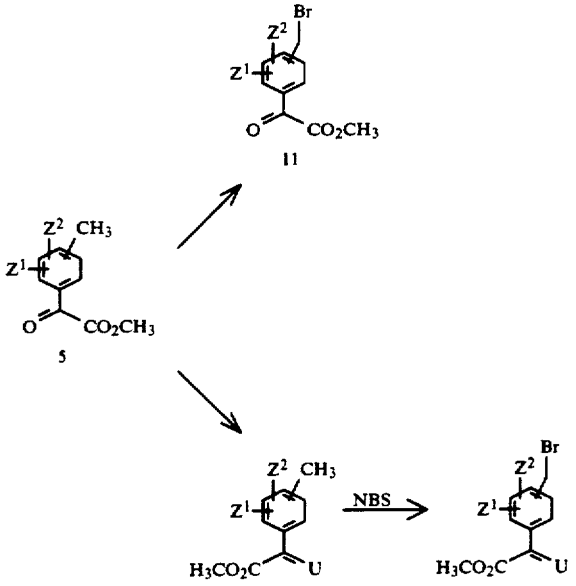

11 5 12 13

U: $=CH-OCH_3$, $=N-OCH_3$ or $=N-NH-CH_3$ $Z^1$ and $Z^2$: as defined above

NBS: N-bromosuccinimide

The benzyl bromides 14 can be reacted with nucleophiles, eg. carboxylates (OZ 39 491), phenolates, alcoholates (EP 251 082), mercaptans (EP 226 917), amines, etc. by standard processes to give the novel compounds 15 (Scheme 5).

Scheme 5

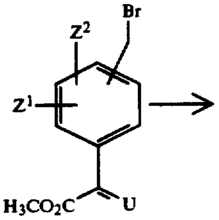

14

-continued

Scheme 5

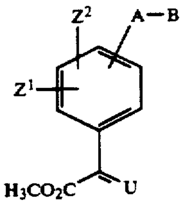

15

U: $=O$, $=CH-OCH$ $=N-OCH_3$, $=N-NH-CH_3$

A: $CH_2-O-(CH_2O)_n$, $CH_2-S-(CH_2)_n$, $CH_2-O-CO(CH_2)_n$ or $CH_2-NR^7-(CH_2)_n$ n, B, $Z^1$, $Z^2$ or $R^7$: as defined above Furthermore, the benzyl bromides 14 can be reacted with phosphites or phosphines to give phosphonates 16 or phosphonium salts 17, which then react with aldehydes to give the styrene derivatives 18. Hydrogenation of these styrene derivatives 18 with a diimine or with $H_2$ in the presence of a suitable hydrogenation catalyst, eg. Pd or Pt, in a suitable organic solvent, such as tetrahydrofuran, methanol or acetic acid, gives the alkylated aromatics 19 (cf. EP 229 974; Scheme 6).

Scheme 6

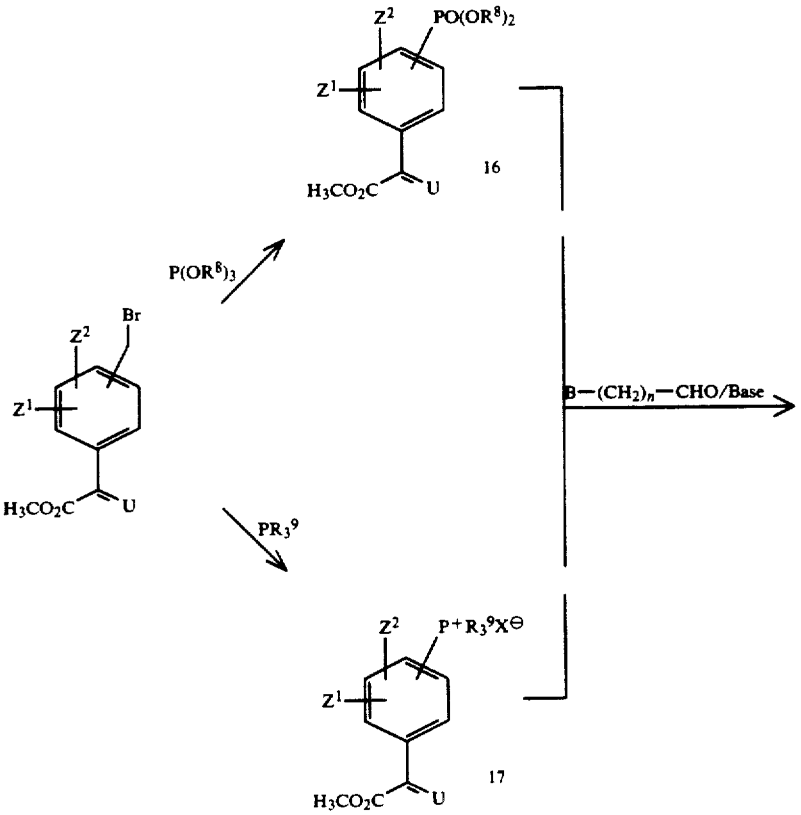

-continued

Scheme 6

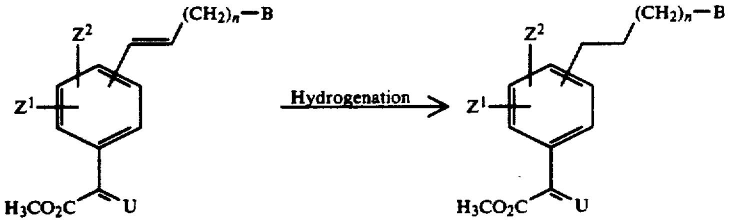

18 19

U: =O, =CH—OCH$_3$, =N—OCH$_3$ or =N—NH—CH$_3$

B, $R^8$, $R^9$ and n: as defined above

The benzyl bromides 14 can also be oxidized with oxidizing agents, such as N-methylmorpholine N-oxide (OZ 50/40842, DE 2948058) or dimethyl sulfoxide (Nace et al., J. Org. Chem. 24 (1959), 1782) to give the aldehydes 20.

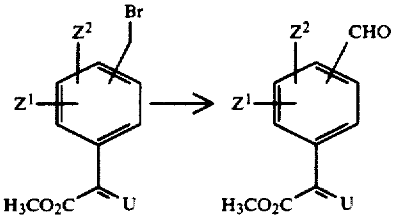

14 20

U: =O, =CH—OCH$_3$, =N—OCH$_3$ or =N—NH—CH$_3$ $Z^1$ and $Z^2$: as defined above These aldehydes 20 react, for example in Wittig reactions similar to Scheme 6, with phosphonates or phosphonium salts to give the styrene derivatives 18.

The aldehydes 20 can also be reacted with, for example, amines or hydroxyamines or HCN to give Schiff's bases or oxime ethers 21 (Scheme 8) or cyanohydrins 22 (Scheme 9).

Scheme 8

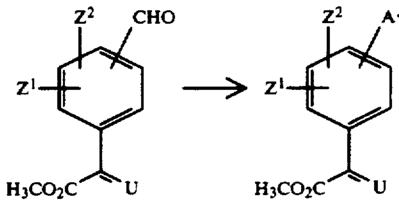

16

20 21

U: =O, =CH—OCH$_3$, =N—OCH$_3$ or =N—NH—CH$_3$

A: CH=N—O—(CH$_2$)$_n$ or CH=N—(CH$_2$)$_n$,

B, $Z^1$, $Z^2$ or n: as defined above

The hydroxyl function of the cyanohydrins 22 can be further reacted. Thus, acylated cyanohydrins 23 are obtained, for example, by reacting the compounds 22 with acyl chlorides (Scheme 9).

Scheme 9

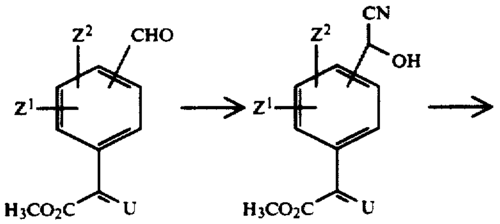

20 22

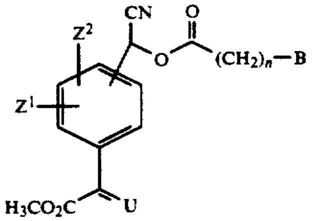

23

U: =O, =CH—OCH$_3$, =N—OCH$_3$ or =N—NH—CH$_3$

B, n, $Z^1$ or $Z^2$: as defined above

The benzyl bromides 11 can likewise (cf. Scheme 5) be reacted with nucleophiles, such as carboxylates, alcoholates, mercaptans, etc., the derivatives 24 being obtained. The compounds 24 can be converted into the active ingredients 25 by means of a Wittig reaction with $(C_6H_5)_3P^+$—CH$_2$—O—CH$_3$Cl$^-$ (EP 178 826), $C_6H_5P^+$—CH$_3$X$^-$ (X=halogen), $(C_6H_5)_3P^+$—CH$_2$—CH$_3$X$^-$ (X=halogen; DE 3705389) or $(C_3H_5)_3P^+$—CH$_2$—CH$_2$—CH$_3$X$^-$ (X=halogen) or by reaction with CH$_3$—O—N$^+$H$_3$Cl$^-$ (EP 253 213) or H$_2$N—NHCH$_3$ (Scheme 10).

Scheme 10

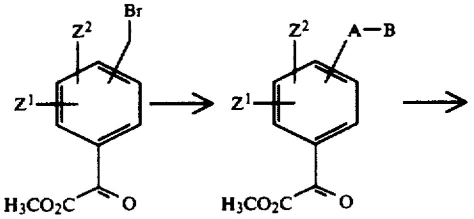

11 24

-continued

Scheme 10

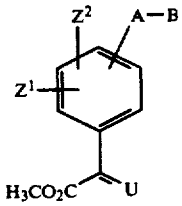

25

A: $CH_2$—O—CO, $CH_2$—O—$(CH_2)_n$, $CH_2$—S—$(CH_2)_n$ or $CH_2$—$NR^7(CH_2)_n$

U: =CH—$OCH_3$, =N—$OCH_3$, =N—NH—$CH_3$, =$CH_2$, =CH—$CH_3$ or =CH—$CH_2$—$CH_3$

B, n, $Z^1$, $Z^2$ or R as defined above.

Active ingredients of the structure 28 are obtained from the corresponding hydroxyphenylacetic esters 26, for example by alkylation of the compounds 26 to give the phenyl ethers 27 and subsequent formulation/methylation of 27 (EP 251 082) to give the active ingredients 28 (Scheme 11).

Scheme 11

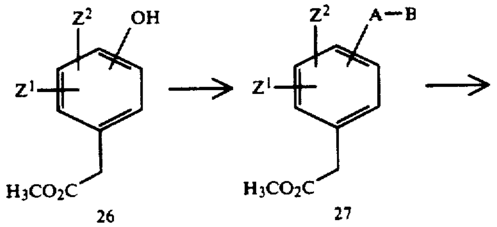

26 27

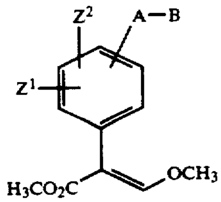

28

A: O—$(CH_2)_n$, O—$(CH_2)_{n+1}$—CO or O—$(CH_2)_{n+2}$—O

B, n, $Z^1$ or $Z^2$: as defined above

Alternatively, the hydroxyl function of the compounds 26 can be protected by a suitable protective group, eg. tetrahydropyranyl or benzyl.

Formylation/methylation (EP 251 082) of these protected phenols 29 then gives the methyl α-phenyl-β-methoxyacrylates 30, from which the phenols 31 can be liberated by treatment with hydrochloric acid in methanol or by catalytic hydrogenation (Scheme 12).

Scheme 12

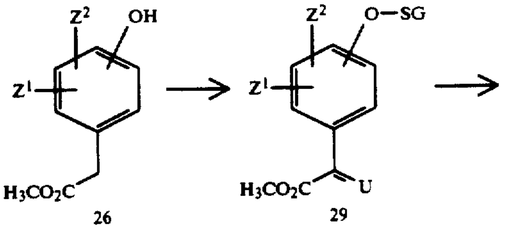

26 29

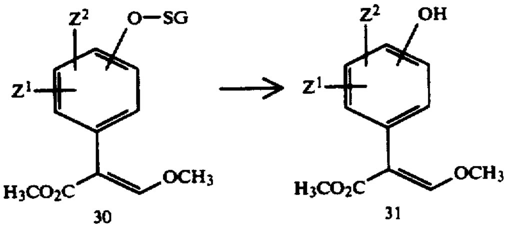

30 31

SG: Protective group, eg. benzyl or tetrahydropyranyl

The phenols 31 can then be reacted with electrophiles under standard conditions, the active ingredients 32 being obtained (Scheme 13).

Scheme 13

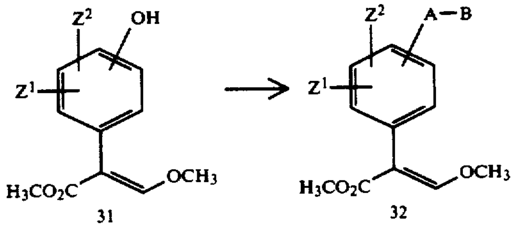

31 32

A: O—$(CH_2)_n$, O—$(CH_2)_n$—CO, O—CO—$(CH_2)_n$, O—$(CH_2)_n$—CO—O or O—$(CH_2)_{n+2}$—O

B, n, $Z^1$or $Z^2$: as defined above

Other useful starting materials for the preparation of the novel compounds 41 are the hydroxybenzaldehydes 33.

The hydroxybenzaldehydes 33 can be reacted with benzyl bromide under base catalysis. The benzylated derivatives 34 thus obtained are converted into the corresponding cyanohydrins 35 by reaction with HCN. These can be reacted with methanol and hydrochloric acid to give the imidoester hydrochlorides 36, which can be hydrolyzed to the mandelic esters 37.

The compounds 37 are oxidized with tetramethylpiperidine-N-oxyl (Tempo: P. Anelli et al., JOC 52 (1987), 2559)/NaOCl to give the ketoesters 38. These can be subjected to hydrogenolysis to give the phenols 39, which in turn react with methoxyamine hydrochloride or $H_2N$—$NHCH_3$ to give the phenolic building blocks 40. These can be etherified or esterified, the novel active ingredients 41 being obtained (Scheme 14). Alternatively, the ketoesters 39 are etherified or esterified to the compounds 42. The derivatives 42 are then converted into the active ingredients 41 by reaction with $CH_3$—O—$NH_3Cl$ or $H_2N$—$NHCH_3$ (Scheme 14).

Scheme 14

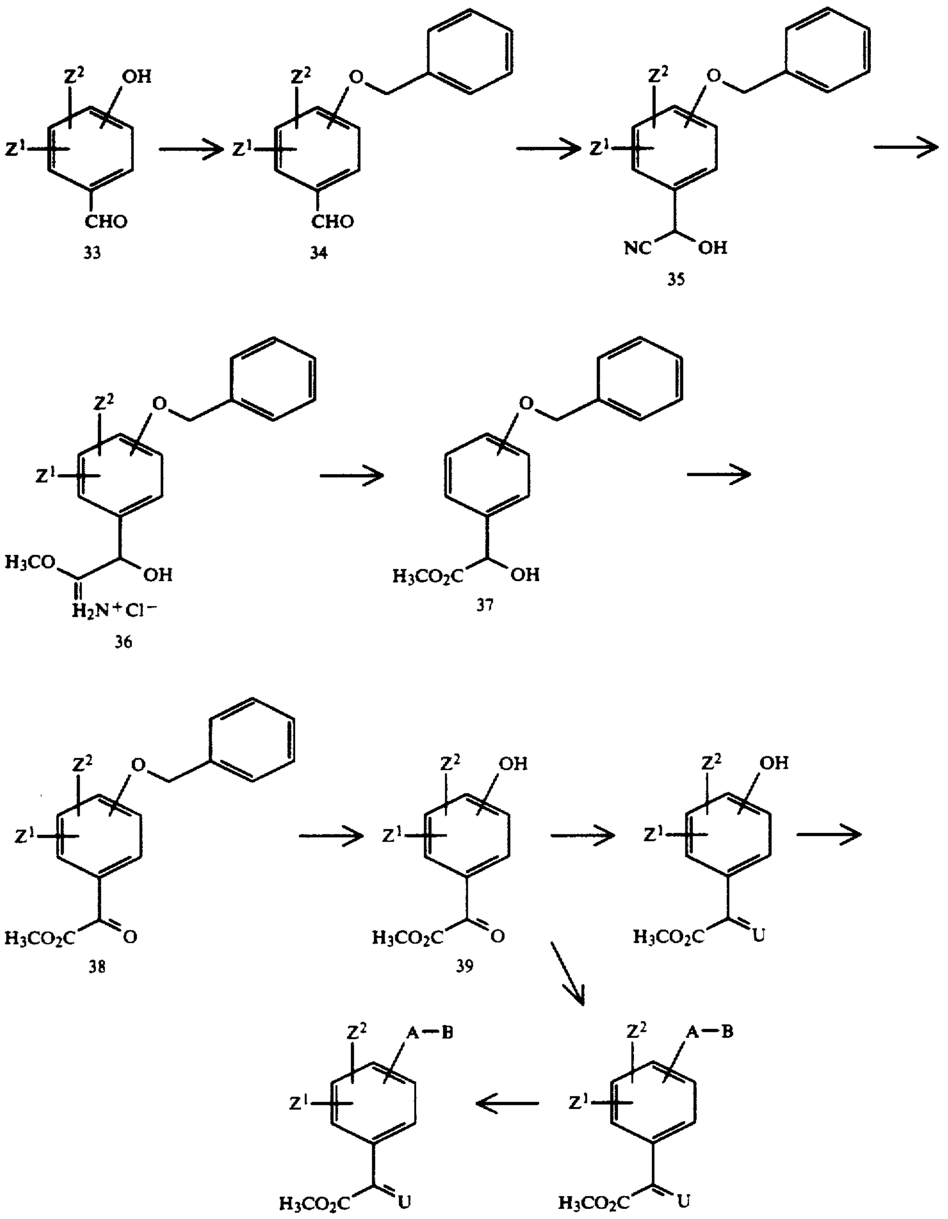

33 34 35 36 37 38 39 41 42

A: $O-(CH_2)_n$, $O-(CH_2)_n-CO$, $O-CO-(CH_2)_n$, $O-(CH_2)_n-CO-O$ or $O-(CH_2)_{n+2}-O$

U: $=N-OCH_3$ or $=N-NH-CH_3$

B, n, $Z^1$ or $Z^2$: as defined above

The ketoesters 38 can on the other hand also be subjected to Wittig reactions under base catalysis with $(C_6H_5)_3P^+-CH_2-O-CH_3X^-$, $(C_6H_5)_3P^+-CH_3X^-$, $(C_6H_5)_3P^+-CH_2-CH_3X^-$ or $(C_6H_5)_3P^+-CH_2-CH_2-CH_3X^-$ to give the benzyl ethers 43 (X = halogen).

The benzyl group can then be eliminated from these by hydrogenolysis or a free radical reaction, the phenols 44 being obtained. These can be etherified or esterified to the active ingredients 45 in reactions similar to Schemes 13 and 14 (Scheme 15).

Scheme 15

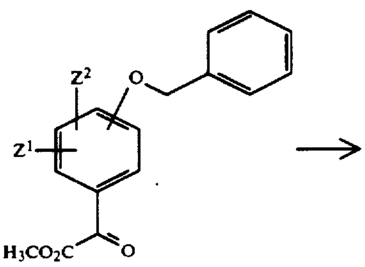

38

-continued

Scheme 15

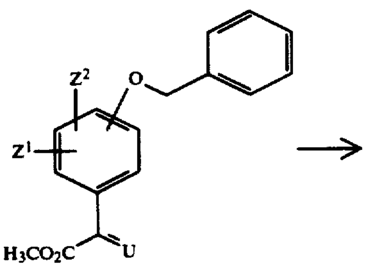

43

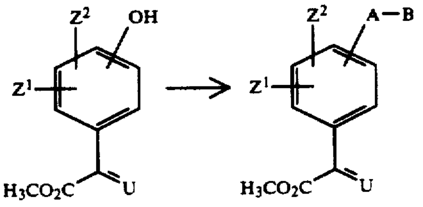

44

U: $=CH-OCH_3$, $=CH_2$, $=CH-CH_3$ or $=CH-CH_2-CH_3$

A: $O-(CH_2)_n$, $O-(CH_2)_n-CO$, $O-CO-(CH_2)_n$, $O-(CH_2)_n-CO-O$ or $O-(CH_2)_{n+2}-O$

B, n, $Z^1$ and $Z^2$: as defined above

Alternatively, the active ingredients 48 can be prepared by a method similar to Schemes 14 and 15 by introducing the side chain into the hydroxybenzaldehydes 33 themselves.

The benzaldehydes 46 thus obtained are then converted by the method described in Scheme 14 into the phenylketoacetates 47, which give the active ingredients 48 by a Wittig reaction with $(C_6H_5)_3P^+-CH_2-O-CH_3X^-$, $(C_6H_5)_3P^+-CH_3X^-$, $(C_6H_5)_3P^+-CH_2-CH_3X^-$ or $(C_6H_5)_3P^+-CH_2-CH_2-CH_3X^+$ (X=halogen) or by reaction with $CH_3-O-N^+H_3Cl^-$ or $H_2N-NHCH_3$ (Scheme 16).

Scheme 16

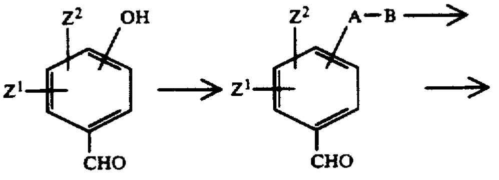

33 46

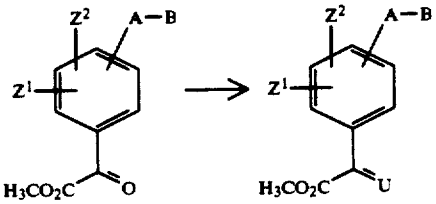

47 48

U: $=CH-OCH_3$, $=N-OCH_3$, $=N-NH-CH_3$, $=CH_2$, $=CH-CH_3$ or $=CH-CH_2-CH_3$

A: $O-(CH_2)_n$, $O-(CH_2)_n-CO$, $O-CO-(CH_2)_n$, $O-(CH_2)_n-CO-O$ or $O-(CH_2)_{n+2}-O$

B, n, $Z^1$ and $Z^2$: as defined above

The benzyl bromides 11 described in Scheme 4 can also be used for the synthesis of further key intermediates (Scheme 17). For example, the benzyl bromides 11 can be reacted with Na acetate or K acetate in highly solvating solvents, such as dimethylformamide or N-methylpyrrolidone, to give the acetates 49. The latter react under base catalysis with $(C_6H_5)_3P^+-CH_2-O-CH_3X^-$, $(C_6H_5)_3P^+-CH_3X^-$, $(C_6H_5)_3P^+-CH_2-CH_3X^-$ or $(C_6H_5)_3P^+-CH_2-CH_2-CH_3X^-$ (X=halogen) in Wittig reactions or with $CH_3ON^+H_3Cl^-$ or $H_2N-NHCH_3$, the derivatives 50 being formed.

The benzyl alcohols 51 and 52 are obtainable from the derivatives 49 and 50 by alkaline ester hydrolyis with aqueous alkali in the presence of a solubilizer, such as acetonitrile, dioxane or tetrahydrofuran.

Scheme 17

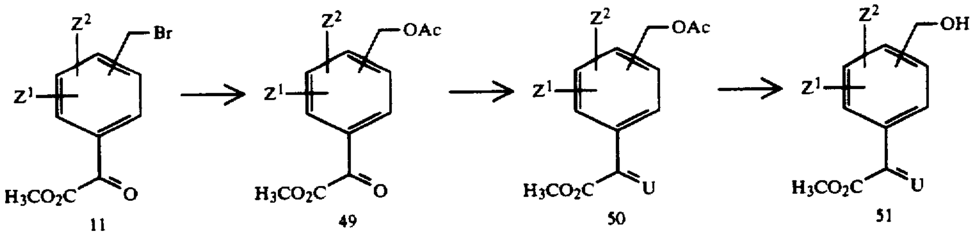

11 49 50 51

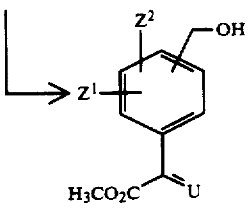

52

U: $=CH-OCH_3$, $=N-OCH_3$, $=N-NH-CH_3$, $=CH_2$, $=CH-CH_3$ or $=CH-CH_2-CH_3$ $Z^1$ and $Z^2$: as defined above The benzyl bromides 13, likewise obtained according to Scheme 4, can be converted into the acetates 53 (Scheme 18) similarly to Scheme 17.

Scheme 18

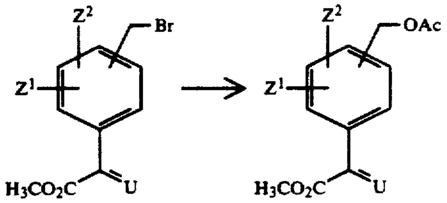

12 53

U: $=CH-OCH_3$, $=N-OCH_3$ or $=N-NH-CH_3$ $Z^1$ and $Z^2$: as defined above

The benzyl alcohols 54 can be converted into the benzaldehydes 55 by oxidation with suitable oxidation agents, such as dimethyl sulfoxide or pyridinium chlorochromate, into the benzoic acid 56 by oxidation with, for example, chromium(VI) oxide in acetone/sulfuric acid and into the bromides 57 or chlorides 58 by reaction with suitable hydrogenating agents, eg. $PBr_3$ or HBr or $PCl_5$, $SOCl_2$ or $PCl_3$ (Scheme 19).

A: $HC{\equiv}CH$, $CH_2-CH_2$, $CH(CN)-OH$, $CH(CN)-O-CO-(CH_2)_n$, $CH{=}N-(CH_2)_n$ or $CH{=}N-O-(CH_2)_n$ U: $=CH-OCH_3$, $=N-OCH_3$, $=N-NH-CH_3$, $=CH_2$, $=CH-CH_3$ or $=CH-CH_2-CH_3$ B, $Z^1$ and $Z^2$: as defined above The benzoic acids 56 can be esterified under standard conditions, the benzoic esters 60 being obtained (Scheme 21).

Scheme 21

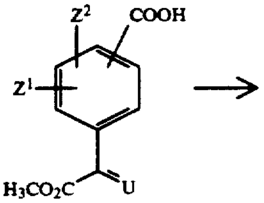

56

Scheme 19

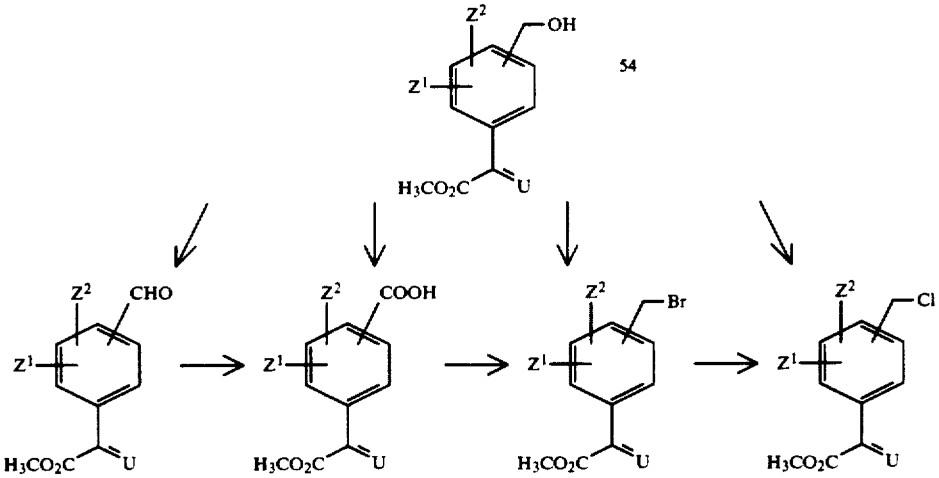

54

55 56 57 58

U: $=O$, $=CH-OCH_3$, $=N-OCH_3$, $=N-NH-CH_3$, $=CH_2$, $=CH-CH_3$ or $=CH-CH_2-CH_3$ $Z^1$ and $Z^2$: as defined above The active ingredients 59 are obtainable (Scheme 19) from the benzaldehydes 55 similarly to the reactions described in Schemes 6, 8 and 9.

Scheme 20

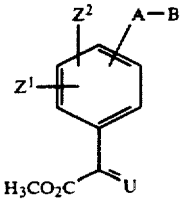

59

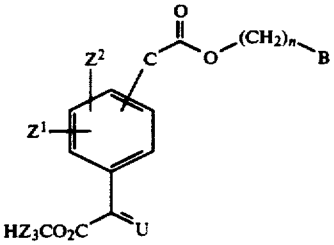

60

U: $=O$, $=CH-OCH_3$, $=N-OCH_3$, $=N-NH-CH_3$, $=CH_2$, $=CH-CH_3$ or $=CH-CH_2-CH_3$ $Z^1$ and $Z^2$: as defined above The benzyl bromides 57 or chlorides 58 can be converted into stilbene or dihydrostilbenes 61 in reactions similar to Scheme 6, via their phosphonium salts or phosphonates (Scheme 22).

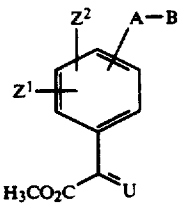

61

U: $=CH-OCH_3$, $=N-OCH_3$, $=N-NH-CH_3$, $=CH_2$, $-CH-CH_3$ or $-CH-CH_2-CH_3$

A: $HC=CH$, $H_2C-CH_2$

B, $Z^1$ and $Z^2$: as defined above

The thioenolethers 63 can be prepared from the corresponding oxo analogs 64 by methods known from the literature (EP 178 826) (Scheme 23).

Scheme 23

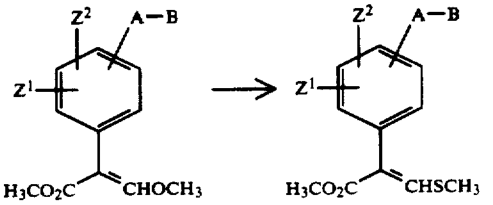

64 63

A, B, $Z^1$ and $Z^2$: as defined above

The Examples which follow illustrate the preparation of the novel compounds.

EXAMPLE 1 a) Methyl m-methylmandelate

A mixture of 65 g (1 mol) of KCN and 53.5 g (1 mol) of $NH_4Cl$ in 300 ml of water and 60 g (0.5 mol) of m-tolylaldehyde in 500 Ml Of ether is stirred overnight at room temperature (20° C.). Thereafter, the organic phase is separated off, extracted twice with water, dried and evaporated down.

67.6 g of the cyanohydrin are obtained as a reddish brown oil.

67.6 g (about 0.5 mol) of the crude cyanohydrin product are dissolved in 600 ml of ether and the solution is cooled to 0° C.

32 g (1 mol) of methanol and 136 ml (0.6 mol) of a 4.4 M solution of hydrochloric acid in ether are added in succession and the mixture is stirred overnight at 10°-15° C. and for a further two days at room temperature. The imidoester hydrochloride which is crystallized out is filtered off under suction, washed with ether, transferred to a flask and hydrolyzed by boiling for 30 minutes with water.

The aqueous phase is cooled to room temperature and extracted twice with ether. The ether phase is filtered over a short silica gel column, dried over $MgSO_4$ and evaporated down. 40 g (0.22 mol; 44% based on m-tolylaldehyde) of methyl m-methylmandelate are obtained as the residue in the form of a yellow oil.

$^1H$-NMR ($CDCl_3$): δ: 2.3 (s, 3H); 3.7 (s, 3H); 4.1 (s, broad, 1H); 5.1 (s, 1H); 7.1 (m, 4H).

b) Methyl m-methylphenylglyoxylate (Table 1, Number 1, abbreviation: 1/1)

170 ml of 12.5% strength NaOCl solution are added dropwise at 20° C. to a stirred mixture of 40 g (0.22 mol) of methyl m-methylmandelate and 1.5 g (9.6 mmol) of tetramethylpiperidine-N-oxyl in 200 ml of $CH_2Cl_2$ and 1.4 g (13 mmol) KBr, 3.5 g (25 mmol) of $NaH_2PO_4.H_2O$ and 4.3 g (25 mmol) of $Na_2HPO_4.2\ H_2O$ in 200 ml of water.

Stirring is carried out for 3 hours at room temperature, after which the organic phase is separated off, washed with $NAHCO_3$ solution and water and evaporated down.

The residue obtained comprises 37.5 g (0.21 mol, 96%) of methyl m-methylphenylglyoxylate as a yellow oil.

$^1H$-NMR ($CDCl_3$): δ: 2.4 (s, 3H); 4.0 (s, 3H); 7.4 (m, 2H); 7.8 (m, 2H).

EXAMPLE 2 a) Methyl m-bromomethylenephenylglyoxylate (Table 1, Number 2, abbreviation 1/2)

18 g (0.1 mol) of methyl m-methylphenylglyoxylate, 20 g (0.11 mol) of N-bromosuccinimide and 0.1 g (0.6 mmol) of azoisobutyronitrile in 200 ml of $CCl_4$ are exposed for 4 hours to a 300 watt UV lamp, the solution heating up to the reflux temperature.

The precipitated succinimide is then filtered off under suction. The organic phase is washed with water, dried with $MgSO_4$ and filtered under suction over a little silica gel, and the filtrate is evaporated down. 28.6 g of a reddish brown oil are obtained, which is shown by NMR analysis to contain 65% of the desired compound methyl m-bromomethylenephenylglyoxylate (70%, based on methyl m-methylphenylglyoxylate), about 20% of the corresponding dibromide and about 15% of starting material.

$^1H$-NMR ($CDCl_3$): δ: 4.0 (s, 3H); 4.55 (s, 2H); 7.3-8.2 (m, 4H).

b) Methyl m- (o-methylphenoxymethylene) -phenylglyoxylate (Table 2, Number 490, abbreviation 2/490)

0.6 g (24 mmol) of NaH is added a little at a time to a solution of 2.2 g (20.4 mmol) of o-cresol in 50 ml of dimethylformamide at room temperature, vigorous evolution of gas occurring. 5.1 g of the crude methyl m-bromomethylenephenylglyoxylate (Example 1c; contains 13 mmol of the benzyl bromide) are then added. The reaction mixture warms up to about 40° C.

Stirring is carried out for 4 hours at room temperature, the reaction mixture is diluted with water and the aqueous phase is extracted several times with ether. The combined ether phases are washed several times with $Na_2CO_3$ solution and water, dried over $MgSO_4$ and evaporated down.

The residue is purified by column chromatography, after which 3.8 g of the desired product, contaminated with o-cresol, are obtained.

Bulb tube distillation (0. 1 mbar; 175°-225° C.) gives 2.4 g (65%) of methyl m-(o-methylphenoxymethylene)-phenylglyoxylate as a yellow oil.

$^1H$-NMR ($CDCl_3$): δ: 4.0 (s, 3H); 5.1 (s, 2H); 6.7-7.2 (m, 4H); 7.5 (t, J=9Hz, 1H); 7.7 (d, J=9Hz, 1H); 8.0 (d, J=9Hz, 1H); 8.1 (d, J=9Hz, 1H).

EXAMPLE 3

Methyl 2-[m-(o-methylphenoxymethylene)-phenyl]-crotonate (Table 6, Number 65, abbreviation 6/65)

5.8 ml of a 15% strength solution of butyllithium in hexane are added to 4.2 g (10 mmol) of ethyltriphenylphosphonium iodide in 20 ml of tetrahydrofuran at 0° C. while stirring.

After 30 minutes at room temperature, the mixture is cooled to −780° C., a pale yellow solid being precipitated, and a solution of 2.4 g (8 mmol) of methyl m-(o-methylphenoxymethylene)-phenylglyoxylate in tetrahydrofuran is added. The color of the reaction mixture changes from orange to yellow.

The reaction mixture is stirred for 2 hours at room temperature, after which it is poured onto water, the phases are separated and the aqueous phase is extracted several times with ether.

The ether phase is dried over $MgSO_4$ and filtered under suction over a short silica gel column, and the filtrate is evaporated down.

The remaining oil is chromatographed once with 5:1 cyclohexane/ethyl acetate and once with 4:1 cyclohexane/methylene chloride. 0.8 g (34%) of methyl 2-[m-(o-methylphenoxymethylene)-phenyl]-crotonate is obtained as a yellow oil.

$^1$H-NMR ($CDCl_3$): δ: 1.7 (d, 8Hz, 3H); 2.3 (s, 3H); 3.7 (s, 3H); 5.1 (s, 2H); 6.8–7.5 (m, 9H).

EXAMPLE 4 m-Methylphenylglyoxylic acid methyl ester O-methyl oxime (Table 1, Number 37, abbreviation 1/37)

15 g (84 mmol) of methyl m-methylphenylglyoxylate and 8.3 g (100 mmol) of O-methylhydroxylamine hydrochloride in 150 ml of methanol are refluxed for 5 hours. Thereafter, the solvent is evaporated off and the residue is filtered with ether over silica gel.

Evaporating off the ether gives 16.2 g (93%) of m-methylphenylglyoxylic acid methyl ester O-methyl oxime as an oily cis/trans mixture (nonpolar isomer:polar isomer=25:1).

$^1$H-NMR ($CDCl_3$): δ (nonpolar isomer): 2.35 (s, 3H); 3.93 (s, 3H); 4.0 (s, 3H); 7.1–7.5 (m, 4H); δ (polar isomer) 2.38 (s, 3H) ; 3.87 (s, 3H) ; 4.05 (s, 3H); 7.1–7.5 (m, 4H).

EXAMPLE 5 m-Bromomethylenephenylglyoxylic acid methyl ester O-methyl oxime (Table 1, Number 38, abbreviation 1/38)

15 g (72.4 mmol) of m-methylphenylglyoxylic acid methyl ester O-methyl oxime, 13.5 g (75.8 mmol) of N-bromosuccinimide and 0.1 g (0.6 mmol) of azobisisobutyrodinitrile in 150 ml of $CH_2Cl_2$ are exposed for 4 hours to a 300 watt UV lamp, the reaction mixture being refluxed. Thereafter, the organic phase is extracted with water, dried over $MgSO_4$ and evaporated down.

Purification by column chromatography gives 10.7 g of the nonpolar isomer and 6.1 g of the polar isomer, each of which contains about 5% of the corresponding dibromide and about 10% of the starting material.

$^1$H-NMR ($CDCl_3$): δ (nonpolar isomer): 3.95 (s, 3H); 4.05 (s, 3H); 4.5 (s, 2H); 7.2–7.5 (m, 3H); 7.6 (s, 1H); δ (polar isomer): 3.90 (s, 3H); 4.10 (s, 3H); 4.5 (s, 2H); 7.2–7.5 (m, 4H).

EXAMPLE 6 m-(6-methyl-2-oxymethylenepyridyl)-phenylglyoxylic acid methyl ester O-methyl oxime (Table 20, Number 2, abbreviation 20/2)

0.18 g (6.3 mmol) of NaH is added to 0.76 g (7 mmol) of 2-hydroxy-6-methylpyridine in 20 ml of dimethylformamide. Stirring is carried out for 30 minutes at room temperature, after which evolution of gas has ceased.

2 g of m-bromomethylenephenylglyoxylic acid methyl ester O-methyl oxime (nonpolar isomer, containing 1.7 g (6 mmol) of the substituted benzyl bromide) are then added and the mixture is stirred overnight at room temperature. Thereafter, the reaction mixture is diluted with water and the aqueous phase is extracted three times with ether. The combined ether phases are extracted with water, dried over $MgSO_4$ and evaporated down.

The oily residue is chromatographed with 1:1 cyclohexane/methylene chloride.

0.5 g (27%) of m-(6-methyl-2-oxymethylenepyridyl)-phenylglyoxylic acid methyl ester O-methyl oxime is obtained as a yellow oil.

$^1$H-NMR ($CDCl_3$): δ: 2.45 (s, 3H); 3.95 (s, 3H); 4.05 (s, 3H); 5.4 (s, 2H); 6.6 (d, J=8Hz, 1H); 6.75 (d, J=8Hz, 1H); 7.3–7.6 (m, 4H); 7.7 (s, 1H).

EXAMPLE 7

2-(N-methyl-N-phenyl-m-aminomethylphenyl)-3-methoxyacrylate (Table 2, Number 88)

2.9 g (10 mmol) of methyl 2-(m-bromomethylphenyl)-3-methoxyacrylate (prepared similarly to EP 226 917) and 1.1 g (10 mmol) of N-methylaniline in 30 ml of $CH_2Cl_2$ are stirred for 1 hour at room temperature and for 5 hours while refluxing. Thereafter, the organic phase is extracted with $NaHCO_3$ solution and water, dried over $MgSO_4$ and evaporated down.

Chromatography with 10:1 cyclohexane/ethyl acetate gives 2.5 g (80%) of the title compound as a pale yellow oil.

$^1$H-NMR ($CDCl_3$): δ: 3.0 (s, 3H); 3.65 (s, 3H); 3.75 (s, 3H); 4.5 (s, 3H); 6.6–6.8 (m, 3H); 7.0–7.4 (m, 6H); 7.5 (s, 1H).

EXAMPLE 8 a) Methyl 2-(m-formylphenyl)-3-methoxyacrylate (Table 1, Number 22)

5.7 g (20 mmol) of methyl 2-(m-bromomethylphenyl)-3-methoxyacrylate and 6.7 g (50 mmol) of N-methylmorpholine N-oxide monohydrate in 100 ml of $CCl_4$ are refluxed for 7 hours. The reaction mixture is cooled and is extracted once with water, once with 2 N HCl and again with water. The organic phase is dried over $MgSO_4$ and evaporated down.

The oily residue is chromatographed with 4:1 cyclohexane/ethyl acetate, after which 3.0 g (13.6 mmol, 68%) of methyl 2-(m-formylphenyl)-3-methoxyacrylate are obtained as a colorless oil.

$^1$H-NMR ($CDCl_3$): δ: 3.75 (s, 3H); 3.85 (s, 3H); 7.5 (t, J=8Hz, 1H); 7.65 (m, 2H); 7.8 (d, broad, J=8Hz, 1H); 7.9 (s, broad, 1H); 10 (s, 1H).

b) Methyl 2-[m-(α-phenylcarboxy)-cyanomethylphenyl]-3-methoxyacrylate ((Table 2, Number 95)

A mixture of 2.9 g (13 mmol) of methyl 2-(m-formylphenyl)-3-methoxyacrylate in 20 ml of ether and 1.7 g (26 mmol) of KCN and 1.5 g (26 mmol) of $NH_4Cl$ in 7.5 ml of water is stirred at room temperature overnight, after which only a small amount of starting material is detectable by thin layer chromatography.

Thereafter, the reaction mixture is diluted with a little water, and the aqueous phase is separated off and is extracted twice with ether. The combined organic phases are dried over $MgSO_4$ and evaporated down.

The remaining oil is subjected to coarse chromatographic purification to give 2.4 g of a colorless oil, which is directly reacted further.

1.4 g (10 mmol) of benzoyl chloride are added dropwise to 2.4 g (about 10 mmol) of the crude cyanohydrin product, 1.1 g (11 mmol) of triethylamine and 0.1 g of p-N-dimethylaminopyridine in 20 ml of $CH_2Cl_2$ while cooling slightly, a white solid being precipitated.

After 1 hour at room temperature, the reaction mixture is washed once with water, twice with Na bisulfite solution and again with water, dried over $MgSO_4$ and evaporated down. The remaining oil is chromatographed once with 8:1 cyclohexane/ethyl acetate and once with 0.1% methanol in methylene chloride, after which 2.1 g (6 mmol), 46% based on methyl 2-(m-formylphenyl)-3-methoxyacrylate) of the title compound are obtained as a colorless oil.

$^1$H-NMR ($CDCl_2$): δ: 3.75 (s, 3H); 3.85 (s, 3H); 6.7 (s, 1H), 7.4-7.7 (m, 9H); 8.1 (d, J=8Hz, 1H).

EXAMPLE 9

2-(p-Benzyloxyphenyl)-3-methoxyacrylate (Table 1, Number 33)

90 g (0.54 mol) of methyl 4-hydroxyphenylacetate, 60 g (0.71 mol) of dihydropyran and 0.1 g of p-toluenesulfonic acid are combined. The temperature of the mixture initially decreases to 5°-10° C. but increases again in the course of the reaction and is kept at 30°-35° C. by cooling in a water bath. After 1 hour, the excess dihydropyran is stripped off under reduced pressure from a water pump.

The crude tetrahydropyranyl ether product is dissolved in 220 ml of methyl formate, and 44 g (0.78 mol) of $NaOCH_3$ are added while cooling to about 10° C.

After 2 hours at room temperature, the reaction mixture is diluted with $CH_2Cl_2$ and water and the aqueous phase is acidified to pH 4.5 with dilute hydrochloric acid and is extracted several times with $CH_2Cl_2$. The combined organic phases are dried over $MgSO_4$ and evaporated down.

The oily crude product obtained as the residue is dissolved in 700 ml of . . . , 90 g (0.65 mol) of $K_2CO_3$ and 74 g (0.59 mol) of dimethyl sulfate are added and the mixture is stirred overnight at room temperature.

The reaction mixture is then evaporated down in a rotary evaporator and the residue is diluted with water. The aqueous phase is extracted several times with ether. The combined ether phases are dried over $MgSO_4$ and evaporated down.

The crude methyl 2-(p-tetrahydropyranyloxyphenyl)-3-methoxyacrylate thus obtained is dissolved in 700 ml of methanol, and 0.5 ml of concentrated hydrochloric acid and 5 ml of water are added. After 2 hours at room temperature, 2 g of $NaHCO_3$ are added and the reaction mixture is evaporated down in a rotary evaporator.

The oily residue is taken up in $CH_2Cl_2$, and the solution is dried over $MgSO_4$ and evaporated down. The residue is partially crystalline and is stirred with methyl tert-butyl ether. The solid is filtered off under suction, the mother liquor is evaporated down and the residue is chromatographed.

The title compound is obtained as a white solid (mp.=107°-109° C.) in a total yield of 66 g (0.32 mol; 59%, based on methyl p-hydroxyphenyl acetate).

$^1$H-NMR ($CDCl_3$): δ: 3.75 (s, 3H); 3.8 (s, 3H); 6.75 (d, J=8Hz, 2H); 7.15 (d, J=8Hz, 2H); 7.5 (s, 1H).

EXAMPLE 10

2-(p-Benzyloxyphenyl)-3-methoxyacrylate (Table 3, Number 14)

1. 8 g (10. 5 mmol) of benzyl bromide are added, at −20° C., to 2.1 g (10 mmol) of methyl 2-(p-hydroxyphenyl)-3-methoxyacrylate and 0.56 g (10 mmol) of KOH powder in 20 ml of dimethylformamide. Stirring is then carried out for 3 hours at room temperature. Thereafter, the reaction mixture is diluted with water and the aqueous phase is extracted three times with ether.

The combined ether phases are extracted with water, dried over $MgSO_4$ and evaporated down. Chromatographic purification of the oily residue gives 2.4 g (8.1 mmol, 80%) of the title compound as a colorless solid (mp.=77°-79° C.).

$^1$H-NMR ($CDCl_3$) : δ: 3.75 (s, 3H); 3.85 (s, 3H); 5.1 (s, 2H); 6.95 (d, J=11Hz, 2H); 7.2-7.5 (m, 7H); 7.55 (s, 1H).

EXAMPLE 11

Methyl 2-m-(phenylcarbonylmethyleneoxyphenyl)-3-methoxyacrylate (Table 2, Number 19)

0.3 g (12 mmol) of sodium hydride is added a little at a time to 2.1 g (10 mmol) of methyl 2-m-hydroxyphenyl-3-methoxyacrylate (Table 1, Number 24; prepared similarly to Example 5a) in 20 ml of dimethylformamide.

After the end of the addition, the reaction mixture is stirred for 30 minutes at room temperature, after which 3.3 g (1.6 mmol) of a-bromoacetophenone are added.

Stirring is continued overnight at room temperature, after which the reaction mixture is diluted with water and the aqueous phase is extracted three times with ether. The ether phase is extracted with water, dried over magnesium sulfate and evaporated down.

The remaining oil is chromatographed, 1.1 g (3.4 mmol, 34%) of the title compound being obtained as a white solid (mp. 103°-105° C.).

$^1$H-NMR ($CDCl_3$): δ: 3.35 (s, 2H); 3.65 (s, 3H); 3.8 (s, 3H); 5.55 (s, 2H); 6.8 (m, 3H); 7.2 (t, J=8Hz, 1H); 7.5-7.8 (m, 4H); 8.05 (d, J=8Hz, 2H).

EXAMPLE 12 a) Methyl m-benzyloxymandelate 61 g (0.5 mol) of m-hydroxybenzaldehyde, 86 g (0.5 mol) of benzyl bromide and 70 g (0.5 mol) of $K_2CO_3$ in 500 ml of ethanol are refluxed for 3 hours.

The solid is then filtered off and the ethanol is evaporated off in a rotary evaporator. Thereafter, the residue is taken up in $CH_2Cl_2$ and the organic phase is extracted with 1 NAOH and twice with water. The solution is dried over $MgSO_4$ and the solvent is evaporated under reduced pressure.

The residue obtained comprises 102.5 g of m-benzyloxybenzaldehyde as a reddish brown oil.

A mixture of 102.5 g of the above crude benzyl ether in 400 ml of ether and 65 g (1 mol) of KCN and 53.5 g (1 mol) of $NH_4Cl$ in 300 ml of water is stirred overnight at room temperature. Thereafter, the organic phase is separated off, extracted twice with NaCl solution, dried over $MgSO_4$ and evaporated down. The residue obtained comprises 113 g of m-benzyloxymandelonitrile as a brown oil which is directly reacted further.

140 ml of 4.4 molar hydrochloric acid solution (0.62 mol) in ether are added, at 0°-50° C., to 113 g of the crude mandelonitrile product and 32 g (1 mol) of methanol in 500 ml of ether. Stirring is carried out overnight at 5°-15° C.; the corresponding imidoester hydrochloride is precipitated and is filtered off under suction and washed with ether (yield: 107 g). The solid is transferred to a round-bottomed flask and boiled for 30 minutes with 500 ml of water. Thereafter, the reaction mixture is cooled to room temperature and the aqueous phase is extracted with ether.

The combined ether phases are filtered with suction through silica gel, dried over $MgSO_4$ and evaporated down.

86 g (0.32 mol; 63%, based on m-hydroxybenzaldehyde) of methyl m-benzyloxymandelate are obtained as a residue.

$^1$H-NMR ($CDCl_3$): δ: 3.5 (s, broad, 1H); 3.7 (s, 3H); 5.05 (s, 2H); 5.15 (s, 1H); 6.8-7.1 (m, 3H); 7.2-7.5 (m, 6H).

b) Methyl m-benzyloxyphenylglyoxylate 245 ml of 12.5% strength NaOCl solution are added dropwise to a stirred mixture of 86 g (0.32 mol) of methyl m-benzyloxymandelate and 2 g (13 mmol) of tetramethylpiperidine-1-oxyl in 250 ml of $CH_2Cl_2$ and 1.95 g (16 mmol) of KBr, 4.9 g (28 mmol) of $Na_2HPO_4.2H_2O$ and 6.1 g (44 mmol) of $NaH_2PO_4.H_2O$ in 250 ml of water, while cooling with a water bath.

Stirring is carried out for 3 hours at room temperature, the aqueous phase is separated off and the organic phase is extracted with $NaHCO_3$ solution and with water. The organic phase is dried over $MgSO_4$ and evaporated down. 78 g (0.29 mol, 90%) of methyl m-benzyloxyphenylglyoxylate are obtained as a residue.

$^1$H-NMR ($CDCl_3$): δ: 3.95 (s, 3H); 5.1 (s, 2H); 7.1-7.7 (m, 9H).

EXAMPLE 13 m-Benzyloxyphenylglyoxylic acid methyl ester O-methyl oxime (Table 2, Number 119)

4 g (15 mmol) of methyl m-benzyloxyphenylglyoxylate and 1.4 g (17 mmol) of O-methylhydroxylamine hydrochloride in 25 ml of ethanol are refluxed for 3 hours. The reaction mixture is then evaporated down. The residue is taken up in ether and the insoluble constituents are filtered off.

The solvent is evaporated off and the remaining residue is purified by column chromatography.

3.1 g (10.4 mmol, 69%) of the nonpolar isomer (colorless crystals, mp.=62°-63° C.) and 0.9 g (3 mmol, 20%) of the polar isomers (colorless crystals, mp.=63°-64° C.) of the title compound are obtained.

$^1$H-NMR ($CDCl_3$) of the nonpolar isomer: δ: 3.9 (s, 3H); 4.0 (s, 3H); 5.05 (s, 2H); 6.95-7.5 (m, 9H).

$^1$H-NMR ($CDCl_3$) of the polar isomer: δ: 3.85 (s, 3H); 4.05 (s, 3H); 5.05 (s, 2H); 7.0 (m, 3H); 7.2-7.5 (m, 6H).

EXAMPLE 14 a) m-Hydroxyphenylglyoxylic acid methyl ester O-methyl oxime (Table 1, Number 42)

65 g (0.24 mol) of methyl m-benzyloxyglyoxylate and 6 g of 10% strength Pd/C in 500 ml of methanol are stirred at 60° C. under hydrogen (1 bar).

After a reaction time of 8 hours in each case, the hydrogenation catalyst is filtered off and the same amount of fresh catalyst is added.

After a total reaction time of 32 hours, the reaction is complete. The catalyst is filtered off and the reaction mixture is evaporated down. The residue obtained comprises 42 g of methyl m-hydroxyphenylglyoxylate as an oily crude product.

21 g of the above crude product and 10 g (0.12 mol) of O-methylhydroxylamine hydrochloride in 200 ml of methanol are refluxed for 2 hours.

Thereafter, the solvent is distilled off, the residue is taken up in ether and the undissolved constituents are filtered off. The ether is evaporated off and the residue thus obtained is purified by column chromatography. 8.7 g (42 mmol; 35%, based on methyl mbenzyloxyphenylglyoxylate) of the nonpolar isomer (pale yellow oil) and 4.2 g (20 mmol; 17%, based on methyl mbenzyloxyphenylglyoxylate) of the polar isomer of the title compound are obtained.

$^1$H-NMR ($CDCl_3$) of the nonpolar isomer: δ: 3.9 (s, 3H); 4.0 (s, 3H); 5.7 (s, broad, 1H); 6.9 (d, J=8Hz, 1H); 7.1 (m, 2H); 7.2 (t, J=8Hz, 1H).

$^1$H-NMR ($CDCl_3$) of the polar isomer: δ: 3.85 (s, 3H); 4.05 (s, 3H); 6.2 (s, broad, 1H); 6.8-7.0 (m, 3H); 7.2 (t, J=8Hz, 1H).

EXAMPLE 15 m-(o-Fluorobenzyloxy)-phenylglyoxylic acid methyl ester O-methyl oxime (Table 5, Number 1)

0.3 g (12.5 mmol) of sodium hydride is added a little at a time to 2.1 g (10 mmol) of m-hydroxyphenylglyoxylic acid methyl ester O-methyl oxime (nonpolar isomer:polar isomer=2:1) in 20 ml of dimethylformamide. Stirring is carried out for 30 minutes at room temperature, 1.9 g (10 mmol) of 2-fluorobenzyl bromide are added and stirring is continued overnight at room temperature.

The reaction mixture is then diluted with water and extracted with ether. The combined ether phases are extracted with water, dried over $MgSO_4$ and evaporated down. Purification of the residue by column chromatography gives 1.7 g (5.4 mmol, 54%) of the nonpolar isomer (pale yellow oil) and 0.5 g (1.6 mmol, 16%) of the polar isomer (colorless solid, mp.=77°-79° C.) of the title compound.

$^1$H-NMR ($CDCl_3$) of the nonpolar isomer: δ: 3.9 (s, 3H); 5.1 (s, 2H); 6.9-7.6 (m, 8H).

$^1$H-NMR ($CDCl_3$) of the polar isomer: δ: 3.85 (s, 3H), 4.05 (s, 3H); 5.1 (s, 2H); 6.9-7.6 (m, 8H).

EXAMPLE 16

Methyl 2-(p-acetoxyphenyl)-3-methoxyacrylate (Table 3, Number 22)

3 g (10.5 mmol) of methyl 2-(p-bromomethylphenyl)-3-methoxyacrylate (prepared similarly to EP 226 917), 1.1 g (11.2 mmol) of potassium acetate and 50 mg of potassium iodide in 70 ml of N-methylpyrrolidone are stirred for 3 hours at 70°-80° C. The reaction mixture is diluted with water and extracted three times with ether. The combined ether phases are washed with water, dried over $MgSO_4$ and evaporated down. Purification of the residue by column chromatography gives 2.3 g (8.7 mmol, 83%) of the title compound as colorless crystals (mp.= 69°-70° C.).

$^1$H-NMR ($CDCl_3$): δ: 2.1 (s, 3H); 3.75 (s, 3H); 3.85 (s, 3H); 5.1 (s, 2H); 7.35 (s, 4H); 7.6 (s, 1H).

EXAMPLE 17

Methyl 2- (p-hydroxymethylphenyl) -3-methoxyacrylate (Table 1, Number 36)

12 g (45 mmol) of methyl 2-(p-acetoxyphenyl)-3-methoxyacrylate in 200 ml of dioxane and 1.9 g (47 mmol) of NAOH in 100 ml of water are stirred for 24 hours at room temperature. A further 1.8 g of NAOH are added, stirring is carried out for 30 minutes and the reaction mixture is evaporated down under reduced pressure.

The residue is taken up with dilute hydrochloric acid and the aqueous phase is extracted three times with ether. The ether phase is filtered under suction over $Al_2O_3$ and the solvent is evaporated off. The residue obtained comprises 4.2 g (19 mmol, 40%) of the title compound as a colorless oil.

$^1$H-NMR ($CDCl_3$): δ: 2.4 (s, broad, 1H); 3.75 (s, 3H); 3.85 (s, 3H); 4.65 (s, 2H); 7.3 (s,-4H); 7.55 (s, 1H)

EXAMPLE 18

Methyl 2-(p-carboxyphenyl)-3-methoxyacrylate (Table 1, Number 32)

5 ml of Jones reagent (L. Chinn, Selection of Oxidants in Synthesis, Marcel Dekker, New York 1971, page 42) are added dropwise, at from −10° to −20° C., to 2.2 g (10 mmol) of methyl 2-(p-hydroxymethylphenyl)-3-methoxyacrylate in 20 ml of acetone. The mixture is allowed to reach room temperature and a further 3 ml of Jones reagent are added to the greenish solution, after which a permanent orange color is obtained.

The excess oxidizing agent is decomposed by adding a little methanol, the precipitated greenish solid is filtered off under suction and the solvent is evaporated under reduced pressure. The residue is taken up in $CH_2Cl_2$ and the organic phase is extracted twice with water, dried over $MgSO_4$ and evaporated down.

The residue is purified by column chromatography, after which 0.8 g (3.4 mmol, 34%) of the title compound is obtained.

$^1$H-NMR ($CDCl_3$): δ: 3.75 (s, 3H) ; 3. 9 (s, 3H) ; 7.45 (d, J=8Hz, 2H) ; 7.6 (s, 1H); 8.1 (d, J=8Hz, 2H); 11.4 (s, broad, 1H).

EXAMPLE 19

Methyl 2-(p-carboxymethylphenyl)-3-methoxyacrylate (Table 3, Number 26)

0.3 g (12.5 mmol) of sodium hydride is added a little at a time to 1 g (4 mmol) of methyl 2-(p-carboxyphenyl)-3-methoxyacrylate in 10 ml of dimethylformamide. Stirring is carried out for 30 minutes at room temperature, after which 1.3 g (10 mmol) of dimethyl sulfate are added. Stirring is continued for a further 30 minutes, the mixture is diluted with 100 ml of 1% strength $NH_4OH$ solution and the aqueous phase is extracted with methylene chloride. The solvent is evaporated off, the residue is taken up in ether and the ether-insoluble residue is filtered off under suction and discarded.

The organic phase is washed with water, dried over $MgSO_4$ and evaporated down.

Purification of the residue by column chromatography gives 0.5 g (2 mmol, 50%) of the title compound as colorless crystals (mp.=81°-84° C.).

$^1$H-NMR ($CDCl_3$): δ=3.75 (s, 3H); 3.9 (s, 3H); 3.95 (s, 3H); 7.45 (d, J=8Hz, 2H); 7.6 (s, 1H); 8.05 (d, J=8Hz, 2H).

TABLE 1

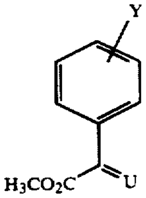

| No. | U | Y | mp | NMR: δ (ppm) |
|---|---|---|---|---|
| 1 | O | 3-$CH_3$ | oil | 2.4(S, 3H,); 4.0(S, 3H) |
| 2 | O | 3-$CH_2Br$ | oil | 4.0(S, 3H); 4.5(S, 2H) |
| 3 | O | 3-$CH_2Cl$ | | |
| 4 | O | 3-CHO | | |
| 5 | O | 3-COOH | | |
| 6 | O | 3-$PO(OCH_3)_2$ | | |
| 7 | O | 3-$P^+(C_6H_5)_3Cl^-$ | | |
| 8 | O | 3-$CH_2OH$ | | |
| 9 | O | 4-$CH_2Br$ | | |
| 10 | O | 4-$CH_2Cl$ | | |
| 11 | O | 4-CHO | | |
| 12 | O | 4-COOH | | |
| 13 | O | 4-$PO(OCH_3)_2$ | | |
| 14 | O | 4-$P^+(C_6H_5)_3Cl^-$ | | |
| 15 | O | 4-$CH_2OH$ | | |
| 16 | $HCOCH_3$ | 3-$CH_3$ | 58-61 | |
| 17 | $HCOCH_3$ | 3-$CH_2Br$ | 90-91 | |
| 18 | $HCOCH_3$ | 3-$CH_2Cl$ | | |
| 19 | $HCOCH_3$ | 3-CHO | oil | 7.6(S, 1H); 10.0(S, 1H) |
| 20 | $HCOCH_3$ | 3-COOH | 158-162 | |
| 21 | $HCOCH_3$ | 3-OH | 94-96 | |
| 22 | $HCOCH_3$ | 3-$PO(OCH_3)_2$ | 93-94 | |
| 23 | $HCOCH_3$ | 3-$P^+(C_6H_5)_3Cl^-$ | | |
| 24 | $HCOCH_3$ | 3-$CH_2OH$ | oil | 4.6(S, 1H); 7.55(S, 1H) |
| 25 | $HCOCH_3$ | 4-$CH_3$ | 62-63 | |
| 26 | $HCOCH_3$ | 4-$CH_2Br$ | 76-81 | |
| 27 | $HCOCH_3$ | 4-$CH_2Cl$ | | |
| 28 | $HCOCH_3$ | 4-CHO | | |
| 29 | $HCOCH_3$ | 4-COOH | 158-162 | |
| 30 | $HCOCH_3$ | 4-OH | 107-109 | |
| 31 | $HCOCH_3$ | 4-$PO(OCH_3)_2$ | | |
| 32 | $HCOCH_3$ | 4-$P^+(C_6H_5)_3Cl^-$ | | |
| 33 | $HCOCH_3$ | 4-$CH_2OH$ | 62-63 | |
| 34a) non-polar isomer | $NOCH_3$ | 3-$CH_3$ | oil | 2.35(S, 3H); 3.9(S, 3H); 4.0(S, 3H) |
| 34b) polar isomer | $NOCH_3$ | 3-$CH_3$ | 66-67 | |

TABLE 1-continued

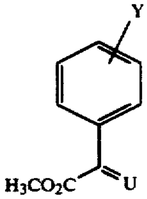

| No. | U | Y | mp | NMR: δ (ppm) |
|---|---|---|---|---|
| 35a) non-polar isomer | $NOCH_3$ | 3-$CH_2Br$ | 74–75 | |
| 35b) | $NOCH_3$ | 3-$CH_2Br$ | 68–69 | |
| 36 | $NOCH_3$ | 3-$CH_2Cl$ | | |
| 37 | $NOCH_3$ | 3-CHO | | |
| 38 | $NOCH_3$ | 3-COOH | | |
| 39 | $NOCH_3$ | 3-$PO(OCH_3)_2$ | | |
| 40 | $NOCH_3$ | 3-$P^+(C_6H_5)_3Cl^-$ | | |
| 41 | $NOCH_3$ | 3-$CH_2{}^-OH$ | | |
| 42 | $NOCH_3$ | 4-$CH_3$ | | |
| 43 | $NOCH_3$ | 4-$CH_2Br$ | | |
| 44 | $NOCH_3$ | 4-$CH_2Cl$ | | |
| 45 | $NOCH_3$ | 4-CHO | | |
| 46 | $NOCH_3$ | 4-COOH | | |
| 47 | $NOCH_3$ | 4-$PO(OCH_3)_2$ | | |
| 48 | $NOCH_3$ | 4-$P^+(C_6H_5)_3Cl^-$ | | |
| 49 | $NOCH_3$ | 4-$CH_2OH$ | | |
| 50 | $CH—CH_3$ | 3-$CH_3$ | | |
| 51 | $CH—CH_3$ | 3-$CH_2Br$ | | |
| 52 | $CH—CH_3$ | 3-$CH_2Cl$ | | |
| 53 | $CH—CH_3$ | 3-CHO | | |
| 54 | $CH—CH_3$ | 3-COOH | | |
| 55 | $CH—CH_3$ | 3-OH | | |
| 56 | $CH—CH_3$ | 3-$PO(OCH_3)_2$ | | |
| 57 | $CH—CH_3$ | 3-$P^+(C_6H_5)_3{}^-Cl$ | | |
| 58 | $CH—CH_3$ | 3-$CH_2OH$ | | |
| 59 | $CH—CH_3$ | 4-$CH_3$ | | |
| 60 | $CH—CH_3$ | 4-$CH_2Br$ | | |
| 61 | $CH—CH_3$ | 4-$CH_2Cl$ | | |
| 62 | $CH—CH_3$ | 4-CHO | | |
| 63 | $CH—CH_3$ | 4-COOH | | |
| 64 | $CH—CH_3$ | 4-OH | | |
| 65 | $CH—CH_3$ | 4-$PO(OCH_3)_2$ | | |
| 66 | $CH—CH_3$ | 4-$P^+(C_6H_5)_3{}^-Cl$ | | |
| 67 | $CH—CH_3$ | 4-$CH_2OH$ | | |

TABLE 2

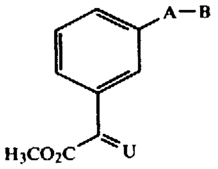

| No. | U | A | B | mp | NMR: δ (ppm) |
|---|---|---|---|---|---|
| 1 | $HCOCH_3$ | $CH_2-CH_2$ | H | | |
| 2 | $HCOCH_3$ | $CH_2-CH_2$ | $CH_3$ | | |
| 3 | $HCOCH_3$ | $CH_2-CH_2$ | cyclohexyl | | |
| 4 | $HCOCH_3$ | $CH_2-CH_2$ | phenyl | oil | 2.95(S, 4H); 7.55(S, 1H) |
| 5 | $HCOCH_3$ | $CH_2-CH_2$ | 2-pyridyl | | |
| 6 | $HCOCH_3$ | $CH=CH$ | H | | |
| 7 | $HCOCH_3$ | $CH=CH$ | $CH_3$ | | |
| 8 | $HCOCH_3$ | $CH=CH$ | cyclohexyl | | |
| 9 | $HCOCH_3$ | $CH=CH$ | 2-naphthyl | | |
| 10 | $HCOCH_3$ | $CH=CH$ | 2-pyridyl | | |
| 11 | $HCOCH_3$ | $O-CH_2$ | H | oil | 3.7; 3, 78; 3.82(3S, 9H); 7.55(S, 1H) |
| 12 | $HCOCH_3$ | $O-CH_2$ | $CH_3$ | 43-45 | |
| 13 | $HCOCH_3$ | $O-CH_2$ | cyclohexyl | | |
| 14 | $HCOCH_3$ | $O-CH_2$ | phenyl | oil | 5.05(S, 2H); 7.55(S, 1H) |
| 15 | $HCOCH_3$ | $O-CH_2$ | 2-pyridyl | | |
| 16 | $HCOCH_3$ | $O-CH_2-CO$ | H | | |
| 17 | $HCOCH_3$ | $O-CH_2-CO$ | $CH_3$ | | |
| 18 | $HCOCH_3$ | $O-CH_2-CO$ | cyclohexyl | | |
| 19 | $HCOCH_3$ | $O-CH_2-CO$ | phenyl | 103-105 | |
| 20 | $HCOCH_3$ | $O-CH_2-CO$ | 2-pyridyl | | |
| 21 | $HCOCH_3$ | $CH_2-O-CO$ | H | oil | 5.2(S, 2H); 7.55(S, 1H) |
| 22 | $HCOCH_3$ | $CH_2-O-CO$ | $CH_3$ | 34-35 | |
| 23 | $HCOCH_3$ | $CH_2-O-CO$ | cyclohexyl | | |
| 24 | $HCOCH_3$ | $CH_2-O-CO$ | phenyl | oil | 5.4(S, 2H); 7.6(S, 1H) |
| 25 | $HCOCH_3$ | $CH_2-O-CO$ | 2-pyridyl | | |
| 26 | $HCOCH_3$ | $CO-O-CH_2$ | H | | |
| 27 | $HCOCH_3$ | $CO-O-CH_2$ | $CH_3$ | | |
| 28 | $HCOCH_3$ | $CO-O-CH_2$ | cyclohexyl | | |
| 29 | $HCOCH_3$ | $CO-O-CH_2$ | phenyl | | |
| 30 | $HCOCH_3$ | $CO-O-CH_2$ | 2-pyridyl | | |
| 31 | $HCOCH_3$ | $O-CO-CH_2$ | H | | |
| 32 | $HCOCH_3$ | $O-CO-CH_2$ | $CH_3$ | | |
| 33 | $HCOCH_3$ | $O-CO-CH_2$ | cyclohexyl | | |
| 34 | $HCOCH_3$ | $O-CO-CH_2$ | phenyl | 65-66 | |
| 35 | $HCOCH_3$ | $O-CO-CH_2$ | 2-pyridyl | | |
| 36 | $HCOCH_3$ | $O-CO-$ | phenyl | 98-99 | |
| 37 | $HCOCH_3$ | $O-CH_2-COO$ | $CH_3$ | 51-53 | |
| 38 | $HCOCH_3$ | $O-(CH_2)_3-COO$ | $CH_3$ | oil | 4.0(t, J=7Hz, 3H); 7.55(S, 1H) |
| 39 | $HCOCH_3$ | $O-(CH_2)_7-COO$ | $CH_3$ | oil | 3.95(t, J=7Hz, 2H); 7.55(S, 1H) |
| 40 | $HCOCH_3$ | $O-(CH_2)_2-O$ | H | oil | 4.1(t, J=5Hz, 2H), 7.55(S, 1H) |
| 41 | $HCOCH_3$ | $O-(CH_2)_2-O$ | $CH_3$ | | |
| 42 | $HCOCH_3$ | $O-(CH_2)_2-O$ | cyclohexyl | | |

TABLE 2-continued

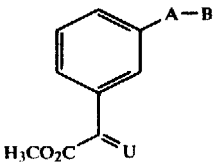

| No. | U | A | B | mp | NMR: δ (ppm) |
|---|---|---|---|---|---|
| 43 | $HCOCH_3$ | $O-(CH_2)_2-O$ | phenyl | oil | 4.3(S, 4H); 7.55(S, 1H) |
| 44 | $HCOCH_3$ | $O-(CH_2)_2-O$ | 2-pyridyl | | |
| 45 | $HCOCH_3$ | $O-(CH_2)_3-O$ | H | oil | 4.1(t, J=6Hz, 2H), 7.55(S, 1H) |
| 46 | $HCOCH_3$ | $O-(CH_2)_3-O$ | $CH_3$ | | |
| 47 | $HCOCH_3$ | $O-(CH_2)_3-O$ | cyclohexyl | | |
| 47 | $HCOCH_3$ | $O-(CH_2)_3-O$ | cyclohexyl | | |
| 48 | $HCOCH_3$ | $O-(CH_2)_3-O$ | phenyl | 68-69 | |
| 49 | $HCOCH_3$ | $O-(CH_2)_3-O$ | 2-pyridyl | | |
| 50 | $HCOCH_3$ | $O-(CH_2)_4-O$ | H | oil | 4.0(t, J=6Hz, 2H); 7.55(S, 1H) |
| 51 | $HCOCH_3$ | $O-(CH_2)_4-O$ | $CH_3$ | | |
| 52 | $HCOCH_3$ | $O-(CH_2)_4-O$ | cyclohexyl | | |
| 53 | $HCOCH_3$ | $O-(CH_2)_4-O$ | phenyl | 92-93 | |
| 54 | $HCOCH_3$ | $O-(CH_2)_4-O$ | 2-pyridyl | | |
| 55 | $HCOCH_3$ | $O-(CH_2)_5-O$ | H | | |
| 56 | $HCOCH_3$ | $O-(CH_2)_5-O$ | $CH_3$ | | |
| 57 | $HCOCH_3$ | $O-(CH_2)_5-O$ | cyclohexyl | | |
| 58 | $HCOCH_3$ | $O-(CH_2)_5-O$ | phenyl | oil | 4.0(t, J=6Hz, 4H); 7.55(S, 1H) |
| 59 | $HCOCH_3$ | $O-(CH_2)_5-O$ | 2-pyridyl | | |
| 60 | $HCOCH_3$ | $O-(CH_2)_6-O$ | H | | |
| 61 | $HCOCH_3$ | $O-(CH_2)_6-O$ | $CH_3$ | | |
| 62 | $HCOCH_3$ | $O-(CH_2)_6-O$ | cyclohexyl | | |
| 63 | $HCOCH_3$ | $O-(CH_2)_6-O$ | phenyl | 78-80 | |
| 64 | $HCOCH_3$ | $O-(CH_2)_6-O$ | 2-pyridyl | | |
| 65 | $HCOCH_3$ | $O-(CH_2)_8-O$ | H | oil | 3.95(t, J=6Hz, 2H); 7.55(S, 1H) |
| 66 | $HCOCH_3$ | $O-(CH_2)_8-O$ | $CH_3$ | | |
| 67 | $HCOCH_3$ | $O-(CH_2)_8-O$ | cyclohexyl | | |
| 68 | $HCOCH_3$ | $O-(CH_2)_8-O$ | phenyl | 69-74 | |
| 69 | $HCOCH_3$ | $O-(CH_2)_8-O$ | 2-pyridyl | | |
| 70 | $HCOCH_3$ | $O-(CH_2)_{10}-O$ | H | | |
| 71 | $HCOCH_3$ | $O-(CH_2)_{10}-O$ | $CH_3$ | | |
| 72 | $HCOCH_3$ | $O-(CH_2)_{10}-O$ | cyclohexyl | | |
| 73 | $HCOCH_3$ | $O-(CH_2)_{10}-O$ | phenyl | 49-52 | |
| 74 | $HCOCH_3$ | $O-(CH_2)_{10}-O$ | 2-pyridyl | | |
| 75 | $HCOCH_3$ | $CH_2-O$ | $CH_3$ | | |
| 76 | $HCOCH_3$ | $CH_2-O$ | cyclohexyl | | |
| 77 | $HCOCH_3$ | $CH_2-O$ | phenyl | 72-74 | |
| 78 | $HCOCH_3$ | $CH_2-O$ | pyridyl | | |
| 79 | $HCOCH_3$ | $CH_2-S-CH_2$ | phenyl | oil | 3.55(S, 4H); 7.55(S, 1H) |
| 80 | $HCOCH_3$ | $CH_2-S-$ | H | | |
| 81 | $HCOCH_3$ | $CH_2-S-$ | $CH_3$ | | |
| 82 | $HCOCH_3$ | $CH_2-S-$ | cyclohexyl | | |
| 83 | $HCOCH_3$ | $CH_2-S-$ | phenyl | 69-70 | |
| 84 | $HCOCH_3$ | $CH_2-S-$ | 2-pyridyl | oil | 4.45(S, 2H); 7.55(S, 1H) |

TABLE 2-continued

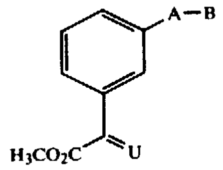

| No. | U | A | B | mp | NMR: δ (ppm) |
|---|---|---|---|---|---|
| 85 | $HCOCH_3$ | $CH_2-N(CH_3)$ | H | | |
| 86 | $HCOCH_3$ | $CH_2-N(CH_3)$ | $CH_3$ | | |
| 87 | $HCOCH_3$ | $CH_2-N(CH_3)$ | cyclohexyl | | |
| 88 | $HCOCH_3$ | $CH_2-N(CH_3)$ | phenyl | oil | 3.65(S, 3H); 3.75(S, 3H); 4.55(S, 2H) |
| 89 | $HCOCH_3$ | $CH_2-N(CH_3)$ | 2-pyridyl | | |
| 90 | $HCOCH_3$ | $CH(CN)-OCO-CH_2$ | H | | |
| 91 | $HCOCH_3$ | $CH(CN)-OCO-CH_2$ | $CH_3$ | | |
| 92 | $HCOCH_3$ | $CH(CN)-OCO-CH_2$ | cyclohexyl | | |
| 93 | $HCOCH_3$ | $CH(CN)-OCO-CH_2$ | phenyl | | |
| 94 | $HCOCH_3$ | $CH(CN)-OCO-CH_2$ | pyridyl | | |
| 95 | $HCOCH_3$ | $CH(CN)-OCO$ | phenyl | oil | 6.7(S, 1H); 7.6(S, 1H) |
| 96 | $HCOCH_3$ | $CH{=}N-$ | H | | |
| 97 | $HCOCH_3$ | $CH{=}N-$ | $CH_3$ | | |
| 98 | $HCOCH_3$ | $CH{=}N-$ | cyclohexyl | | |
| 99 | $HCOCH_3$ | $CH{=}N-$ | phenyl | | |
| 100 | $HCOCH_3$ | $CH{=}N-$ | 2-pyridyl | | |
| 101 | $HCOCH_3$ | $CH{=}N-O-CH_2$ | H | | |
| 102 | $HCOCH_3$ | $CH{=}N-O-CH_2$ | $CH_3$ | | |
| 103 | $HCOCH_3$ | $CH{=}N-O-CH_2$ | cyclohexyl | | |
| 104 | $HCOCH_3$ | $CH{=}N-O-CH_2$ | phenyl | | |
| 105 | $HCOCH_3$ | $CH{=}N-O-CH_2$ | 2-pyridyl | | |
| 106 | $NOCH_3$ | $CH_2-CH_2$ | H | | |
| 107 | $NOCH_3$ | $CH_2-CH_2$ | $CH_3$ | | |
| 108 | $NOCH_3$ | $CH_2-CH_2$ | cyclohexyl | | |
| 109 | $NOCH_3$ | $CH_2-CH_2$ | phenyl | | |
| 110 | $NOCH_3$ | $CH_2-CH_2$ | 2-pyridyl | | |
| 111 | $NOCH_3$ | $CH{=}CH$ | H | | |
| 112 | $NOCH_3$ | $CH{=}CH$ | $CH_3$ | | |
| 113 | $NOCH_3$ | $CH{=}CH$ | cyclohexyl | | |
| 114 | $NOCH_3$ | $CH{=}CH$ | phenyl | | |
| 115 | $NOCH_3$ | $CH{=}CH$ | 2-pyridyl | | |
| 116 | $NOCH_3$ | $O-CH_2$ | H | | |
| 117 | $NOCH_3$ | $O-CH_2$ | $CH_3$ | | |
| 118 | $NOCH_3$ | $O-CH_2$ | cyclohexyl | | |
| 119a) | $NOCH_3$ | $O-CH_2$ | phenyl | 62-63 | non-polar isomer 3.9(S, 3H); 4.0(S, 3H); 5.05(S, 2H) |
| 119b) | $NOCH_3$ | $O-CH_2$ | phenyl | 63-64 | polar isomer 3.85(S, 3H), 4.05(S, 3H); 5.05(S, 2H) |
| 120 | $NOCH_3$ | $O-CH_2$ | 2-pyridyl | | |
| 121 | $NOCH_3$ | $O-CH_2-CO$ | H | | |
| 122 | $NOCH_3$ | $O-CH_2-CO$ | $CH_3$ | | |

TABLE 2-continued

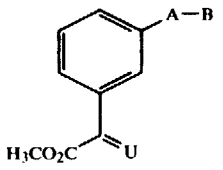

| No. | U | A | B | mp | NMR: δ (ppm) |
|---|---|---|---|---|---|
| 123 | $NOCH_3$ | $O-CH_2-CO$ | cyclohexyl | | |
| 124 | $NOCH_3$ | $O-CH_2-CO$ | phenyl | | |
| 125 | $NOCH_3$ | $O-CH_2-CO$ | 2-pyridyl | | |
| 126 | $NOCH_3$ | $CH_2-O-CO$ | H | | |
| 127 | $NOCH_3$ | $CH_2-O-CO$ | $CH_3$ | | |
| 128 | $NOCH_3$ | $CH_2-O-CO$ | cyclohexyl | | |
| 129 | $NOCH_3$ | $CH_2-O-CO$ | phenyl | | |
| 130 | $NOCH_3$ | $CH_2-O-CO$ | 2-pyridyl | | |
| 131 | $NOCH_3$ | $CO-O-CH_2$ | H | | |
| 132 | $NOCH_3$ | $CO-O-CH_2$ | $CH_3$ | | |
| 133 | $NOCH_3$ | $CO-O-CH_2$ | cyclohexyl | | |
| 134 | $NOCH_3$ | $CO-O-CH_2$ | phenyl | | |
| 135 | $NOCH_3$ | $CO-O-CH_2$ | 2-pyridyl | | |
| 136 | $NOCH_3$ | $O-CO-CH_2$ | H | | |
| 137 | $NOCH_3$ | $O-CO-CH_2$ | $CH_3$ | | |
| 138 | $NOCH_3$ | $O-CO-CH_2$ | cyclohexyl | | |
| 139 | $NOCH_3$ | $O-CO-CH_2$ | phenyl | | |
| 140 | $NOCH_3$ | $O-CO-CH_2$ | 2-pyridyl | | |
| 141 | $NOCH_3$ | $O-CO-$ ' | phenyl | | |
| 142 | $NOCH_3$ | $O-CH_2-COO$ | $CH_3$ | | |
| 143 | $NOCH_3$ | $O-(CH_2)_3-COO$ | $CH_3$ | | |
| 144 | $NOCH_3$ | $O-(CH_2)_7-COO$ | $CH_3$ | | |
| 145 | $NOCH_3$ | $O-(CH_2)_2-O$ | H | | |
| 146 | $NOCH_3$ | $O-(CH_2)_2-O$ | $CH_3$ | | |
| 147 | $NOCH_3$ | $O-(CH_2)_2-O$ | cyclohexyl | | |
| 148 | $NOCH_3$ | $O-(CH_2)_2-O$ | phenyl | | |
| 149 | $NOCH_3$ | $O-(CH_2)_2-O$ | 2-pyridyl | | |
| 150 | $NOCH_3$ | $O-(CH_2)_3-O$ | H | | |
| 151 | $NOCH_3$ | $O-(CH_2)_3-O$ | $CH_3$ | | |
| 152 | $NOCH_3$ | $O-(CH_2)_3-O$ | cyclohexyl | | |
| 153 | $NOCH_3$ | $O-(CH_2)_3-O$ | phenyl | | |
| 154 | $NOCH_3$ | $O-(CH_2)_3-O$ | 2-pyridyl | | |
| 155 | $NOCH_3$ | $O-(CH_2)_4-O$ | H | | |
| 156 | $NOCH_3$ | $O-(CH_2)_4-O$ | $CH_3$ | | |
| 157 | $NOCH_3$ | $O-(CH_2)_4-O$ | cyclohexyl | | |
| 158 | $NOCH_3$ | $O-(CH_2)_4-O$ | phenyl | | |
| 159 | $NOCH_3$ | $O-(CH_2)_4-O$ | 2-pyridyl | | |
| 160 | $NOCH_3$ | $O-(CH_2)_5-O$ | H | | |
| 161 | $NOCH_3$ | $O-(CH_2)_5-O$ | $CH_3$ | | |
| 162 | $NOCH_3$ | $O-(CH_2)_5-O$ | cyclohexyl | | |
| 163 | $NOCH_3$ | $O-(CH_2)_5-O$ | phenyl | | |
| 164 | $NOCH_3$ | $O-(CH_2)_5-O$ | 2-pyridyl | | |
| 165 | $NOCH_3$ | $O-(CH_2)_6-O$ | H | | |

TABLE 2-continued

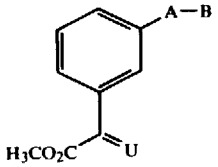

| No. | U | A | B | mp | NMR: δ (ppm) |
|---|---|---|---|---|---|
| 166 | $NOCH_3$ | $O-(CH_2)_6-O$ | $CH_3$ | | |
| 167 | $NOCH_3$ | $O-(CH_2)_6-O$ | cyclohexyl | | |
| 168 | $NOCH_3$ | $O-(CH_2)_6-O$ | phenyl | | |
| 169 | $NOCH_3$ | $O-(CH_2)_6-O$ | 2-pyridyl | | |
| 170 | $NOCH_3$ | $O-(CH_2)_8-O$ | H | | |
| 171 | $NOCH_3$ | $O-(CH_2)_8-O$ | $CH_3$ | | |
| 172 | $NOCH_3$ | $O-(CH_2)_8-O$ | cyclohexyl | | |
| 173 | $NOCH_3$ | $O-(CH_2)_8-O$ | phenyl | | |
| 174 | $NOCH_3$ | $O-(CH_2)_8-O$ | 2-pyridyl | | |
| 175 | $NOCH_3$ | $O-(CH_2)_{10}-O$ | H | | |
| 176 | $NOCH_3$ | $O-(CH_2)_{10}-O$ | $CH_3$ | | |
| 177 | $NOCH_3$ | $O-(CH_2)_{10}-O$ | cyclohexyl | | |
| 178 | $NOCH_3$ | $O-(CH_2)_{10}-O$ | phenyl | | |
| 179 | $NOCH_3$ | $O-(CH_2)_{10}-O$ | 2-pyridyl | | |
| 180 | $NOCH_3$ | $CH_2-O-$ | H | | |
| 181 | $NOCH_3$ | $CH_2-O-$ | $CH_3$ | | |
| 182 | $NOCH_3$ | $CH_2-O-$ | cyclohexyl | | |
| 183 | $NOCH_3$ | $CH_2-O-$ | phenyl | | |
| 184 | $NOCH_3$ | $CH_2-O-$ | pyridyl | | |
| 185 | $NOCH_3$ | $CH_2-S-CH_2$ | H | | |
| 186 | $NOCH_3$ | $CH_2-S-CH_2$ | $CH_3$ | | |
| 187 | $NOCH_3$ | $CH_2-S-CH_2$ | cyclohexyl | | |
| 188 | $NOCH_3$ | $CH_2-S-CH_2$ | phenyl | | |
| 189 | $NOCH_3$ | $CH_2-S-CH_2$ | 2-pyridyl | | |
| 190 | $NOCH_3$ | $CH_2-N(CH_3)$ | H | | |
| 191 | $NOCH_3$ | $CH_2-N(CH_3)$ | $CH_3$ | | |
| 192 | $NOCH_3$ | $CH_2-N(CH_3)$ | cyclohexyl | | |
| 193 | $NOCH_3$ | $CH_2-N(CH_3)$ | phenyl | | |
| 194 | $NOCH_3$ | $CH_2-N(CH_3)$ | 2-pyridyl | | |
| 195 | $NOCH_3$ | $CH(CN)-OCO-CH_2$ | H | | |
| 196 | $NOCH_3$ | $CH(CN)-OCO-CH_2$ | $CH_3$ | | |
| 197 | $NOCH_3$ | $CH(CN)-OCO-CH_2$ | cyclohexyl | | |
| 198 | $NOCH_3$ | $CH(CN)-OCO-CH_2$ | phenyl | | |
| 199 | $NOCH_3$ | $CH(CN)-OCO-CH_2$ | pyridyl | | |
| 200 | $NOCH_3$ | $CH(CN)-OCO$ | phenyl | | |
| 201 | $NOCH_3$ | $CH=N-$ | H | | |
| 202 | $NOCH_3$ | $CH=N-$ | $CH_3$ | | |
| 203 | $NOCH_3$ | $CH=N-$ | cyclohexyl | | |
| 204 | $NOCH_3$ | $CH=N-$ | phenyl | | |
| 205 | $NOCH_3$ | $CH=N-$ | 2-pyridyl | | |
| 206 | $NOCH_3$ | $CH=N-O-CH_2$ | H | | |
| 207 | $NOCH_3$ | $CH=N-O-CH_2$ | $CH_3$ | | |
| 208 | $NOCH_3$ | $CH=N-O-CH_2$ | cyclohexyl | | |

TABLE 2-continued

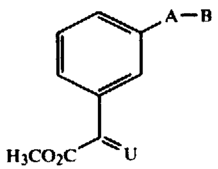

| No. | U | A | B | mp | NMR: δ (ppm) |
|---|---|---|---|---|---|
| 209 | $NOCH_3$ | $CH{=}N{-}O{-}CH_2$ | phenyl | | |
| 210 | $NOCH_3$ | $CH{=}N{-}O{-}CH_2$ | 2-pyridyl | | |
| 211 | $HC{-}CH_3$ | $CH_2{-}CH_2$ | H | | |
| 212 | $HC{-}CH_3$ | $CH_2{-}CH_2$ | $CH_3$ | | |
| 213 | $HC{-}CH_3$ | $CH_2{-}CH_2$ | cyclohexyl | | |
| 214 | $HC{-}CH_3$ | $CH_2{-}CH_2$ | phenyl | | |
| 215 | $HC{-}CH_3$ | $CH_2{-}CH_2$ | 2-pyridyl | | |
| 216 | $HC{-}CH_3$ | $CH{=}CH$ | H | | |
| 217 | $HC{-}CH_3$ | $CH{=}CH$ | $CH_3$ | | |
| 218 | $HC{-}CH_3$ | $CH{=}CH$ | cyclohexyl | | |
| 219 | $HC{-}CH_3$ | $CH{=}CH$ | phenyl | | |
| 220 | $HC{-}CH_3$ | $CH{=}CH$ | 2-pyridyl | | |
| 221 | $HC{-}CH_3$ | $OCH_2$ | H | | |
| 222 | $HC{-}CH_3$ | $OCH_2$ | $CH_3$ | | |
| 223 | $HC{-}CH_3$ | $OCH_2$ | cyclohexyl | | |
| 224 | $HC{-}CH_3$ | $OCH_2$ | phenyl | | |
| 225 | $HC{-}CH_3$ | $OCH_2$ | 2-pyridyl | | |
| 226 | $HC{-}CH_3$ | $O{-}CH_2{-}CO$ | H | | |
| 227 | $HC{-}CH_3$ | $O{-}CH_2{-}CO$ | $CH_3$ | | |
| 228 | $HC{-}CH_3$ | $O{-}CH_2{-}CO$ | cyclohexyl | | |
| 229 | $HC{-}CH_3$ | $O{-}CH_2{-}CO$ | phenyl | | |
| 230 | $HC{-}CH_3$ | $O{-}CH_2{-}CO$ | 2-pyridyl | | |
| 231 | $HC{-}CH_3$ | $CH_2{-}O{-}CO$ | H | | |
| 232 | $HC{-}CH_3$ | $CH_2{-}O{-}CO$ | $CH_3$ | | |
| 233 | $HC{-}CH_3$ | $CH_2{-}O{-}CO$ | cyclohexyl | | |
| 234 | $HC{-}CH_3$ | $CH_2{-}O{-}CO$ | phenyl | | |
| 235 | $HC{-}CH_3$ | $CH_2{-}O{-}CO$ | 2-pyridyl | | |
| 236 | $HC{-}CH_3$ | $CO{-}O{-}CH_2$ | H | | |
| 237 | $HC{-}CH_3$ | $CO{-}O{-}CH_2$ | $CH_3$ | | |
| 238 | $HC{-}CH_3$ | $CO{-}O{-}CH_2$ | cyclohexyl | | |
| 239 | $HC{-}CH_3$ | $CO{-}O{-}CH_2$ | phenyl | | |
| 240 | $HC{-}CH_3$ | $CO{-}O{-}CH_2$ | 2-pyridyl | | |
| 241 | $HC{-}CH_3$ | $O{-}CO{-}CH_2$ | H | | |
| 242 | $HC{-}CH_3$ | $O{-}CO{-}CH_2$ | $CH_3$ | | |
| 243 | $HC{-}CH_3$ | $O{-}CO{-}CH_2$ | cyclohexyl | | |
| 244 | $HC{-}CH_3$ | $O{-}CO{-}CH_2$ | phenyl | | |
| 245 | $HC{-}CH_3$ | $O{-}CO{-}CH_2$ | 2-pyridyl | | |
| 246 | $HC{-}CH_3$ | $O{-}CO{-}$ | phenyl | | |
| 247 | $HC{-}CH_3$ | $O{-}CO{-}COO$ | $CH_3$ | | |
| 248 | $HC{-}CH_3$ | $O{-}(CH_2)_3{-}COO$ | $CH_3$ | | |
| 249 | $HC{-}CH_3$ | $O{-}(CH_2)_3{-}COO$ | $CH_3$ | | |
| 250 | $HC{-}CH_3$ | $O{-}(CH_2)_2{-}O$ | H | | |
| 251 | $HC{-}CH_3$ | $O{-}(CH_2)_2{-}O$ | $CH_3$ | | |

TABLE 2-continued

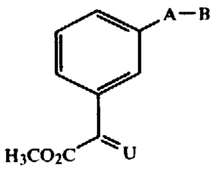

| No. | U | A | B | mp | NMR: δ (ppm) |
|---|---|---|---|---|---|
| 252 | HC—CH$_3$ | O—(CH$_2$)$_2$—O | cyclohexyl | | |
| 253 | HC—CH$_3$ | O—(CH$_2$)$_2$—O | phenyl | | |
| 254 | HC—CH$_3$ | O—(CH$_2$)$_2$—O | 2-pyridyl | | |
| 255 | HC—CH$_3$ | O—(CH$_2$)$_3$—O | H | | |
| 256 | HC—CH$_3$ | O—(CH$_2$)$_3$—O | CH$_3$ | | |
| 257 | HC—CH$_3$ | O—(CH$_2$)$_3$—O | cyclohexyl | | |
| 258 | HC—CH$_3$ | O—(CH$_2$)$_3$—O | phenyl | | |
| 259 | HC—CH$_3$ | O—(CH$_2$)$_3$—O | 2-pyridyl | | |
| 260 | HC—CH$_3$ | O—(CH$_2$)$_4$—O | H | | |
| 261 | HC—CH$_3$ | O—(CH$_2$)$_4$—O | CH$_3$ | | |
| 262 | HC—CH$_3$ | O—(CH$_2$)$_4$—O | cyclohexyl | | |
| 263 | HC—CH$_3$ | O—(CH$_2$)$_4$—O | phenyl | | |
| 264 | HC—CH$_3$ | O—(CH$_2$)$_4$—O | 2-pyridyl | | |
| 265 | HC—CH$_3$ | O—(CH$_2$)$_5$—O | H | | |
| 266 | HC—CH$_3$ | O—(CH$_2$)$_5$—O | CH$_3$ | | |
| 267 | HC—CH$_3$ | O—(CH$_2$)$_5$—O | cyclohexyl | | |
| 268 | HC—CH$_3$ | O—(CH$_2$)$_5$—O | phenyl | | |
| 269 | HC—CH$_3$ | O—(CH$_2$)$_5$—O | 2-pyridyl | | |
| 270 | HC—CH$_3$ | O—(CH$_2$)$_6$—O | H | | |
| 271 | HC—CH$_3$ | O—(CH$_2$)$_6$—O | CH$_3$ | | |
| 272 | HC—CH$_3$ | O—(CH$_2$)$_6$—O | cyclohexyl | | |
| 273 | HC—CH$_3$ | O—(CH$_2$)$_6$—O | phenyl | | |
| 274 | HC—CH$_3$ | O—(CH$_2$)$_6$—O | 2-pyridyl | | |
| 275 | HC—CH$_3$ | O—(CH$_2$)$_8$—O | H | | |
| 276 | HC—CH$_3$ | O—(CH$_2$)$_8$—O | CH$_3$ | | |
| 277 | HC—CH$_3$ | O—(CH$_2$)$_8$—O | cyclohexyl | | |
| 278 | HC—CH$_3$ | O—(CH$_2$)$_8$—O | phenyl | | |
| 279 | HC—CH$_3$ | O—(CH$_2$)$_8$—O | 2-pyridyl | | |
| 280 | HC—CH$_3$ | O—(CH$_2$)$_{10}$—O | H | | |
| 281 | HC—CH$_3$ | O—(CH$_2$)$_{10}$—O | CH$_3$ | | |
| 282 | HC—CH$_3$ | O—(CH$_2$)$_{10}$—O | cyclohexyl | | |
| 283 | HC—CH$_3$ | O—(CH$_2$)$_{10}$—O | phenyl | | |
| 284 | HC—CH$_3$ | O—(CH$_2$)$_{10}$—O | 2-pyridyl | | |
| 285 | HC—CH$_3$ | CH$_2$—O— | H | | |
| 286 | HC—CH$_3$ | CH$_2$—O— | CH$_3$ | | |
| 287 | HC—CH$_3$ | CH$_2$—O— | cyclohexyl | | |
| 288 | HC—CH$_3$ | CH$_2$—O— | phenyl | oil | 1.75(d, J=8Hz, 3H); 3.75/S, 3H); 5.1(S, 2H) |
| 289 | HC—CH$_3$ | CH$_2$—O— | pyridyl | | |
| 290 | HC—CH$_3$ | CH$_2$—S—CH$_2$ | H | | |
| 291 | HC—CH$_3$ | CH2—S—CH2 | CH3 | | |
| 292 | HC—CH$_3$ | CH2—S—CH2 | cyclohexyl | | |
| 293 | HC—CH$_3$ | CH2—S—CH2 | phenyl | | |

TABLE 2-continued

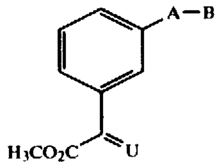

| No. | U | A | B | mp | NMR: δ (ppm) |
|---|---|---|---|---|---|
| 294 | $HC-CH_3$ | CH2—S—CH2 | 2-pyridyl | | |
| 295 | $HC-CH_3$ | CH2—N—(CH3) | H | | |
| 296 | $HC-CH_3$ | CH2—N—(CH3) | CH3 | | |
| 297 | $HC-CH_3$ | CH2—N—(CH3) | cyclohexyl | | |
| 298 | $HC-CH_3$ | CH2—N—(CH3) | phenyl | | |
| 299 | $HC-CH_3$ | CH2—N—(CH3) | 2-pyridyl | | |
| 300 | $HC-CH_3$ | $CH(CN)-OCO-CH_2$ | H | | |
| 301 | $HC-CH_3$ | $CH(CN)-OCO-CH_2$ | $CH_3$ | | |
| 302 | $HC-CH_3$ | $CH(CN)-OCO-CH_2$ | cyclohexyl | | |
| 303 | $HC-CH_3$ | $CH(CN)-OCO-CH_2$ | phenyl | | |
| 304 | $HC-CH_3$ | $CH(CN)-OCO-CH_2$ | pyridyl | | |
| 305 | $HC-CH_3$ | CH(CN)OCO | phenyl | | |
| 306 | $HC-CH_3$ | CH=N— | H | | |
| 307 | $HC-CH_3$ | CH=N— | $CH_3$ | | |
| 308 | $HC-CH_3$ | CH=N— | cyclohexyl | | |
| 309 | $HC-CH_3$ | CH=N— | phenyl | | |
| 310 | $HC-CH_3$ | CH=N— | 2-pyridyl | | |
| 311 | $HC-CH_3$ | $CH=N-O-CH_2$ | H | | |
| 312 | $HC-CH_3$ | $CH=N-O-CH_2$ | $CH_3$ | | |
| 313 | $HC-CH_3$ | $CH=N-O-CH_2$ | cyclohexyl | | |
| 314 | $HC-CH_3$ | $CH=N-O-CH_2$ | phenyl | | |
| 315 | $HC-CH_3$ | $CH=N-O-CH_2$ | 2-pyridyl | | |
| 316 | O | $CH_2-CH_2$ | H | | |
| 317 | O | $CH_2-CH_2$ | $CH_3$ | | |
| 318 | O | $CH_2-CH_2$ | cyclohexyl | | |
| 319 | O | $CH_2-CH_2$ | phenyl | | |
| 320 | O | $CH_2-CH_2$ | 2-pyridyl | | |
| 321 | O | CH=CH | H | | |
| 322 | O | CH=CH | $CH_3$ | | |
| 323 | O | CH=CH | cyclohexyl | | |
| 324 | O | CH=CH | phenyl | | |
| 325 | O | CH=CH | 2-pyridyl | | |
| 326 | O | $O-CH_2$ | H | | |
| 327 | O | $O-CH_2$ | $CH_3$ | | |
| 328 | O | $O-CH_2$ | cyclohexyl | | |
| 329 | O | $O-CH_2$ | phenyl | | |
| 330 | O | $O-CH_2$ | 2-pyridyl | | |
| 331 | O | $CH_2-O$ | H | | |
| 332 | O | $CH_2-O$ | $CH_3$ | | |
| 333 | O | $CH_2-O$ | cyclohexyl | | |
| 334 | O | $CH_2-O$ | phenyl | | |
| 335 | O | $CH_2-O$ | 2-pyridyl | | |
| 336 | O | $CH_2-O-CO$ | H | | |

TABLE 2-continued

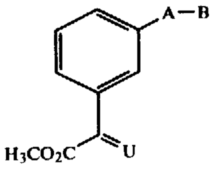

| No. | U | A | B | mp | NMR: δ (ppm) |
|---|---|---|---|---|---|
| 337 | O | $CH_2-O-CO$ | $CH_3$ | | |
| 338 | O | $CH_2-O-CO$ | cyclohexyl | | |
| 339 | O | $CH_2-O-CO$ | phenyl | | |
| 340 | O | $CH_2-O-CO$ | 2-pyridyl | | |
| 341 | $N-NHCH_3$ | $CH_2-CH_2$ | H | | |
| 342 | $N-NHCH_3$ | $CH_2-CH_2$ | $CH_3$ | | |
| 343 | $N-NHCH_3$ | $CH_2-CH_2$ | cyclohexyl | | |
| 344 | $N-NHCH_3$ | $CH_2-CH_2$ | phenyl | | |
| 345 | $N-NHCH_3$ | $CH_2-CH_2$ | 2-pyridyl | | |
| 346 | $N-NHCH_3$ | $CH=CH$ | H | | |
| 347 | $N-NHCH_3$ | $CH=CH$ | $CH_3$ | | |
| 348 | $N-NHCH_3$ | $CH=CH$ | cyclohexyl | | |
| 349 | $N-NHCH_3$ | $CH=CH$ | phenyl | | |
| 350 | $N-NHCH_3$ | $CH=CH$ | 2-pyridyl | | |
| 351 | $N-NHCH_3$ | $O-CH_2$ | H | | |
| 352 | $N-NHCH_3$ | $O-CH_2$ | $CH_3$ | | |
| 353 | $N-NHCH_3$ | $O-CH_2$ | cyclohexyl | | |
| 354 | $N-NHCH_3$ | $O-CH_2$ | phenyl | | |
| 355 | $N-NHCH_3$ | $O-CH_2$ | 2-pyridyl | | |
| 356 | $N-NHCH_3$ | $CH_2-O$ | H | | |
| 357 | $N-NHCH_3$ | $CH_2-O$ | $CH_3$ | | |
| 358 | $N-NHCH_3$ | $CH_2-O$ | cyclohexyl | | |
| 359 | $N-NHCH_3$ | $CH_2-O$ | phenyl | | |
| 360 | $N-NHCH_3$ | $CH_2-O$ | 2-pyridyl | | |
| 361 | $N-NHCH_3$ | $CH_2-O-CO$ | H | | |
| 362 | $N-NHCH_3$ | $CH_2-O-CO$ | $CH_3$ | | |
| 363 | $N-NHCH_3$ | $CH_2-O-CO$ | cyclohexyl | | |
| 364 | $N-NHCH_3$ | $CH_2-O-CO$ | phenyl | | |
| 365 | $N-NHCH_3$ | $CH_2-O-CO$ | 2-pyridyl | | |
| 366 | $CH_2$ | $CH_2-CH_2$ | H | | |
| 367 | $CH_2$ | $CH_2-CH_2$ | $CH_3$ | | |
| 368 | $CH_2$ | $CH_2-CH_2$ | cyclohexyl | | |
| 369 | $CH_2$ | $CH_2-CH_2$ | phenyl | | |
| 370 | $CH_2$ | $CH_2-CH_2$ | 2-pyridyl | | |
| 371 | $CH_2$ | $CH=CH$ | H | | |
| 372 | $CH_2$ | $CH=CH$ | $CH_3$ | | |
| 373 | $CH_2$ | $CH=CH$ | cyclohexyl | | |
| 374 | $CH_2$ | $CH=CH$ | phenyl | | |
| 375 | $CH_2$ | $CH=CH$ | 2-pyridyl | | |
| 376 | $CH_2$ | $O-CH_2$ | H | | |
| 377 | $CH_2$ | $O-CH_2$ | $CH_3$ | | |
| 378 | $CH_2$ | $O-CH_2$ | cyclohexyl | | |
| 379 | $CH_2$ | $O-CH_2$ | phenyl | | |

TABLE 2-continued

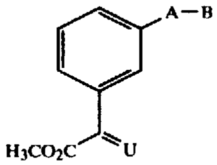

| No. | U | A | B | mp | NMR: δ (ppm) |
|---|---|---|---|---|---|
| 380 | $CH_2$ | $O-CH_2$ | 2-pyridyl | | |
| 381 | $CH_2$ | $CH_2-O$ | H | | |
| 382 | $CH_2$ | $CH_2-O$ | $CH_3$ | | |
| 383 | $CH_2$ | $CH_2-O$ | cyclohexyl | | |
| 384 | $CH_2$ | $CH_2-O$ | phenyl | | |
| 385 | $CH_2$ | $CH_2-O$ | 2-pyridyl | | |
| 386 | $CH_2$ | $CH_2-O-CO$ | H | | |
| 387 | $CH_2$ | $CH_2-O-CO$ | $CH_3$ | | |
| 388 | $CH_2$ | $CH_2-O-CO$ | cyclohexyl | | |
| 389 | $CH_2$ | $CH_2-O-CO$ | phenyl | | |
| 390 | $CH_2$ | $CH_2-O-CO$ | 2-pyridyl | | |
| 391 | $CH-CH_2-CH_3$ | $CH_2-CH_2$ | H | | |
| 392 | $CH-CH_2-CH_3$ | $CH_2-CH_2$ | $CH_3$ | | |
| 393 | $CH-CH_2-CH_3$ | $CH_2-CH_2$ | cyclohexyl | | |
| 394 | $CH-CH_2-CH_3$ | $CH_2-CH_2$ | phenyl | | |
| 395 | $CH-CH_2-CH_3$ | $CH_2-CH_2$ | 2-pyridyl | | |
| 396 | $CH-CH_2-CH_3$ | $CH=CH$ | H | | |
| 397 | $CH-CH_2-CH_3$ | $CH=CH$ | $CH_3$ | | |
| 398 | $CH-CH_2-CH_3$ | $CH=CH$ | cyclohexyl | | |
| 399 | $CH-CH_2-CH_3$ | $CH=CH$ | phenyl | | |
| 400 | $CH-CH_2-CH_3$ | $CH=CH$ | 2-pyridyl | | |
| 401 | $CH-CH_2-CH_3$ | $O-CH_2$ | H | | |
| 402 | $CH-CH_2-CH_3$ | $O-CH_2$ | $CH_3$ | | |
| 403 | $CH-CH_2-CH_3$ | $O-CH_2$ | cyclohexyl | | |
| 404 | $CH-CH_2-CH_3$ | $O-CH_2$ | phenyl | | |
| 405 | $CH-CH_2-CH_3$ | $O-CH_2$ | 2-pyridyl | | |
| 406 | $CH-CH_2-CH_3$ | $CH_2-O$ | H | | |
| 407 | $CH-CH_2-CH_3$ | $CH_2-O$ | $CH_3$ | | |
| 408 | $CH-CH_2-CH_3$ | $CH_2-O$ | cyclohexyl | | |
| 409 | $CH-CH_2-CH_3$ | $CH_2-O$ | phenyl | | |
| 410 | $CH-CH_2-CH_3$ | $CH_2-O$ | 2-pyridyl | | |
| 411 | $CH-CH_2-CH_3$ | $CH_2-O-CO$ | H | | |
| 412 | $CH-CH_2-CH_3$ | $CH_2-O-CO$ | $CH_3$ | | |
| 413 | $CH-CH_2-CH_3$ | $CH_2-O-CO$ | cyclohexyl | | |
| 414 | $CH-CH_2-CH_3$ | $CH_2-O-CO$ | phenyl | | |
| 415 | $CH-CH_2-CH_3$ | $CH_2-O-CO$ | 2-pyridyl | | |
| 416 | $CH-S-CH_3$ | $CH_2-CH_2$ | H | | |
| 417 | $CH-S-CH_3$ | $CH_2-CH_2$ | $CH_3$ | | |
| 418 | $CH-S-CH_3$ | $CH_2-CH_2$ | cyclohexyl | | |
| 419 | $CH-S-CH_3$ | $CH_2-CH_2$ | phenyl | | |
| 420 | $CH-S-CH_3$ | $CH_2-CH_2$ | 2-pyridyl | | |
| 421 | $CH-S-CH_3$ | $CH=CH$ | H | | |
| 422 | $CH-S-CH_3$ | $CH=CH$ | $CH_3$ | | |

TABLE 2-continued

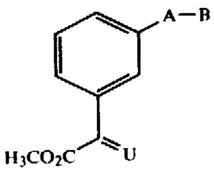

| No. | U | A | B | mp | NMR: δ (ppm) |
|---|---|---|---|---|---|
| 423 | $CH-S-CH_3$ | $CH=CH$ | cyclohexyl | | |
| 424 | $CH-S-CH_3$ | $CH=CH$ | phenyl | | |
| 425 | $CH-S-CH_3$ | $CH=CH$ | 2-pyridyl | | |
| 426 | $CH-S-CH_3$ | $O-CH_2$ | H | | |
| 427 | $CH-S-CH_3$ | $O-CH_2$ | $CH_3$ | | |
| 428 | $CH-S-CH_3$ | $O-CH_2$ | cyclohexyl | | |
| 429 | $CH-S-CH_3$ | $O-CH_2$ | phenyl | | |
| 430 | $CH-S-CH_3$ | $O-CH_2$ | 2-pyridyl | | |
| 431 | $CH-S-CH_3$ | $CH_2-O$ | H | | |
| 432 | $CH-S-CH_3$ | $CH_2-O$ | $CH_3$ | | |
| 433 | $CH-S-CH_3$ | $CH_2-O$ | cyclohexyl | | |
| 434 | $CH-S-CH_3$ | $CH_2-O$ | phenyl | | |
| 435 | $CH-S-CH_3$ | $CH_2-O$ | 2-pyridyl | | |
| 436 | $CH-S-CH_3$ | $CH_2-O-CO$ | H | | |
| 437 | $CH-S-CH_3$ | $CH_2-O-CO$ | $CH_3$ | | |
| 438 | $CH-S-CH_3$ | $CH_2-O-CO$ | cyclohexyl | | |
| 439 | $CH-S-CH_3$ | $CH_2-O-CO$ | phenyl | | |
| 440 | $CH-S-CH_3$ | $CH_2-O-CO$ | 2-pyridyl | | |
| 441 | $HCOCH_3$ | $CH_2-O-CO$ | 1-(4-methoxy-phenyl)-cyclopropyl | 66–69 | |
| 442 | $HCOCH_3$ | $CH_2-O-CO$ | 2-pyridyl | 70–74 | |
| 443 | $HCOCH_3$ | $CH_2-O-CO$ | 3-pyridyl | | |
| 444 | $HCOCH_3$ | $CH_2-O-CO$ | 4-pyridyl | oil | 5.45(S, 2H); 7.55(S, 1H) |
| 445 | $HCOCH_3$ | $CH_2-O-CO$ | 1-phenyl-cyclopropyl | 79–81 | |
| 446 | $HCOCH_3$ | $CH_2-O-CO$ | 1-(4-chloro-phenyl)-cyclopropyl | 102–103 | |
| 447 | $HCOCH_3$ | $CH_2-O-CO$ | 1-Indanyl- | oil | 5.15(S, 2H); 7.55(S, 1H) |
| 448 | $HCOCH_3$ | $CH_2-O-CO$ | 4-phenyl-phenyl | 132 | |
| 449 | $HCOCH_3$ | $CH_2-O-CO$ | 4-phenyl-benzyl | oil | 5.15(S, 2H); .55(S, 1H) |
| 450 | $HCOCH_3$ | $CH_2-O-CO$ | 2-phenyl-phenyl | 85–87 | |
| 451 | $HCOCH_3$ | $CH_2-O-CO$ | 2-phenoxyphenyl | oil | 5.3(S, 2H); 7.55(S, 1H) |
| 452 | $HCOCH_3$ | $CH_2-O-CO$ | 2-naphthyl | oil | 5.45(S, 2H); 7.6(S, 1H) |
| 453 | $HCOCH_3$ | $CH_2-O-CO$ | 2-naphthylmethyl | oil | 5.15(S, 2H); 7.5(S, 1H) |
| 454 | $HCOCH_3$ | $CH_2-O-CO$ | 1-naphthyl | 123–124 | |
| 455 | $HCOCH_3$ | $CH_2-O-CO$ | 1-naphthylmethyl | oil | 5.15(S, 2H); 7.55(S, 1H) |
| 456 | $HCOCH_3$ | $CH_2-O-CO$ | 3-phenoxyphenyl | oil | 5.35(S, 2H); 7.55(S, 1H) |
| 457 | $HCOCH_3$ | $CH_2-O-CO$ | n-heptodecyl | 38–40 | |
| 458 | $HCOCH_3$ | $CH_2-O-CO$ | n-heptyl | oil | 5.1(S, 2H); 7.55(S, 1H) |
| 459 | $HCOCH_3$ | $CH_2-O-CO$ | t-butyl | oil | 5.1(S, 2H); 7.55(S, 1H) |
| 460 | $HCOCH_3$ | $CH_2-O-CO$ | iso-butyl | oil | 5.1(S, 2H); 7.55(S, 1H) |
| 461 | $HCOCH_3$ | $CH_2-O-CO$ | n-butyl | oil | 5.1(S, 2H); 7.55(S, 1H) |
| 462 | $HCOCH_3$ | $CH_2-O-CO$ | n-Propyl | oil | 5.1(S, 2H); 7.55(S, 1H) |

TABLE 2-continued

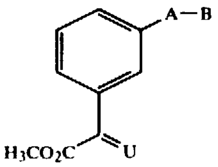

| No. | U | A | B | mp | NMR: δ (ppm) |
|---|---|---|---|---|---|
| 463 | $HCOCH_3$ | $CH_2-O-CO$ | Ethyl | oil | 5.1(S, 2H); 7.55(S, 1H) |
| 464 | $HCOCH_3$ | $CH_2-O-CO-CH_2$ | phenyl | oil | 5.15(S, 2H); 7.6(S, 1H) |
| 465 | $HCOCH_3$ | $CH_2-O-CO-(CH_2)_2$ | phenyl | oil | 5.1(S, 2H); 7.55(S, 1H) |
| 466 | $HCOCH_3$ | $CH_2-O-CO-(CH_2)_3$ | phenyl | oil | 5.15(S, 2H); 7.55(S, 1H) |
| 467 | $HCOCH_3$ | $CH_2-O-CO$ | 1-methylcyclo-propyl | 45-47 | |
| 468 | $HCOCH_3$ | $CH_2-O-CO$ | n-pentyl | oil | 5.1(S, 2H); 7.55(S, 1H) |
| 469 | $HCOCH_3$ | $CH_2-O-CO$ | n-hexyl | oil | 5.1(S, 2H); 7.55(S, 1H) |
| 470 | $HCOCH_3$ | $CH_2-O-CO$ | n-nonyl | oil | 5.1(S, 2H); 7.55(S, 1H) |
| 471 | $HCOCH_3$ | $CH_2-O-CO$ | n-undecyl | oil | 5.1(S, 2H); 7.55(S, 1H) |
| 472 | $HCOCH_3$ | $CH_2-S-$ | n-octyl | oil | 3.7(S, 2H); 7.55(S, 1H) |
| 473 | $HCOCH_3$ | $O-(CH_2)_2$ | phenyl | oil | 4.2(t, J=7Hz.2H); 7.55(S, 1H) |
| 474 | $HCOCH_3$ | $O-(CH_2)_3$ | phenyl | oil | 3.95(t, J=7Hz, 2H); 7.55(S, 1H) |
| 475 | $HCOCH_3$ | $CH_2-O$ | 2-naphthyl | 164-165 | |
| 476 | $HCOCH_3$ | $O-CH_2$ | 2-naphthyl | 74-75 | |
| 477 | $HCOCH_3$ | $O-(CH_2)_2$ | $CH_3$ | oil | 3.9(t, J=8Hz, 2H); 7.55(S, 1H) |
| 478 | $HCOCH_3$ | $O-(CH_2)_3$ | $CH_3$ | oil | 3.95(t, J=8Hz, 2H); 7.55(S, 1H) |
| 479 | $HCOCH_3$ | $O-(CH_2)_5$ | $CH_3$ | oil | 3.95(t, J=7Hz, 2H); 7.55(S, 1H) |
| 480 | $HCOCH_3$ | $O-(CH_2)_7$ | $CH_3$ | 38-39 | |
| 481 | $HCOCH_3$ | $O-(CH_2)_9$ | $CH_3$ | 53-54 | |
| 482 | $HCOCH_3$ | $O-(CH_2)_{19}$ | $CH_3$ | 62-63 | |
| 483 | $HCOCH_3$ | $O-CH_2$ | 2,6-dimethylheptyl | oil | 4.0(m, 2H); 7.55(S, 1H) |
| 484 | $HCOCH_3$ | $O-CH_2$ | 2,6-dimethyl-heptenyl-(5) | oil | 4.0(m, 2H); 7.55(S, 1H) |
| 485 | $HCOCH_3$ | $O-CH_2$ | (trans)-2,6-dimethyl-heptadienyl-(1,5) | oil | 4.5(d, J=7Hz, 2H); 7.55(S, 1H) |
| 486 | $HCOCH_3$ | $O-CH_2$ | (cis)-2,6-dimethyl-heptadienyl-(1,5) | oil | 4.5(d, J=7Hz, 2H); 7.55(S, 1H) |
| 487 (isomer mixture) | $HCOCH_3$ | $O-CH_2$ | (trans, trans)-2,6,10-tri-methylundecatrienyl-(1,5,9) | oil | 4.5(d, J=7Hz, 2H); 7.55(S, 1H) |
| 488 (isomer mixture) | $HCOCH_3$ | $O-CH_2$ | (trans)-1,5,9,13-tetramethylpentadecen-(1) | oil | 4.5(d, J=7Hz, 2H); 7.55(S, 1H) |
| 489 | $HCOCH_3$ | $O-CH_2$ | 1-[2-methyl-3-(4-fluorophenyl]-propenyl | oil | 3.75(d, J=7Hz, 2H); 7.55(S, 1H) |
| 490 | O | $CH_2O$ | 2-methylphenyl | oil | 5.1(s, 2H) |
| 491 | O | $CH_2O$ | 3-methylphenyl | | |
| 492 | O | $CH_2O$ | 4-methylphenyl | | |
| 493 | O | $CH_2O$ | 2,3-dimethylphenyl | | |
| 494 | O | $CH_2O$ | 2,4-dimethylphenyl | | |
| 495 | O | $CH_2O$ | 2,5-dimethylphenyl | | |
| 496 | O | $CH_2O$ | 2,6-dimethylphenyl | | |
| 497 | O | $CH_2O$ | 3,4-dimethylphenyl | | |
| 498 | O | $CH_2O$ | 3,5-dimethylphenyl | | |

TABLE 3

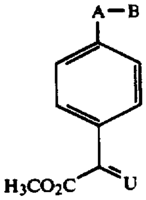

| No. | U | A | B | mp | NMR: δ(ppm) |
|---|---|---|---|---|---|
| 1 | $HCOCH_3$ | $CH_2-CH_2$ | H | | |
| 2 | $HCOCH_3$ | $CH_2-CH_2$ | $CH_3$ | | |
| 3 | $HCOCH_3$ | $CH_2-CH_2$ | cyclohexyl | | |
| 4 | $HCOCH_3$ | $CH_2-CH_2$ | phenyl | | |
| 5 | $HCOCH_3$ | $CH_2-CH_2$ | 2-pyridyl | | |
| 6 | $HCOCH_3$ | $CH=CH$ | H | | |
| 7 | $HCOCH_3$ | $CH=CH$ | $CH_3$ | | |
| 8 | $HCOCH_3$ | $CH=CH$ | cyclohexyl | | |
| 9 | $HCOCH_3$ | $CH=CH$ | 2-naphthyl | | |
| 10 | $HCOCH_3$ | $CH=CH$ | 2-pyridyl | | |
| 11 | $HCOCH_3$ | $O-CH_2$ | H | | |
| 12 | $HCOCH_3$ | $O-CH_2$ | $CH_3$ | | |
| 13 | $HCOCH_3$ | $O-CH_2$ | cyclohexyl | | |
| 14 | $HCOCH_3$ | $O-CH_2$ | phenyl | 77-79 | |
| 15 | $HCOCH_3$ | $O-CH_2$ | 2-pyridyl | | |
| 16 | $HCOCH_3$ | $O-CH_2-CO$ | H | | |
| 17 | $HCOCH_3$ | $O-CH_2-CO$ | $CH_3$ | | |
| 18 | $HCOCH_3$ | $O-CH_2-CO$ | cyclohexyl | | |
| 19 | $HCOCH_3$ | $O-CH_2-CO$ | phenyl | | |
| 20 | $HCOCH_3$ | $O-CH_2-CO$ | 2-pyridyl | | |
| 21 | $HCOCH_3$ | $CH_2-O-CO$ | H | oil | 5.2(S, 2H); 7.6(S, 1H) |
| 22 | $HCOCH_3$ | $CH_2-O-CO$ | $CH_3$ | 69-70 | |
| 23 | $HCOCH_3$ | $CH_2-O-CO$ | cyclohexyl | | |
| 24 | $HCOCH_3$ | $CH_2-O-CO$ | phenyl | 74-75 | |
| 25 | $HCOCH_3$ | $CH_2-O-CO$ | 2-pyridyl | | |
| 26 | $HCOCH_3$ | $CO-O-CH_2$ | H | 81-84 | |
| 27 | $HCOCH_3$ | $CO-O-CH_2$ | $CH_3$ | | |
| 28 | $HCOCH_3$ | $CO-O-CH_2$ | cyclohexyl | | |
| 29 | $HCOCH_3$ | $CO-O-CH_2$ | phenyl | | |
| 30 | $HCOCH_3$ | $CO-O-CH_2$ | 2-pyridyl | | |
| 31 | $HCOCH_3$ | $O-CO-CH_2$ | H | | |
| 32 | $HCOCH_3$ | $O-CO-CH_2$ | $CH_3$ | | |
| 33 | $HCOCH_3$ | $O-CO-CH_2$ | cyclohexyl | | |
| 34 | $HCOCH_3$ | $O-CO-CH_2$ | phenyl | | |
| 35 | $HCOCH_3$ | $O-CO-CH_2$ | 2-pyridyl | | |
| 36 | $HCOCH_3$ | $O-CO-$ | phenyl | | |
| 37 | $HCOCH_3$ | $O-CH_2-COO$ | $CH_3$ | | |
| 38 | $HCOCH_3$ | $O-(CH_2)_3-COO$ | $CH_3$ | 57-58 | |
| 39 | $HCOCH_3$ | $O-(CH_2)_7-COO$ | $CH_3$ | 44 | |
| 40 | $HCOCH_3$ | $O-(CH_2)_2-O$ | H | | |
| 41 | $HCOCH_3$ | $O-(CH_2)_2-O$ | $CH_3$ | | |
| 42 | $HCOCH_3$ | $O-(CH_2)_2-O$ | cyclohexyl | | |
| 43 | $HCOCH_3$ | $O-(CH_2)_2-O$ | phenyl | | |
| 44 | $HCOCH_3$ | $O-(CH_2)_2-O$ | 2-pyridyl | | |
| 45 | $HCOCH_3$ | $O-(CH_2)_3-O$ | H | | |
| 46 | $HCOCH_3$ | $O-(CH_2)_3-O$ | $CH_3$ | | |
| 47 | $HCOCH_3$ | $O-(CH_2)_3-O$ | cyclohexyl | | |
| 47 | $HCOCH_3$ | $O-(CH_2)_3-O$ | cyclohexyl | | |
| 48 | $HCOCH_3$ | $O-(CH_2)_3-O$ | phenyl | | |
| 49 | $HCOCH_3$ | $O-(CH_2)_3-O$ | 2-pyridyl | | |
| 50 | $HCOCH_3$ | $O-(CH_2)_4-O$ | H | | |
| 51 | $HCOCH_3$ | $O-(CH_2)_4-O$ | $CH_3$ | | |
| 52 | $HCOCH_3$ | $O-(CH_2)_4-O$ | cycloheyl | | |
| 53 | $HCOCH_3$ | $O-(CH_2)_4-O$ | phenyl | | |
| 54 | $HCOCH_3$ | $O-(CH_2)_4-O$ | 2-pyridyl | | |
| 55 | $HCOCH_3$ | $O-(CH_2)_5-O$ | H | | |
| 56 | $HCOCH_3$ | $O-(CH_2)_5-O$ | $CH_3$ | | |
| 57 | $HCOCH_3$ | $O-(CH_2)_5-O$ | cyclohexyl | | |
| 58 | $HCOCH_3$ | $O-(CH_2)_5-O$ | phenyl | | |
| 59 | $HCOCH_3$ | $O-(CH_2)_5-O$ | 2-pyridyl | | |
| 60 | $HCOCH_3$ | $O-(CH_2)_6-O$ | H | | |
| 61 | $HCOCH_3$ | $O-(CH_2)_6-O$ | $CH_3$ | | |
| 62 | $HCOCH_3$ | $O-(CH_2)_6-O$ | cyclohexyl | | |
| 63 | $HCOCH_3$ | $O-(CH_2)_6-O$ | phenyl | | |
| 64 | $HCOCH_3$ | $O-(CH_2)_6-O$ | 2-pyridyl | | |
| 65 | $HCOCH_3$ | $O-(CH_2)_8-O$ | H | | |
| 66 | $HCOCH_3$ | $O-(CH_2)_8-O$ | $CH_3$ | | |
| 67 | $HCOCH_3$ | $O-(CH_2)_8-O$ | cyclohexyl | | |
| 68 | $HCOCH_3$ | $O-(CH_2)_8-O$ | phenyl | | |
| 69 | $HCOCH_3$ | $O-(CH_2)_8-O$ | 2-pyridyl | | |

TABLE 3-continued

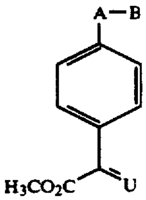

| No. | U | A | B | mp | NMR: δ(ppm) |
|---|---|---|---|---|---|
| 70 | $HCOCH_3$ | $O-(CH_2)_{10}-O$ | H | | |
| 71 | $HCOCH_3$ | $O-(CH_2)_{10}-O$ | $CH_3$ | | |
| 72 | $HCOCH_3$ | $O-(CH_2)_{10}-O$ | cyclohexyl | | |
| 73 | $HCOCH_3$ | $O-(CH_2)_{10}-O$ | phenyl | | |
| 74 | $HCOCH_3$ | $O-(CH_2)_{10}-O$ | 2-pyridyl | | |
| 75 | $HCOCH_3$ | O | phenyl | 99-100 | |
| 76 | $HCOCH_3$ | $CH_2-O$ | $CH_3$ | | |
| 77 | $HCOCH_3$ | $CH_2-O$ | cyclohexyl | | |
| 78 | $HCOCH_3$ | $CH_2-O$ | phenyl | | |
| 79 | $HCOCH_3$ | $CH_2-O$ | pyridyl | | |
| 80 | $HCOCH_3$ | $CH_2-S-CH_2$ | H | | |
| 81 | $HCOCH_3$ | $CH_2-S-CH_2$ | $CH_3$ | | |
| 82 | $HCOCH_3$ | $CH_2-S-CH_2$ | cyclohexyl | | |
| 83 | $HCOCH_3$ | $CH_2-S-CH_2$ | phenyl | | |
| 84 | $HCOCH_3$ | $CH_2-S-CH_2$ | 2-pyridyl | | |
| 85 | $HCOCH_3$ | $CH_2-N(CH_3)$ | H | | |
| 86 | $HCOCH_3$ | $CH_2-N(CH_3)$ | $CH_3$ | | |
| 87 | $HCOCH_3$ | $CH_2-N(CH_3)$ | cyclohexyl | | |
| 88 | $HCOCH_3$ | $CH_2-N(CH_3)$ | phenyl | | |
| 89 | $HCOCH_3$ | $CH_2-N(CH_3)$ | 2-pyridyl | | |
| 90 | $HCOCH_3$ | $CH(CN)-OCO-CH_2$ | H | | |
| 91 | $HCOCH_3$ | $CH(CN)-OCO-CH_2$ | $CH_3$ | | |
| 92 | $HCOCH_3$ | $CH(CN)-OCO-CH_2$ | cyclohexyl | | |
| 93 | $HCOCH_3$ | $CH(CN)-OCO-CH_2$ | phenyl | | |
| 94 | $HCOCH_3$ | $CH(CN)-OCO-CH_2$ | pyridyl | | |
| 95 | $HCOCH_3$ | $CH(CN)-OCO$ | phenyl | | |
| 96 | $HCOCH_3$ | $CH=N-$ | H | | |
| 97 | $HCOCH_3$ | $CH=N-$ | $CH_3$ | | |
| 98 | $HCOCH_3$ | $CH=N-$ | cyclohexyl | | |
| 99 | $HCOCH_3$ | $CH=N-$ | phenyl | | |
| 100 | $HCOCH_3$ | $CH=N-$ | 2-pyridyl | | |
| 101 | $HCOCH_3$ | $CH=N-O-CH_2$ | H | | |
| 102 | $HCOCH_3$ | $CH=N-O-CH_2$ | $CH_3$ | | |
| 103 | $HCOCH_3$ | $CH=N-O-CH_2$ | cyclohexyl | | |
| 104 | $HCOCH_3$ | $CH=N-O-CH_2$ | phenyl | | |
| 105 | $HCOCH_3$ | $CH=N-O-CH_2$ | 2-pyridyl | | |
| 106 | $NOCH_3$ | $CH_2-CH_2$ | H | | |
| 107 | $NOCH_3$ | $CH_2-CH_2$ | $CH_3$ | | |
| 108 | $NOCH_3$ | $CH_2-CH_2$ | cyclohexyl | | |
| 109 | $NOCH_3$ | $CH_2-CH_2$ | phenyl | | |
| 110 | $NOCH_3$ | $CH_2-CH_2$ | 2-pyridyl | | |
| 111 | $NOCH_3$ | $CH=CH$ | H | | |
| 112 | $NOCH_3$ | $CH=CH$ | $CH_3$ | | |
| 113 | $NOCH_3$ | $CH=CH$ | cyclohexyl | | |
| 114 | $NOCH_3$ | $CH=CH$ | phenyl | | |
| 115 | $NOCH_3$ | $CH=CH$ | 2-pyridyl | | |
| 116 | $NOCH_3$ | $O-CH_2$ | H | | |
| 117 | $NOCH_3$ | $O-CH_2$ | $CH_3$ | | |
| 118 | $NOCH_3$ | $O-CH_2$ | cyclohexyl | | |
| 119 | $NOCH_3$ | $O-CH_2$ | phenyl | | |
| 120 | $NOCH_3$ | $O-CH_2$ | 2-pyridyl | | |
| 121 | $NOCH_3$ | $O-CH_2-CO$ | H | | |
| 122 | $NOCH_3$ | $O-CH_2-CO$ | $CH_3$ | | |
| 123 | $NOCH_3$ | $O-CH_2-CO$ | cyclohexyl | | |
| 124 | $NOCH_3$ | $O-CH_2-CO$ | phenyl | | |
| 125 | $NOCH_3$ | $O-CH_2-CO$ | 2-pyridyl | | |
| 126 | $NOCH_3$ | $CH_2-O-CO$ | H | | |
| 127 | $NOCH_3$ | $CH_2-O-CO$ | $CH_3$ | | |
| 128 | $NOCH_3$ | $CH_2-O-CO$ | cyclohexyl | | |
| 129 | $NOCH_3$ | $CH_2-O-CO$ | phenyl | | |
| 130 | $NOCH_3$ | $CH_2-O-CO$ | 2-pyridyl | | |
| 131 | $NOCH_3$ | $CO-O-CH_2$ | H | | |
| 132 | $NOCH_3$ | $CO-O-CH_2$ | $CH_3$ | | |
| 133 | $NOCH_3$ | $CO-O-CH_2$ | cyclohexyl | | |
| 134 | $NOCH_3$ | $CO-O-CH_2$ | phenyl | | |
| 135 | $NOCH_3$ | $CO-O-CH_2$ | 2-pyridyl | | |
| 136 | $NOCH_3$ | $O-CO-CH_2$ | H | | |
| 137 | $NOCH_3$ | $O-CO-CH_2$ | $CH_3$ | | |
| 138 | $NOCH_3$ | $O-CO-CH_2$ | cyclohexyl | | |
| 139 | $NOCH_3$ | $O-CO-CH_2$ | phenyl | | |

TABLE 3-continued

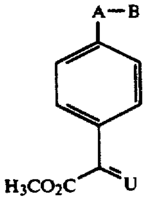

| No. | U | A | B | mp | NMR: δ(ppm) |
|---|---|---|---|---|---|
| 140 | $NOCH_3$ | $O-CO-CH_2$ | 2-pyridyl | | |
| 141 | $NOCH_3$ | $O-CO-$ | phenyl | | |
| 142 | $NOCH_3$ | $O-CH_2-COO$ | $CH_3$ | | |
| 143 | $NOCH_3$ | $O-(CH_2)_3-COO$ | $CH_3$ | | |
| 144 | $NOCH_3$ | $O-(CH_2)_7-COO$ | $CH_3$ | | |
| 145 | $NOCH_3$ | $O-(CH_2)_2-O$ | H | | |
| 146 | $NOCH_3$ | $O-(CH_2)_2-O$ | $CH_3$ | | |
| 147 | $NOCH_3$ | $O-(CH_2)_2-O$ | cyclohexyl | | |
| 148 | $NOCH_3$ | $O-(CH_2)_2-O$ | phenyl | | |
| 149 | $NOCH_3$ | $O-(CH_2)_2-O$ | 2-pyridyl | | |
| 150 | $NOCH_3$ | $O-(CH_2)_3-O$ | H | | |
| 151 | $NOCH_3$ | $O-(CH_2)_3-O$ | $CH_3$ | | |
| 152 | $NOCH_3$ | $O-(CH_2)_3-O$ | cyclohexyl | | |
| 153 | $NOCH_3$ | $O-(CH_2)_3-O$ | phenyl | | |
| 154 | $NOCH_3$ | $O-(CH_2)_3-O$ | 2-pyridyl | | |
| 155 | $NOCH_3$ | $O-(CH_2)_4-O$ | H | | |
| 156 | $NOCH_3$ | $O-(CH_2)_4-O$ | $CH_3$ | | |
| 157 | $NOCH_3$ | $O-(CH_2)_4-O$ | cyclohexyl | | |
| 158 | $NOCH_3$ | $O-(CH_2)_4-O$ | phenyl | | |
| 159 | $NOCH_3$ | $O-(CH_2)_4-O$ | 2-pyridyl | | |
| 160 | $NOCH_3$ | $O-(CH_2)_5-O$ | H | | |
| 161 | $NOCH_3$ | $O-(CH_2)_5-O$ | $CH_3$ | | |
| 162 | $NOCH_3$ | $O-(CH_2)_5-O$ | cyclohexyl | | |
| 163 | $NOCH_3$ | $O-(CH_2)_5-O$ | phenyl | | |
| 164 | $NOCH_3$ | $O-(CH_2)_5-O$ | 2-pyridyl | | |
| 165 | $NOCH_3$ | $O-(CH_2)_6-O$ | H | | |
| 166 | $NOCH_3$ | $O-(CH_2)_6-O$ | $CH_3$ | | |
| 167 | $NOCH_3$ | $O-(CH_2)_6-O$ | cyclohexyl | | |
| 168 | $NOCH_3$ | $O-(CH_2)_6-O$ | phenyl | | |
| 169 | $NOCH_3$ | $O-(CH_2)_6-O$ | 2-pyridyl | | |
| 170 | $NOCH_3$ | $O-(CH_2)_8-O$ | H | | |
| 171 | $NOCH_3$ | $O-(CH_2)_8-O$ | $CH_3$ | | |
| 172 | $NOCH_3$ | $O-(CH_2)_8-O$ | cyclohexyl | | |
| 173 | $NOCH_3$ | $O-(CH_2)_8-O$ | phenyl | | |
| 174 | $NOCH_3$ | $O-(CH_2)_8-O$ | 2-pyridyl | | |
| 175 | $NOCH_3$ | $O-(CH_2)_{10}-O$ | H | | |
| 176 | $NOCH_3$ | $O-(CH_2)_{10}-O$ | $CH_3$ | | |
| 177 | $NOCH_3$ | $O-(CH_2)_{10}-O$ | cyclohexyl | | |
| 178 | $NOCH_3$ | $O-(CH_2)_{10}-O$ | phenyl | | |
| 179 | $NOCH_3$ | $O-(CH_2)_{10}-O$ | 2-pyridyl | | |
| 180 | $NOCH_3$ | $CH_2-O-$ | H | | |
| 181 | $NOCH_3$ | $CH_2-O-$ | $CH_3$ | | |
| 182 | $NOCH_3$ | $CH_2-O-$ | cyclohexyl | | |
| 183 | $NOCH_3$ | $CH_2-O-$ | phenyl | | |
| 184 | $NOCH_3$ | $CH_2-O-$ | pyridyl | | |
| 185 | $NOCH_3$ | $CH_2-S-CH_2$ | H | | |
| 186 | $NOCH_3$ | $CH_2-S-CH_2$ | $CH_3$ | | |
| 187 | $NOCH_3$ | $CH_2-S-CH_2$ | cyclohexyl | | |
| 188 | $NOCH_3$ | $CH_2-S-CH_2$ | phenyl | | |
| 189 | $NOCH_3$ | $CH_2-S-CH_2$ | 2-pyridyl | | |
| 190 | $NOCH_3$ | $CH_2-N(CH_3)$ | H | | |
| 191 | $NOCH_3$ | $CH_2-N(CH_3)$ | $CH_3$ | | |
| 192 | $NOCH_3$ | $CH_2-N(CH_3)$ | cyclohexyl | | |
| 193 | $NOCH_3$ | $CH_2-N(CH_3)$ | phenyl | | |
| 194 | $NOCH_3$ | $CH_2-N(CH_3)$ | 2-pyridyl | | |
| 195 | $NOCH_3$ | $CH(CN)-OCO-CH_2$ | H | | |
| 196 | $NOCH_3$ | $CH(CN)-OCO-CH_2$ | $CH_3$ | | |
| 197 | $NOCH_3$ | $CH(CN)-OCO-CH_2$ | cyclohexyl | | |
| 198 | $NOCH_3$ | $CH(CN)-OCO-CH_2$ | phenyl | | |
| 199 | $NOCH_3$ | $CH(CN)-OCO-CH_2$ | pyridyl | | |
| 200 | $NOCH_3$ | $CH(CN)-OCO$ | phenyl | | |
| 201 | $NOCH_3$ | $CH=N-$ | H | | |
| 202 | $NOCH_3$ | $CH=N-$ | $CH_3$ | | |
| 203 | $NOCH_3$ | $CH=N-$ | cyclohexyl | | |
| 204 | $NOCH_3$ | $CH=N-$ | phenyl | | |
| 205 | $NOCH_3$ | $CH=N-$ | 2-pyridyl | | |
| 206 | $NOCH_3$ | $CH=N-O-CH_2$ | H | | |
| 207 | $NOCH_3$ | $CH=N-O-CH_2$ | $CH_3$ | | |
| 208 | $NOCH_3$ | $CH=N-O-CH_2$ | cyclohexyl | | |
| 209 | $NOCH_3$ | $CH=N-O-CH_2$ | phenyl | | |

TABLE 3-continued

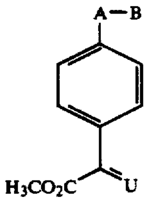

| No. | U | A | B | mp | NMR: δ(ppm) |
|---|---|---|---|---|---|
| 210 | $NOCH_3$ | $CH{=}N{-}O{-}CH_2$ | 2-pyridyl | | |
| 211 | $HC{-}CH_3$ | $CH_2{-}CH_2$ | H | | |
| 212 | $HC{-}CH_3$ | $CH_2{-}CH_2$ | $CH_3$ | | |
| 213 | $HC{-}CH_3$ | $CH_2{-}CH_2$ | cyclohexyl | | |
| 214 | $HC{-}CH_3$ | $CH_2{-}CH_2$ | phenyl | | |
| 215 | $HC{-}CH_3$ | $CH_2{-}CH_2$ | 2-pyridyl | | |
| 216 | $HC{-}CH_3$ | $CH{=}CH$ | H | | |
| 217 | $HC{-}CH_3$ | $CH{=}CH$ | $CH_3$ | | |
| 218 | $HC{-}CH_3$ | $CH{=}CH$ | cyclohexyl | | |
| 219 | $HC{-}CH_3$ | $CH{=}CH$ | phenyl | | |
| 220 | $HC{-}CH_3$ | $CH{=}CH$ | 2-pyridyl | | |
| 221 | $HC{-}CH_3$ | $OCH_2$ | H | | |
| 222 | $HC{-}CH_3$ | $OCH_2$ | $CH_3$ | | |
| 223 | $HC{-}CH_3$ | $OCH_2$ | cyclohexyl | | |
| 224 | $HC{-}CH_3$ | $OCH_2$ | phenyl | | |
| 225 | $HC{-}CH_3$ | $OCH_2$ | 2-pyridyl | | |
| 226 | $HC{-}CH_3$ | $O{-}CH_2{-}CO$ | H | | |
| 227 | $HC{-}CH_3$ | $O{-}CH_2{-}CO$ | $CH_3$ | | |
| 228 | $HC{-}CH_3$ | $O{-}CH_2{-}CO$ | cyclohexyl | | |
| 229 | $HC{-}CH_3$ | $O{-}CH_2{-}CO$ | phenyl | | |
| 230 | $HC{-}CH_3$ | $O{-}CH_2{-}CO$ | 2-pyridyl | | |
| 231 | $HC{-}CH_3$ | $CH_2{-}O{-}CO$ | H | | |
| 232 | $HC{-}CH_3$ | $CH_2{-}O{-}CO$ | $CH_3$ | | |
| 233 | $HC{-}CH_3$ | $CH_2{-}O{-}CO$ | cyclohexyl | | |
| 234 | $HC{-}CH_3$ | $CH_2{-}O{-}CO$ | phenyl | | |
| 235 | $HC{-}CH_3$ | $CH_2{-}O{-}CO$ | 2-pyridyl | | |
| 236 | $HC{-}CH_3$ | $CO{-}O{-}CH_2$ | H | | |
| 237 | $HC{-}CH_3$ | $CO{-}O{-}CH_2$ | $CH_3$ | | |
| 238 | $HC{-}CH_3$ | $CO{-}O{-}CH_2$ | cyclohexyl | | |
| 239 | $HC{-}CH_3$ | $CO{-}O{-}CH_2$ | phenyl | | |
| 240 | $HC{-}CH_3$ | $CO{-}O{-}CH_2$ | 2-pyridyl | | |
| 241 | $HC{-}CH_3$ | $O{-}CO{-}CH_2$ | H | | |
| 242 | $HC{-}CH_3$ | $O{-}CO{-}CH_2$ | $CH_3$ | | |
| 243 | $HC{-}CH_3$ | $O{-}CO{-}CH_2$ | cyclohexyl | | |
| 244 | $HC{-}CH_3$ | $O{-}CO{-}CH_2$ | phenyl | | |
| 245 | $HC{-}CH_3$ | $O{-}CO{-}CH_2$ | 2-pyridyl | | |
| 246 | $HC{-}CH_3$ | $O{-}CO{-}$ | phenyl | | |
| 247 | $HC{-}CH_3$ | $O{-}CH_2{-}COO$ | $CH_3$ | | |
| 248 | $HC{-}CH_3$ | $O{-}(CH_2)_3{-}COO$ | $CH_3$ | | |
| 249 | $HC{-}CH_3$ | $O{-}(CH_2)_7{-}COO$ | $CH_3$ | | |
| 250 | $HC{-}CH_3$ | $O{-}(CH_2)_2{-}O$ | H | | |
| 251 | $HC{-}CH_3$ | $O{-}(CH_2)_2{-}O$ | $CH_3$ | | |
| 252 | $HC{-}CH_3$ | $O{-}(CH_2)_2{-}O$ | cyclohexyl | | |
| 253 | $HC{-}CH_3$ | $O{-}(CH_2)_2{-}O$ | phenyl | | |
| 254 | $HC{-}CH_3$ | $O{-}(CH_2)_2{-}O$ | 2-pyridyl | | |
| 255 | $HC{-}CH_3$ | $O{-}(CH_2)_3{-}O$ | H | | |
| 256 | $HC{-}CH_3$ | $O{-}(CH_2)_3{-}O$ | $CH_3$ | | |
| 257 | $HC{-}CH_3$ | $O{-}(CH_2)_3{-}O$ | cyclohexyl | | |
| 258 | $HC{-}CH_3$ | $O{-}(CH_2)_3{-}O$ | phenyl | | |
| 259 | $HC{-}CH_3$ | $O{-}(CH_2)_3{-}O$ | 2-pryidyl | | |
| 260 | $HC{-}CH_3$ | $O{-}(CH_2)_4{-}O$ | H | | |
| 261 | $HC{-}CH_3$ | $O{-}(CH_2)_4{-}O$ | $CH_3$ | | |
| 262 | $HC{-}CH_3$ | $O{-}(CH_2)_4{-}O$ | cyclohexyl | | |
| 263 | $HC{-}CH_3$ | $O{-}(CH_2)_4{-}O$ | phenyl | | |
| 264 | $HC{-}CH_3$ | $O{-}(CH_2)_4{-}O$ | 2-pyridyl | | |
| 265 | $HC{-}CH_3$ | $O{-}(CH_2)_5{-}O$ | H | | |
| 266 | $HC{-}CH_3$ | $O{-}(CH_2)_5{-}O$ | $CH_3$ | | |
| 267 | $HC{-}CH_3$ | $O{-}(CH_2)_5{-}O$ | cyclohexyl | | |
| 268 | $HC{-}CH_3$ | $O{-}(CH_2)_5{-}O$ | phenyl | | |
| 269 | $HC{-}CH_3$ | $O{-}(CH_2)_5{-}O$ | 2-pyridyl | | |
| 270 | $HC{-}CH_3$ | $O{-}(CH_2)_6{-}O$ | H | | |
| 271 | $HC{-}CH_3$ | $O{-}(CH_2)_6{-}O$ | $CH_3$ | | |
| 272 | $HC{-}CH_3$ | $O{-}(CH_2)_6{-}O$ | cyclohexyl | | |
| 273 | $HC{-}CH_3$ | $O{-}(CH_2)_6{-}O$ | phenyl | | |
| 274 | $HC{-}CH_3$ | $O{-}(CH_2)_6{-}O$ | 2-pyridyl | | |
| 275 | $HC{-}CH_3$ | $O{-}(CH_2)_8{-}O$ | H | | |
| 276 | $HC{-}CH_3$ | $O{-}(CH_2)_8{-}O$ | $CH_3$ | | |
| 277 | $HC{-}CH_3$ | $O{-}(CH_2)_8{-}O$ | cyclohexyl | | |
| 278 | $HC{-}CH_3$ | $O{-}(CH_2)_8{-}O$ | phenyl | | |
| 279 | $HC{-}CH_3$ | $O{-}(CH_2)_8{-}O$ | 2-pyridyl | | |

TABLE 3-continued

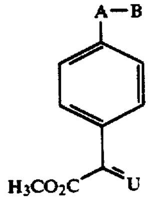

| No. | U | A | B | mp | NMR: δ(ppm) |
|---|---|---|---|---|---|
| 280 | $HC-CH_3$ | $O-(CH_2)_{10}-O$ | H | | |
| 281 | $HC-CH_3$ | $O-(CH_2)_{10}-O$ | $CH_3$ | | |
| 282 | $HC-CH_3$ | $O-(CH_2)_{10}-O$ | cyclohexyl | | |
| 283 | $HC-CH_3$ | $O-(CH_2)_{10}-O$ | phenyl | | |
| 284 | $HC-CH_3$ | $O-(CH_2)_{10}-O$ | 2-pyridyl | | |
| 285 | $HC-CH_3$ | $CH_2-O-$ | H | | |
| 286 | $HC-CH_3$ | $CH_2-O-$ | $CH_3$ | | |
| 287 | $HC-CH_3$ | $CH_2-O-$ | cyclohexyl | | |
| 288 | $HC-CH_3$ | $CH_2-O-$ | phenyl | | |
| 289 | $HC-CH_3$ | $CH_2-O-$ | pyridyl | | |
| 290 | $HC-CH_3$ | $CH_2-S-CH_2$ | H | | |
| 291 | $HC-CH_3$ | $CH_2-S-CH_2$ | $CH_3$ | | |
| 292 | $HC-CH_3$ | $CH_2-S-CH_2$ | cyclohexyl | | |
| 293 | $HC-CH_3$ | $CH_2-S-CH_2$ | phenyl | | |
| 294 | $HC-CH_3$ | $CH_2-S-CH_2$ | 2-pyridyl | | |
| 295 | $HC-CH_3$ | $CH_2-N(CH_3)$ | H | | |
| 296 | $HC-CH_3$ | $CH_2-N(CH_3)$ | $CH_3$ | | |
| 297 | $HC-CH_3$ | $CH_2-N(CH_3)$ | cyclohexyl | | |
| 298 | $HC-CH_3$ | $CH_2-N(CH_3)$ | phenyl | | |
| 299 | $HC-CH_3$ | $CH_2-N(CH_3)$ | 2-pyridyl | | |
| 300 | $HC-CH_3$ | $CH(CN)-OCO-CH_2$ | H | | |
| 301 | $HC-CH_3$ | $CH(CN)-OCO-CH_2$ | $CH_3$ | | |
| 302 | $HC-CH_3$ | $CH(CN)-OCO-CH_2$ | cyclohexyl | | |
| 303 | $HC-CH_3$ | $CH(CN)-OCO-CH_2$ | phenyl | | |
| 304 | $HC-CH_3$ | $CH(CN)-OCO-CH_2$ | pyridyl | | |
| 305 | $HC-CH_3$ | $CH(CN)-OCO$ | phenyl | | |
| 306 | $HC-CH_3$ | $CH=N-$ | H | | |
| 307 | $HC-CH_3$ | $CH=N-$ | $CH_3$ | | |
| 308 | $HC-CH_3$ | $CH=N-$ | cyclohexyl | | |
| 309 | $HC-CH_3$ | $CH=N-$ | phenyl | | |
| 310 | $HC-CH_3$ | $CH=N-$ | 2-pyridyl | | |
| 311 | $HC-CH_3$ | $CH=N-O-CH_2$ | H | | |
| 312 | $HC-CH_3$ | $CH=N-O-CH_2$ | $CH_3$ | | |
| 313 | $HC-CH_3$ | $CH=N-O-CH_2$ | cyclohexyl | | |
| 314 | $HC-CH_3$ | $CH=N-O-CH_2$ | phenyl | | |
| 315 | $HC-CH_3$ | $CH=N-O-CH_2$ | 2-pyridyl | | |
| 316 | O | $CH_2-CH_2$ | H | | |
| 317 | O | $CH_2-CH_2$ | $CH_3$ | | |
| 318 | O | $CH_2-CH_2$ | cyclohexyl | | |
| 319 | O | $CH_2-CH_2$ | phenyl | | |
| 320 | O | $CH_2-CH_2$ | 2-pyridyl | | |
| 312 | O | $CH=CH$ | H | | |
| 322 | O | $CH=CH$ | $CH_3$ | | |
| 323 | O | $CH=CH$ | cyclohexyl | | |
| 324 | O | $CH=CH$ | phenyl | | |
| 325 | O | $CH=CH$ | 2-pyridyl | | |
| 326 | O | $O-CH_2$ | H | | |
| 327 | O | $O-CH_2$ | $CH_3$ | | |
| 328 | O | $O-CH_2$ | cyclohexyl | | |
| 329 | O | $O-CH_2$ | phenyl | | |
| 330 | O | $O-CH_2$ | 2-pyridyl | | |
| 331 | O | $CH_2-O$ | H | | |
| 332 | O | $CH_2-O$ | $CH_3$ | | |
| 333 | O | $CH_2-O$ | cyclohexyl | | |
| 334 | O | $CH_2-O$ | phenyl | | |
| 335 | O | $CH_2-O$ | 2-pyridyl | | |
| 336 | O | $CH_2-O-CO$ | H | | |
| 337 | O | $CH_2-O-CO$ | $CH_3$ | | |
| 338 | O | $CH_2-O-CO$ | cyclohexyl | | |
| 339 | O | $CH_2-O-CO$ | phenyl | | |
| 340 | O | $CH_2-O-CO$ | 2-pyridyl | | |
| 341 | $N-NHCH_3$ | $CH_2-CH_2$ | H | | |
| 342 | $N-NHCH_3$ | $CH_2-CH_2$ | $CH_3$ | | |
| 343 | $N-NHCH_3$ | $CH_2-CH_2$ | cyclohexyl | | |
| 344 | $N-NHCH_3$ | $CH_2-CH_2$ | phenyl | | |
| 345 | $N-NHCH_3$ | $CH_2-CH_2$ | 2-pyridyl | | |
| 346 | $N-NHCH_3$ | $CH=CH$ | H | | |
| 347 | $N-NHCH_3$ | $CH=CH$ | $CH_3$ | | |
| 348 | $N-NHCH_3$ | $CH=CH$ | cyclohexyl | | |
| 349 | $N-NHCH_3$ | $CH=CH$ | phenyl | | |

TABLE 3-continued

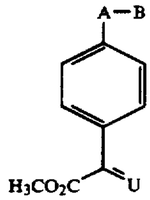

| No. | U | A | B | mp | NMR: δ(ppm) |
|---|---|---|---|---|---|
| 350 | N—$NHCH_3$ | CH═CH | 2-pyridyl | | |
| 351 | N—$NHCH_3$ | O—$CH_2$ | H | | |
| 352 | N—$NHCH_3$ | O—$CH_2$ | $CH_3$ | | |
| 353 | N—$NHCH_3$ | O—$CH_2$ | cyclohexyl | | |
| 354 | N—$NHCH_3$ | O—$CH_2$ | phenyl | | |
| 355 | N—$NHCH_3$ | O—$CH_2$ | 2-pyridyl | | |
| 356 | N—$NHCH_3$ | $CH_2$—O | H | | |
| 357 | N—$NHCH_3$ | $CH_2$—O | $CH_3$ | | |
| 358 | N—$NHCH_3$ | $CH_2$—O | cyclohexyl | | |
| 359 | N—$NHCH_3$ | $CH_2$—O | phenyl | | |
| 360 | N—$NHCH_3$ | $CH_2$—O | 2-pyridyl | | |
| 361 | N—$NHCH_3$ | $CH_2$—O—CO | H | | |
| 362 | N—$NHCH_3$ | $CH_2$—O—CO | $CH_3$ | | |
| 363 | N—$NHCH_3$ | $CH_2$—O—CO | cyclohexyl | | |
| 364 | N—$NHCH_3$ | $CH_2$—O—CO | phenyl | | |
| 365 | N—$NHCH_3$ | $CH_2$—O—CO | 2-pyridyl | | |
| 366 | $CH_2$ | $CH_2$—$CH_2$ | H | | |
| 367 | $CH_2$ | $CH_2$—$CH_2$ | $CH_3$ | | |
| 368 | $CH_2$ | $CH_2$—$CH_2$ | cyclohexyl | | |
| 369 | $CH_2$ | $CH_2$—$CH_2$ | phenyl | | |
| 370 | $CH_2$ | $CH_2$—$CH_2$ | 2-pyridyl | | |
| 371 | $CH_2$ | CH═CH | H | | |
| 372 | $CH_2$ | CH═CH | $CH_3$ | | |
| 373 | $CH_2$ | CH═CH | cyclohexyl | | |
| 374 | $CH_2$ | CH═CH | phenyl | | |
| 375 | $CH_2$ | CH═CH | 2-pyridyl | | |
| 376 | $CH_2$ | O—$CH_2$ | H | | |
| 377 | $CH_2$ | O—$CH_2$ | $CH_3$ | | |
| 378 | $CH_2$ | O—$CH_2$ | cyclohexyl | | |
| 379 | $CH_2$ | O—$CH_2$ | phenyl | | |
| 380 | $CH_2$ | O—$CH_2$ | 2-pyridyl | | |
| 381 | $CH_2$ | $CH_2$—O | H | | |
| 382 | $CH_2$ | $CH_2$—O | $CH_3$ | | |
| 383 | $CH_2$ | $CH_2$—O | cyclohexyl | | |
| 384 | $CH_2$ | $CH_2$—O | phenyl | | |
| 385 | $CH_2$ | $CH_2$—O | 2-pyridyl | | |
| 386 | $CH_2$ | $CH_2$—O—CO | H | | |
| 387 | $CH_2$ | $CH_2$—O—CO | $CH_3$ | | |
| 388 | $CH_2$ | $CH_2$—O—CO | cyclohexyl | | |
| 389 | $CH_2$ | $CH_2$—O—CO | phenyl | | |
| 390 | $CH_2$ | $CH_2$—O—CO | 2-pyridyl | | |
| 391 | CH—$CH_2$—$CH_3$ | $CH_2$—$CH_2$ | H | | |
| 392 | CH—$CH_2$—$CH_3$ | $CH_2$—$CH_2$ | $CH_3$ | | |
| 393 | CH—$CH_2$—$CH_3$ | $CH_2$—$CH_2$ | cyclohexyl | | |
| 394 | CH—$CH_2$—$CH_3$ | $CH_2$—$CH_2$ | phenyl | | |
| 395 | CH—$CH_2$—$CH_3$ | $CH_2$—$CH_2$ | 2-pyridyl | | |
| 396 | CH—$CH_2$—$CH_3$ | CH═CH | H | | |
| 397 | CH—$CH_2$—$CH_3$ | CH═CH | $CH_3$ | | |
| 398 | CH—$CH_2$—$CH_3$ | CH═CH | cyclohexyl | | |
| 399 | CH—$CH_2$—$CH_3$ | CH═CH | phenyl | | |
| 400 | CH—$CH_2$—$CH_3$ | CH═CH | 2-pyridyl | | |
| 401 | CH—$CH_2$—$CH_3$ | O—$CH_2$ | H | | |
| 402 | CH—$CH_2$—$CH_3$ | O—$CH_2$ | $CH_3$ | | |
| 403 | CH—$CH_2$—$CH_3$ | O—$CH_2$ | cyclohexyl | | |
| 404 | CH—$CH_2$—$CH_3$ | O—$CH_2$ | phenyl | | |
| 405 | CH—$CH_2$—$CH_3$ | O—$CH_2$ | 2-pyridyl | | |
| 406 | CH—$CH_2$—$CH_3$ | $CH_2$—O | H | | |
| 407 | CH—$CH_2$—$CH_3$ | $CH_2$—O | $CH_3$ | | |
| 408 | CH—$CH_2$—$CH_3$ | $CH_2$—O | cyclohexyl | | |
| 409 | CH—$CH_2$—$CH_3$ | $CH_2$—O | phenyl | | |
| 410 | CH—$CH_2$—$CH_3$ | $CH_2$—O | 2-pyridyl | | |
| 411 | CH—$CH_2$—$CH_3$ | $CH_2$—O—CO | H | | |
| 412 | CH—$CH_2$—$CH_3$ | $CH_2$—O—CO | $CH_3$ | | |
| 413 | CH—$CH_2$—$CH_3$ | $CH_2$—O—CO | cyclohexyl | | |
| 414 | CH—$CH_2$—$CH_3$ | $CH_2$—O—CO | phenyl | | |
| 415 | CH—$CH_2$—$CH_3$ | $CH_2$—O—CO | 2-pyridyl | | |
| 416 | CH—S—$CH_3$ | $CH_2$—$CH_2$ | H | | |
| 417 | CH—S—$CH_3$ | $CH_2$—$CH_2$ | $CH_3$ | | |
| 418 | CH—S—$CH_3$ | $CH_2$—$CH_2$ | cyclohexyl | | |
| 419 | CH—S—$CH_3$ | $CH_2$—$CH_2$ | phenyl | | |

TABLE 3-continued

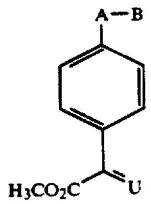

| No. | U | A | B | mp | NMR: δ(ppm) |
|---|---|---|---|---|---|
| 420 | CH—S—$CH_3$ | $CH_2$—$CH_2$ | 2-pyridyl | | |
| 421 | CH—S—$CH_3$ | CH═CH | H | | |
| 422 | CH—S—$CH_3$ | CH═CH | $CH_3$ | | |
| 423 | CH—S—$CH_3$ | CH═CH | cyclohexyl | | |
| 424 | CH—S—$CH_3$ | CH═CH | phenyl | | |
| 425 | CH—S—$CH_3$ | CH═CH | 2-pyridyl | | |
| 426 | CH—S—$CH_3$ | O—$CH_2$ | H | | |
| 427 | CH—S—$CH_3$ | O—$CH_2$ | $CH_3$ | | |
| 428 | CH—S—$CH_3$ | O—$CH_2$ | cyclohexyl | | |
| 429 | CH—S—$CH_3$ | O—$CH_2$ | phenyl | | |
| 430 | CH—S—$CH_3$ | O—$CH_2$ | 2-pyridyl | | |
| 431 | CH—S—$CH_3$ | $CH_2$—O | H | | |
| 432 | CH—S—$CH_3$ | $CH_2$—O | $CH_3$ | | |
| 433 | CH—S—$CH_3$ | $CH_2$—O | cyclohexyl | | |
| 434 | CH—S—$CH_3$ | $CH_2$—O | phenyl | | |
| 435 | CH—S—$CH_3$ | $CH_2$—O | 2-pyridyl | | |
| 436 | CH—S—$CH_3$ | $CH_2$—O—CO | H | | |
| 437 | CH—S—$CH_3$ | $CH_2$—O—CO | $CH_3$ | | |
| 438 | CH—S—$CH_3$ | $CH_2$—O—CO | cyclohexyl | | |
| 439 | CH—S—$CH_3$ | $CH_2$—O—CO | phenyl | | |
| 440 | CH—S—$CH_3$ | $CH_2$—O—CO | 2-pyridyl | | |
| 441 | $HCOCH_3$ | $CH_2$—O—CO | n-heptadecyl | 37–38 | |
| 442 | $HCOCH_3$ | $CH_2$—O—CO | n-heptyl | oil | 5.1(S, 2H); 7.55(S, 1H) |
| 443 | $HCOCH_3$ | $CH_2$—O—CO | t-butyl | oil | 5.1(S, 2H); 7.6(S, 1H) |
| 444 | $HCOCH_3$ | $CH_2$—O—CO | iso-butyl | oil | 5.1(S, 2H); 7.55(S, 1H) |
| 445 | $HCOCH_3$ | $CH_2$—O—CO | n-butyl | oil | 5.1(S, 2H); 7.55(S, 1H) |
| 446 | $HCOCH_3$ | $CH_2$—O—CO | n-propyl | oil | 5.1(S, 2H); 7.55(S, 1H) |
| 447 | $HCOCH_3$ | $CH_2$—O—CO | n-ethyl | oil | 5.1(S, 2H); 7.55(S, 1H) |
| 448 | $HCOCH_3$ | $CH_2$—O—CO—$CH_2$ | phenyl | 59–60 | |
| 449 | $HCOCH_3$ | $CH_2$—O—CO—$(CH_2)_2$ | phenyl | oil | 5.1(S, 2H); 7.55(S, 1H) |
| 450 | $HCOCH_3$ | $CH_2$—O—CO—$(CH_2)_3$ | phenyl | oil | 5.1(S, 2H); 7.55(S, 1H) |
| 451 | $HCOCH_3$ | O—$(CH_2)_2$—O | A | oil | 4.1(t, J=5Hz, 2H); 7.55(S, 1H) |
| 452 | $HCOCH_3$ | O—$(CH_2)_3$—O | H | oil | 4.1(t, J=6Hz, 2H); 7.55(S, 1H) |
| 453 | $HCOCH_3$ | O—$(CH_2)_4$—O | H | oil | 4.0(t, J=6Hz, 2H); 7.55(S, 1H) |
| 454 | $HCOCH_3$ | O—$(CH_2)_8$—O | H | 54–55 | |

TABLE 4

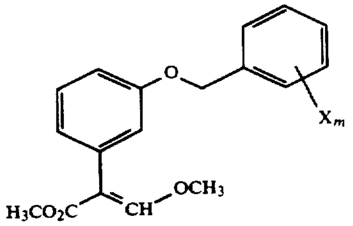

| No. | $X_m$ | mp | NMR: δ(ppm) |
|---|---|---|---|
| 1 | 2-F | oil | 5.15(S, 2H); 7.55(S, 1H) |
| 2 | 3-F | | |
| 3 | 4-F | | |
| 4 | 2,4-$F_2$ | | |
| 5 | 2,4,6-$F_3$ | | |
| 6 | 2,3,4,5,6-$F_5$ | | |
| 7 | 2,3-$F_2$ | | |
| 8 | 2-Cl | oil | 5.15(S, 2H); 7.55(S, 1H) |
| 9 | 3-Cl | oil | 5.05(S, 2H); 7.55(S, 1H) |
| 10 | 4-Cl | 64–67 | |
| 11 | 2,3-$Cl_2$ | 106–108 | |
| 12 | 2,4-$Cl_2$ | | |
| 13 | 2,5-$Cl_2$ | | |
| 14 | 2,6-$Cl_2$ | | |

TABLE 4-continued

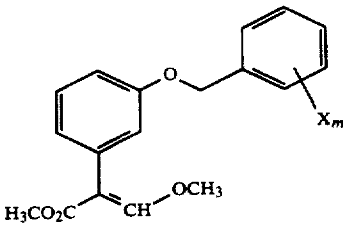

| No. | $X_m$ | mp | NMR: δ(ppm) |
|---|---|---|---|
| 205 | 3,4-$Cl_2$ | | |
| 16 | 3,5-$Cl_2$ | | |
| 17 | 2,3,4-$Cl_3$ | | |
| 18 | 2,3,5-$Cl_3$ | | |
| 19 | 2,3,6-$Cl_3$ | | |
| 20 | 2,4,5-$Cl_3$ | | |
| 21 | 2,4,6-$Cl_3$ | | |
| 22 | 3,4,5-$Cl_3$ | | |
| 23 | 2,3,4,6-$Cl_4$ | | |
| 24 | 2,3,5,6-$Cl_4$ | | |
| 25 | 2,3,4,5,6-$Cl_5$ | | |
| 26 | 2-Br | | |
| 27 | 3-Br | | |
| 28 | 4-Br | | |
| 29 | 2,4-$Br_2$ | | |
| 30 | 2,5-$Br_5$ | | |
| 31 | 2,6-$Br_2$ | | |

TABLE 4-continued

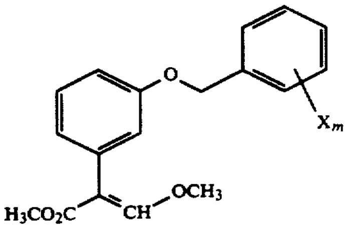

| No. | $X_m$ | mp | NMR: δ(ppm) |
|---|---|---|---|
| 32 | 2,4,6-$Br_3$ | | |
| 33 | 2,3,4,5,6-$Br_5$ | | |
| 34 | 2-J | | |
| 35 | 3-I | | |
| 36 | 4-I | | |
| 37 | 2,4-$I_2$ | | |
| 38 | 2-Cl, 3-F | | |
| 39 | 2-Cl, 4-F | | |
| 40 | 2-Cl, 5-F | | |
| 41 | 2-Cl, 6-F | | |
| 42 | 2-Cl, 3-Br | | |
| 43 | 2-Cl, 4-Br | | |
| 44 | 2-Cl, 6-Br | | |
| 45 | 2-Cl, 6-Br | | |
| 46 | 2-Br, 3-Cl | | |
| 47 | 2-Br, 4-Cl | | |
| 48 | 2-Br, 5-Cl | | |
| 49 | 2-Br, 3-F | | |
| 50 | 2-Br, 4-F | | |
| 51 | 2-Br, 5-F | | |
| 52 | 2-Br, 6-F | | |
| 53 | 2-F, 3-Cl | | |
| 54 | 2-F, 4-Cl | | |
| 55 | 2-F, 5-Cl | | |
| 56 | 3-Cl, 4-F | | |
| 57 | 3-Cl, 5-F | | |
| 58 | 3-Cl, 4-Br | | |
| 59 | 3-Cl, 5-Br | | |
| 60 | 3-F, 4-Cl | | |
| 61 | 3-F, 4-Br | | |
| 62 | 3-Br, 4-Cl | | |
| 63 | 3-Br, 4-F | | |
| 64 | 2,6-$Cl_2$, 4-Br | | |
| 65 | 2-$CH_3$ | 78-79 | |
| 66 | 3-$CH_3$ | 88-90 | |
| 67 | 4-$CH_3$ | 116-118 | |
| 68 | 2,3-$(CH_3)_2$ | 69-71 | |
| 69 | 2,4-$(CH_3)_2$ | 79-82 | |
| 70 | 2,5-$(CH_3)_2$ | 82-84 | |
| 71 | 2,6-$(CH_3)_2$ | 59-61 | |
| 72 | 3,4-$(CH_3)_2$ | 83-84 | |
| 73 | 3,5-$(CH_3)_2$ | 76-77 | |
| 74 | 3,5-$(CH_3)_2$ | | |
| 75 | 2,3,4-$(CH_3)_3$ | | |
| 76 | 2,3,6-$(CH_3)_3$ | | |
| 77 | 2,4,5-$(CH_3)_3$ | | |
| 78 | 2,3,6-$(CH_3)_3$ | | |
| 79 | 2,3,4-$(CH_3)_3$ | | |
| 80 | 2,3,4,6-$(CH_3)_4$ | | |
| 81 | 2,3,5,6-$(CH_3)_4$ | | |
| 82 | 2,3,4,5,6-$(CH_3)_5$ | | |
| 83 | 2-$C_2H_5$ | | |
| 84 | 3-$C_2H_5$ | | |
| 85 | 4-$C_2H_5$ | | |
| 86 | 2,4-$(C_2H_5)_2$ | | |
| 87 | 2,6-$(C_2H_5)_2$ | | |
| 88 | 3,5-$(C_2H_5)_2$ | | |
| 89 | 2,4,6-$(C_2H_5)_3$ | | |
| 90 | 2-n-$C_3H_7$ | | |
| 91 | 3-n-$C_3H_7$ | | |
| 92 | 4-n-$C_3H_7$ | | |
| 93 | 2-i-$C_3H_7$ | | |
| 94 | 3-i-$C_3H_7$ | | |
| 95 | 4-i-$C_3H_7$ | | |
| 96 | 2,4-(i-$C_3H_7)_2$ | | |
| 97 | 2,6-(i-$C_3H_7)_2$ | | |
| 98 | 3,5-(i-$C_3H_7)_2$ | | |
| 99 | 2,4,6-(i-$C_3H_7)_3$ | | |
| 100 | 2-S—$C_4H_9$ | | |

TABLE 4-continued

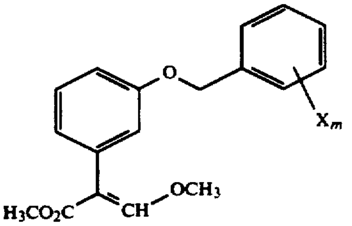

| No. | $X_m$ | mp | NMR: δ(ppm) |
|---|---|---|---|
| 101 | 3-S—$C_4H_9$ | | |
| 102 | 4-S—$C_4H_9$ | | |
| 103 | 2-t-$C_4H_9$ | | |
| 104 | 3-t-$C_4H_9$ | | |
| 105 | 4-t-$C_4H_9$ | | |
| 106 | 2,3-(t-$C_4H_9)_2$ | | |
| 107 | 2,4-(t-$C_4H_9)_2$ | | |
| 108 | 2,5-(t-$C_4H_9)_2$ | | |
| 109 | 2,6-(t-$C_4H_9)_2$ | | |
| 110 | 3,4-(t-$C_4H_9)_2$ | | |
| 111 | 2,4,6-(t-$C_4H_9)_3$ | | |
| 112 | 4-n-$C_9H_{19}$ | | |
| 113 | 4-n-$C_{12}H_{25}$ | | |
| 114 | 3-n-$C_{15}H_{31}$ | | |
| 115 | 4-(1,1,3,3-tetramethylbutyl) | | |
| 116 | 4-(2,4,4-trimethylpropyl) | | |
| 117 | 2-t-$C_4H_9$, 4-$CH_3$ | | |
| 118 | 2-t-$C_4H_9$, 5-$CH_3$ | | |
| 119 | 2,6-(t-$C_4H_9$), 4-$CH_3$ | | |
| 120 | 2-$CH_3$, 4-t-$C_4H_9$ | | |
| 121 | 2-$CH_3$, 6-t-$C_4H_9$ | | |
| 122 | 2-$CH_3$, 4-i-$C_3H_7$ | | |
| 123 | 2-$CH_3$, 5-i-$C_3H_7$ | | |
| 124 | 3-$CH_3$, 4-i-$C_3H_7$ | | |
| 125 | 2-i-$C_3H_7$, 5 $CH_3$ | | |
| 126 | 2,4-(t-$C_4H_9$), 6-i-$C_3H_7$ | | |
| 127 | 2-allyl | | |
| 128 | 3-allyl | | |
| 129 | 4-allyl | | |
| 130 | 2-allyl, 6-$CH_3$ | | |
| 131 | 2-cyclo-$C_6H_{11}$ | | |
| 132 | 3-cyclo-$C_6H_{11}$ | | |
| 133 | 4-cyclo-$C_6H_{11}$ | | |
| 134 | 2,4-(cyclo-$C_6H_{11})_2$, 6-$CH_3$ | | |
| 135 | 2-$CH_3$, 4-cyclo-$C_6H_{11}$ | | |
| 136 | 2-$CH_2$—$C_6H_5$ | | |
| 137 | 3-$CH_2$—$C_6H_5$ | | |
| 138 | 4-$CH_2$—$C_6H_5$ | | |
| 139 | 2-$CH_2$—$C_6H_5$, 4-$CH_3$ | | |
| 140 | 2-$CH_3$, 4-$CH_2$—$C_6H_5$ | | |
| 141 | 2-$C_6H_5$ | | |
| 142 | 3-$C_6H_5$ | | |
| 143 | 4-$C_6H_5$ | 149-150 | |
| 144 | 4-(2-i-$C_3H_7$—$C_6H_4$) | | |
| 145 | 4-$C_6H_5$, 2,6-$(CH_3)_2$ | | |
| 146 | 2-Cl, 4-$C_6H_5$ | | |
| 147 | 2-Br, 4-$C_6H_5$ | | |
| 148 | 2-$C_6H_5$, 4-Cl | | |
| 149 | 2-$C_6H_5$, 4-Br | | |
| 150 | 2-$CH_2C_6H_5$, 4-Cl | | |
| 151 | 2-$CH_2C_6H_5$, 4-Br | | |
| 152 | 2-Cl, 4-$CH_2C_6H_5$ | | |
| 153 | 2-Br, 4-$CH_2C_6H_5$ | | |
| 154 | 2-cyclo-$C_6H_{11}$, 4-Cl | | |
| 155 | 2-cyclo-$C_6H_{11}$, 4-Br | | |
| 156 | 2-Cl, 4-cyclo-$C_6H_{11}$ | | |
| 157 | 2-Br, 4-cyclo-$C_6H_{11}$ | | |
| 158 | 2-$OCH_3$ | oil | 5.15(S, 2H); 7.55(S, 1H) |
| 159 | 3-$OCH_3$ | oil | 5.05(S, 2H); 7.55(S, 1H) |
| 200 | 4-$OCH_3$ | 107-109 | |
| 161 | 2-$OC_2H_5$ | | |
| 162 | 3-O—$C_2H_5$ | | |
| 163 | 4-O—$C_2H_5$ | | |
| 164 | 2-O-n-$C_3H_7$ | | |
| 165 | 3-O-n-$C_3H_7$ | | |
| 166 | 4-O-n-$C_3H_7$ | | |
| 167 | 2-O-i-$C_3H_7$ | | |

TABLE 4-continued

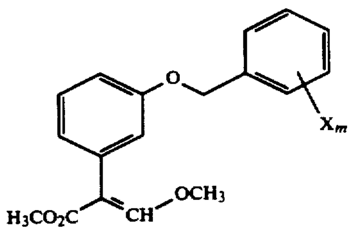

| No. | $X_m$ | mp | NMR: δ(ppm) |
|---|---|---|---|
| 168 | 3-O-i-$C_3H_7$ | | |
| 169 | 4-O-i-$C_3H_7$ | | |
| 170 | 2-O-n-$C_6H_{13}$ | | |
| 171 | 3-O-n-$C_6H_{13}$ | | |
| 172 | 4-O-n-$C_6H_{13}$ | | |
| 173 | 2-O-n-$C_8H_{17}$ | | |
| 174 | 3-O-n-$C_8H_{17}$ | | |
| 175 | 4-O-n-$C_8H_{17}$ | | |
| 176 | 2-O—$CH_2C_6H_5$ | | |
| 177 | 3-O—$CH_2C_6H_5$ | | |
| 178 | 4-O—$CH_2C_6H_5$ | | |
| 179 | 2-O—$(CH_2)_3C_6H_5$ | | |
| 180 | 3-O—$(CH_2)_3C_6H_5$ | | |
| 181 | 4-O—$(CH_2)_3C_6H_5$ | | |
| 182 | 2,4-$(OCH_3)_2$ | | |
| 183 | 2-$CF_3$ | oil | 5.2(S, 2H); 7.55(S, 1H) |
| 184 | 3-$CF_3$ | | |
| 185 | 4-$CF_3$ | | |
| 186 | 2-$OCF_3$ | | |
| 187 | 3-$OCF_3$ | | |
| 188 | 4-$OCF_3$ | | |
| 189 | 3-$OCH_2CHF_2$ | | |
| 190 | 2-$NO_2$ | | |
| 191 | 3-$NO_2$ | | |
| 192 | 4-$NO_2$ | | |
| 193 | 2-CN | | |
| 194 | 3-CN | | |
| 195 | 4-CN | | |
| 196 | 2-$CH_3$, 3-Cl | | |
| 197 | 2-$CH_3$, 4-Cl | | |
| 198 | 2-$CH_3$, 5-Cl | | |
| 199 | 2-$CH_3$, 6-Cl | | |
| 200 | 2-$CH_3$, 3-F | | |
| 201 | 2-$CH_3$, 4-F | | |
| 202 | 2-$CH_3$, 5-F | | |
| 203 | 2-$CH_3$, 6-F | | |
| 204 | 2-$CH_3$, 3-Br | | |
| 205 | 2-$CH_3$, 4-Br | | |
| 206 | 2-$CH_3$, 5-Br | | |
| 207 | 2-$CH_3$, 6-Br | | |
| 208 | 2-Cl, 3-$CH_3$ | | |
| 209 | 2-Cl, 4-$CH_3$ | | |
| 210 | 2-Cl, 5-$CH_3$ | | |
| 211 | 2-F, 3-$CH_3$ | | |
| 212 | 2-F, 4-$CH_3$ | | |
| 213 | 2-F, 5-$CH_3$ | | |
| 214 | 2-Br, 3-$CH_3$ | | |
| 215 | 2-Br, 4-$CH_3$ | | |
| 216 | 2-Br, 5-$CH_3$ | | |
| 217 | 3-$CH_3$, 4-Cl | | |
| 218 | 3-$CH_3$, 5-Cl | | |
| 219 | 3-$CH_3$, 4-F | | |
| 220 | 3-$CH_3$, 4-Br | | |
| 221 | 3-$CH_3$, 4-Br | | |
| 222 | 3-$CH_3$, 5-Br | | |
| 223 | 3-F, 4-$CH_3$ | | |
| 224 | 3-Cl, 4-$CH_3$ | | |
| 225 | 3-Br, 4-$CH_3$ | | |
| 226 | 2-Cl, 4,5-$(CH_3)_2$ | | |
| 227 | 2-Br, 4,5-$(CH_3)_2$ | | |
| 228 | 2-Cl, 3,5-$(CH_3)_2$ | | |
| 229 | 2-Br, 3,5-$(CH_3)_2$ | | |
| 230 | 2,6-$Cl_2$, 4-$CH_3$ | | |
| 231 | 2,6-$F_2$, 4-$CH_3$ | | |
| 232 | 2,6-$Br_2$, 4-$CH_3$ | | |
| 233 | 2,4-$Cl_2$, 6-$CH_3$ | | |
| 234 | 2,4-$F_2$, 6-$CH_3$ | | |
| 235 | 2,4-$Br_2$, 6-$CH_3$ | | |

TABLE 4-continued

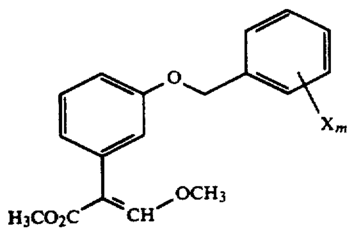

| No. | $X_m$ | mp | NMR: δ(ppm) |
|---|---|---|---|
| 236 | 2,6-$(CH_3)_2$, 4-F | | |
| 237 | 2,6-$(CH_3)_2$, 4-Cl | | |
| 238 | 2,6-$(CH_3)_2$, 4-Br | | |
| 239 | 3,5-$(CH_3)_2$, 4-F | | |
| 240 | 3,5-$(CH_3)_2$, 4-Cl | | |
| 241 | 3,5-$(CH_3)_2$, 4-Br | | |
| 242 | 2,3,6-$(CH_3)_3$, 4-F | | |
| 243 | 2,3,6-$(CH_3)_3$, 4-Cl | | |
| 244 | 2,3,6-$(CH_3)_3$, 4-Br | | |
| 245 | 2,4-$(CH_3)_2$, 6-F | | |
| 246 | 2,4-$(CH_3)_2$, 6-Cl | | |
| 247 | 2,4-$(CH_3)_2$, 6-Br | | |
| 248 | 2-i-$C_3H_7$, 4-Cl, 5-$CH_3$ | | |
| 249 | 2-Cl, 4-$NO_2$ | | |
| 250 | 2-$NO_2$, 4-Cl | | |
| 251 | 2-$OCH_3$, 5-$NO_2$ | | |
| 252 | 2,4-$Cl_2$, 5-$NO_2$ | | |
| 253 | 2,4-$Cl_2$, 6-$NO_2$ | | |
| 254 | 2,6-$Cl_2$, 4-$NO_2$ | | |
| 255 | 2,6-$Br_2$, 4-$NO_2$ | | |
| 256 | 2,6-$I_2$, 4-$NO_2$ | | |
| 257 | 2-$CH_3$, 5-i-$C_3H_7$, 4-Cl | | |
| 258 | 2-$C_6H_5O$ | | |
| 259 | 3-$C_6H_5O$ | | |
| 260 | 4-$C_6H_5O$ | | |
| 261 | 2-$CHNOCH_3$ | oil | 5.1(s, 2H); 7.6(s, 1H) |
| 262 | 3-$CHNOCH_3$ | 65-68 | |
| 263 | 4-$CHNOCH_3$ | 69-72 | |
| 264 | 2-$CHNOC_2H_5$ | | |
| 265 | 3-$CHNOC_2H_5$ | | |
| 266 | 4-$CHNOC_2H_5$ | | |
| 267 | 2-CHNO(n-$C_3H_7$) | | |
| 268 | 3-CHNO(n-$C_3H_7$) | | |
| 269 | 4-CHNO(n-$C_3H_7$) | | |
| 270 | 2-CHNO(i-$C_3H_7$) | | |
| 271 | 3-CHNO(i-$C_3H_7$) | | |
| 272 | 4-CHNO(i-$C_3H_7$) | | |
| 273 | 2-CHNO(n-$C_6H_{13}$) | oil | 5.1(s, 2H); 7.6(s, 1H) |
| 274 | 3-CHNO(n-$C_6H_{13}$) | oil | 5.1(s, 2H); 7.6(s, 1H) |
| 275 | 4-CHNO(n-$C_6H_{13}$) | oil | 5.1(s, 2H); 7.6(s, 1H) |
| 276 | 2-CHNO(n-$C_8H_{17}$) | | |
| 277 | 3-CHNO(n-$C_8H_{17}$) | | |
| 278 | 4-CHNO(n-$C_8H_{17}$) | | |
| 279 | 2-$CHNOCH_2(C_6H_5)$ | oil | 5.1(s, 2H). 7.55(s, 1H) |
| 280 | 3-$CHNOCH_2(C_6H_5)$ | oil | 5.1(s, 2H); 7.6(s, 1H) |
| 281 | 4-$CHNOCH_2(C_6H_5)$ | 93-96 | |
| 282 | 2-$CO_2CH_3$ | 65-66 | |
| 283 | 3-$CO_2CH_3$ | 69-72 | |
| 284 | 4-$CO_2CH_3$ | 106-107 | |
| 285 | 2-$CO_2(C_2H_5)$ | | |
| 286 | 3-$CO_2(C_2H_5)$ | | |
| 287 | 4-$CO_2(C_2H_5)$ | | |
| 288 | 2-$CO_2$(n-$C_3H_7$) | | |
| 289 | 3-$CO_2$(n-$C_3H_7$) | | |
| 290 | 4-$CO_2$(n-$C_3H_7$) | | |
| 291 | 2-$CO_2$(i-$C_3H_7$) | | |
| 292 | 3-$CO_2$(i-$C_3H_7$) | | |
| 293 | 4-$CO_2$(i-$C_3H_7$) | | |
| 294 | 2-$CO_2$(n-$C_6H_{13}$) | | |
| 295 | 3-$CO_2$(n-$C_6H_{13}$) | | |
| 296 | 4-$CO_2$(n-$C_6H_{13}$) | | |
| 297 | 2-$CO_2$(n-$C_8H_{17}$) | | |
| 298 | 3-$CO_2$(n-$C_8H_{17}$) | | |

TABLE 4-continued

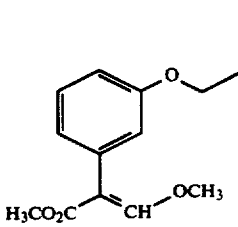

| No. | $X_m$ | mp | NMR: δ(ppm) |
|---|---|---|---|
| 299 | $4\text{-}CO_2(n\text{-}C_8H_{17})$ | | |
| 300 | $2\text{-}CHN{-}O{-}CH_2{-}CH{=}CH_2$ | oil | 5.1(s, 2H); 7.6(s, 1H) |
| 301 | $3\text{-}CHN{-}O{-}CH_2{-}CH{=}CH_2$ | oil | 5.1(s, 2H); 7.6(s, 1H) |
| 302 | $4\text{-}CHN{-}O{-}CH_2{-}CH{=}CH_2$ | oil | 5.1(s, 2H); 7.6(s, 1H) |
| 303 | $2\text{-}CHNO(CH_2)_3(C_6H_5)$ | | |
| 304 | $3\text{-}CHNO(CH_2)_3(C_6H_5)$ | | |
| 305 | $4\text{-}CHNO(CH_2)_3(C_6H_5)$ | | |
| 306 | $2\text{-}CH_2OCH_3$ | | |
| 307 | $3\text{-}CH_2OCH_3$ | | |
| 308 | $4\text{-}CH_2OCH_3$ | | |
| 309 | $2\text{-}CH_2O(C_2H_5)$ | | |
| 310 | $3\text{-}CH_2O(C_2H_5)$ | | |
| 311 | $4\text{-}CH_2O(C_2H_5)$ | | |
| 312 | $2\text{-}CH_2O(n\text{-}C_3H_7)$ | | |
| 313 | $3\text{-}CH_2O(n\text{-}C_3H_7)$ | | |
| 314 | $4\text{-}CH_2O(n\text{-}C_3H_7)$ | | |
| 315 | $2\text{-}CH_2O(i\text{-}C_3H_7)$ | | |
| 316 | $3\text{-}CH_2O(i\text{-}C_3H_7)$ | | |
| 317 | $4\text{-}(CH_2O(i\text{-}C_3H_7)$ | | |
| 318 | $2\text{-}CH_2O(n\text{-}C_6H_{13})$ | | |
| 319 | $3\text{-}CH_2O(n\text{-}C_6H_{13})$ | | |
| 320 | $4\text{-}CH_2O(n\text{-}C_6H_{13})$ | | |
| 321 | $2\text{-}CH_2O(n\text{-}C_8H_{17})$ | | |
| 322 | $3\text{-}CH_2O(n\text{-}C_8H_{17})$ | | |
| 323 | $4\text{-}CH_2O(n\text{-}C_8H_{17})$ | | |
| 324 | $2\text{-}CH_2OCH_2(C_6H_5)$ | | |
| 325 | $3\text{-}CH_2OCH_2(C_6H_5)$ | | |
| 326 | $4\text{-}CH_2OCH_2(C_6H_5)$ | | |
| 327 | $2\text{-}CH_2O(CH_2)_3$ | | |
| 328 | $3\text{-}CH_2O(CH_2)_3(C_6H_5)$ | | |
| 329 | $4\text{-}CH_2O(CH_2)_3(C_6H_5)$ | | |
| 330 | 2-CHO | 95-96 | |
| 331 | 3-CHO | | |
| 332 | 4-CHO | 123-125 | |
| 333 | $2\text{-}CH_3\text{-}4\text{-}CHNO$-allyl | oil | 5.1(s, 2H); 7.55(s, 1H) |
| 334 | $2\text{-}CH_3\text{-}5\text{-}CHNO$-allyl | oil | 5.1(s, 2H); 7.6(s, 1H) |
| 335 | $2\text{-}CH_3\text{-}6\text{-}CHNO$-allyl | oil | 4.85(s, 2H); 7.6(s, 1H) |
| 336 | $3\text{-}CH_3\text{-}6\text{-}CHNO$-allyl | 97-98 | |
| 337 | $4\text{-}CH_3\text{-}6\text{-}CHNO$-allyl | oil | 5.05(s, 2H); 7.6(s, 1H) |

TABLE 5

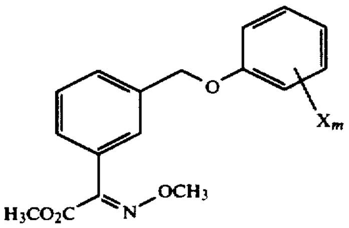

| No. | $X_m$ | mp | NMR: δ (ppm) |
|---|---|---|---|
| 1 | 2-F | | |
| 2 | 3-F | | |
| 3 | 4-F | | |
| 4 | $2,4\text{-}F_2$ | | |
| 5 | $2,4,6\text{-}F_3$ | | |

TABLE 5-continued

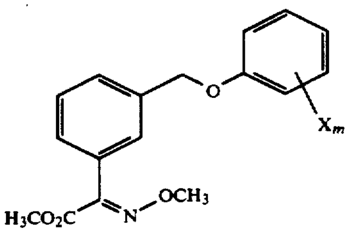

| No. | $X_m$ | mp | NMR: δ (ppm) |
|---|---|---|---|
| 6 | $2,3,4,5,6\text{-}F_5$ | | |
| 7 | $2,3\text{-}F_2$ | | |
| 8 | 2-Cl | | |
| 9a) | 3-Cl; non-polar isomer | oil | 3.95(s, 3H); 4.05(s, 3H); 5.05(s, 2H) |
| 9b | 3-Cl; polar isomer | 82-85 | |
| 10 | 4-Cl | | |
| 11 | $2,3\text{-}Cl_2$ | | |
| 12 | $2,4\text{-}Cl_2$ | | |
| 13 | $2,5\text{-}Cl_2$ | | |
| 14 | $2,6\text{-}Cl_2$ | | |
| 15 | $3,4\text{-}Cl_2$ | | |
| 16 | $3,5\text{-}Cl_2$ | | |
| 17 | $2.3,4\text{-}Cl_3$ | | |
| 18 | $2,3,5\text{-}Cl_3$ | | |
| 19 | $2,3,6\text{-}Cl_3$ | | |
| 20 | $2,4,5\text{-}Cl_3$ | | |
| 21 | $2,4,6\text{-}Cl_3$ | | |
| 22 | $3,4,5\text{-}Cl_3$ | | |
| 23 | $2,3,4,6\text{-}Cl_4$ | | |
| 24 | $2,3,5,6\text{-}Cl_4$ | | |
| 25 | $2,3,4,5,6\text{-}Cl_5$ | | |
| 26 | 2-Br | | |
| 27 | 3-Br | | |
| 28 | 4-Br | | |
| 29 | $2,4\text{-}Br_2$ | | |
| 30 | $2,5\text{-}Br_5$ | | |
| 31 | $2,6\text{-}Br_2$ | | |
| 32 | $2,4,6\text{-}Br_3$ | | |
| 33 | $2,3,4,5,6\text{-}Br_5$ | | |
| 34 | 2-I | | |
| 35 | 3-I | | |
| 36 | 4-I | | |
| 37 | $2,4\text{-}I_2$ | | |
| 38 | 2-Cl, 3-F | | |
| 39 | 2-Cl, 4-F | | |
| 40 | 2-Cl, 5-F | | |
| 41 | 2-Cl, 6-F | | |
| 42 | 2-Cl, 3-Br | | |
| 43 | 2-Cl, 4-Br | | |
| 44 | 2-Cl, 6-Br | | |
| 45 | 2-Cl, 6-Br | | |
| 46 | 2-Br, 3-Cl | | |
| 47 | 2-Br, 4-Cl | | |
| 48 | 2-Br, 5-Cl | | |
| 49 | 2-Br, 3-F | | |
| 50 | 2-Br, 4-F | | |
| 51 | 2-Br, 5-F | | |
| 52 | 2-Br, 6-F | | |
| 53 | 2-F, 3-Cl | | |
| 54 | 2-F, 4-Cl | | |
| 55 | 2-F, 5-Cl | | |
| 56 | 3-Cl, 4-F | | |
| 57 | 3-Cl, 5-F | | |
| 58 | 3-Cl, 4-Br | | |
| 59 | 3-Cl, 5-Br | | |
| 60 | 3-F, 4-Cl | | |
| 61 | 3-F, 4-Br | | |
| 62 | 3-Br, 4-Cl | | |
| 63 | 3-Br, 4-F | | |
| 64 | $2,6\text{-}Cl_2$, 4-Br | | |
| 65a) | $2\text{-}CH_3$:non-polar isomer | oil | 3.95(S, 3H); 4.05(S, 3H); 5.05(S, 2H) |
| 65b) | $2\text{-}CH_3$:polar isomer | 99-100 | |
| 66a) | $3\text{-}CH_3$:non-polar isomer | oil | 3.9(S, 3H); 4.0(S, 3H); 5.05(S, 2H) |
| 66b) | $3\text{-}CH_3$:polar isomer | 51-54 | |

TABLE 5-continued

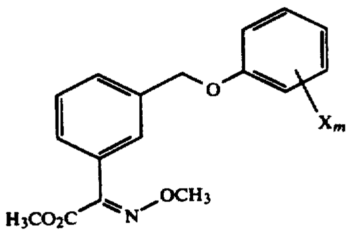

| No. | $X_m$ | mp | NMR: δ (ppm) |
|---|---|---|---|
| 67a) | 4-$CH_3$:non-polar isomer | oil | 3.9(S, 3H); 4.0(S, 3H); 5.0(S, 2H) |
| 67b) | 4-$CH_3$:polar isomer | 102–103 | |
| 68a) | non-polar isomer; 2,3-$(CH_3)_2$ | oil | 3.95(s, 3H); 4.05(s, 3H); 5.05(s, 2H) |
| 68b) | polar isomer; 2,3-$(CH_3)_2$ | 86–89 | |
| 69a) | non-polar isomer; 2,4-$(CH_3)_2$ | oil | 3.95(s, 3H); 4.05(s, 3H); 5.05(s, 2H) |
| 69b) | polar isomer; 2,4-$(CH_3)_2$ | oil | 3.90(s, 3H); 4.05(s, 3H); 5.05(s, 2H) |
| 70a) | non-polar isomer; 2,5-$(CH_3)_2$ | oil | 3.95(s, 3H); 4.05(s, 3H); 5.05(s, 2H) |
| 70b) | polar isomer; 2,5-$(CH_3)_2$ | 85–88 | |
| 71a) | non-polar isomer; 2,6-$(CH_3)_2$ | oil | 3.95(s, 3H); 4.05(s, 3H); 4.80(s, 2H) |
| 71b) | polar isomer; 2,6-$(CH_3)_2$ | 79–81 | |
| 72a) | non-polar isomer; 3,4-$(CH_3)_2$ | oil | 3.95(s, 3H); 4.05(s, 3H); 5.05(s, 2H) |
| 72b) | polar isomer; 3,4-$(CH_3)_2$ | oil | 3.90(s, 3H); 4.05(s, 3H); 5.05(s, 2H) |
| 73a) | non-polar isomer; 3,5-$(CH_3)_2$ | oil | 3.95(s, 3H); 4.05(s, 3H); 5.05(s, 2H) |
| 73b) | polar isomer; 3,5-$(CH_3)_2$ | oil | 3.90(s, 3H); 4.05(s, 3H); 5.05(s, 2H) |
| 74 | 3,5-$(CH_3)_2$ | | |
| 75 | 2,3,4-$(CH_3)_3$ | | |
| 76 | 2,3,6-$(CH_3)_3$ | | |
| 77 | 2,4,5-$(CH_3)_3$ | | |
| 78 | 2,4,6-$(CH_3)_3$ | | |
| 79 | 3,4,5-$(CH_3)_3$ | | |
| 80 | 2,3,4,6-$(CH_3)_4$ | | |
| 81 | 2,3,5,6,-$(CH_3)_4$ | | |
| 82 | 2,3,4,5,6-$(CH_3)_5$ | | |
| 83 | 2-$C_2H_5$ | | |
| 84 | 3-$C_2H_5$ | | |
| 85 | 4-$C_2H_5$ | | |
| 86 | 2,4-$(C_2H_5)_2$ | | |
| 87 | 2,6-$(C_2H_5)_2$ | | |
| 88 | 3,5-$(C_2H_5)_2$ | | |
| 89 | 2,4,6-$(C_2H_5)_3$ | | |
| 90 | 2-n-$C_3H_7$ | | |
| 91 | 3-n-$C_3H_7$ | | |
| 92 | 4-n-$C_3H_7$ | | |
| 93 | 2-i-$C_3H_7$ | | |
| 94 | 3-i-$C_3H_7$ | | |
| 95 | 4-i-$C_3H_7$ | | |
| 96 | 2,4-(i-$C_3H_7)_2$ | | |
| 97 | 2,6-(i-$C_3H_7)_2$ | | |
| 98 | 3,5-(i-$C_3H_7)_2$ | | |
| 99 | 2,4,6-(i-$C_3H_7)_3$ | | |
| 100 | 2-S-$C_4H_9$ | | |
| 101 | 3-S-$C_4H_9$ | | |
| 102 | 4-S-$C_4H_9$ | | |
| 103 | 2-t-$C_4H_9$ | | |
| 104 | 3-t-$C_4H_9$ | | |
| 105 | 4-t-$C_4H_9$ | | |
| 106 | 2,3-(t-$C_4H_9)_2$ | | |
| 107 | 2,4-(t-$C_4H_9)_2$ | | |
| 108 | 2,5-(t-$C_4H_9)_2$ | | |
| 109 | 2,6-(t-$C_4H_9)_2$ | | |
| 110 | 3,4-(t-$C_4H_9)_2$ | | |
| 111 | 2,4,6-(t-$C_4H_9)_3$ | | |
| 112 | 4-n-$C_9H_{19}$ | | |
| 113 | 4-n-$C_{12}H_{25}$ | | |
| 114 | 3-n-$C_{15}H_{31}$ | | |

TABLE 5-continued

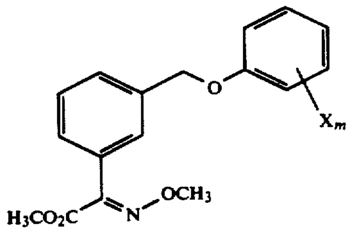

| No. | $X_m$ | mp | NMR: δ (ppm) |
|---|---|---|---|
| 115 | 4-(1,1,3,3-tetramethyl-butyl) | | |
| 116 | 4-(2,4,4-trimethylpropyl | | |
| 117 | 2-t-$C_4H_9$, 4-$CH_3$ | | |
| 118 | 2-t-$C_4H_9$, 5-$CH_3$ | | |
| 119 | 2,6-(t-$C_4H_9$), 4-$CH_3$ | | |
| 120 | 2-$CH_3$, 4-t-$C_4H_9$ | | |
| 121 | 2-$CH_3$, 6-t-$C_4H_9$ | | |
| 122 | 2-$CH_3$, 4-i-$C_3H_7$ | | |
| 123 | 2-$CH_3$, 5-i-$C_3H_7$ | | |
| 124 | 3-$CH_3$, 4-i-$C_3H_7$ | | |
| 125 | 2-i-$C_3H_7$, 5 $CH_3$ | | |
| 126 | 2,4-(t-$C_4H_9$), 6-i-$C_3H_7$ | | |
| 127 | 2-allyl | | |
| 128 | 3-allyl | | |
| 129 | 4-allyl | | |
| 130 | 2-allyl, 6-$CH_3$ | | |
| 131 | 2-cyclo-$C_6H_{11}$ | | |
| 132 | 3-cyclo-$C_6H_{11}$ | | |
| 133 | 4-cyclo-$C_6H_{11}$ | | |
| 134 | 2,4-(cyclo-$C_6H_{11})_2$, 6-$CH_3$ | | |
| 135 | 2-$CH_3$, 4-cyclo-$C_6H_{11}$ | | |
| 136 | 2-$CH_2$, $C_6H_5$ | | |
| 137 | 3-$CH_2$, $C_6H_5$ | | |
| 138 | 4-$CH_2$, $C_6H_5$ | | |
| 139 | 2-$CH_2$—$C_6H_5$, 4-$CH_3$ | | |
| 140 | 2-$CH_3$, 4-$CH_2$—$C_6H_5$ | | |
| 141 | 2-$C_6H_5$ | | |
| 142 | 3-$C_6H_5$ | | |
| 143 | 4-$C_6H_5$ | | |
| 144 | 4-(2-i-$C_3H_7$—$C_6H_4$) | | |
| 145 | 4-$C_6H_5$, 2,6-$(CH_3)_2$ | | |
| 146 | 2-Cl, 4-$C_6H_5$ | | |
| 147 | 2-Br, 4-$C_6H_5$ | | |
| 148 | 2-$C_6H_5$, 4-Cl | | |
| 149 | 2-$C_6H_5$, 4-Br | | |
| 150 | 2-$CH_2C_6H_5$, 4-Cl | | |
| 151 | 2-$CH_2C_6H_5$, 4-Br | | |
| 152 | 2-Cl, 4-$CH_2C_6H_5$ | | |
| 153 | 2-Br, 4-$CH_2C_6H_5$ | | |
| 154 | 2-cyclo-$C_6H_{11}$, 4-Cl | | |
| 155 | 2-cyclo-$C_6H_{11}$, 4-Br | | |
| 156 | 2-Cl, 4-cyclo-$C_6H_{11}$ | | |
| 157 | 2-Br, 4-cyclo-$C_6H_{11}$ | | |
| 158a) | 2-$OCH_3$; non-polar isomer | oil | 3.85; 3.90; 5.0(3s, 3H in each case); 5.1(s, 2H) |
| 158b) | 2-$OCH_3$ polar isomer | 63–67 | |
| 159a) | 3-$OCH_3$; non-polar isomer | oil | 3.80; 3,95; 4.05(3s, 3H in each case); 5.1(s, 2H) |
| 159b) | 3-$OCH_3$ polar isomer | 35 | |
| 160a) | 4-$OCH_3$; non-polar isomer | oil | 3.75; 3.95; 4.05(3s, 3H in each case); 5.05(s, 2H) |
| 160b) | 4-$OCH_3$ polar isomer | 75–78 | |
| 161 | 3-$OC_2H_5$ | | |
| 162 | 3-O-$C_2H_5$ | | |
| 163 | 4-O-$C_2H_7$ | | |
| 164 | 2-O-n-$C_3H_7$ | | |
| 165 | 3-O-n-$C_3H_7$ | | |
| 166 | 4-O-n-$C_3H_7$ | | |
| 167 | 2-O-i-$C_3H_7$ | | |
| 168 | 3-O-i-$C_3H_7$ | | |
| 169 | 4-O-i-$C_3H_7$ | | |
| 170 | 2-O-n-$C_6H_{13}$ | | |
| 171 | 3-O-n-$C_6H_{13}$ | | |

TABLE 5-continued

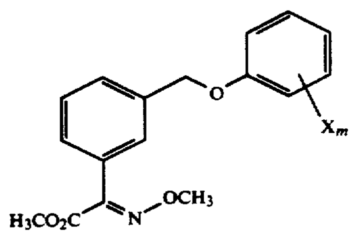

| No. | $X_m$ | mp | NMR: δ (ppm) |
|---|---|---|---|
| 172 | 4-O-n-$C_6H_{13}$ | | |
| 173 | 2-O-n-$C_8H_{17}$ | | |
| 174 | 3-O-n-$C_8H_{17}$ | | |
| 175 | 4-O-n-$C_8H_{17}$ | | |
| 176 | 2-O-$CH_2C_6H_5$ | | |
| 177 | 3-O-$CH_2C_6H_5$ | | |
| 178 | 4-O-$CH_2C_6H_5$ | | |
| 179 | 2-O-$(CH_2)_3C_6H_5$ | | |
| 180 | 3-O-$(CH_2)_3C_6H_5$ | | |
| 181 | 4-O-$(CH_2)_3C_6H_5$ | | |
| 182 | 2,4-$(OCH_3)_2$ | | |
| 183 | 2-$CF_3$ | | |
| 184 | 3-$CF_3$ | | |
| 185 | 4-$CF_3$ | | |
| 186 | 2-$OCF_3$ | | |
| 187 | 3-$OCF_3$ | | |
| 188 | 4-$OCF_3$ | | |
| 189 | 3-$OCH_2CHF_2$ | | |
| 190 | 2-$NO_2$ | | |
| 191 | 3-$NO_2$ | | |
| 192 | 4-$NO_2$ | | |
| 193 | 2-CN | | |
| 194 | 3-CN | | |
| 195 | 4-CN | | |
| 196 | 2-$CH_3$, 3-Cl | | |
| 197 | 2-$CH_3$, 4-Cl | | |
| 198 | 2-$CH_3$, 5-Cl | | |
| 199 | 2-$CH_3$, 6-Cl | | |
| 200 | 2-$CH_3$, 3-F | | |
| 201 | 2-$CH_3$, 4-F | | |
| 202 | 2-$CH_3$, 5-F | | |
| 203 | 2-$CH_3$, 6-F | | |
| 204 | 2-$CH_3$, 3-Br | | |
| 205 | 2-$CH_3$, 4-Br | | |
| 206 | 2-$CH_3$, 5-Br | | |
| 207 | 2-$CH_3$, 6-Br | | |
| 208 | 2-Cl, 3-$CH_3$ | | |
| 209 | 2-Cl, 4-$CH_3$ | | |
| 210 | 2-Cl, 5-$CH_3$ | | |
| 211 | 2-F, 3-$CH_3$ | | |
| 212 | 2-F, 4-$CH_3$ | | |
| 213 | 2-F, 5-$CH_3$ | | |
| 214 | 2-Br, 3-$CH_3$ | | |
| 215 | 2-Br, 4-$CH_3$ | | |
| 216 | 2-Br, 5-$CH_3$ | | |
| 217 | 3-$CH_3$, 4-Cl | | |
| 218 | 3-$CH_3$, 5-Cl | | |
| 219 | 3-$CH_3$, 3-F | | |
| 220 | 3-$CH_3$, 4-Br | | |
| 221 | 3-$CH_3$, 4-Br | | |
| 222 | 3-$CH_3$, 5-Br | | |
| 223 | 3-F, 4-$CH_3$ | | |
| 224 | 3-Cl, 4-$CH_3$ | | |
| 225 | 3-Br, 4-$CH_3$ | | |
| 226 | 2-Cl, 4,5-$(CH_3)_2$ | | |
| 227 | 2-Br, 4,5-$(CH_3)_2$ | | |
| 228 | 2-Cl, 3,5-$(CH_3)_2$ | | |
| 229 | 2-Br, 3,5-$(CH_3)_2$ | | |
| 230 | 2,6-$Cl_2$, 4-$CH_3$ | | |
| 231 | 2,6-$F_2$, 4-$CH_3$ | | |
| 232 | 2,6-$Br_2$, 4-$CH_3$ | | |
| 233 | 2,4-$Cl_2$, 6-$CH_3$ | | |
| 234 | 2,4-$F_2$, 6-$CH_3$ | | |
| 235 | 2,4-$Br_2$, 6-$CH_3$ | | |
| 236 | 2,6-$(CH_3)_2$, 4-F | | |
| 237 | 2,6-$(CH_3)_2$, 4-Cl | | |
| 238 | 2,6-$(CH_3)_2$, 4-Br | | |
| 239 | 3,5-$(CH_3)_2$, 4-F | | |

TABLE 5-continued

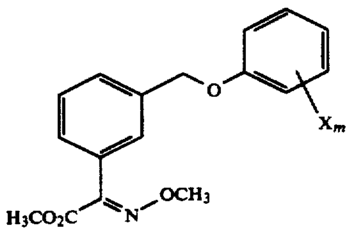

| No. | $X_m$ | mp | NMR: δ (ppm) |
|---|---|---|---|
| 240 | 3,5-$(CH_3)_2$, 4-Cl | | |
| 241 | 3,5-$(CH_3)_2$, 4-Br | | |
| 242 | 2,3,6-$(CH_3)_3$, 4-F | | |
| 243 | 2,3,6-$(CH_3)_3$, 4-Cl | | |
| 244 | 2,3,6-$(CH_3)_3$, 4-Br | | |
| 245 | 2,4-$(CH_3)_2$, 6-F | | |
| 246 | 2,4-$(CH_3)_2$, 6-Cl | | |
| 247 | 2,4-$(CH_3)_2$, 6-Br | | |
| 248 | 2-i-$C_3H_7$, 4-Cl, 5-$CH_3$ | | |
| 249 | 2-Cl, 4-$NO_2$ | | |
| 250 | 2-$NO_2$, 4-Cl | | |
| 251 | 2-$OCH_3$, 5-$NO_2$ | | |
| 252 | 2,4-$Cl_2$, 5-$NO_2$ | | |
| 253 | 2,4-$Cl_2$, 6-$NO_2$ | | |
| 254 | 2,6-$Cl_2$, 4-$NO_2$ | | |
| 255 | 2,6-$Br_2$, 4-$NO_2$ | | |
| 256 | 2,6-$I_2$, 4-$NO_2$ | | |
| 257 | 2-$CH_3$, 5-i-$C_3H_7$, 4-Cl | | |
| 258 | 2-$C_6H_5O$ | | |
| 259 | 3-$C_6H_5O$ | | |
| 260 | 4-$C_6H_5O$ | | |
| 261 | 2-$CHNOCH_3$ | | |
| 262 | 3-$CHNOCH_3$ | | |
| 263 | 4-$CHNOCH_3$; | | |
| 264 | 2-$CHNOC_2H_5$ | | |
| 265 | 3-$CHNOC_2H_5$ | | |
| 266 | 4-$CHNOC_2H_5$ | | |
| 267 | 2-CHNO(n-$C_3H_7$) | | |
| 268 | 3-CHNO(n-$C_3H_7$) | | |
| 269 | 4-CHNO(n-$C_3H_7$) | | |
| 270a) | 2-CHNO(n-$C_4H_9$); non-polar isomer | oil | 3.95(s, 3H); 4.05(s, 3H); 5.1(s, 2H) |
| 270b) | 2-CHNO(n-$C_4H_9$): polar isomer | oil | 3.90(s, 3H); 4.05(s, 3H); 5.1(s, 2H) |
| 271a) | 3-CHNO(n-$C_4H_9$): non-polar isomer | oil | 3.95(s, 3H); 4.05(s, 3H); 5.1(s, 2H) |
| 271b) | 3-CHNO(n-$C_4H_9$): polar isomer | oil | 3.90(s, 3H); 4.05(s, 3H); 5.1(s, 2H) |
| 272a) | 4-CHNO(n-$C_4H_9$): non-polar isomer | oil | 3.95(s, 3H); 4.05(s, 3H); 5.05(s, 2H) |
| 272b) | 4-CHNO(n-$C_4H_9$): polar isomer | 88-89 | |
| 273a) | 2-CHNO(n-$C_6H_{13}$): non-polar isomer | oil | 3.95(s, 3H); 4.05(s, 3H); 5.1(s, 2H) |
| 273b) | 2-CHNO(n-$C_6H_{13}$): polar isomer | oil | 3.90(s, 3H); 4.05(s, 3H); 5.1(s, 2H) |
| 274a) | 3-CHNO(n-$C_6H_{13}$): non-polar isomer | oil | 3.95(s, 3H); 4.05(s, 3H); 5.1(s, 2H) |
| 274b) | 3-CHNO(n-$C_6H_{13}$): polar isomer | oil | 3.90(s, 3H); 4.05(s, 3H); 5.1(s, 2H) |
| 275a) | 4-CHNO(n-$C_6H_{13}$): non-polar isomer | oil | 3.95(s, 3H); 4.05(s, 3H); 5.1(s, 2H) |
| 275b) | 4-CHNO(n-$C_6H_{13}$): polar isomer | 77-80 | |
| 276 | 2-CHNO(n-$C_8H_{17}$) | | |
| 277 | 3-CHNO(n-$C_8H_{17}$) | | |
| 278 | 4-CHNO(n-$C_8H_{17}$) | | |
| 279 | 2-$CHNOCH_2(C_6H_5)$ | | |
| 280 | 3-$CHNOCH_2(C_6H_5)$ | | |
| 281 | 4-$CHNOCH_2(C_6H_5)$ | | |
| 282 | 2-$CO_2CH_3$ | | |
| 283 | 3-$CO_2CH_3$ | | |
| 284 | 4-$CO_2CH_3$ | | |
| 285 | 2-$CO_2(C_2H_5)$ | | |
| 286 | 3-$CO_2(C_2H_5)$ | | |
| 287 | 4-$CO_2(C_2H_5)$ | | |
| 288 | 2-$CO_2$(n-$C_3H_7$) | | |
| 289 | 3-$CO_2$(n-$C_3H_7$) | | |

TABLE 5-continued

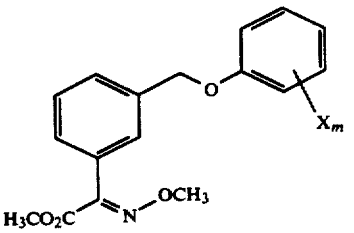

| No. | X$_m$ | mp | NMR: δ (ppm) |
| --- | --- | --- | --- |
| 290 | 4-CO$_2$(n-C$_3$H$_7$) | | |
| 291 | 2-CO$_2$(i-C$_3$H$_7$) | | |
| 292 | 3-CO$_2$(i-C$_3$H$_7$) | | |
| 293 | 4-CO$_2$(i-C$_3$H$_7$) | | |
| 294 | 2-CO$_2$(n-C$_6$H$_{13}$) | | |
| 295 | 3-CO$_2$(n-C$_6$H$_{13}$) | | |
| 296 | 4-CO$_2$(n-C$_6$H$_{13}$) | | |
| 297 | 2-CO$_2$(n-C$_8$H$_{17}$) | | |
| 298 | 3-CO$_2$(n-C$_8$H$_{17}$) | | |
| 299 | 4-CO$_2$(n-C$_8$H$_{17}$) | | |
| 300a) | 2-CH=NO-allyl: non-polar isomer | oil | 3.95(s, 3H); 4.05(s, 3H); 5.1(s, 2H) |
| 300b) | 2-CH=NO-allyl: polar isomer | oil | 3.90(s, 3H); 4.10(s, 3H); 5.1(s, 2H) |
| 301a) | 3-CH=NO-allyl: non-polar isomer | oil | 3.95(s, 3H); 4.05(s, 3H); 5.1(s, 2H) |
| 301b) | 3-CH=NO-allyl: polar isomer | oil | 3.90(s, 3H); 4.05(s, 3H); 5.1(s, 2H) |
| 302a) | 4-CH=NO-allyl: non-polar isomer | oil | 3.90(s, 3H); 4.0(s, 3H); 5.1(s, 2H) |
| 302b) | 4-CH=NO-allyl: polar isomer | 89 | |
| 303 | 2-CHNO(CH$_2$)$_3$ (C$_6$H$_5$) | | |
| 304 | 3-CHNO(CH$_2$)$_3$ (C$_6$H$_5$) | | |
| 305 | 4-CHNO(CH$_2$)$_3$ (C$_6$H$_5$) | | |
| 306 | 2-CH$_2$OCH$_3$ | | |
| 307 | 3-CH$_2$OCH$_3$ | | |
| 308 | 4-CH$_2$OCH$_3$ | | |
| 309 | 2-CH$_2$O(C$_2$H$_5$) | | |
| 310 | 3-CH$_2$O(C$_2$H$_5$) | | |
| 311 | 4-CH$_2$O(C$_2$H$_5$) | | |
| 312 | 2-CH$_2$O(n-C$_3$H$_7$) | | |
| 313 | 3-CH$_2$O(n-C$_3$H$_7$) | | |
| 314 | 4-CH$_2$O(n-C$_3$H$_7$) | | |
| 315 | 2-CH$_2$O(i-C$_3$H$_7$) | | |
| 316 | 3-CH$_2$O(i-C$_3$H$_7$) | | |
| 317 | 4-(CH$_2$O(i-C$_3$H$_7$) | | |
| 318 | 2-CH$_2$O(n-C$_6$H$_{13}$) | | |
| 319 | 3-CH$_2$O(n-C$_6$H$_{13}$) | | |
| 320 | 2-CH$_2$O(n-C$_6$H$_{13}$) | | |
| 321 | 2-CH$_2$O(n-C$_8$H$_{17}$) | | |
| 322 | 3-CH$_2$O(n-C$_8$H$_{17}$) | | |
| 323 | 4-CH$_2$O(n-C$_8$H$_7$) | | |
| 324 | 2-CH$_2$OCH$_2$(C$_6$H$_5$) | | |
| 325 | 3-CH$_2$OCH$_2$(C$_6$H$_5$) | | |
| 325 | 4-CH$_2$OCH$_2$(C$_6$H$_5$) | | |
| 327 | 2-CH$_2$O(CH$_2$)$_3$ | | |
| 328 | 3-CH$_2$O(CH$_2$)$_3$(C$_6$H$_5$) | | |
| 329 | 4-CH$_2$O(CH$_2$)$_3$(C$_6$H$_5$) | | |
| 330 | 2-CHO | | |
| 331 | 3-CHO | | |
| 332 | 4-CHO | | |

TABLE 6

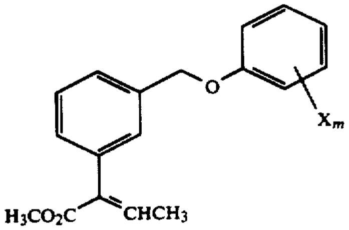

| No. | X$_m$ | mp | NMR: δ(ppm) |
| --- | --- | --- | --- |
| 1 | 2-F | | |
| 2 | 3-F | | |
| 3 | 4-F | | |
| 4 | 2,4-F$_2$ | | |
| 5 | 2,4,6-F$_3$ | | |
| 6 | 2,3,4,5,6-F$_5$ | | |
| 7 | 2,3-F$_2$ | | |
| 8 | 2-Cl | | |
| 9 | 3-Cl | | |
| 10 | 4-Cl | | |
| 11 | 2,3-Cl$_2$ | | |
| 12 | 2,4-Cl$_2$ | | |
| 13 | 2,5-Cl$_2$ | | |
| 14 | 2,6-Cl$_2$ | | |
| 15 | 3,4-Cl$_2$ | | |
| 16 | 3,5-Cl$_2$ | | |
| 17 | 2,3,4-Cl$_3$ | | |
| 18 | 2,3,5-Cl$_3$ | | |
| 19 | 2,3,6-Cl$_3$ | | |
| 20 | 2,4,5-Cl$_3$ | | |
| 21 | 2,4,6-Cl$_3$ | | |
| 22 | 3,4,5-Cl$_3$ | | |
| 23 | 2,3,4,6-Cl$_4$ | | |
| 24 | 2,3,5,6-Cl$_4$ | | |
| 25 | 2,3,4,5,6-Cl$_5$ | | |
| 26 | 2-Br | | |
| 27 | 3-Br | | |
| 28 | 4-Br | | |
| 29 | 2,4-Br$_2$ | | |
| 30 | 2,5-Br$_5$ | | |
| 31 | 2,6-Br$_2$ | | |
| 32 | 2,4,6-Br$_3$ | | |
| 33 | 2,3,4,5,6-Br$_5$ | | |
| 34 | 2-I | | |
| 35 | 3-I | | |
| 36 | 4-I | | |
| 37 | 2,4-I$_2$ | | |
| 38 | 2-Cl, 3-F | | |
| 39 | 2-Cl, 4-F | | |
| 40 | 2-Cl, 5-F | | |
| 41 | 2-Cl, 6-F | | |
| 42 | 2-Cl, 3-Br | | |
| 43 | 2-Cl, 4-Br | | |
| 44 | 2-Cl, 6-Br | | |
| 45 | 2-Cl, 6-Br | | |
| 46 | 2-Br, 3-Cl | | |
| 47 | 2-Br, 4-Cl | | |
| 48 | 2-Br, 5-Cl | | |
| 49 | 2-Br, 3-F | | |
| 50 | 2-Br, 4-F | | |
| 51 | 2-Br, 5-F | | |
| 52 | 2-Br, 6-F | | |
| 53 | 2-F, 3-Cl | | |
| 54 | 2-F, 4-Cl | | |
| 55 | 2-F, 5-Cl | | |
| 56 | 3-Cl, 4-F | | |
| 57 | 3-Cl, 5-F | | |
| 58 | 3-Cl, 4-Br | | |
| 59 | 3-Cl, 5-Br | | |
| 60 | 3-F, 4-Cl | | |
| 61 | 3-F, 4-Br | | |
| 62 | 3-Br, 4-Cl | | |
| 63 | 3-Br, 4-F | | |
| 64 | 2,6-Cl$_2$, 4-Br | | |
| 65 | 2-CH$_3$ | oil | 1.75(d, J=8Hz, 3H); 3.7(S, 3H); 5.1(S, 2H) |
| 66 | 3-CH$_3$ | | |
| 67 | 4-CH$_3$ | | |

TABLE 6-continued

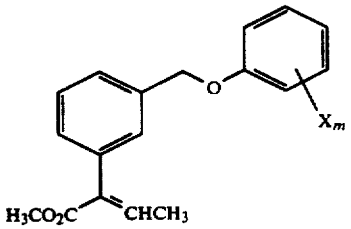

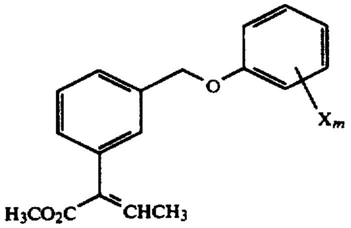

| No. | $X_m$ | mp | NMR: δ(ppm) |
|---|---|---|---|
| 68 | 2,3-$(CH_3)_2$ | | |
| 69 | 2,4-$(CH_3)_2$ | | |
| 70 | 2,5-$(CH_3)_2$ | | |
| 71 | 2,6-$(CH_3)_2$ | | |
| 72 | 3,4-$(CH_3)_2$ | | |
| 73 | 3,5-$(CH_3)_2$ | | |
| 74 | 3,5-$(CH_3)_2$ | | |
| 75 | 2,3,4-$(CH_3)_3$ | | |
| 76 | 2,3,6-$(CH_3)_3$ | | |
| 77 | 2,4,5-$(CH_3)_3$ | | |
| 78 | 2,4,6-$(CH_3)_3$ | | |
| 79 | 3,4,5-$(CH_3)_3$ | | |
| 80 | 2,3,4,6-$(CH_3)_4$ | | |
| 81 | 2,3,5,6-$(CH_3)_4$ | | |
| 82 | 2,3,4,5,6-$(CH_3)_5$ | | |
| 83 | 2-$C_2H_5$ | | |
| 84 | 3-$C_2H_5$ | | |
| 85 | 4-$C_2H_5$ | | |
| 86 | 2,4-$(C_2H_5)_2$ | | |
| 87 | 2,6-$(C_2H_5)_2$ | | |
| 88 | 3,5-$(C_2H_5)_2$ | | |
| 89 | 2,4,6-$(C_2H_5)_3$ | | |
| 90 | 2-n-$C_3H_7$ | | |
| 91 | 3-n-$C_3H_7$ | | |
| 92 | 4-n-$C_3H_7$ | | |
| 93 | 2-i-$C_3H_7$ | | |
| 94 | 3-i-$C_3H_7$ | | |
| 95 | 4-i-$C_3H_7$ | | |
| 96 | 2,4-(i-$C_3H_7)_2$ | | |
| 97 | 2,6-(i-$C_3H_7)_2$ | | |
| 98 | 3,5-(i-$C_3H_7)_2$ | | |
| 99 | 2,4,6-(i-$C_3H_7)_3$ | | |
| 100 | 2-S—$C_4H_9$ | | |
| 101 | 3-S—$C_4H_9$ | | |
| 102 | 4-S—$C_4H_9$ | | |
| 103 | 2-t-$C_4H_9$ | | |
| 104 | 3-t-$C_4H_9$ | | |
| 105 | 4-t-$C_4H_9$ | | |
| 106 | 2,3-(t-$C_4H_9)_2$ | | |
| 107 | 2,4-(t-$C_4H_9)_2$ | | |
| 108 | 2,5-(t-$C_4H_9)_2$ | | |
| 109 | 2,6-(t-$C_4H_9)_2$ | | |
| 110 | 3,4-(t-$C_4H_9)_2$ | | |
| 111 | 2,4,6-(t-$C_4H_9)_3$ | | |
| 112 | 4-n-$C_9H_{19}$ | | |
| 113 | 4-n-$C_{12}H_{25}$ | | |
| 114 | 3-n-$C_{15}H_{31}$ | | |
| 115 | 4-(1,1,3,3-tetramethylbutyl) | | |
| 116 | 4-(2,4,4-trimethylpropyl | | |
| 117 | 2-t-$C_4H_9$, 4-$CH_3$ | | |
| 118 | 2-t-$C_4H_9$, 5-$CH_3$ | | |
| 119 | 2,6-(t-$C_4H_9$), 4-$CH_3$ | | |
| 120 | 2-$CH_3$, 4-t-$C_4H_9$ | | |
| 121 | 2-$CH_3$, 6-t-$C_4H_9$ | | |
| 122 | 2-$CH_3$, 4-i-$C_3H_7$ | | |
| 123 | 2-$CH_3$, 5-i-$C_3H_7$ | | |
| 124 | 3-$CH_3$, 4-i-$C_3H_7$ | | |
| 125 | 2-i-$C_3H_7$, 5 $CH_3$ | | |
| 126 | 2,4-(t-$C_4H_9$), 6-i-$C_3H_7$ | | |
| 127 | 2-allyl | | |
| 128 | 3-allyl | | |
| 129 | 4-allyl | | |
| 130 | 2-allyl, 6-$CH_3$ | | |
| 131 | 2-cyclo-$C_6H_{11}$ | | |
| 132 | 3-cyclo-$C_6H_{11}$ | | |
| 133 | 4-cyclo-$C_6H_{11}$ | | |
| 134 | 2,4-(cyclo-$C_6H_{11})_2$, 6-$CH_3$ | | |
| 135 | 2-$CH_3$, 4-cyclo-$C_6H_{11}$ | | |
| 136 | 2-$CH_2$—$C_6H_5$ | | |
| 137 | 3-$CH_2$—$C_6H_5$ | | |
| 138 | 4-$CH_2$—$C_6H_5$ | | |
| 139 | 2-$CH_2$—$C_6H_5$, 4-$CH_3$ | | |
| 140 | 2-$CH_3$, 4-$CH_2$—$C_6H_5$ | | |
| 141 | 2-$C_6H_5$ | | |
| 142 | 3-$C_6H_5$ | | |
| 143 | 4-$C_6H_5$ | | |
| 144 | 4-(2-i-$C_3H_7$—$C_6H_4$) | | |
| 145 | 4-$C_6H_5$, 2,6-$(CH_3)_2$ | | |
| 146 | 2-Cl, 4-$C_6H_5$ | | |
| 147 | 2-Br, 4-$C_6H_5$ | | |
| 148 | 2-$C_6H_5$, 4-Cl | | |
| 149 | 2-$C_6H_5$, 4-Br | | |
| 150 | 2-$CH_2C_6H_5$, 4-Cl | | |
| 151 | 2-$CH_2C_6H_5$, 4-Br | | |
| 152 | 2-Cl, 4-$CH_2C_6H_5$ | | |
| 153 | 2-Br, 4-$CH_2C_6H_5$ | | |
| 154 | 2-cyclo-$C_6H_{11}$, 4-Cl | | |
| 155 | 2-cyclo-$C_6H_{11}$, 4-Br | | |
| 156 | 2-Cl, 4-cyclo-$C_6H_{11}$ | | |
| 157 | 2-Br, 4-cyclo-$C_6H_{11}$ | | |
| 158 | 2-$OCH_3$ | | |
| 159 | 3-$OCH_3$ | | |
| 160 | 4-$OCH_3$ | | |
| 161 | 2-$OC_2H_5$ | | |
| 162 | 3-O—$C_2H_5$ | | |
| 163 | 4-O—$C_2H_5$ | | |
| 164 | 2-O-n-$C_3H_7$ | | |
| 165 | 3-O-n-$C_3H_7$ | | |
| 166 | 4-O-n-$C_3H_7$ | | |
| 167 | 2-O-i-$C_3H_7$ | | |
| 168 | 3-O-i-$C_3H_7$ | | |
| 169 | 4-O-i-$C_3H_7$ | | |
| 170 | 2-O-n-$C_6H_{13}$ | | |
| 171 | 3-O-n-$C_6H_{13}$ | | |
| 172 | 4-O-n-$C_6H_{13}$ | | |
| 173 | 2-O-n-$C_8H_{17}$ | | |
| 174 | 3-O-n-$C_8H_{17}$ | | |
| 175 | 4-O-n-$C_8H_{17}$ | | |
| 176 | 2-O—$CH_2C_6H_5$ | | |
| 177 | 3-O—$CH_2C_6H_5$ | | |
| 178 | 4-O—$CH_2C_6H_5$ | | |
| 179 | 2-O—$(CH_2)_3C_6H_5$ | | |
| 180 | 3-O—$(CH_2)_3C_6H_5$ | | |
| 181 | 4-O—$(CH_2)_3C_6H_5$ | | |
| 182 | 2,4-$(OCH_3)_2$ | | |
| 183 | 2-$CF_3$ | | |
| 184 | 3-$CF_3$ | | |
| 185 | 4-$CF_3$ | | |
| 186 | 2-$OCF_3$ | | |
| 187 | 3-$OCF_3$ | | |
| 188 | 4-$OCF_3$ | | |
| 189 | 3-$OCH_2CHF_2$ | | |
| 190 | 2-$NO_2$ | | |
| 191 | 3-$NO_2$ | | |
| 192 | 4-$NO_2$ | | |
| 193 | 2-CN | | |
| 194 | 3-CN | | |
| 195 | 4-CN | | |
| 196 | 2-$CH_3$, 3-Cl | | |
| 197 | 2-$CH_3$, 4-Cl | | |
| 198 | 2-$CH_3$, 5-Cl | | |
| 199 | 2-$CH_3$, 6-Cl | | |
| 200 | 2-$CH_3$, 3-F | | |
| 201 | 2-$CH_3$, 4-F | | |
| 202 | 2-$CH_3$, 5-F | | |
| 203 | 2-$CH_3$, 6-F | | |

TABLE 6-continued

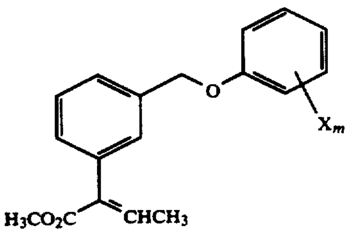

| No. | $X_m$ | mp | NMR: δ(ppm) |
|---|---|---|---|
| 204 | 2-$CH_3$, 3-Br | | |
| 205 | 2-$CH_3$, 4-Br | | |
| 206 | 2-$CH_3$, 5-Br | | |
| 207 | 2-$CH_3$, 6-Br | | |
| 208 | 2-Cl, 3-$CH_3$ | | |
| 209 | 2-Cl, 4-$CH_3$ | | |
| 210 | 2-Cl, 5-$CH_3$ | | |
| 211 | 2-F, 3-$CH_3$ | | |
| 212 | 2-F, 4-$CH_3$ | | |
| 213 | 2-F, 5-$CH_3$ | | |
| 214 | 2-Br, 3-$CH_3$ | | |
| 215 | 2-Br, 4-$CH_3$ | | |
| 216 | 2-Br, 5-$CH_3$ | | |
| 217 | 3-$CH_3$, 4-Cl | | |
| 218 | 3-$CH_3$, 5-Cl | | |
| 219 | 3-$CH_3$, 4-F | | |
| 220 | 3-$CH_3$, 4-Br | | |
| 221 | 3-$CH_3$, 4-Br | | |
| 222 | 3-$CH_3$, 5-Br | | |
| 223 | 3-F, 4-$CH_3$ | | |
| 224 | 3-Cl, 4-$CH_3$ | | |
| 225 | 3-Br, 4-$CH_3$ | | |
| 226 | 2-Cl, 4,5-$(CH_3)_2$ | | |
| 227 | 2-Br, 4,5-$(CH_3)_2$ | | |
| 228 | 2-Cl, 3,5-$(CH_3)_2$ | | |
| 229 | 2-Br, 3,5-$(CH_3)_2$ | | |
| 230 | 2,6-$Cl_2$, 4-$CH_3$ | | |
| 231 | 2,6-$F_2$, 4-$CH_3$ | | |
| 232 | 2,6-$Br_2$, 4-$CH_3$ | | |
| 233 | 2,4-$Cl_2$, 6-$CH_3$ | | |
| 234 | 2,4-$F_2$, 6-$CH_3$ | | |
| 235 | 2,4-$Br_2$, 6-$CH_3$ | | |
| 236 | 2,6-$(CH_3)_2$, 4-F | | |
| 237 | 2,6-$(CH_3)_2$, 4-Cl | | |
| 238 | 2,6-$(CH_3)_2$, 4-Br | | |
| 239 | 3,5-$(CH_3)_2$, 4-F | | |
| 240 | 3,5-$(CH_3)_2$, 4-Cl | | |
| 241 | 3,5-$(CH_3)_2$, 4-Br | | |
| 242 | 2,3,6-$(CH_3)_3$, 4-F | | |
| 243 | 2,3,6-$(CH_3)_3$, 4-Cl | | |
| 244 | 2,3,6-$(CH_3)_3$, 4-Br | | |
| 245 | 2,4-$(CH_3)_2$, 6-F | | |
| 246 | 2,4-$(CH_3)_2$, 6-Cl | | |
| 247 | 2,4-$(CH_3)_{62}$, 6-Br | | |
| 248 | 2-i-$C_3H_7$, 4-Cl, 5-$CH_3$ | | |
| 249 | 2-Cl, 4-$NO_2$ | | |
| 250 | 2-$NO_2$, 4-Cl | | |
| 251 | 2-$OCH_3$, 5-$NO_2$ | | |
| 252 | 2,4-$Cl_2$, 5-$NO_2$ | | |
| 253 | 2,4-$Cl_2$, 6-$NO_2$ | | |
| 254 | 2,6-$Cl_2$, 4-$NO_2$ | | |
| 255 | 2,6-$Br_2$, 4-$NO_2$ | | |
| 256 | 2,6-$I_2$, 4-$NO_2$ | | |
| 257 | 2-$CH_3$, 5-i-$C_3H_7$, 4-Cl | | |
| 258 | 2-$C_6H_5O$ | | |
| 259 | 3-$C_6H_5O$ | | |
| 260 | 4-$C_6H_5O$ | | |
| 261 | 2-$CHNOCH_3$ | | |
| 262 | 3-$CHNOCH_3$ | | |
| 263 | 4-$CHNOCH_3$ | | |
| 264 | 2-$CHNOC_2H_5$ | | |
| 265 | 3-$CHNOC_2H_5$ | | |
| 266 | 4-$CHNOC_2H_5$ | | |
| 267 | 2-CHNO(n-$C_3H_7$) | | |
| 268 | 3-CHNO(n-$C_3H_7$) | | |
| 269 | 4-CHNO(n-$C_3H_7$) | | |
| 270 | 2-CHNO(i-$C_3H_7$) | | |
| 271 | 3-CHNO(i-$C_3H_7$) | | |

TABLE 6-continued

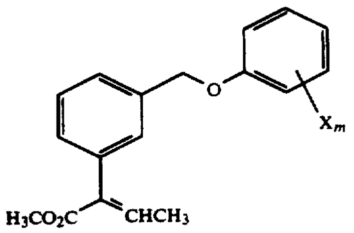

| No. | $X_m$ | mp | NMR: δ(ppm) |
|---|---|---|---|
| 272 | 4-CHNO(i-$C_3H_7$) | | |
| 273 | 2-CHNO(n-$C_6H_{13}$) | | |
| 274 | 3-CHNO(n-$C_6H_{13}$) | | |
| 275 | 4-CHNO(n-$C_6H_{13}$) | | |
| 276 | 2-CHNO(n-$C_8H_{17}$) | | |
| 277 | 3-CHNO(n-$C_8H_{17}$) | | |
| 278 | 4-CHNO(n-$C_8H_{17}$) | | |
| 279 | 2-$CHNOCH_2(C_6H_5)$ | | |
| 280 | 3-$CHNOCH_2(C_6H_5)$ | | |
| 281 | 4-$CHNOCH_2(C_6H_5)$ | | |
| 282 | 2-$CO_2CH_3$ | | |
| 283 | 3-$CO_2CH_3$ | | |
| 284 | 4-$CO_2CH_3$ | | |
| 285 | 2-$CO_2(C_2H_5)$ | | |
| 286 | 3-$CO_2(C_2H_5)$ | | |
| 287 | 4-$CO_2(C_2H_5)$ | | |
| 288 | 2-$CO_2$(n-$C_3H_7$) | | |
| 289 | 3-$CO_2$(n-$C_3H_7$) | | |
| 290 | 4-$CO_2$(n-$C_3H_7$) | | |
| 291 | 2-$CO_2$(i-$C_3H_7$) | | |
| 292 | 3-$CO_2$(i-$C_3H_7$) | | |
| 293 | 4-$CO_2$(i-$C_3H_7$) | | |
| 294 | 2-$CO_2$(n-$C_6H_{13}$) | | |
| 295 | 3-$CO_2$(n-$C_6H_{13}$) | | |
| 296 | 4-$CO_2$(n-$C_6H_{13}$) | | |
| 297 | 2-$CO_2$(n-$C_8H_{17}$) | | |
| 298 | 3-$CO_2$(n-$C_8H_{17}$) | | |
| 299 | 4-$CO_2$(n-$C_8H_{17}$) | | |
| 300 | 2-$CHNO{-}CH_2{-}CH{=}CH_2$ | | |
| 301 | 3-$CHNO{-}CH_2{-}CH{=}CH_2$ | | |
| 302 | 4-$CHNO{-}CH_2{-}CH{=}CH_2$ | | |
| 303 | 2-$CHNO(CH_2)_3(C_6H_5)$ | | |
| 304 | 3-$CHNO(CH_2)_3(C_6H_5)$ | | |
| 305 | 4-$CHNO(CH_2)_3(C_6H_5)$ | | |
| 306 | 2-$CH_2OCH_3$ | | |
| 307 | 3-$CH_2OCH_3$ | | |
| 308 | 4-$CH_2OCH_3$ | | |
| 309 | 2-$CH_2O(C_2H_5)$ | | |
| 310 | 3-$CH_2O(C_2H_5)$ | | |
| 311 | 4-$CH_2O(C_2H_5)$ | | |
| 312 | 2-$CH_2O$(n-$C_3H_7$) | | |
| 313 | 3-$CH_2O$(n-$C_3H_7$) | | |
| 314 | 4-$CH_2O$(n-$C_3H_7$) | | |
| 315 | 2-$CH_2O$(i-$C_3H_7$) | | |
| 316 | 3-$CH_2O$(i-$C_3H_7$) | | |
| 317 | 4-($CH_2O$(i-$C_3H_7$) | | |
| 318 | 2-$CH_2O$(n-$C_6H_{13}$) | | |
| 319 | 3-$CH_2O$(n-$C_6H_{13}$) | | |
| 320 | 4-$CH_2O$(n-$C_6H_{13}$) | | |
| 321 | 2-$CH_2O$(n-$C_8H_{17}$) | | |
| 322 | 3-$CH_2O$(n-$C_8H_{17}$) | | |
| 323 | 4-$CH_2O$(n-$C_8H_7$) | | |
| 324 | 2-$CH_2OCH_2(C_6H_5)$ | | |
| 325 | 3-$CH_2OCH_2(C_6H_5)$ | | |
| 326 | 4-$CH_2OCH_2(C_6H_5)$ | | |
| 327 | 2-$CH_2O(CH_2)_3$ | | |
| 328 | 3-$CH_2O(CH_2)_3(C_6H_5)$ | | |
| 329 | 4-$CH_2O(CH_2)_3(C_6H_5)$ | | |
| 330 | 2-CHO | | |
| 331 | 3-CHO | | |
| 332 | 4-CHO | | |

TABLE 7

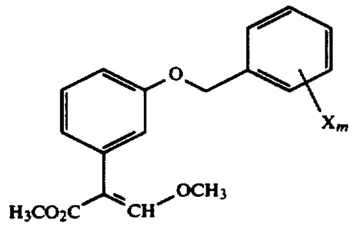

| No. | $X_m$ | mp | NMR: δ(ppm) |
|---|---|---|---|
| 1 | 2-F | | |
| 2 | 3-F | | |
| 3 | 4-F | | |
| 4 | 2,4-$F_2$ | | |
| 5 | 2,4,6-$F_3$ | | |
| 6 | 2,3,4,5,6-$F_4$ | | |
| 7 | 2,3-$F_2$ | | |
| 8 | 2-Cl | 72–74 | |
| 9 | 3-Cl | oil | 5.0(S, 2H); 7.55(S, 1H) |
| 10 | 4-Cl | 80–81 | |
| 11 | 2,3-$Cl_2$ | | |
| 12 | 2,4-$Cl_2$ | 59–61 | |
| 13 | 2,5-$Cl_2$ | | |
| 14 | 2,6-$Cl_2$ | | |
| 15 | 3,4-$Cl_2$ | oil | 5.0(S, 2H); 7.55(S, 1H) |
| 16 | 3,5-$Cl_2$ | 93–95 | |
| 17 | 2,3,4-$Cl_3$ | | |
| 18 | 2,3,5-$Cl_3$ | | |
| 19 | 2,3,6-$Cl_3$ | | |
| 20 | 2,4,5-$Cl_3$ | | |
| 21 | 2,4,6-$Cl_3$ | | |
| 22 | 3,4,5-$Cl_3$ | | |
| 23 | 2,3,4,6-$Cl_4$ | | |
| 24 | 2,3,5,6-$Cl_4$ | | |
| 25 | 2,3,4,5,6-$Cl_5$ | | |
| 26 | 2-Br | | |
| 27 | 3-Br | | |
| 28 | 4-Br | | |
| 29 | 2,4-$Br_2$ | | |
| 30 | 2,5-$Br_5$ | | |
| 31 | 2,6-$Br_2$ | | |
| 32 | 2,4,6-$Br_3$ | | |
| 33 | 2,3,4,5,6-$Br_5$ | | |
| 34 | 2-I | | |
| 35 | 3-I | | |
| 36 | 4-I | | |
| 37 | 2,4-$I_2$ | | |
| 38 | 2-Cl, 3-F | | |
| 39 | 2-Cl, 4-F | | |
| 40 | 2-Cl, 5-F | | |
| 41 | 2-Cl, 6-F | | |
| 42 | 2-Cl, 3-Br | | |
| 43 | 2-Cl, 4-Br | | |
| 44 | 2-Cl, 6-Br | | |
| 45 | 2-Cl, 6-Br | | |
| 46 | 2-Br, 3-Cl | | |
| 47 | 2-Br, 4-Cl | | |
| 48 | 2-Br, 5-Cl | | |
| 49 | 2-Br, 3-F | | |
| 50 | 2-Br, 4-F | | |
| 51 | 2-Br, 5-F | | |
| 52 | 2-Br, 6-F | | |
| 53 | 2-F, 3-Cl | | |
| 54 | 2-F, 4-Cl | | |
| 55 | 2-F, 5-Cl | | |
| 56 | 3-Cl, 4-F | | |
| 57 | 3-Cl, 5-F | | |
| 58 | 3-Cl, 4-Br | | |
| 59 | 3-Cl, 5-Br | | |
| 60 | 3-F, 4-Cl | | |
| 61 | 3-F, 4-Br | | |
| 62 | 3-Br, 4-Cl | | |
| 63 | 3-Br, 4-F | | |
| 64 | 2,6-$Cl_2$, 4-Br | | |
| 65 | 2-$CH_3$ | oil | 5.0(S, 2H); 7.55(S, 1H) |
| 66 | 3-$CH_3$ | oil | 5.0(S, 2H); |

TABLE 7-continued

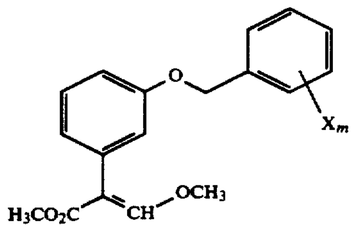

| No. | $X_m$ | mp | NMR: δ(ppm) |
|---|---|---|---|
| | | | 7.55(S, 1H) |
| 67 | 4-$CH_3$ | 69–71 | |
| 68 | 2,3-$(CH_3)_2$ | | |
| 69 | 2,4-$(CH_3)_2$ | | |
| 70 | 2,5-$(CH_3)_2$ | | |
| 71 | 2,6-$(CH_3)_2$ | | |
| 72 | 3,4-$(CH_3)_2$ | | |
| 73 | 3,5-$(CH_3)_2$ | | |
| 74 | 3,5-$(CH_3)_2$ | | |
| 75 | 2,3,4-$(CH_3)_3$ | | |
| 76 | 2,3,6-$(CH_3)_3$ | | |
| 77 | 2,4,5-$(CH_3)_3$ | | |
| 78 | 2,4,6-$(CH_3)_3$ | | |
| 79 | 3,4,5-$(CH_3)_3$ | | |
| 80 | 2,3,4,6-$(CH_3)_4$ | | |
| 81 | 2,3,5,6-$(CH_3)_4$ | | |
| 82 | 2,3,4,5,6-$(CH_3)_5$ | | |
| 83 | 2-$C_2H_5$ | | |
| 84 | 3-$C_2H_5$ | | |
| 85 | 4-$C_2H_5$ | | |
| 86 | 2,4-$(C_2H_5)_2$ | | |
| 87 | 2,6-$(C_2H_5)_2$ | | |
| 88 | 3,5-$(C_2H_5)_2$ | | |
| 89 | 2,4,6-$(C_2H_5)_3$ | | |
| 90 | 2-n-$C_3H_7$ | | |
| 91 | 3-n-$C_3H_7$ | | |
| 92 | 4-n-$C_3H_7$ | | |
| 93 | 2-i-$C_3H_7$ | | |
| 94 | 3-i-$C_3H_7$ | | |
| 95 | 4-i-$C_3H_7$ | | |
| 96 | 2,4-(i-$C_3H_7)_2$ | | |
| 97 | 2,6-(i-$C_3H_7)_2$ | | |
| 98 | 3,5-(i-$C_3H_7)_2$ | | |
| 99 | 2,4,6-(i-$C_3H_7)_3$ | | |
| 100 | 2-S-$C_4H_9$ | | |
| 101 | 3-S-$C_4H_9$ | | |
| 102 | 4-S-$C_4H_9$ | | |
| 103 | 2-t-$C_4H_9$ | | |
| 104 | 3-t-$C_4H_9$ | | |
| 105 | 4-t-$C_4H_9$ | | |
| 106 | 2,3-(t-$C_4H_9)_2$ | | |
| 107 | 2,4-(t-$C_4H_9)_2$ | | |
| 108 | 2,5-(t-$C_4H_9)_2$ | | |
| 109 | 2,6-(t-$C_4H_9)_2$ | | |
| 110 | 3,4-(t-$C_4H_9)_2$ | | |
| 111 | 2,4,6-(t-$C_4H_9)_3$ | | |
| 112 | 4-n-$C_9H_{19}$ | | |
| 113 | 4-n-$C_{12}H_{25}$ | | |
| 114 | 3-n-$C_{15}H_{31}$ | | |
| 115 | 4-(1,1,3,3-tetramethylbutyl) | | |
| 116 | 4-(2,4,4-trimethylpropyl | | |
| 117 | 2-t-$C_4H_9$, 4-$CH_3$ | | |
| 118 | 2-t-$C_4H_9$, 5-$CH_3$ | | |
| 119 | 2,6-(t-$C_4H_9$), 4-$CH_3$ | | |
| 120 | 2-$CH_3$, 4-t-$C_4H_9$ | | |
| 121 | 2-$CH_3$, 6-t-$C_4H_9$ | | |
| 122 | 2-$CH_3$, 4-i-$C_3H_7$ | | |
| 123 | 2-$CH_3$, 5-i-$C_3H_7$ | | |
| 124 | 3-$CH_3$, 4-i-$C_3H_7$ | | |
| 125 | 2-i-$C_3H_7$, 5 $CH_3$ | | |
| 126 | 2,4-(t-$C_4H_9$), 6-i-$C_3H_7$ | | |
| 127 | 2-allyl | | |
| 128 | 3-allyl | | |
| 129 | 4-allyl | | |
| 130 | 2-allyl, 6-$CH_3$ | | |
| 131 | 2-cyclo-$C_6H_{11}$ | | |
| 132 | 3-cyclo-$C_6H_{11}$ | | |
| 133 | 4-cyclo-$C_6H_{11}$ | | |
| 134 | 2,4-(cyclo-$C_6H_{11})_2$, 6-$CH_3$ | | |

TABLE 7-continued

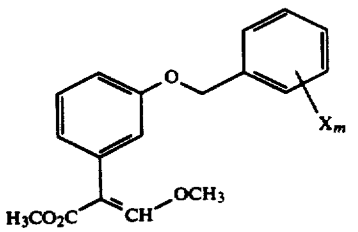

| No. | $X_m$ | mp | NMR: δ(ppm) |
|---|---|---|---|
| 135 | 2-$CH_3$, 4-cyclo-$C_6H_{11}$ | | |
| 136 | 2-$CH_2$—$C_6H_5$ | | |
| 137 | 3-$CH_2$—$C_6H_5$ | | |
| 138 | 4-$CH_2$—$C_2H_5$ | | |
| 139 | 2-$CH_2$—$C_6H_5$, 4-$CH_3$ | | |
| 140 | 2-$CH_3$, 4-$CH_2$—$C_6H_5$ | | |
| 141 | 2-$C_6H_5$ | | |
| 142 | 3-$C_6H_5$ | | |
| 143 | 4-$C_6H_5$ | | |
| 144 | 4-(2-i-$C_3H_7$—$C_6H_4$) | | |
| 145 | 4-$C_6H_5$, 2,6-$(CH_3)_2$ | | |
| 146 | 2-Cl, 4-$C_6H_5$ | | |
| 147 | 2-Br, 4-$C_6H_5$ | | |
| 148 | 2-$C_6H_5$, 4-Cl | | |
| 149 | 2-$C_6H_5$, 4-Br | | |
| 150 | 2-$CH_2C_6H_5$, 4-Cl | | |
| 151 | 2-$CH_2C_6H_5$, 4-Br | | |
| 152 | 2-Cl, 4-$CH_2C_6H_5$ | | |
| 153 | 2-Br, 4-$CH_2C_6H_5$ | | |
| 154 | 2-cyclo-$C_6H_{11}$, 4-Cl | | |
| 155 | 2-cyclo-$C_6H_{11}$, 4-Br | | |
| 156 | 2-Cl, 4-cyclo-$C_6H_{11}$ | | |
| 157 | 2-Br, 4-cyclo-$C_6H_{11}$ | | |
| 158 | 2-$OCH_3$ | | |
| 159 | 3-$OCH_3$ | | |
| 160 | 4-$OCH_3$ | | |
| 161 | 2-$OC_2H_5$ | | |
| 162 | 3-O—$C_2H_5$ | | |
| 163 | 4-O—$C_2H_5$ | | |
| 164 | 2-O-n-$C_3H_7$ | | |
| 165 | 3-O-n-$C_3H_7$ | | |
| 166 | 4-O-n-$C_3H_7$ | | |
| 167 | 2-O-i-$C_3H_7$ | | |
| 168 | 3-O-i-$C_3H_7$ | | |
| 169 | 4-O-i-$C_3H_7$ | | |
| 170 | 2-O-n-$C_6H_{13}$ | | |
| 171 | 3-O-n-$C_6H_{13}$ | | |
| 172 | 4-O-i-$C_6H_{13}$ | | |
| 173 | 2-O-n-$C_8H_{17}$ | | |
| 174 | 3-O-n-$C_8H_{17}$ | | |
| 175 | 4-O-n-$C_8H_{17}$ | | |
| 176 | 2-O—$CH_2C_6H_5$ | | |
| 177 | 3-O—$CH_2C_6H_5$ | | |
| 178 | 4-O—$CH_2C_6H_5$ | | |
| 179 | 2-O—$(CH_2)_3C_6H_5$ | | |
| 180 | 3-O—$(CH_2)_3C_6H_5$ | | |
| 181 | 4-O—$(CH_2)_3C_6H_5$ | | |
| 182 | 2,4-$(OCH_3)_2$ | | |
| 183 | 2-$CF_3$ | | |
| 184 | 3-$CF_3$ | | |
| 185 | 4-$CF_3$ | | |
| 186 | 2-$OCF_3$ | | |
| 187 | 3-$OCF_3$ | | |
| 188 | 4-$OCF_3$ | | |
| 189 | 3-$OCH_2CHF_2$ | | |
| 190 | 2-$NO_2$ | | |
| 191 | 3-$NO_2$ | | |
| 192 | 4-$NO_2$ | | |
| 193 | 2-CN | | |
| 194 | 3-CN | | |
| 195 | 4-CN | | |
| 196 | 2-$CH_3$, 3-Cl | | |
| 197 | 2-$CH_3$, 4-Cl | | |
| 198 | 2-$CH_3$, 5-Cl | | |
| 199 | 2-$CH_3$, 6-Cl | | |
| 200 | 2-$CH_3$, 3-F | | |
| 201 | 2-$CH_3$, 4-F | | |
| 202 | 2-$CH_3$, 5-F | | |
| 203 | 2-$CH_3$, 6-F | | |

TABLE 7-continued

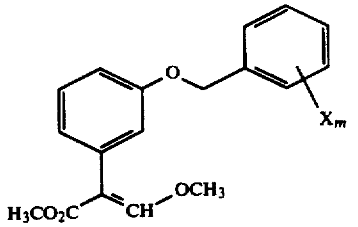

| No. | $X_m$ | mp | NMR: δ(ppm) |
|---|---|---|---|
| 204 | 2-$CH_3$, 3-Br | | |
| 205 | 2-$CH_3$, 3-Br | | |
| 206 | 2-$CH_3$, 5-Br | | |
| 207 | 2-$CH_3$, 6-Br | | |
| 208 | 2-Cl, 3-$CH_3$ | | |
| 209 | 2-Cl, 4-$CH_3$ | | |
| 210 | 2-Cl, 5-$CH_3$ | | |
| 211 | 2-F, 3-$CH_3$ | | |
| 212 | 2-F, 4-$CH_3$ | | |
| 213 | 2-F, 5-$CH_3$ | | |
| 214 | 2-Br, 3-$CH_3$ | | |
| 215 | 2-Br, 4-$CH_3$ | | |
| 216 | 2-Br, 5-$CH_3$ | | |
| 217 | 3-$CH_3$, 4-Cl | | |
| 218 | 3-$CH_3$, 5-Cl | | |
| 219 | 3-$CH_3$, 4-F | | |
| 220 | 3-$CH_3$, 4-Br | | |
| 221 | 3-$CH_3$, 4-Br | | |
| 222 | 3-$CH_3$, 5-Br | | |
| 223 | 3-F, 4-$CH_3$ | | |
| 224 | 3-Cl, 4-$CH_3$ | | |
| 225 | 3-Br, 4-$CH_3$ | | |
| 226 | 2-Cl, 4,5-$(CH_3)_2$ | | |
| 227 | 2-Br, 4,5-$(CH_3)_2$ | | |
| 228 | 2-Cl, 3,5-$(CH_3)_2$ | | |
| 229 | 2-Br, 3,5-$(CH_3)_2$ | | |
| 230 | 2,6-$Cl_2$, 4-$CH_3$ | | |
| 231 | 2,6-$F_2$, 4-$CH_3$ | | |
| 232 | 2,6-$Br_2$, 4-$CH_3$ | | |
| 233 | 2,4-$Cl_2$, 6-$CH_3$ | | |
| 234 | 2,4-$F_2$, 6-$CH_3$ | | |
| 235 | 2,4-$Br_2$, 6-$CH_3$ | | |
| 236 | 2,6-$(CH_3)_2$, 4-F | | |
| 237 | 2,6-$(CH_3)_2$, 4-Cl | | |
| 238 | 2,6-$(CH_3)_2$, 4-Br | | |
| 239 | 3,5-$(CH_3)_2$, 4-F | | |
| 240 | 3,5-$(CH_3)_2$, 4-Cl | | |
| 241 | 3,5-$(CH_3)_2$, 4-Br | | |
| 242 | 2,3,6-$(CH_3)_3$, 4-F | | |
| 243 | 2,3,6-$(CH_3)_3$, 4-Cl | | |
| 244 | 2,3,6-$(CH_3)_3$, 4-Br | | |
| 245 | 2,4-$(CH_3)_2$, 6-F | | |
| 246 | 2,4-$(CH_3)_2$, 6-Cl | | |
| 247 | 2,4-$(CH_3)_{62}$, 6-Br | | |
| 248 | 2-i-$C_3H_7$, 4-Cl, 5-$CH_3$ | | |
| 249 | 2-Cl, 4-$NO_2$ | | |
| 250 | 2-$NO_2$, 4-Cl | | |
| 251 | 2-$OCH_3$, 5-$NO_2$ | | |
| 252 | 2,4-$Cl_2$, 5-$NO_2$ | | |
| 253 | 2,4-$Cl_2$, 6-$NO_2$ | | |
| 254 | 2,6-$Cl_2$, 4-$NO_2$ | | |
| 255 | 2,6-$Br_2$, 4-$NO_2$ | | |
| 256 | 2,6-$J_2$, 4-$NO_2$ | | |
| 257 | 2-$CH_3$, 5-i-$C_3H_7$, 4-Cl | | |
| 258 | 2-$C_6H_5O$ | | |
| 259 | 3-$C_6H_5O$ | | |
| 260 | 4-$C_6H_5O$ | | |
| 261 | 2-$CHNOCH_3$ | | |
| 262 | 3-$CHNOCH_3$ | | |
| 263 | 4-$CHNOCH_3$ | | |
| 264 | 2-$CHNOC_2H_5$ | | |
| 265 | 3-$CHNOC_2H_5$ | | |
| 266 | 4-$CHNOC_2H_5$ | | |
| 267 | 2-CHNO(n-$C_3H_7$) | | |
| 268 | 3-CHNO(n-$C_3H_7$) | | |
| 269 | 4-CHNO(n-$C_3H_7$) | | |
| 270 | 2-CHNO(i-$C_3H_7$) | | |
| 271 | 3-CHNO(i-$C_3H_7$) | | |
| 272 | 4-CHNO(i-$C_3H_7$) | | |

TABLE 7-continued

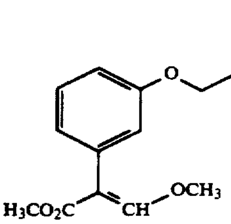

| No. | $X_m$ | mp | NMR: δ(ppm) |
|---|---|---|---|
| 273 | 2-CHNO(n-$C_6H_{13}$) | | |
| 274 | 3-CHNO(n-$C_6H_{13}$) | | |
| 275 | 4-CHNO(n-$C_6H_{13}$) | | |
| 276 | 2-CHNO(n-$C_8H_{17}$) | | |
| 277 | 3-CHNO(n-$C_8H_{17}$) | | |
| 278 | 4-CHNO(n-$C_8H_{17}$) | | |
| 279 | 2-$CHNOCH_2(C_6H_5)$ | | |
| 280 | 3-$CHNOCH_2(C_6H_5)$ | | |
| 281 | 4-$CHNOCH_2(C_6H_5)$ | | |
| 282 | 2-$CO_2CH_3$ | | |
| 283 | 3-$CO_2CH_3$ | | |
| 284 | 4-$CO_2CH_3$ | | |
| 285 | 2-$CO_2(C_2H_5)$ | | |
| 286 | 3-$CO_2(C_2H_5)$ | | |
| 287 | 4-$CO_2(C_2H_5)$ | | |
| 288 | 2-$CO_2$(n-$C_3H_7$) | | |
| 289 | 3-$CO_2$(n-$C_3H_7$) | | |
| 290 | 4-$CO_2$(n-$C_3H_7$) | | |
| 291 | 2-$CO_2$(i-$C_3H_7$) | | |
| 292 | 3-$CO_2$(i-$C_3H_7$) | | |
| 293 | 4-$CO_2$(i-$C_3H_7$) | | |
| 294 | 2-$CO_2$(n-$C_6H_{13}$) | | |
| 295 | 3-$CO_2$(n-$C_6H_{13}$) | | |
| 296 | 4-$CO_2$(n-$C_6H_{13}$) | | |
| 297 | 2-$CO_2$(n-$C_8H_{17}$) | | |
| 298 | 3-$CO_2$(n-$C_8H_{17}$) | | |
| 299 | 4-$CO_2$(n-$C_8H_{17}$) | | |
| 300 | 2-CHNO$-CH_2-CH=CH_2$ | | |
| 301 | 3-CHNO$-CH_2-CH=CH_2$ | | |
| 302 | 4-CHNO$-CH_2-CH=CH_2$ | | |
| 303 | 2-CHNO$(CH_2)_3(C_6H_5)$ | | |
| 304 | 3-CHNO$(CH_2)_3(C_6H_5)$ | | |

TABLE 7-continued

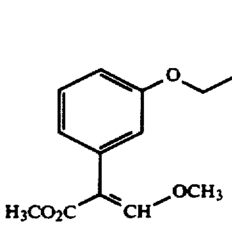

| No. | $X_m$ | mp | NMR: δ(ppm) |
|---|---|---|---|
| 305 | 4-CHNO$(CH_2)_3(C_6H_5)$ | | |
| 306 | 2-$CH_2OCH_3$ | | |
| 307 | 3-$CH_2OCH_3$ | | |
| 308 | 4-$CH_2OCH_3$ | | |
| 309 | 2-$CH_2O(C_2H_5)$ | | |
| 310 | 3-$CH_2O(C_2H_5)$ | | |
| 311 | 4-$CH_2O(C_2H_5)$ | | |
| 312 | 2-$CH_2O$(n-$C_3H_7$) | | |
| 313 | 3-$CH_2O$(n-$C_3H_7$) | | |
| 314 | 4-$CH_2O$(n-$C_3H_7$) | | |
| 315 | 2-$CH_2O$(i-$C_3H_7$) | | |
| 316 | 3-$CH_2O$(i-$C_3H_7$) | | |
| 317 | 4-($CH_2O$(i-$C_3H_7$) | | |
| 318 | 2-$CH_2O$(n-$C_6H_{13}$) | | |
| 319 | 3-$CH_2O$(n-$C_6H_{13}$) | | |
| 320 | 4-$CH_2O$(n-$C_6H_{13}$) | | |
| 321 | 2-$CH_2O$(n-$C_8H_{17}$) | | |
| 322 | 3-$CH_2O$(n-$C_8H_{17}$) | | |
| 323 | 4-$CH_2O$(n-$C_8H_{17}$) | | |
| 324 | 2-$CH_2OCH_2(C_6H_5)$ | | |
| 325 | 3-$CH_2OCH_2(C_6H_5)$ | | |
| 326 | 4-$CH_2OCH_2(C_6H_5)$ | | |
| 327 | 2-$CH_2O(CH_2)_3$ | | |
| 328 | 3-$CH_2O(CH_2)_3(C_6H_5)$ | | |
| 329 | 4-$CH_2O(CH_2)_3(C_6H_5)$ | | |
| 330 | 2-CHO | | |
| 331 | 3-CHO | | |
| 332 | 4-CHO | | |
| 333 | 3-benzoyl | oil | 5.15(s, 2H); 7.55 (s, 1H) |

TABLE 8

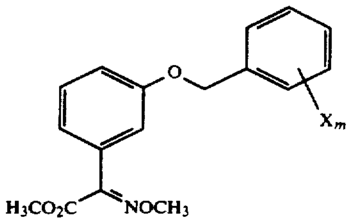

| No. | $X_m$ | mp | NMR: δ (ppm) |
|---|---|---|---|
| 1a) | 2-F: non-polar isomer | oil | 3.9(S, 3H); 4.0(S, 3H); 5.15(S, 2H) |
| 1b) | 2-F: polar isomer | 77-79 | |
| 2 | 3-F | | |
| 3 | 4-F | | |
| 4 | 2,4-$F_2$ | | |
| 5 | 2,4,6-$F_3$ | | |
| 6 | 2,3,4,5,6-$F_5$ | | |
| 7 | 2,3-$F_2$ | | |
| 8a) | 2-Cl: non-polar isomer | oil | 3.9(S, 3H); 4.0(S, 3H); 5.15(S, 2H) |
| 8b) | 2-Cl: polar isomer | 78-80 | |
| 9a) | 3-Cl: non-polar isomer | oil | 3.9(S, 3H); 4.0(S, 3H); 5.05(S, 2H) |
| 9b) | 3-Cl: polar isomer | 64-66 | |
| 10a) | 4-Cl: non-polar isomer | 58-70 | 3.9(S, 3H); 4.0(S, 3H); 5.0(S, 2H) |
| 10b) | 4-Cl: polar isomer | 112-120 | 3.85(S, 3H); 4.05(S, 3H); 5.0(S, 2H) |
| 11 | 2,3-$Cl_2$ | | |
| 12a) | 2,4-$Cl_2$: non-polar isomer | 89-93 | |

TABLE 8-continued

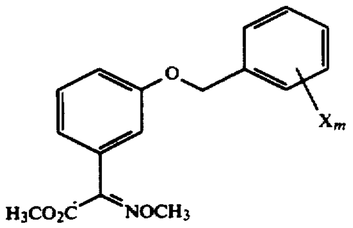

| No. | $X_m$ | mp | NMR: δ (ppm) |
|---|---|---|---|
| 12b) | 2,4-$Cl_2$: polar isomer | 83-86 | |
| 13 | 2,5-$Cl_2$ | | |
| 14 | 2,6-$Cl_2$ | | |
| 15 | 3,4-$Cl_2$ | | |
| 16 | 3,5-$Cl_2$ | | |
| 17 | 2,3,4-$Cl_3$ | | |
| 18 | 2,3,5-$Cl_3$ | | |
| 19 | 2,3,6-$Cl_3$ | | |
| 20 | 2,4,5-$Cl_3$ | | |
| 21 | 2,4,6-$Cl_3$ | | |
| 22 | 3,4,5-$Cl_3$ | | |
| 23 | 2,3,4,6-$Cl_4$ | | |
| 24 | 2,3,5,6-$Cl_4$ | | |
| 25 | 2,3,4,5,6-$Cl_5$ | | |
| 26 | 2-Br | | |
| 27 | 3-Br | | |
| 28 | 4-Br | | |
| 29 | 2,4-$Br_2$ | | |
| 30 | 2,5-$Br_5$ | | |
| 31 | 2,6-$Br_2$ | | |
| 32 | 2,4,6-$Br_3$ | | |
| 33 | 2,3,4,5,6-$Br_5$ | | |
| 34 | 2-I | | |
| 35 | 3-I | | |
| 36 | 4-I | | |
| 37 | 2,4-$I_2$ | | |
| 38 | 2-Cl, 3-F | | |
| 39 | 2-Cl, 4-F | | |
| 40 | 2-Cl, 5-F | | |
| 41 | 2-Cl, 6-F | | |
| 42 | 2-Cl, 3-Br | | |
| 43 | 2-Cl, 4-Br | | |
| 44 | 2-Cl, 6-Br | | |
| 45 | 2-Cl, 6-Br | | |
| 46 | 2-Br, 3-Cl | | |
| 47 | 2-Br, 4-Cl | | |
| 48 | 2-Br, 5-Cl | | |
| 49 | 2-Br, 3-F | | |
| 50 | 2-Br, 4-F | | |
| 51 | 2-Br, 5-F | | |
| 52 | 2-Br, 6-F | | |
| 53 | 2-F, 3-Cl | | |
| 54 | 2-F, 4-Cl | | |
| 55 | 2-F, 5-Cl | | |
| 56 | 3-Cl, 4-F | | |
| 57 | 3-Cl, 5-F | | |
| 58 | 3-Cl, 4-Br | | |
| 59 | 3-Cl, 5-Br | | |
| 60 | 3-F, 4-Cl | | |
| 61 | 3-F, 4-Br | | |
| 62 | 3-Br, 4-Cl | | |
| 63 | 3-Br, 4-F | | |
| 64 | 2,6-$Cl_2$, 4-Br | | |
| 65a) | 2-$CH_3$: non-polar isomer | 51-53 | |
| 65b) | 2-$CH_3$: polar isomer | 79-83 | |
| 66a | 3-$CH_3$: non-polar isomer | oil | 3.9(s, 3H); 4.0(s, 3H); 5.0(s, 2H) |
| 66b | 3-$CH_3$: polar isomer | 87-89 | |
| 67a | 4-$CH_3$: non-polar isomer | oil | 3.95(s, 3H); 4.05(s, 3H); 5.05(s, 2H) |
| 67b | 3-$CH_3$: polar isomer | 78-79 | |
| 68 | 2,3-$(CH_3)_2$ | | |
| 69 | 2,4-$(CH_3)_2$ | | |
| 70 | 2,5-$(CH_3)_2$ | | |
| 71 | 2,6-$(CH_3)_2$ | | |
| 72 | 3,4-$(CH_3)_2$ | | |
| 73 | 3,5-$(CH_3)_2$ | | |
| 74 | 3,5-$(CH_3)_2$ | | |
| 75 | 2,3,4-$(CH_3)_3$ | | |

TABLE 8-continued

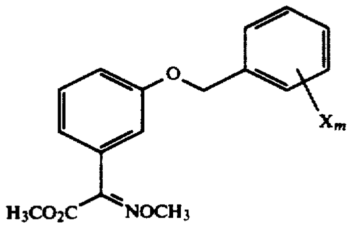

| No. | $X_m$ | mp | NMR: δ (ppm) |
|---|---|---|---|
| 76 | 2,3,6-$(CH_3)_3$ | | |
| 77 | 2,4,5-$(CH_3)_3$ | | |
| 78 | 2,4,6-$(CH_3)_3$ | | |
| 79 | 3,4,5-$(CH_3)_3$ | | |
| 80 | 2,3,4,6-$(CH_3)_4$ | | |
| 81 | 2,3,5,6-$(CH_3)_4$ | | |
| 82 | 2,3,4,5,6-$(CH_3)_5$ | | |
| 83 | 2-$C_2H_5$ | | |
| 84 | 3-$C_2H_5$ | | |
| 85 | 4-$C_2H_5$ | | |
| 86 | 2,4-$(C_2H_5)_2$ | | |
| 87 | 2,6-$(C_2H_5)_2$ | | |
| 88 | 3,5-$(C_2H_5)_2$ | | |
| 89 | 2,4,6-$(C_2H_5)_3$ | | |
| 90 | 2-n-$C_3H_7$ | | |
| 91 | 3-n-$C_3H_7$ | | |
| 92 | 4-n-$C_3H_7$ | | |
| 93 | 2-i-$C_3H_7$ | | |
| 94 | 3-i-$C_3H_7$ | | |
| 95 | 4-i-$C_3H_7$ | | |
| 96 | 2,4-(i-$C_3H_7)_2$ | | |
| 97 | 2,6-(i-$C_3H_7)_2$ | | |
| 98 | 3,5-(i-$C_3H_7)_2$ | | |
| 99 | 2,4,6-(i-$C_3H_7)_3$ | | |
| 100 | 2-S-$C_4H_9$ | | |
| 101 | 3-S-$C_4H_9$ | | |
| 102 | 4-S-$C_4H_9$ | | |
| 103 | 2-t-$C_4H_9$ | | |
| 104 | 3-t-$C_4H_9$ | | |
| 105 | 4-t-$C_4H_9$ | | |
| 106 | 2,3-(t-$C_4H_9)_2$ | | |
| 107 | 2,4-(t-$C_4H_9)_2$ | | |
| 108 | 2,5-(t-$C_4H_9)_2$ | | |
| 109 | 2,6-(t-$C_4H_9)_2$ | | |
| 110 | 3,4-(t-$C_4H_9)_2$ | | |
| 111 | 2,4,6-(t-$C_4H_9)_3$ | | |
| 112 | 4-n-$C_9H_{19}$ | | |
| 113 | 4-n-$C_{12}H_{25}$ | | |
| 114 | 3-n-$C_{15}H_{31}$ | | |
| 115 | 4-(1,1,3,3-tetramethylbutyl) | | |
| 116 | 4-(2,4,4-trimethylpropyl | | |
| 117 | 2-t-$C_4H_9$, 4-$CH_3$ | | |
| 118 | 2-t-$C_4H_9$, 5-$CH_3$ | | |
| 119 | 2,6-(t-$C_4H_9$), 4-$CH_3$ | | |
| 120 | 2-$CH_3$, 4-t-$C_4H_9$ | | |
| 121 | 2-$CH_3$, 6-t-$C_4H_9$ | | |
| 122 | 2-$CH_3$, 4-i-$C_3H_7$ | | |
| 123 | 2-$CH_3$, 5-i-$C_3H_7$ | | |
| 124 | 3-$CH_3$, 4-i-$C_3H_7$ | | |
| 125 | 2-i-$C_3H_7$, 5 $CH_3$ | | |
| 126 | 2,4-(t-$C_4H_9$), 6-i-$C_3H_7$ | | |
| 127 | 2-allyl | | |
| 128 | 3-allyl | | |
| 129 | 4-allyl | | |
| 130 | 2-allyl, 6-$CH_3$ | | |
| 131 | 2-cyclo-$C_6H_{11}$ | | |
| 132 | 3-cyclo-$C_6H_{11}$ | | |
| 133 | 4-cyclo-$C_6H_{11}$ | | |
| 134 | 2,4-(cyclo-$C_6H_{11})_2$, 6-$CH_3$ | | |
| 135 | 2-$CH_3$, 4-cyclo-$C_6H_{11}$ | | |
| 136 | 2-$CH_2$—$C_6H_5$ | | |
| 137 | 3-$CH_2$—$C_6H_5$ | | |
| 138 | 4-$CH_2$—$C_2H_5$ | | |
| 139 | 2-$CH_2$—$C_6H_5$, 4-$CH_3$ | | |
| 140 | 2-$CH_3$, 4-$CH_2$—$C_6H_5$ | | |
| 141 | 2-$C_6H_5$ | | |
| 142 | 3-$C_6H_5$ | | |
| 143 | 4-$C_6H_5$ | | |
| 144 | 4-(2-i-$C_3H_7$—$C_6H_4$) | | |

TABLE 8-continued

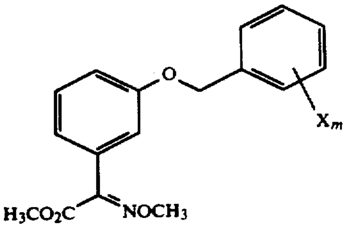

| No. | $X_m$ | mp | NMR: δ (ppm) |
|---|---|---|---|
| 145 | 4-$C_6H_5$, 2,6-$(CH_3)_2$ | | |
| 146 | 2-Cl, 4-$C_6H_5$ | | |
| 147 | 2-Br, 4-$C_6H_5$ | | |
| 148 | 2-$C_6H_5$, 4-Cl | | |
| 149 | 2-$C_6H_5$, 4-Br | | |
| 150 | 2-$CH_2C_6H_5$, 4-Cl | | |
| 151 | 2-$CH_2C_6H_5$, 4-Br | | |
| 152 | 2-Cl, 4-$CH_2C_6H_5$ | | |
| 153 | 2-Br, 4-$CH_2C_6H_5$ | | |
| 154 | 2-cyclo-$C_6H_{11}$, 4-Cl | | |
| 155 | 2-cyclo-$C_6H_{11}$, 4-Br | | |
| 156 | 2-Cl, 4-cyclo-$C_6H_{11}$ | | |
| 157 | 2-Br, 4-cyclo-$C_6H_{11}$ | | |
| 158 | 2-$OCH_3$ | | |
| 159a | 3-$OCH_3$: non-polar isomer | oil | 3.80; 3, 95, 4.05(3s, 3H in each case); 5.05(s, 2H) |
| 159b | 3-$OCH_3$: polar isomer | oil | 3.80; 3.90, 4.05(3s, 3H in each case); 5.05(s, 2H) |
| 160 | 4-$OCH_3$ | | |
| 161 | 2-$OC_2H_5$ | | |
| 162 | 3-O-$C_2H_5$ | | |
| 163 | 4-O-$C_2H_5$ | | |
| 164 | 2-O-n-$C_3H_7$ | | |
| 165 | 3-O-n-$C_3H_7$ | | |
| 166 | 4-O-n-$C_3H_7$ | | |
| 167 | 2-O-i-$C_3H_7$ | | |
| 168 | 3-O-i-$C_3H_7$ | | |
| 169 | 4-O-i-$C_3H_7$ | | |
| 170 | 2-O-n-$C_6H_{13}$ | | |
| 171 | 3-O-n-$C_6H_{13}$ | | |
| 172 | 4-O-n-$C_6H_{13}$ | | |
| 173 | 2-O-n-$C_8H_{17}$ | | |
| 174 | 3-O-n-$C_8H_{17}$ | | |
| 175 | 4-O-n-$C_8H_{17}$ | | |
| 176 | 2-O-$CH_2C_6H_5$ | | |
| 177 | 3-O-$CH_2C_6H_5$ | | |
| 178 | 4-O-$CH_2C_6H_5$ | | |
| 179 | 2-O-$(CH_2)_3C_6H_5$ | | |
| 180 | 3-O-$(CH_2)_3C_6H_5$ | | |
| 181 | 4-O-$(CH_2)_3C_6H_5$ | | |
| 182 | 2,4-$(OCH_3)_2$ | | |
| 183 | 2-$CF_3$ | | |
| 184 | 3-$CF_3$ | | |
| 185 | 4-$CF_3$ | | |
| 186 | 2-$OCF_3$ | | |
| 187 | 3-$OCF_3$ | | |
| 188 | 4-$OCF_3$ | | |
| 189 | 3-$OCH_2CHF_2$ | | |
| 190 | 2-$NO_2$ | | |
| 191 | 3-$NO_2$ | | |
| 192 | 4-$NO_2$ | | |
| 193 | 2-CN | | |
| 194 | 3-CN | | |
| 195 | 4-CN | | |
| 196 | 2-$CH_3$, 3-Cl | | |
| 197 | 2-$CH_3$, 4-Cl | | |
| 198 | 2-$CH_3$, 5-Cl | | |
| 199 | 2-$CH_3$, 6-Cl | | |
| 200 | 2-$CH_3$, 3-F | | |
| 201 | 2-$CH_3$, 4-F | | |
| 202 | 2-$CH_3$, 5-F | | |
| 203 | 2-$CH_3$, 6-F | | |
| 204 | 2-$CH_3$, 3-Br | | |
| 205 | 2-$CH_3$, 4-Br | | |
| 206 | 2-$CH_3$, 5-Br | | |
| 207 | 2-$CH_3$, 6-Br | | |
| 208 | 2-Cl, 3-$CH_3$ | | |
| 209 | 2-Cl, 4-$CH_3$ | | |
| 210 | 2-Cl, 5-$CH_3$ | | |

TABLE 8-continued

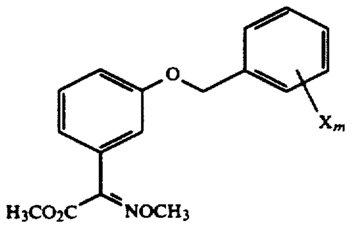

| No. | $X_m$ | mp | NMR: δ (ppm) |
|---|---|---|---|
| 211 | 2-F, 3-$CH_3$ | | |
| 212 | 2-F, 4-$CH_3$ | | |
| 213 | 2-F, 5-$CH_3$ | | |
| 214 | 2-Br, 3-$CH_3$ | | |
| 215 | 2-Br, 4-$CH_3$ | | |
| 216 | 2-Br, 5-$CH_3$ | | |
| 217 | 3-$CH_3$, 4-Cl | | |
| 218 | 3-$CH_3$, 5-Cl | | |
| 219 | 3-$CH_3$, 4-F | | |
| 220 | 3-$CH_3$, 4-Br | | |
| 221 | 3-$CH_3$, 4-Br | | |
| 222 | 3-$CH_3$, 5-Br | | |
| 223 | 3-F, 4-$CH_3$ | | |
| 224 | 3-Cl, 4-$CH_3$ | | |
| 225 | 3-Br, 4-$CH_3$ | | |
| 226 | 2-Cl, 4,5-$(CH_3)_2$ | | |
| 227 | 2-Br, 4,5-$(CH_3)_2$ | | |
| 228 | 2-Cl, 3,5-$(CH_3)_2$ | | |
| 229 | 2-Br, 3,5-$(CH_3)_2$ | | |
| 230 | 2,6-$Cl_2$, 4-$CH_3$ | | |
| 231 | 2,6-$F_2$, 4-$CH_3$ | | |
| 232 | 2,6-$Br_2$, 4-$CH_3$ | | |
| 233 | 2,4-$Cl_2$, 6-$CH_3$ | | |
| 234 | 2,4-$F_2$, 6-$CH_3$ | | |
| 235 | 2,4-$Br_2$, 6-$CH_3$ | | |
| 236 | 2,6-$(CH_3)_2$, 4-F | | |
| 237 | 2,6-$(CH_3)_2$, 4-Cl | | |
| 238 | 2,6-$(CH_3)_2$, 4-Br | | |
| 239 | 3,5-$(CH_3)_2$, 4-F | | |
| 240 | 3,5-$(CH_3)_2$, 4-Cl | | |
| 241 | 3,5-$(CH_3)_2$, 4-Br | | |
| 242 | 2,3,6-$(CH_3)_3$, 4-F | | |
| 243 | 2,3,6-$(CH_3)_3$, 4-Cl | | |
| 244 | 2,3,6-$(CH_3)_3$, 4-Br | | |
| 245 | 2,4-$(CH_3)_2$, 6-F | | |
| 246 | 2,4-$(CH_3)_2$, 6-Cl | | |
| 247 | 2,4-$(CH_3)_{62}$, 6-Br | | |
| 248 | 2-i-$C_3H_7$, 4-Cl, 5-$CH_3$ | | |
| 249 | 2-Cl, 4-$NO_2$ | | |
| 250 | 2-$NO_2$, 4-Cl | | |
| 251 | 2-$OCH_3$, 5-$NO_2$ | | |
| 252 | 2,4-$Cl_2$, 5-$NO_2$ | | |
| 253 | 2,4-$Cl_2$, 6-$NO_2$ | | |
| 254 | 2,6-$Cl_2$, 4-$NO_2$ | | |
| 255 | 2,6-$Br_2$, 4-$NO_2$ | | |
| 256 | 2,6-$I_2$, 4-$NO_2$ | | |
| 257 | 2-$CH_3$, 5-i-$C_3H_7$, 4-Cl | | |
| 258 | 2-$C_6H_5O$ | | |
| 259 | 3-$C_6H_5O$ | | |
| 260 | 4-$C_6H_5O$ | | |
| 261 | 2-$CHNOCH_3$ | | |
| 262 | 3-$CHNOCH_3$ | | |
| 263 | 4-$CHNOCH_3$ | | |
| 264 | 2-$CHNOC_2H_5$ | | |
| 265 | 3-$CHNOC_2H_5$ | | |
| 266 | 4-$CHNOC_2H_5$ | | |
| 267 | 2-CHNO(n-$C_3H_7$) | | |
| 268 | 3-CHNO(n-$C_3H_7$) | | |
| 269 | 4-CHNO(n-$C_3H_7$) | | |
| 270 | 2-CHNO(i-$C_3H_7$) | | |
| 271 | 3-CHNO(i-$C_3H_7$) | | |
| 272 | 4-CHNO(i-$C_3H_7$) | | |
| 273 | 2-CHNO(n-$C_6H_{13}$) | | |
| 274 | 3-CHNO(n-$C_6H_{13}$) | | |
| 275 | 4-CHNO(n-$C_6H_{13}$) | | |
| 276 | 2-CHNO(n-$C_8H_{17}$) | | |
| 277 | 3-CHNO(n-$C_8H_{17}$) | | |
| 278 | 4-CHNO(n-$C_8H_{17}$) | | |
| 279 | 2-$CHNOCH_2(C_6H_5)$ | | |

TABLE 8-continued

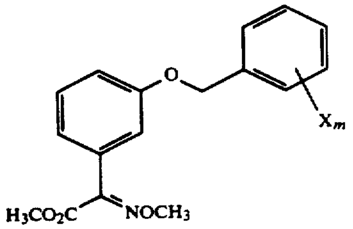

| No. | $X_m$ | mp | NMR: δ (ppm) |
|---|---|---|---|
| 280 | 3-$CHNOCH_2(C_6H_5)$ | | |
| 281 | 4-$CHNOCH_2(C_6H_5)$ | | |
| 282 | 2-$CO_2CH_3$ | | |
| 283 | 3-$CO_2CH_3$ | | |
| 284 | 4-$CO_2CH_3$ | | |
| 285 | 2-$CO_2(C_2H_5)$ | | |
| 286 | 3-$CO_2(C_2H_5)$ | | |
| 287 | 4-$CO_2(C_2H_5)$ | | |
| 288 | 2-$CO_2$(n-$C_3H_7$) | | |
| 289 | 3-$CO_2$(n-$C_3H_7$) | | |
| 290 | 4-$CO_2$(n-$C_3H_7$) | | |
| 291 | 2-$CO_2$(i-$C_3H_7$) | | |
| 292 | 3-$CO_2$(i-$C_3H_7$) | | |
| 293 | 4-$CO_2$(i-$C_3H_7$) | | |
| 294 | 2-$CO_2$(n-$C_6H_{13}$) | | |
| 295 | 3-$CO_2$(n-$C_6H_{13}$) | | |
| 296 | 4-$CO_2$(n-$C_6H_{13}$) | | |
| 297 | 2-$CO_2$(n-$C_8H_{17}$) | | |
| 298 | 3-$CO_2$(n-$C_8H_{17}$) | | |
| 299 | 4-$CO_2$(n-$C_8H_{17}$) | | |
| 300 | 2-$CHNO-CH_2-CH=CH_2$ | | |
| 301 | 3-$CHNO-CH_2-CH=CH_2$ | | |
| 302 | 4-$CHNO-CH_2-CH=CH_2$ | | |
| 303 | 2-$CHNO(CH_2)_3(C_6H_5)$ | | |
| 304 | 3-$CHNO(CH_2)_3(C_6H_5)$ | | |
| 305 | 4-$CHNO(CH_2)_3(C_6H_5)$ | | |
| 306 | 2-$CH_2OCH_3$ | | |
| 307 | 3-$CH_2OCH_3$ | | |
| 308 | 4-$CH_2OCH_3$ | | |
| 309 | 2-$CH_2O(C_2H_5)$ | | |
| 310 | 3-$CH_2O(C_2H_5)$ | | |
| 311 | 4-$CH_2O(C_2H_5)$ | | |
| 312 | 2-$CH_2O$(n-$C_3H_7$) | | |
| 313 | 3-$CH_2O$(n-$C_3H_7$) | | |
| 314 | 4-$CH_2O$(n-$C_3H_7$) | | |
| 315 | 2-$CH_2O$(i-$C_3H_7$) | | |
| 316 | 3-$CH_2O$(i-$C_3H_7$) | | |
| 317 | 4-($CH_2O$(i-$C_3H_7$) | | |
| 318 | 2-$CH_2O$(n-$C_6H_{13}$) | | |
| 319 | 3-$CH_2O$(n-$C_6H_{13}$) | | |
| 320 | 4-$CH_2O$(n-$C_6H_{13}$) | | |
| 321 | 2-$CH_2O$(n-$C_8H_{17}$) | | |
| 322 | 3-$CH_2O$(n-$C_8H_{17}$) | | |
| 323 | 4-$CH_2O$(n-$C_8H_7$) | | |
| 324 | 2-$CH_2OCH_2(C_6H_5)$ | | |
| 325 | 3-$CH_2OCH_2(C_6H_5)$ | | |
| 326 | 4-$CH_2OCH_2(C_6H_5)$ | | |
| 327 | 2-$CH_2O(CH_2)_3$ | | |
| 328 | 3-$CH_2O(CH_2)_3(C_6H_5)$ | | |
| 329 | 4-$CH_2O(CH_2)_3(C_6H_5)$ | | |
| 330 | 2-CHO | | |
| 331 | 3-CHO | | |
| 332 | 4-CHO | | |

TABLE 9

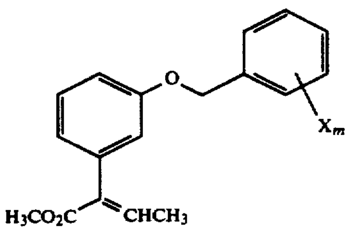

TABLE 9-continued

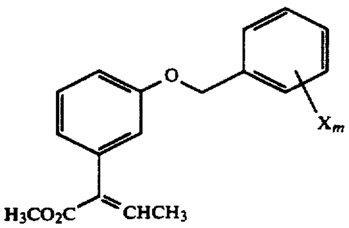

| No. | $X_m$ | mp | NMR: δ (ppm) |
|---|---|---|---|
| 1 | 2-F | | |
| 2 | 3-F | | |
| 3 | 4-F | | |
| 4 | 2,4-$F_2$ | | |
| 5 | 2,4,6-$F_3$ | | |
| 6 | 2,3,4,5,6,-$F_5$ | | |
| 7 | 2,3-$F_2$ | | |
| 8 | 2-Cl | | |
| 9 | 3-Cl | | |
| 10 | 4-Cl | | |
| 11 | 2,3-$Cl_2$ | | |
| 12 | 2,4-$Cl_2$ | | |
| 13 | 2,5-$Cl_2$ | | |
| 14 | 2,6-$Cl_2$ | | |
| 15 | 3,4-$Cl_2$ | | |
| 16 | 3,5-$Cl_2$ | | |
| 17 | 2,3,4-$Cl_3$ | | |
| 18 | 2,3,5-$Cl_3$ | | |
| 19 | 2,3,6-$Cl_3$ | | |
| 20 | 2,4,5-$Cl_3$ | | |
| 21 | 2,4,6-$Cl_3$ | | |
| 22 | 3,4,5-$Cl_3$ | | |
| 23 | 2,3,4,6-$Cl_4$ | | |
| 24 | 2,3,5,6-$Cl_4$ | | |
| 25 | 2,3,4,5,6,-$Cl_5$ | | |
| 26 | 2-Br | | |
| 27 | 3-Br | | |
| 28 | 4-Br | | |
| 29 | 2,4-$Br_2$ | | |
| 30 | 2,5-$Br_5$ | | |
| 31 | 2,6-$Br_2$ | | |
| 32 | 2,4,6-$Br_3$ | | |
| 33 | 2,3,4,5,6-$Br_5$ | | |
| 34 | 2-I | | |
| 35 | 3-I | | |
| 36 | 4-I | | |
| 37 | 2,4-$I_2$ | | |
| 38 | 2-Cl, 3-F | | |
| 39 | 2-Cl, 4-F | | |
| 40 | 2-Cl, 5-F | | |
| 41 | 2-Cl, 6-F | | |
| 42 | 2-Cl, 3-Br | | |
| 43 | 2-Cl, 4-Br | | |
| 44 | 2-Cl, 6-Br | | |
| 45 | 2-Cl, 6-Br | | |
| 46 | 2-Br, 3-Cl | | |
| 47 | 2-Br, 4-Cl | | |
| 48 | 2-Br, 5-Cl | | |
| 49 | 2-Br, 3-F | | |
| 50 | 2-Br, 4-F | | |
| 51 | 2-Br, 5-F | | |
| 52 | 2-Br, 6-F | | |
| 53 | 2-F, 3-Cl | | |
| 54 | 2-F, 4-Cl | | |
| 55 | 2-F, 5-Cl | | |
| 56 | 3-Cl, 4-F | | |
| 57 | 3-Cl, 5-F | | |
| 58 | 3-Cl, 4-Br | | |
| 59 | 3-Cl, 5-Br | | |
| 60 | 3-F, 4-Cl | | |
| 61 | 3-F, 4-Br | | |
| 62 | 3-Br, 4-Cl | | |
| 63 | 3-Br, 4-F | | |
| 64 | 2,6-$Cl_2$, 4-Br | | |
| 65 | 2-$CH_3$ | | |
| 66 | 3-$CH_3$ | | |
| 67 | 4-$CH_3$ | | |
| 68 | 2,3-$(CH_3)_2$ | | |
| 69 | 2,4-$(CH_3)_2$ | | |
| 70 | 2,5-$(CH_3)_2$ | | |
| 71 | 2,6-$(CH_3)_2$ | | |
| 72 | 3,4-$(CH_3)_2$ | | |
| 73 | 3,5-$(CH_3)_2$ | | |
| 74 | 3,5-$(CH_3)_2$ | | |
| 75 | 2,3,4-$(CH_3)_3$ | | |
| 76 | 2,3,6-$(CH_3)_3$ | | |
| 77 | 2,4,5-$(CH_3)_3$ | | |
| 78 | 2,4,6-$(CH_3)_3$ | | |
| 79 | 3,4,5-$(CH_3)_3$ | | |
| 80 | 2,3,4,6-$(CH_3)_4$ | | |
| 81 | 2,3,5,6-$(CH_3)_4$ | | |
| 82 | 2,3,4,5,6-$(CH_3)_5$ | | |
| 83 | 2-$C_2H_5$ | | |
| 84 | 3-$C_2H_5$ | | |
| 85 | 4-$C_2H_5$ | | |
| 86 | 2,4-$(C_2H_5)_2$ | | |
| 87 | 2,6-$(C_2H_5)_2$ | | |
| 88 | 3,5-$(C_2H_5)_2$ | | |
| 89 | 2,4,6-$(C_2H_5)_3$ | | |
| 90 | 2-n-$C_3H_7$ | | |
| 91 | 3-n-$C_3H_7$ | | |
| 92 | 4-n-$C_3H_7$ | | |
| 93 | 2-i-$C_3H_7$ | | |
| 94 | 3-i-$C_3H_7$ | | |
| 95 | 4-i-$C_3H_7$ | | |
| 96 | 2,4-(i-$C_3H_7$)$_2$ | | |
| 97 | 2,6-(i-$C_3H_7$)$_2$ | | |
| 98 | 3,5-(i-$C_3H_7$)$_2$ | | |
| 99 | 2,4,6-(i-$C_3H_7$)$_3$ | | |
| 100 | 2-S-$C_4H_9$ | | |
| 101 | 3-S-$C_4H_9$ | | |
| 102 | 4-S-$C_4H_9$ | | |
| 103 | 2-t-$C_4H_9$ | | |
| 104 | 3-t-$C_4H_9$ | | |
| 105 | 4-t-$C_4H_9$ | | |
| 106 | 2,3-(t-$C_4H_9$)$_2$ | | |
| 107 | 2,4-(t-$C_4H_9$)$_2$ | | |
| 108 | 2,5-(t-$C_4H_9$)$_2$ | | |
| 109 | 2,6-(t-$C_4H_9$)$_2$ | | |
| 110 | 3,4-(t-$C_4H_9$)$_2$ | | |
| 111 | 2,4,6-(t-$C_4H_9$)$_3$ | | |
| 112 | 4-n-$C_9H_{19}$ | | |
| 113 | 4-n-$C_{12}H_{25}$ | | |
| 114 | 3-n-$C_{15}H_{31}$ | | |
| 115 | 4-(1,1,3,3-tetramethylbutyl) | | |
| 116 | 4-(2,4,4-trimethylpropyl) | | |
| 117 | 2-t-$C_4H_9$, 4-$CH_3$ | | |
| 118 | 2-t-$C_4H_9$, 5-$CH_3$ | | |
| 119 | 2,6-(t-$C_4H_9$), 4-$CH_3$ | | |
| 120 | 2-$CH_3$, 4-t-$C_4H_9$ | | |
| 121 | 2-$CH_3$, 6-t-$C_4H_9$ | | |
| 122 | 2-$CH_3$, 4-i-$C_3H_7$ | | |
| 123 | 2-$CH_3$, 5-i-$C_3H_7$ | | |
| 124 | 3-$CH_3$, 4-i-$C_3H_7$ | | |
| 125 | 2-i-$C_3H_7$, 5 $CH_3$ | | |
| 126 | 2,4-(t-$C_4H_9$), 6-i-$C_3H_7$ | | |
| 127 | 2-allyl | | |
| 128 | 3-allyl | | |
| 129 | 4-allyl | | |
| 130 | 2-allyl, 6-$CH_3$ | | |
| 131 | 2-cyclo-$C_6H_{11}$ | | |
| 132 | 3-cyclo-$C_6H_{11}$ | | |
| 133 | 4-cyclo-$C_6H_{11}$ | | |
| 134 | 2,4-(cyclo-$C_6H_{11}$)$_2$, 6-$CH_3$ | | |
| 135 | 2-$CH_3$, 4-cyclo-$C_6H_{11}$ | | |
| 136 | 2-$CH_2$-$C_6H_5$ | | |
| 137 | 3-$CH_2$-$C_6H_5$ | | |
| 138 | 4-$CH_2$-$C_2H_5$ | | |

TABLE 9-continued

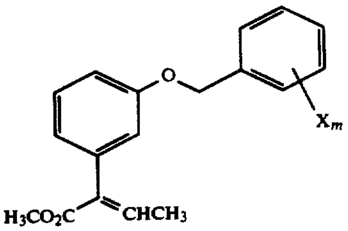

| No. | $X_m$ | mp | NMR: δ (ppm) |
|---|---|---|---|
| 139 | 2-$CH_2$-$C_6H_5$, 4-$CH_3$ | | |
| 140 | 2-$CH_3$, 4-$CH_2$-$C_6H_5$ | | |
| 141 | 2-$C_6H_5$ | | |
| 142 | 3-$C_6H_5$ | | |
| 143 | 4-$C_6H_5$ | | |
| 144 | 4-(2-i-$C_3H_7$-$C_6H_4$) | | |
| 145 | 4-$C_6H_5$, 2,6-$(CH_3)_2$ | | |
| 146 | 2-Cl, 4-$C_6H_5$ | | |
| 147 | 2-Br, 4-$C_6H_5$ | | |
| 148 | 2-$C_6H_5$, 4-Cl | | |
| 149 | 2-$C_6H_5$, 4-Br | | |
| 150 | 2-$CH_2C_6H_5$, 4-Cl | | |
| 151 | 2-$CH_2C_6H_5$, 5-Br | | |
| 152 | 2-Cl, 4-$CH_2C_6H_5$ | | |
| 153 | 2-Br, 4-$CH_2C_6H_5$ | | |
| 154 | 2-cyclo-$C_6H_{11}$, 4-Cl | | |
| 155 | 2-cyclo-$C_6H_{11}$, 4-Br | | |
| 156 | 2-Cl, 4-cyclo-$C_6H_{11}$ | | |
| 157 | 2-Br, 4-cyclo-$C_6H_{11}$ | | |
| 158 | 2-$OCH_3$ | | |
| 159 | 3-$OCH_3$ | | |
| 160 | 4-$OCH_3$ | | |
| 161 | 2-$OC_2H_5$ | | |
| 162 | 3-O-$C_2H_5$ | | |
| 163 | 4-O-$C_2H_5$ | | |
| 164 | 2-O-n-$C_3H_7$ | | |
| 165 | 3-O-n-$C_3H_7$ | | |
| 166 | 4-O-n-$C_3H_7$ | | |
| 167 | 2-O-i-$C_3H_7$ | | |
| 168 | 3-O-i-$C_3H_7$ | | |
| 169 | 4-O-i-$C_3H_7$ | | |
| 170 | 2-O-n-$C_6H_{13}$ | | |
| 171 | 3-O-n-$C_6H_{13}$ | | |
| 172 | 4-O-n-$C_6H_{13}$ | | |
| 173 | 2-O-n-$C_8H_{17}$ | | |
| 174 | 3-O-n-$C_8H_{17}$ | | |
| 175 | 4-O-n-$C_8H_{17}$ | | |
| 176 | 2-O-$CH_2C_6H_5$ | | |
| 177 | 3-O-$CH_2C_6H_5$ | | |
| 178 | 4-O-$CH_2C_6H_5$ | | |
| 179 | 2-O-$(CH_2)_3C_6H_5$ | | |
| 180 | 3-O-$(CH_2)_3C_6H_5$ | | |
| 181 | 4-O-$(CH_2)_3C_6H_5$ | | |
| 182 | 2,4-$(OCH_3)_2$ | | |
| 183 | 2-$CF_3$ | | |
| 184 | 3-$CF_3$ | | |
| 185 | 4-$CF_3$ | | |
| 186 | 2-$OCF_3$ | | |
| 187 | 3-$OCF_3$ | | |
| 188 | 4-$OCF_3$ | | |
| 189 | 3-$OCH_2CHF_2$ | | |
| 190 | 2-$NO_2$ | | |
| 191 | 3-$NO_2$ | | |
| 192 | 4-$NO_2$ | | |
| 193 | 2-CN | | |
| 194 | 3-CN | | |
| 195 | 4-CN | | |
| 196 | 2-$CH_3$, 3-Cl | | |
| 197 | 2-$CH_3$, 4-Cl | | |
| 198 | 2-$CH_3$, 5-Cl | | |
| 199 | 2-$CH_3$, 6-Cl | | |
| 200 | 2-$CH_3$, 3-F | | |
| 201 | 2-$CH_3$, 4-F | | |
| 202 | 2-$CH_3$, 5-F | | |
| 203 | 2-$CH_3$, 6-F | | |
| 204 | 2-$CH_3$, 3-Br | | |
| 205 | 2-$CH_3$, 4-Br | | |
| 206 | 2-$CH_3$, 5-Br | | |
| 207 | 2-$CH_3$, 6-Br | | |

TABLE 9-continued

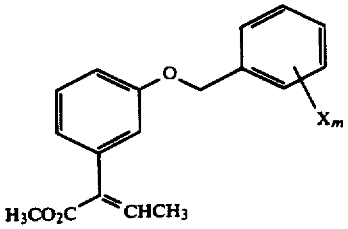

| No. | $X_m$ | mp | NMR: δ (ppm) |
|---|---|---|---|
| 208 | 2-Cl, 3-$CH_3$ | | |
| 209 | 2-Cl, 4-$CH_3$ | | |
| 210 | 2-Cl, 5-$CH_3$ | | |
| 211 | 2-F, 3-$CH_3$ | | |
| 212 | 2-F, 4-$CH_3$ | | |
| 213 | 2-F, 5-$CH_3$ | | |
| 214 | 2-Br, 3-$CH_3$ | | |
| 215 | 2-Br, 4-$CH_3$ | | |
| 216 | 2-Br, 5-$CH_3$ | | |
| 217 | 3-$CH_3$, 4-Cl | | |
| 218 | 3-$CH_3$, 5-Cl | | |
| 219 | 3-$CH_3$, 4-F | | |
| 220 | 3-$CH_3$, 4-Br | | |
| 221 | 3-$CH_3$, 4-Br | | |
| 222 | 3-$CH_3$, 5-Br | | |
| 223 | 3-F, 4-$CH_3$ | | |
| 224 | 3-Cl, 4-$CH_3$ | | |
| 225 | 3-Br, 4-$CH_3$ | | |
| 226 | 2-Cl, 4,5-$(CH_3)_2$ | | |
| 227 | 2-Br, 4,5-$(CH_3)_2$ | | |
| 228 | 2-Cl, 3,5-$(CH_3)_2$ | | |
| 229 | 2-Br, 3,5-$(CH_3)_2$ | | |
| 230 | 2,6-$Cl_2$, 4-$CH_3$ | | |
| 231 | 2,6-$F_2$, 4-$CH_3$ | | |
| 232 | 2,6-$Br_2$, 4-$CH_3$ | | |
| 233 | 2,4-$Cl_2$, 6-$CH_3$ | | |
| 234 | 2,4-$F_2$, 6-$CH_3$ | | |
| 235 | 2,4-$Br_2$, 6-$CH_3$ | | |
| 236 | 2,6-$(CH_3)_2$, 4-F | | |
| 237 | 2,6-$(CH_3)_2$, 4-Cl | | |
| 238 | 2,6-$(CH_3)_2$, 4-Br | | |
| 239 | 3,5-$(CH_3)_2$, 4-F | | |
| 240 | 3,5-$(CH_3)_2$, 4-Cl | | |
| 241 | 3,5-$(CH_3)_2$, 4-Br | | |
| 242 | 2,3,6-$(CH_3)_3$, 4-F | | |
| 243 | 2,3,6-$(CH_3)_3$, 4-Cl | | |
| 244 | 2,3,6-$(CH_3)_3$, 4-Br | | |
| 245 | 2,4-$(CH_3)_2$, 6-F | | |
| 246 | 2,4-$(CH_3)_2$, 6-Cl | | |
| 247 | 2,4-$(CH_3)$62, 6-Br | | |
| 248 | 2-i-$C_3H_7$, 4-Cl, 5-$CH_3$ | | |
| 249 | 2-Cl, 4-$NO_2$ | | |
| 250 | 2-$NO_2$, 4-Cl | | |
| 251 | 2-$OCH_3$, 5-$NO_2$ | | |
| 252 | 2,4-$Cl_2$, 5-$NO_2$ | | |
| 253 | 2,4-$Cl_2$, 6-$NO_2$ | | |
| 254 | 2,6-$Cl_2$, 4-$NO_2$ | | |
| 255 | 2,6-$Br_2$, 4-$NO_2$ | | |
| 256 | 2,6-$I_2$, 4-$NO_2$ | | |
| 257 | 2-$CH_3$, 5-i-$C_3H_7$, 4-Cl | | |
| 258 | 2-$C_6H_5O$ | | |
| 259 | 3-$C_6H_5O$ | | |
| 260 | 4-$C_6H_5O$ | | |
| 261 | 2-$CHNOCH_3$ | | |
| 262 | 3-$CHNOCH_3$ | | |
| 263 | 4-$CHNOCH_3$ | | |
| 264 | 2-$CHNOC_2H_5$ | | |
| 265 | 3-$CHNOC_2H_5$ | | |
| 266 | 4-$CHNOC_2H_5$ | | |
| 267 | 2-CHNO(n-$C_3H_7$) | | |
| 268 | 3-CHNO(n-$C_3H_7$) | | |
| 269 | 4-CHNO(n-$C_3H_7$) | | |
| 270 | 2-CHNO(i-$C_3H_7$) | | |
| 271 | 3-CHNO(i-$C_3H_7$) | | |
| 272 | 4-CHNO(i-$C_3H_7$) | | |
| 273 | 2-CHNO(n-$C_6H_{13}$) | | |
| 274 | 3-CHNO(n-$C_6H_{13}$) | | |
| 275 | 4-CHNO(n-$C_6H_{13}$) | | |
| 276 | 2-CHNO(n-$C_8H_{17}$) | | |

TABLE 9-continued

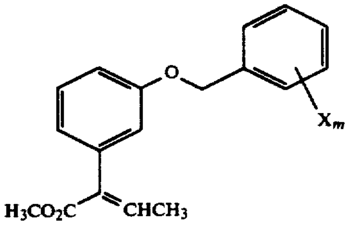

| No. | $X_m$ | mp | NMR: δ (ppm) |
|---|---|---|---|
| 277 | 3-CHNO(n-$C_8H_{17}$) | | |
| 278 | 4-CHNO(n-$C_8H_{17}$) | | |
| 279 | 2-CHNOCH$_2$($C_6H_5$) | | |
| 280 | 3-CHNOCH$_2$($C_6H_5$) | | |
| 281 | 4-CHNOCH$_2$($C_6H_5$) | | |
| 282 | 2-$CO_2CH_3$ | | |
| 283 | 3-$CO_2CH_3$ | | |
| 284 | 4-$CO_2CH_3$ | | |
| 285 | 2-$CO_2$($C_2H_5$) | | |
| 286 | 3-$CO_2$($C_2H_5$) | | |
| 287 | 4-$CO_2$($C_2H_5$) | | |
| 288 | 2-$CO_2$(n-$C_3H_7$) | | |
| 289 | 3-$CO_2$(n-$C_3H_7$) | | |
| 290 | 4-$CO_2$(n-$C_3H_7$) | | |
| 291 | 2-$CO_2$(i-$C_3H_7$) | | |
| 292 | 3-$CO_2$(i-$C_3H_7$) | | |
| 293 | 4-$CO_2$(i-$C_3H_7$) | | |
| 294 | 2-$CO_2$(n-$C_6H_{13}$) | | |
| 295 | 3-$CO_2$(n-$C_6H_{13}$) | | |
| 296 | 4-$CO_2$(n-$C_6H_{13}$) | | |
| 297 | 2-$CO_2$(n-$C_8H_{17}$) | | |
| 298 | 3-$CO_2$(n-$C_8H_{17}$) | | |
| 299 | 4-$CO_2$(n-$C_8H_{17}$) | | |
| 300 | 2-CHNO—$CH_2$—CH=$CH_2$ | | |
| 301 | 3-CHNO—$CH_2$—CH=$CH_2$ | | |
| 302 | 4-CHNO—$CH_2$—CH=$CH_2$ | | |
| 303 | 2-CHNO($CH_2$)$_3$($C_6H_5$) | | |
| 304 | 3-CHNO($CH_2$)$_3$($C_6H_5$) | | |
| 305 | 4-CHNO($CH_2$)$_3$($C_6H_5$) | | |
| 306 | 2-$CH_2OCH_3$ | | |
| 307 | 3-$CH_2OCH_3$ | | |
| 308 | 4-$CH_2OCH_3$ | | |
| 309 | 2-$CH_2O$($C_2H_5$) | | |
| 310 | 3-$CH_2O$($C_2H_5$) | | |
| 311 | 4-$CH_2O$($C_2H_5$) | | |
| 312 | 2-$CH_2O$(n-$C_3H_7$) | | |
| 313 | 3-$CH_2O$(n-$C_3H_7$) | | |
| 314 | 4-$CH_2O$(n-$C_3H_7$) | | |
| 315 | 2-$CH_2O$(i-$C_3H_7$) | | |
| 316 | 3-$CH_2O$(i-$C_3H_7$) | | |
| 317 | 4-($CH_2O$(i-$C_3H_7$) | | |
| 318 | 2-$CH_2O$(n-$C_6H_{13}$) | | |
| 319 | 3-$CH_2O$(n-$C_6H_{13}$) | | |
| 320 | 4-$CH_2O$(n-$C_6H_{13}$) | | |
| 321 | 2-$CH_2O$(n-$C_8H_{17}$) | | |
| 322 | 3-$CH_2O$(n-$C_8H_{17}$) | | |
| 323 | 4-$CH_2O$(n-$C_8H_7$) | | |
| 324 | 2-$CH_2OCH_2$($C_6H_5$) | | |
| 325 | 3-$CH_2OCH_2$($C_6H_5$) | | |
| 326 | 4-$CH_2OCH_2$($C_6H_5$) | | |
| 327 | 2-$CH_2O$($CH_2$)$_3$ | | |
| 328 | 3-$CH_2O$($CH_2$)$_3$($C_6H_5$) | | |
| 329 | 4-$CH_2O$($CH_2$)$_3$($C_6H_5$) | | |
| 330 | 2-CHO | | |
| 331 | 3-CHO | | |
| 332 | 4-CHO | | |

TABLE 10

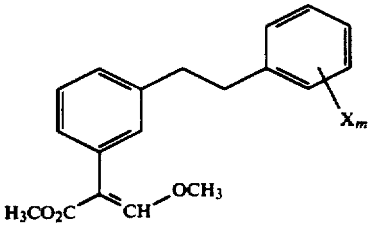

| No. | $X_m$ | mp | NMR: δ (ppm) |
|---|---|---|---|
| 1 | 2-F | | |
| 2 | 3-F | | |
| 3 | 4-F | | |
| 4 | 2,4-$F_2$ | | |
| 5 | 2,4,6-$F_3$ | | |
| 6 | 2,3,4,5,6-$F_5$ | | |
| 7 | 2,3-$F_2$ | | |
| 8 | 2-Cl | | |
| 9 | 3-Cl | | |
| 10 | 4-Cl | | |
| 11 | 2,3-$Cl_2$ | | |
| 12 | 2,4-$Cl_2$ | | |
| 13 | 2,5-$Cl_2$ | | |
| 14 | 2,6-$Cl_2$ | | |
| 15 | 3,4-$Cl_2$ | | |
| 16 | 3,5-$Cl_2$ | | |
| 17 | 2,3,4-$Cl_3$ | | |
| 18 | 2,3,5-$Cl_3$ | | |
| 19 | 2,3,6-$Cl_3$ | | |
| 20 | 2,4,5-$Cl_3$ | | |
| 21 | 2,4,6-$Cl_3$ | | |
| 22 | 3,4,5-$Cl_3$ | | |
| 23 | 2,3,4,6-$Cl_4$ | | |
| 24 | 2,3,5,6-$Cl_4$ | | |
| 25 | 2,3,4,5,6-$Cl_5$ | | |
| 26 | 2-Br | | |
| 27 | 3-Br | | |
| 28 | 4-Br | | |
| 29 | 2,4-$Br_2$ | | |
| 30 | 2,5-$Br_5$ | | |
| 31 | 2,6-$Br_2$ | | |
| 32 | 2,4,6-$Br_3$ | | |
| 33 | 2,3,4,5,6-$Br_5$ | | |
| 34 | 2-I | | |
| 35 | 3-I | | |
| 36 | 4-I | | |
| 37 | 2,4-$I_2$ | | |
| 38 | 2-Cl, 3-F | | |
| 39 | 2-Cl, 4-F | | |
| 40 | 2-Cl, 5-F | | |
| 41 | 2-Cl, 6-F | | |
| 42 | 2-Cl, 3-Br | | |
| 43 | 2-Cl, 4-Br | | |
| 44 | 2-Cl, 6-Br | | |
| 45 | 2-Cl, 6-Br | | |
| 46 | 2-Br, 3-Cl | | |
| 47 | 2-Br, 4-Cl | | |
| 48 | 2-Br, 5-Cl | | |
| 49 | 2-Br, 3-F | | |
| 50 | 2-Br, 4-F | | |
| 51 | 2-Br, 5-F | | |
| 52 | 2-Br, 6-F | | |
| 53 | 2-F, 3-Cl | | |
| 54 | 2-F, 4-Cl | | |
| 55 | 2-F, 5-Cl | | |
| 56 | 3-Cl, 4-F | | |
| 57 | 3-Cl, 5-F | | |
| 58 | 3-Cl, 4-Br | | |
| 59 | 3-Cl, 5-Br | | |
| 60 | 3-F, 4-Cl | | |
| 61 | 3-F, 4-Br | | |
| 62 | 3-Br, 4-Cl | | |
| 63 | 3-Br, 4-F | | |
| 64 | 2,6-$Cl_2$, 4-Br | | |
| 65 | 2-$CH_3$ | | |
| 66 | 3-$CH_3$ | | |
| 67 | 4-$CH_3$ | | |
| 68 | 2,3-($CH_3$)$_2$ | | |
| 69 | 2,4-($CH_3$)$_2$ | | |

TABLE 10-continued

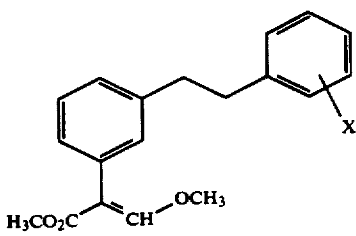

| No. | $X_m$ | mp | NMR: δ (ppm) |
|---|---|---|---|
| 70 | 2,5-$(CH_3)_2$ | | |
| 71 | 2,6-$(CH_3)_2$ | | |
| 72 | 3,4-$(CH_3)_2$ | | |
| 73 | 3,5-$(CH_3)_2$ | | |
| 74 | 3,5-$(CH_3)_2$ | | |
| 75 | 2,3,4-$(CH_3)_3$ | | |
| 76 | 2,3,6-$(CH_3)_3$ | | |
| 77 | 2,4,5-$(CH_3)_3$ | | |
| 78 | 2,4,6-$(CH_3)_3$ | | |
| 79 | 3,4,5-$(CH_3)_3$ | | |
| 80 | 2,3,4,6-$(CH_3)_4$ | | |
| 81 | 2,3,5,6-$(CH_3)_4$ | | |
| 82 | 2,3,4,5,6-$(CH_3)_5$ | | |
| 83 | 2-$C_2H_5$ | | |
| 84 | 3-$C_2H_5$ | | |
| 85 | 4-$C_2H_5$ | | |
| 86 | 2,4-$(C_2H_5)_2$ | | |
| 87 | 2,6-$(C_2H_5)_2$ | | |
| 88 | 3,5-$(C_2H_5)_2$ | | |
| 89 | 2,4,6-$(C_2H_5)_3$ | | |
| 90 | 2-n-$C_3H_7$ | | |
| 91 | 3-n-$C_3H_7$ | | |
| 92 | 4-n-$C_3H_7$ | | |
| 93 | 2-i-$C_3H_7$ | | |
| 94 | 3-i-$C_3H_7$ | | |
| 95 | 4-i-$C_3H_7$ | | |
| 96 | 2,4-(i-$C_3H_7)_2$ | | |
| 97 | 2,6-(i-$C_3H_7)_2$ | | |
| 98 | 3,5-(i-$C_3H_7)_2$ | | |
| 99 | 2,4,6-(i-$C_3H_7)_3$ | | |
| 100 | 2-S—$C_4H_9$ | | |
| 101 | 3-S—$C_4H_9$ | | |
| 102 | 4-S—$C_4H_9$ | | |
| 103 | 2-t-$C_4H_9$ | | |
| 104 | 3-t-$C_4H_9$ | | |
| 105 | 4-t-$C_4H_9$ | | |
| 106 | 2,3-(t-$C_4H_9)_2$ | | |
| 107 | 2,4-(t-$C_4H_9)_2$ | | |
| 108 | 2,5-(t-$C_4H_9)_2$ | | |
| 109 | 2,6-(t-$C_4H_9)_2$ | | |
| 110 | 3,4-(t-$C_4H_9)_2$ | | |
| 111 | 2,4,6-(t-$C_4H_9)_3$ | | |
| 112 | 4-n-$C_9H_{19}$ | | |
| 113 | 4-n-$C_{12}H_{25}$ | | |
| 114 | 3-n-$C_{15}H_{31}$ | | |
| 115 | 4-(1,1,3,3-tetramethylbutyl) | | |
| 116 | 4-(2,4,4-trimethylpropyl | | |
| 117 | 2-t-$C_4H_9$, 4-$CH_3$ | | |
| 118 | 2-t-$C_4H_9$, 5-$CH_3$ | | |
| 119 | 2,6-(t-$C_4H_9$), 4-$CH_3$ | | |
| 120 | 2-$CH_3$, 4-t-$C_4H_9$ | | |
| 121 | 2-$CH_3$, 6-t-$C_4H_9$ | | |
| 122 | 2-$CH_3$, 4-i-$C_3H_7$ | | |
| 123 | 2-$CH_3$, 5-i-$C_3H_7$ | | |
| 124 | 3-$CH_3$, 4-i-$C_3H_7$ | | |
| 125 | 2-i-$C_3H_7$, 5 $CH_3$ | | |
| 126 | 2,4-(t-$C_4H_9$), 6-i-$C_3H_7$ | | |
| 127 | 2-allyl | | |
| 128 | 3-allyl | | |
| 129 | 4-allyl | | |
| 130 | 2-allyl, 6-$CH_3$ | | |
| 131 | 2-cyclo-$C_6H_{11}$ | | |
| 132 | 3-cyclo-$C_6H_{11}$ | | |
| 133 | 4-cyclo-$C_6H_{11}$ | | |
| 134 | 2,4-(cyclo-$C_6H_{11})_2$, 6-$CH_3$ | | |
| 135 | 2-$CH_3$, 4-cyclo-$C_6H_{11}$ | | |
| 136 | 2-$CH_2$—$C_6H_5$ | | |
| 137 | 3-$CH_2$—$C_6H_5$ | | |
| 138 | 4-$CH_2$—$C_6H_5$ | | |

TABLE 10-continued

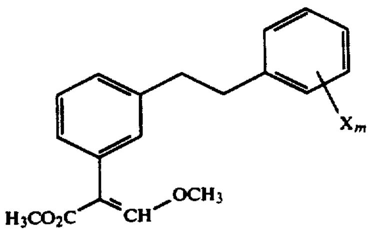

| No. | $X_m$ | mp | NMR: δ (ppm) |
|---|---|---|---|
| 139 | 2-$CH_2$—$C_6H_5$, 4-$CH_3$ | | |
| 140 | 2-$CH_3$, 4-$CH_2$—$C_6H_5$ | | |
| 141 | 2-$C_6H_5$ | | |
| 142 | 3-$C_6H_5$ | | |
| 143 | 4-$C_6H_5$ | | |
| 144 | 4-(2-i-$C_3H_7$—$C_6H_4$) | | |
| 145 | 4-$C_6H_5$, 2,6-$(CH_3)_2$ | | |
| 146 | 2-Cl, 4-$C_6H_5$ | | |
| 147 | 2-Br, 4-$C_6H_5$ | | |
| 148 | 2-$C_6H_5$, 4-Cl | | |
| 149 | 2-$C_6H_5$, 4-Br | | |
| 150 | 2-$CH_2C_6H_5$, 4-Cl | | |
| 151 | 2-$CH_2C_6H_5$, 4-Br | | |
| 152 | 2-Cl, 4-$CH_2C_6H_5$ | | |
| 153 | 2-Br, 4-$CH_2C_6H_5$ | | |
| 154 | 2-cyclo-$C_6H_{11}$, 4-Cl | | |
| 155 | 2-cyclo-$C_6H_{11}$, 4-Br | | |
| 156 | 2-Cl, 4-cyclo-$C_6H_{11}$ | | |
| 157 | 2-Br, 4-cyclo-$C_6H_{11}$ | | |
| 158 | 2-$OCH_3$ | | |
| 159 | 3-$OCH_3$ | | |
| 160 | 4-$OCH_3$ | | |
| 161 | 2-$OC_2H_5$ | | |
| 162 | 3-O—$C_2H_5$ | | |
| 163 | 4-O—$C_2H_5$ | | |
| 164 | 2-O-n-$C_3H_7$ | | |
| 165 | 3-O-n-$C_3H_7$ | | |
| 166 | 4-O-n-$C_3H_7$ | | |
| 167 | 2-O-i-$C_3H_7$ | | |
| 168 | 3-O-i-$C_3H_7$ | | |
| 169 | 4-O-i-$C_3H_7$ | | |
| 170 | 2-O-n-$C_6H_{13}$ | | |
| 171 | 3-O-n-$C_6H_{13}$ | | |
| 172 | 4-O-n-$C_6H_{13}$ | | |
| 173 | 2-O-n-$C_8H_{17}$ | | |
| 174 | 3-O-n-$C_8H_{17}$ | | |
| 175 | 4-O-n-$C_8H_{17}$ | | |
| 176 | 2-O—$CH_2C_6H_5$ | | |
| 177 | 3-O—$CH_2C_6H_5$ | | |
| 178 | 4-O—$CH_2C_6H_5$ | | |
| 179 | 2-O—$(CH_2)_3C_6H_5$ | | |
| 180 | 3-O—$(CH_2)_3C_6H_5$ | | |
| 181 | 4-O—$(CH_2)_3C_6H_5$ | | |
| 182 | 2,4-$(OCH_3)_2$ | | |
| 183 | 2-$CF_3$ | | |
| 184 | 3-$CF_3$ | | |
| 185 | 4-$CF_3$ | | |
| 186 | 2-$OCF_3$ | | |
| 187 | 3-$OCF_3$ | | |
| 188 | 4-$OCF_3$ | | |
| 189 | 3-$OCH_2CHF_2$ | | |
| 190 | 2-$NO_2$ | | |
| 191 | 3-$NO_2$ | | |
| 192 | 4-$NO_2$ | | |
| 193 | 2-CN | | |
| 194 | 3-CN | | |
| 195 | 4-CN | | |
| 196 | 2-$CH_3$, 3-Cl | | |
| 197 | 2-$CH_3$, 4-Cl | | |
| 198 | 2-$CH_3$, 5-Cl | | |
| 199 | 2-$CH_3$, 6-Cl | | |
| 200 | 2-$CH_3$, 3-F | | |
| 201 | 2-$CH_3$, 4-F | | |
| 202 | 2-$CH_3$, 5-F | | |
| 203 | 2-$CH_3$, 6-F | | |
| 204 | 2-$CH_3$, 3-Br | | |
| 205 | 2-$CH_3$, 4-Br | | |
| 206 | 2-$CH_3$, 5-Br | | |
| 207 | 2-$CH_3$, 6-Br | | |

TABLE 10-continued

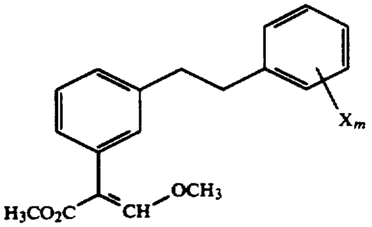

| No. | $X_m$ | mp | NMR: δ (ppm) |
|---|---|---|---|
| 208 | 2-Cl, 3-$CH_3$ | | |
| 209 | 2-Cl, 4-$CH_3$ | | |
| 210 | 2-Cl, 5-$CH_3$ | | |
| 211 | 2-F, 3-$CH_3$ | | |
| 212 | 2-F, 4-$CH_3$ | | |
| 213 | 2-F, 5-$CH_3$ | | |
| 214 | 2-Br, 3-$CH_3$ | | |
| 215 | 2-Br, 4-$CH_3$ | | |
| 216 | 2-Br, 5-$CH_3$ | | |
| 217 | 3-$CH_3$, 4-Cl | | |
| 218 | 3-$CH_3$, 5-Cl | | |
| 219 | 3-$CH_3$, 4-F | | |
| 220 | 3-$CH_3$, 4-Br | | |
| 221 | 3-$CH_3$, 4-Br | | |
| 222 | 3-$CH_3$, 5-Br | | |
| 223 | 3-F, 4-$CH_3$ | | |
| 224 | 3-Cl, 4-$CH_3$ | | |
| 225 | 3-Br, 4-$CH_3$ | | |
| 226 | 2-Cl, 4,5-$(CH_3)_2$ | | |
| 227 | 2-Br, 4,5-$(CH_3)_2$ | | |
| 228 | 2-Cl, 3,5-$(CH_3)_2$ | | |
| 229 | 2-Br, 3,5-$(CH_3)_2$ | | |
| 230 | 2,6-$Cl_2$, 4-$CH_3$ | | |
| 231 | 2,6-$F_2$, 4-$CH_3$ | | |
| 232 | 2,6-$Br_2$, 4-$CH_3$ | | |
| 233 | 2,4-$Cl_2$, 6-$CH_3$ | | |
| 234 | 2,4-$F_2$, 6-$CH_3$ | | |
| 235 | 2,4-$Br_2$, 6-$CH_3$ | | |
| 236 | 2,6-$(CH_3)_2$, 4-F | | |
| 237 | 2,6-$(CH_3)_2$, 4-Cl | | |
| 238 | 2,6-$(CH_3)_2$, 4-Br | | |
| 239 | 3,5-$(CH_3)_2$, 4-F | | |
| 240 | 3,5-$(CH_3)_2$, 4-Cl | | |
| 241 | 3,5-$(CH_3)_2$, 4-Br | | |
| 242 | 2,3,6-$(CH_3)_3$, 4-F | | |
| 243 | 2,3,6-$(CH_3)_3$, 4-Cl | | |
| 244 | 2,3,6-$(CH_3)_3$, 4-Br | | |
| 245 | 2,4-$(CH_3)_2$, 6-F | | |
| 246 | 2,4-$(CH_3)_2$, 6-Cl | | |
| 247 | 2,4-$(CH_3)_{62}$, 6-Br | | |
| 248 | 2-i-$C_3H_7$, 4-Cl, 5-$CH_3$ | | |
| 249 | 2-Cl, 4-$NO_2$ | | |
| 250 | 2-$NO_2$, 4-Cl | | |
| 251 | 2-$OCH_3$, 5-$NO_2$ | | |
| 252 | 2,4-$Cl_2$, 5-$NO_2$ | | |
| 253 | 2,4-$Cl_2$, 6-$NO_2$ | | |
| 254 | 2,6-$Cl_2$, 4-$NO_2$ | | |
| 255 | 2,6-$Br_2$, 4-$NO_2$ | | |
| 256 | 2,6-$I_2$, 4-$NO_2$ | | |
| 257 | 2-$CH_3$, 5-i-$C_3H_7$, 4-Cl | | |
| 258 | 2-$C_6H_5O$ | | |
| 259 | 3-$C_6H_5O$ | | |
| 260 | 4-$C_6H_5O$ | | |
| 261 | 2-$CHNOCH_3$ | | |
| 262 | 3-$CHNOCH_3$ | | |
| 263 | 4-$CHNOCH_3$ | | |
| 264 | 2-$CHNOC_2H_5$ | | |
| 265 | 3-$CHNOC_2H_5$ | | |
| 266 | 4-$CHNOC_2H_5$ | | |
| 267 | 2-CHNO(n-$C_3H_7$) | | |
| 268 | 3-CHNO(n-$C_3H_7$) | | |
| 269 | 4-CHNO(n-$C_3H_7$) | | |
| 270 | 2-CHNO(i-$C_3H_7$) | | |
| 271 | 3-CHNO(i-$C_3H_7$) | | |
| 272 | 4-CHNO(i-$C_3H_7$) | | |
| 273 | 2-CHNO(i-$C_6H_{13}$) | | |
| 274 | 3-CHNO(i-$C_6H_{13}$) | | |
| 275 | 4-CHNO(i-$C_6H_{13}$) | | |
| 276 | 2-CHNO(n-$C_8H_{17}$) | | |

TABLE 10-continued

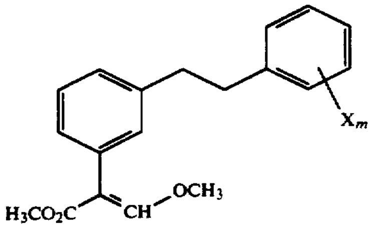

| No. | $X_m$ | mp | NMR: δ (ppm) |
|---|---|---|---|
| 277 | 3-CHNO(n-$C_8H_{17}$) | | |
| 278 | 4-CHNO(n-$C_8H_{17}$) | | |
| 279 | 2-$CHNOCH_2(C_6H_5)$ | | |
| 280 | 3-$CHNOCH_2(C_6H_5)$ | | |
| 281 | 4-$CHNOCH_2(C_6H_5)$ | | |
| 282 | 2-$CO_2CH_3$ | | |
| 283 | 3-$CO_2CH_3$ | | |
| 284 | 4-$CO_2CH_3$ | | |
| 285 | 2-$CO_2(C_2H_5)$ | | |
| 286 | 3-$CO_2(C_2H_5)$ | | |
| 287 | 4-$CO_2(C_2H_5)$ | | |
| 288 | 2-$CO_2$(n-$C_3H_7$) | | |
| 289 | 3-$CO_2$(n-$C_3H_7$) | | |
| 290 | 4-$CO_2$(n-$C_3H_7$) | | |
| 291 | 2-$CO_2$(i-$C_3H_7$) | | |
| 292 | 3-$CO_2$(i-$C_3H_7$) | | |
| 293 | 4-$CO_2$(i-$C_3H_7$) | | |
| 294 | 2-$CO_2$(i-$C_6H_{13}$) | | |
| 295 | 3-$CO_2$(i-$C_6H_{13}$) | | |
| 296 | 4-$CO_2$(i-$C_6H_{13}$) | | |
| 297 | 2-$CO_2$(n-$C_8H_{17}$) | | |
| 298 | 3-$CO_2$(n-$C_8H_{17}$) | | |
| 299 | 4-$CO_2$(n-$C_8H_{17}$) | | |
| 300 | 2-CHNO—$CH_2$—CH=$CH_2$ | | |
| 301 | 3-CHNO—$CH_2$—CH=$CH_2$ | | |
| 302 | 4-CHNO—$CH_2$—CH=$CH_2$ | | |
| 303 | 2-$CHNO(CH_2)_3(C_6H_5)$ | | |
| 304 | 3-$CHNO(CH_2)_3(C_6H_5)$ | | |
| 305 | 4-$CHNO(CH_2)_3(C_6H_5)$ | | |
| 306 | 2-$CH_2OCH_3$ | | |
| 307 | 3-$CH_2OCH_3$ | | |
| 308 | 4-$CH_2OCH_3$ | | |
| 309 | 2-$CH_2O(C_2H_5)$ | | |
| 310 | 3-$CH_2O(C_2H_5)$ | | |
| 311 | 4-$CH_2O(C_2H_5)$ | | |
| 312 | 2-$CH_2O$(n-$C_3H_7$) | | |
| 313 | 3-$CH_2O$(n-$C_3H_7$) | | |
| 314 | 4-$CH_2O$(n-$C_3H_7$) | | |
| 315 | 2-$CH_2O$(i-$C_3H_7$) | | |
| 316 | 3-$CH_2O$(i-$C_3H_7$) | | |
| 317 | 4-($CH_2O$(i-$C_3H_7$) | | |
| 318 | 2-$CH_2O$(n-$C_6H_{13}$) | | |
| 319 | 3-$CH_2O$(n-$C_6H_{13}$) | | |
| 320 | 4-$CH_2O$(n-$C_6H_{13}$) | | |
| 321 | 2-$CH_2O$(n-$C_8H_{17}$) | | |
| 322 | 3-$CH_2O$(n-$C_8H_{17}$) | | |
| 323 | 4-$CH_2O$(n-$C_8H_7$) | | |
| 324 | 2-$CH_2OCH_2(C_6H_5)$ | | |
| 325 | 3-$CH_2OCH_2(C_6H_5)$ | | |
| 326 | 4-$CH_2OCH_2(C_6H_5)$ | | |
| 327 | 2-$CH_2O(CH_2)_3$ | | |
| 328 | 3-$CH_2O(CH_2)_3(C_6H_5)$ | | |
| 329 | 4-$CH_2O(CH_2)_3(C_6H_5)$ | | |
| 330 | 2-CHO | | |
| 331 | 3-CHO | | |
| 332 | 4-CHO | | |

TABLE 11

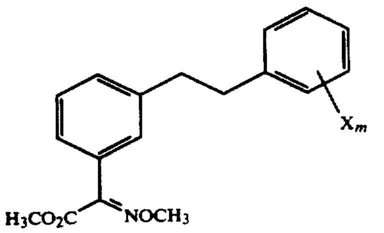

| No. | $X_m$ | mp | NMR: δ (ppm) |
|---|---|---|---|
| 1 | 2-F | | |
| 2 | 3-F | | |
| 3 | 4-F | | |
| 4 | 2,4-$F_2$ | | |
| 5 | 2,4,6-$F_3$ | | |
| 6 | 2,3,4,5,6-$F_5$ | | |
| 7 | 2,3-$F_2$ | | |
| 8 | 2-Cl | | |
| 9 | 3-Cl | | |
| 10 | 4-Cl | | |
| 11 | 2,3-$Cl_2$ | | |
| 12 | 2,4-$Cl_2$ | | |
| 13 | 2,5-$Cl_2$ | | |
| 14 | 2,6-$Cl_2$ | | |
| 15 | 3,4-$Cl_2$ | | |
| 16 | 3,5-$Cl_2$ | | |
| 17 | 2,3,4-$Cl_3$ | | |
| 18 | 2,3,5-$Cl_3$ | | |
| 19 | 2,3,6-$Cl_3$ | | |
| 20 | 2,4,5-$Cl_3$ | | |
| 21 | 2,4,6-$Cl_3$ | | |
| 22 | 3,4,5-$Cl_3$ | | |
| 23 | 2,3,4,6-$Cl_4$ | | |
| 24 | 2,3,5,6-$Cl_4$ | | |
| 25 | 2,3,4,5,6-$Cl_5$ | | |
| 26 | 2-Br | | |
| 27 | 3-Br | | |
| 28 | 4-Br | | |
| 29 | 2,4-$Br_2$ | | |
| 30 | 2,5-$Br_5$ | | |
| 31 | 2,6-$Br_2$ | | |
| 32 | 2,4,6-$Br_3$ | | |
| 33 | 2,3,4,5,6-$Br_5$ | | |
| 34 | 2-I | | |
| 35 | 3-I | | |
| 36 | 4-I | | |
| 37 | 2,4-$I_2$ | | |
| 38 | 2-Cl, 3-F | | |
| 39 | 2-Cl, 4-F | | |
| 40 | 2-Cl, 5-F | | |
| 41 | 2-Cl, 6-F | | |
| 42 | 2-Cl, 3-Br | | |
| 43 | 2-Cl, 4-Br | | |
| 44 | 2-Cl, 6-Br | | |
| 45 | 2-Cl, 6-Br | | |
| 46 | 2-Br, 3-Cl | | |
| 47 | 2-Br, 4-Cl | | |
| 48 | 2-Br, 5-Cl | | |
| 49 | 2-Br, 3-F | | |
| 50 | 2-Br, 4-F | | |
| 51 | 2-Br, 5-F | | |
| 52 | 2-Br, 6-F | | |
| 53 | 2-F, 3-Cl | | |
| 54 | 2-F, 4-Cl | | |
| 55 | 2-F, 5-Cl | | |
| 56 | 3-Cl, 4-F | | |
| 57 | 3-Cl, 5-F | | |
| 58 | 3-Cl, 4-Br | | |
| 59 | 3-Cl, 5-Br | | |
| 60 | 3-F, 4-Cl | | |
| 61 | 3-F, 4-Br | | |
| 62 | 3-Br, 4-Cl | | |
| 63 | 3-Br, 4-F | | |
| 64 | 2,6-$Cl_2$, 4-Br | | |
| 65 | 2-$CH_3$ | | |
| 66 | 3-$CH_3$ | | |
| 67 | 4-$CH_3$ | | |
| 68 | 2,3-$(CH_3)_2$ | | |
| 69 | 2,4-$(CH_3)_2$ | | |

TABLE 11-continued

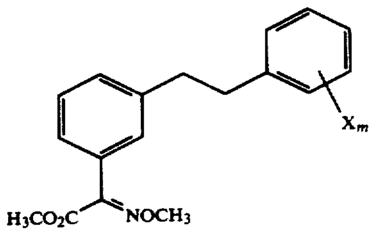

| No. | $X_m$ | mp | NMR: δ (ppm) |
|---|---|---|---|
| 70 | 2,5-$(CH_3)_2$ | | |
| 71 | 2,6-$(CH_3)_2$ | | |
| 72 | 3,4-$(CH_3)_2$ | | |
| 73 | 3,5-$(CH_3)_2$ | | |
| 74 | 3,5-$(CH_3)_2$ | | |
| 75 | 2,3,4-$(CH_3)_3$ | | |
| 76 | 2,3,6-$(CH_3)_3$ | | |
| 77 | 2,4,5-$(CH_3)_3$ | | |
| 78 | 2,4,6-$(CH_3)_3$ | | |
| 79 | 3,4,5-$(CH_3)_3$ | | |
| 80 | 2,3,4,6-$(CH_3)_4$ | | |
| 81 | 2,3,5,6-$(CH_3)_4$ | | |
| 82 | 2,3,4,5,6-$(CH_3)_5$ | | |
| 83 | 2-$C_2H_5$ | | |
| 84 | 3-$C_2H_5$ | | |
| 85 | 4-$C_2H_5$ | | |
| 86 | 2,4-$(C_2H_5)_2$ | | |
| 87 | 2,6-$(C_2H_5)_2$ | | |
| 88 | 3,5-$(C_2H_5)_2$ | | |
| 89 | 2,4,6-$(C_2H_5)_3$ | | |
| 90 | 2-n-$C_3H_7$ | | |
| 91 | 3-n-$C_3H_7$ | | |
| 92 | 4-n-$C_3H_7$ | | |
| 93 | 2-i-$C_3H_7$ | | |
| 94 | 3-i-$C_3H_7$ | | |
| 95 | 4-i-$C_3H_7$ | | |
| 96 | 2,4-(i-$C_3H_7)_2$ | | |
| 97 | 2,6-(i-$C_3H_7)_2$ | | |
| 98 | 3,5-(i-$C_3H_7)_2$ | | |
| 99 | 2,4,6-(i-$C_3H_7)_3$ | | |
| 100 | 2-S—$C_4H_9$ | | |
| 101 | 3-S—$C_4H_9$ | | |
| 102 | 4-S—$C_4H_9$ | | |
| 103 | 2-t-$C_4H_9$ | | |
| 104 | 3-t-$C_4H_9$ | | |
| 105 | 4-t-$C_4H_9$ | | |
| 106 | 2,3-(t-$C_4H_9)_2$ | | |
| 107 | 2,4-(t-$C_4H_9)_2$ | | |
| 108 | 2,5-(t-$C_4H_9)_2$ | | |
| 109 | 2,6-(t-$C_4H_9)_2$ | | |
| 110 | 3,4-(t-$C_4H_9)_2$ | | |
| 111 | 2,4,6-(t-$C_4H_9)_3$ | | |
| 112 | 4-n-$C_9H_{19}$ | | |
| 113 | 4-n-$C_{12}H_{25}$ | | |
| 114 | 3-n-$C_{15}H_{31}$ | | |
| 115 | 4-(1,1,3,3-tetramethylbutyl) | | |
| 116 | 4-(2,4,4-trimethylpropyl | | |
| 117 | 2-t-$C_4H_9$, 4-$CH_3$ | | |
| 118 | 2-t-$C_4H_9$, 5-$CH_3$ | | |
| 119 | 2,6-(t-$C_4H_9$), 4-$CH_3$ | | |
| 120 | 2-$CH_3$, 4-t-$C_4H_9$ | | |
| 121 | 2-$CH_3$, 6-t-$C_4H_9$ | | |
| 122 | 2-$CH_3$, 4-i-$C_3H_7$ | | |
| 123 | 2-$CH_3$, 5-i-$C_3H_7$ | | |
| 124 | 3-$CH_3$, 4-i-$C_3H_7$ | | |
| 125 | 2-i-$C_3H_7$, 5 $CH_3$ | | |
| 126 | 2,4-(t-$C_4H_9$), 6-i-$C_3H_7$ | | |
| 127 | 2-allyl | | |
| 128 | 3-allyl | | |
| 129 | 4-allyl | | |
| 130 | 2-allyl, 6-$CH_3$ | | |
| 131 | 2-cyclo-$C_6H_{11}$ | | |
| 132 | 3-cyclo-$C_6H_{11}$ | | |
| 133 | 4-cyclo-$C_6H_{11}$ | | |
| 134 | 2,4-(cyclo-$C_6H_{11})_2$, 6-$CH_3$ | | |
| 135 | 2-$CH_3$, 4-cyclo-$C_6H_{11}$ | | |
| 136 | 2-$CH_2$—$C_6H_5$ | | |
| 137 | 3-$CH_2$—$C_6H_5$ | | |
| 138 | 4-$CH_2$—$C_6H_5$ | | |

TABLE 11-continued

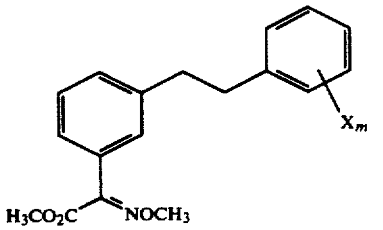

| No. | $X_m$ | mp | NMR: δ (ppm) |
|---|---|---|---|
| 139 | 2-$CH_2$—$C_6H_5$, 4-$CH_3$ | | |
| 140 | 2-$CH_3$, 4-$CH_2$—$C_6H_5$ | | |
| 141 | 2-$C_6H_5$ | | |
| 142 | 3-$C_6H_5$ | | |
| 143 | 4-$C_6H_5$ | | |
| 144 | 4-(2-i-$C_3H_7$—$C_6H_4$) | | |
| 145 | 4-$C_6H_5$, 2,6-$(CH_3)_2$ | | |
| 146 | 2-Cl, 4-$C_6H_5$ | | |
| 147 | 2-Br, 4-$C_6H_5$ | | |
| 148 | 2-$C_6H_5$, 4-Cl | | |
| 149 | 2-$C_6H_5$, 4-Br | | |
| 150 | 2-$CH_2C_6H_5$, 4-Cl | | |
| 151 | 2-$CH_2C_6H_5$, 4-Br | | |
| 152 | 2-Cl, 4-$CH_2C_6H_5$ | | |
| 153 | 2-Br, 4-$CH_2C_6H_5$ | | |
| 154 | 2-cyclo-$C_6H_{11}$, 4-Cl | | |
| 155 | 2-cyclo-$C_6H_{11}$, 4-Br | | |
| 156 | 2-Cl, 4-cyclo-$C_6H_{11}$ | | |
| 157 | 2-Br, 4-cyclo-$C_6H_{11}$ | | |
| 158 | 2-$OCH_3$ | | |
| 159 | 3-$OCH_3$ | | |
| 160 | 4-$OCH_3$ | | |
| 161 | 2-$OC_2H_5$ | | |
| 162 | 3-O—$C_2H_5$ | | |
| 163 | 4-O—$C_2H_5$ | | |
| 164 | 2-O-n-$C_3H_7$ | | |
| 165 | 3-O-n-$C_3H_7$ | | |
| 166 | 4-O-n-$C_3H_7$ | | |
| 167 | 2-O-i-$C_3H_7$ | | |
| 168 | 3-O-i-$C_3H_7$ | | |
| 169 | 4-O-i-$C_3H_7$ | | |
| 170 | 2-O-n-$C_6H_{13}$ | | |
| 171 | 3-O-n-$C_6H_{13}$ | | |
| 172 | 4-O-n-$C_6H_{13}$ | | |
| 173 | 2-O-n-$C_8H_{17}$ | | |
| 174 | 3-O-n-$C_8H_{17}$ | | |
| 175 | 4-O-n-$C_8H_{17}$ | | |
| 176 | 2-O—$CH_2C_6H_5$ | | |
| 177 | 3-O—$CH_2C_6H_5$ | | |
| 178 | 4-O—$CH_2C_6H_5$ | | |
| 179 | 2-O—$(CH_2)_3C_6H_5$ | | |
| 180 | 3-O—$(CH_2)_3C_6H_5$ | | |
| 181 | 4-O—$(CH_2)_3C_6H_5$ | | |
| 182 | 2,4-$(OCH_3)_2$ | | |
| 183 | 2-$CF_3$ | | |
| 184 | 3-$CF_3$ | | |
| 185 | 4-$CF_3$ | | |
| 186 | 2-$OCF_3$ | | |
| 187 | 3-$OCF_3$ | | |
| 188 | 4-$OCF_3$ | | |
| 189 | 3-$OCH_2CHF_2$ | | |
| 190 | 2-$NO_2$ | | |
| 191 | 3-$NO_2$ | | |
| 192 | 4-$NO_2$ | | |
| 193 | 2-CN | | |
| 194 | 3-CN | | |
| 195 | 4-CN | | |
| 196 | 2-$CH_3$, 3-Cl | | |
| 197 | 2-$CH_3$, 4-Cl | | |
| 198 | 2-$CH_3$, 5-Cl | | |
| 199 | 2-$CH_3$, 6-Cl | | |
| 200 | 2-$CH_3$, 3-F | | |
| 201 | 2-$CH_3$, 4-F | | |
| 202 | 2-$CH_3$, 5-F | | |
| 203 | 2-$CH_3$, 6-F | | |
| 204 | 2-$CH_3$, 3-Br | | |
| 205 | 2-$CH_3$, 4-Br | | |
| 206 | 2-$CH_3$, 5-Br | | |
| 207 | 2-$CH_3$, 6-Br | | |

TABLE 11-continued

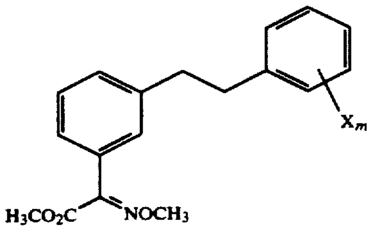

| No. | $X_m$ | mp | NMR: δ (ppm) |
|---|---|---|---|
| 208 | 2-Cl, 3-$CH_3$ | | |
| 209 | 2-Cl, 4-$CH_3$ | | |
| 210 | 2-Cl, 5-$CH_3$ | | |
| 211 | 2-F, 3-$CH_3$ | | |
| 212 | 2-F, 4-$CH_3$ | | |
| 213 | 2-F, 5-$CH_3$ | | |
| 214 | 2-Br, 3-$CH_3$ | | |
| 215 | 2-Br, 4-$CH_3$ | | |
| 216 | 2-Br, 5-$CH_3$ | | |
| 217 | 3-$CH_3$, 4-Cl | | |
| 218 | 3-$CH_3$, 5-Cl | | |
| 219 | 3-$CH_3$, 4-F | | |
| 220 | 3-$CH_3$, 4-Br | | |
| 221 | 3-$CH_3$, 4-Br | | |
| 222 | 3-$CH_3$, 5-Br | | |
| 223 | 3-F, 4-$CH_3$ | | |
| 224 | 3-Cl, 4-$CH_3$ | | |
| 225 | 3-Br, 4-$CH_3$ | | |
| 226 | 2-Cl, 4,5-$(CH_3)_2$ | | |
| 227 | 2-Br, 4,5-$(CH_3)_2$ | | |
| 228 | 2-Cl, 3,5-$(CH_3)_2$ | | |
| 229 | 2-Br, 3,5-$(CH_3)_2$ | | |
| 230 | 2,6-$Cl_2$, 4-$CH_3$ | | |
| 231 | 2,6-$F_2$, 4-$CH_3$ | | |
| 232 | 2,6-$Br_2$, 4-$CH_3$ | | |
| 233 | 2,4-$Cl_2$, 6-$CH_3$ | | |
| 234 | 2,4-$F_2$, 6-$CH_3$ | | |
| 235 | 2,4-$Br_2$, 6-$CH_3$ | | |
| 236 | 2,6-$(CH_3)_2$, 4-F | | |
| 237 | 2,6-$(CH_3)_2$, 4-Cl | | |
| 238 | 2,6-$(CH_3)_2$, 4-Br | | |
| 239 | 3,5-$(CH_3)_2$, 4-F | | |
| 240 | 3,5-$(CH_3)_2$, 4-Cl | | |
| 241 | 3,5-$(CH_3)_2$, 4-Br | | |
| 242 | 2,3,6-$(CH_3)_3$, 4-F | | |
| 243 | 2,3,6-$(CH_3)_3$, 4-Cl | | |
| 244 | 2,3,6-$(CH_3)_3$, 4-Br | | |
| 245 | 2,4-$(CH_3)_2$, 6-F | | |
| 246 | 2,4-$(CH_3)_2$, 6-Cl | | |
| 247 | 2,4-$(CH_3)_{62}$, 6-Br | | |
| 248 | 2-i-$C_3H_7$, 4-Cl, 5-$CH_3$ | | |
| 249 | 2-Cl, 4-$NO_2$ | | |
| 250 | 2-$NO_2$, 4-Cl | | |
| 251 | 2-$OCH_3$, 5-$NO_2$ | | |
| 252 | 2,4-$Cl_2$, 5-$NO_2$ | | |
| 253 | 2,4-$Cl_2$, 6-$NO_2$ | | |
| 254 | 2,6-$Cl_2$, 4-$NO_2$ | | |
| 255 | 2,6-$Br_2$, 4-$NO_2$ | | |
| 256 | 2,6-$I_2$, 4-$NO_2$ | | |
| 257 | 2-$CH_3$, 5-i-$C_3H_7$, 4-Cl | | |
| 258 | 2-$C_6H_5O$ | | |
| 259 | 3-$C_6H_5O$ | | |
| 260 | 4-$C_6H_5O$ | | |
| 261 | 2-$CHNOCH_3$ | | |
| 262 | 3-$CHNOCH_3$ | | |
| 263 | 4-$CHNOCH_3$ | | |
| 264 | 2-$CHNOC_2H_5$ | | |
| 265 | 3-$CHNOC_2H_5$ | | |
| 266 | 4-$CHNOC_2H_5$ | | |
| 267 | 2-CHNO(n-$C_3H_7$) | | |
| 268 | 3-CHNO(n-$C_3H_7$) | | |
| 269 | 4-CHNO(n-$C_3H_7$) | | |
| 270 | 2-CHNO(i-$C_3H_7$) | | |
| 271 | 3-CHNO(i-$C_3H_7$) | | |
| 272 | 4-CHNO(i-$C_3H_7$) | | |
| 273 | 2-CHNO(i-$C_6H_{13}$) | | |
| 274 | 3-CHNO(i-$C_6H_{13}$) | | |
| 275 | 4-CHNO(i-$C_6H_{13}$) | | |
| 276 | 2-CHNO(n-$C_8H_{17}$) | | |

TABLE 11-continued

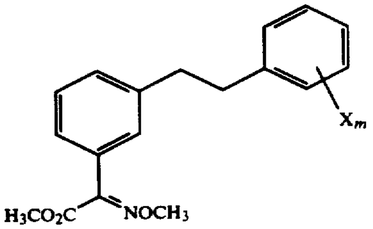

| No. | $X_m$ | mp | NMR: δ (ppm) |
|---|---|---|---|
| 277 | 3-CHNO(n-$C_8H_{17}$) | | |
| 278 | 4-CHNO(n-$C_8H_{17}$) | | |
| 279 | 2-CHNOCH$_2$($C_6H_5$) | | |
| 280 | 3-CHNOCH$_2$($C_6H_5$) | | |
| 281 | 4-CHNOCH$_2$($C_6H_5$) | | |
| 282 | 2-$CO_2CH_3$ | | |
| 283 | 3-$CO_2CH_3$ | | |
| 284 | 4-$CO_2CH_3$ | | |
| 285 | 2-$CO_2$($C_2H_5$) | | |
| 286 | 3-$CO_2$($C_2H_5$) | | |
| 287 | 4-$CO_2$($C_2H_5$) | | |
| 288 | 2-$CO_2$(n-$C_3H_7$) | | |
| 289 | 3-$CO_2$(n-$C_3H_7$) | | |
| 290 | 4-$CO_2$(n-$C_3H_7$) | | |
| 291 | 2-$CO_2$(i-$C_3H_7$) | | |
| 292 | 3-$CO_2$(i-$C_3H_7$) | | |
| 293 | 4-$CO_2$(i-$C_3H_7$) | | |
| 294 | 2-$CO_2$(i-$C_6H_{13}$) | | |
| 295 | 3-$CO_2$(i-$C_6H_{13}$) | | |
| 296 | 4-$CO_2$(i-$C_6H_{13}$) | | |
| 297 | 2-$CO_2$(n-$C_8H_{17}$) | | |
| 298 | 3-$CO_2$(n-$C_8H_{17}$) | | |
| 299 | 4-$CO_2$(n-$C_8H_{17}$) | | |
| 300 | 2-CHNO—$CH_2$—CH=$CH_2$ | | |
| 301 | 3-CHNO—$CH_2$—CH=$CH_2$ | | |
| 302 | 4-CHNO—$CH_2$—CH=$CH_2$ | | |
| 303 | 2-CHNO($CH_2$)$_3$($C_6H_5$) | | |
| 304 | 3-CHNO($CH_2$)$_3$($C_6H_5$) | | |
| 305 | 4-CHNO($CH_2$)$_3$($C_6H_5$) | | |
| 306 | 2-$CH_2OCH_3$ | | |
| 307 | 3-$CH_2OCH_3$ | | |
| 308 | 4-$CH_2OCH_3$ | | |
| 309 | 2-$CH_2O$($C_2H_5$) | | |
| 310 | 3-$CH_2O$($C_2H_5$) | | |
| 311 | 4-$CH_2O$($C_2H_5$) | | |
| 312 | 2-$CH_2O$(n-$C_3H_7$) | | |
| 313 | 3-$CH_2O$(n-$C_3H_7$) | | |
| 314 | 4-$CH_2O$(n-$C_3H_7$) | | |
| 315 | 2-$CH_2O$(i-$C_3H_7$) | | |
| 316 | 3-$CH_2O$(i-$C_3H_7$) | | |
| 317 | 4-($CH_2O$(i-$C_3H_7$) | | |
| 318 | 2-$CH_2O$(n-$C_6H_{13}$) | | |
| 319 | 3-$CH_2O$(n-$C_6H_{13}$) | | |
| 320 | 4-$CH_2O$(n-$C_6H_{13}$) | | |
| 321 | 2-$CH_2O$(n-$C_8H_{17}$) | | |
| 322 | 3-$CH_2O$(n-$C_8H_{17}$) | | |
| 323 | 4-$CH_2O$(n-$C_8H_7$) | | |
| 324 | 2-$CH_2OCH_2$($C_6H_5$) | | |
| 325 | 3-$CH_2OCH_2$($C_6H_5$) | | |
| 326 | 4-$CH_2OCH_2$($C_6H_5$) | | |
| 327 | 2-$CH_2O$($CH_2$)$_3$ | | |
| 328 | 3-$CH_2O$($CH_2$)$_3$($C_6H_5$) | | |
| 329 | 4-$CH_2O$($CH_2$)$_3$($C_6H_5$) | | |
| 330 | 2-CHO | | |
| 331 | 3-CHO | | |
| 332 | 4-CHO | | |

TABLE 12

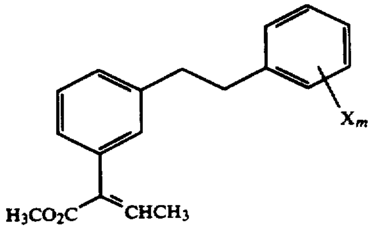

| No. | $X_m$ | mp | NMR: δ (ppm) |
|---|---|---|---|
| 1 | 2-F | | |
| 2 | 3-F | | |
| 3 | 4-F | | |
| 4 | 2,4-$F_2$ | | |
| 5 | 2,4,6-$F_3$ | | |
| 6 | 2,3,4,5,6-$F_5$ | | |
| 7 | 2,3-$F_2$ | | |
| 8 | 2-Cl | | |
| 9 | 3-Cl | | |
| 10 | 4-Cl | | |
| 11 | 2,3-$Cl_2$ | | |
| 12 | 2,4-$Cl_2$ | | |
| 13 | 2,5-$Cl_2$ | | |
| 14 | 2,6-$Cl_2$ | | |
| 15 | 3,4-$Cl_2$ | | |
| 16 | 3,5-$Cl_2$ | | |
| 17 | 2,3,4-$Cl_3$ | | |
| 18 | 2,3,5-$Cl_3$ | | |
| 19 | 2,3,6-$Cl_3$ | | |
| 20 | 2,4,5-$Cl_3$ | | |
| 21 | 2,4,6-$Cl_3$ | | |
| 22 | 3,4,5-$Cl_3$ | | |
| 23 | 2,3,4,6-$Cl_4$ | | |
| 24 | 2,3,5,6-$Cl_4$ | | |
| 25 | 2,3,4,5,6-$Cl_5$ | | |
| 26 | 2-Br | | |
| 27 | 3-Br | | |
| 28 | 4-Br | | |
| 29 | 2,4-$Br_2$ | | |
| 30 | 2,5-$Br_5$ | | |
| 31 | 2,6-$Br_2$ | | |
| 32 | 2,4,6-$Br_3$ | | |
| 33 | 2,3,4,5,6-$Br_5$ | | |
| 34 | 2-I | | |
| 35 | 3-I | | |
| 36 | 4-I | | |
| 37 | 2,4-$I_2$ | | |
| 38 | 2-Cl, 3-F | | |
| 39 | 2-Cl, 4-F | | |
| 40 | 2-Cl, 5-F | | |
| 41 | 2-Cl, 6-F | | |
| 42 | 2-Cl, 3-Br | | |
| 43 | 2-Cl, 4-Br | | |
| 44 | 2-Cl, 6-Br | | |
| 45 | 2-Cl, 6-Br | | |
| 46 | 2-Br, 3-Cl | | |
| 47 | 2-Br, 4-Cl | | |
| 48 | 2-Br, 5-Cl | | |
| 49 | 2-Br, 3-F | | |
| 50 | 2-Br, 4-F | | |
| 51 | 2-Br, 5-F | | |
| 52 | 2-Br, 6-F | | |
| 53 | 2-F, 3-Cl | | |
| 54 | 2-F, 4-Cl | | |
| 55 | 2-F, 5-Cl | | |
| 56 | 3-Cl, 4-F | | |
| 57 | 3-Cl, 5-F | | |
| 58 | 3-Cl, 4-Br | | |
| 59 | 3-Cl, 5-Br | | |
| 60 | 3-F, 4-Cl | | |
| 61 | 3-F, 4-Br | | |
| 62 | 3-Br, 4-Cl | | |
| 63 | 3-Br, 4-F | | |
| 64 | 2,6-$Cl_2$, 4-Br | | |
| 65 | 2-$CH_3$ | | |
| 66 | 3-$CH_3$ | | |
| 67 | 4-$CH_3$ | | |
| 68 | 2,3-($CH_3$)$_2$ | | |
| 69 | 2,4-($CH_3$)$_2$ | | |

TABLE 12-continued

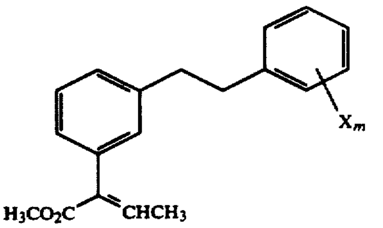

| No. | $X_m$ | mp | NMR: δ (ppm) |
|---|---|---|---|
| 70 | 2,5-$(CH_3)_2$ | | |
| 71 | 2,6-$(CH_3)_2$ | | |
| 72 | 3,4-$(CH_3)_2$ | | |
| 73 | 3,5-$(CH_3)_2$ | | |
| 74 | 3,5-$(CH_3)_2$ | | |
| 75 | 2,3,4-$(CH_3)_3$ | | |
| 76 | 2,3,6-$(CH_3)_3$ | | |
| 77 | 2,4,5-$(CH_3)_3$ | | |
| 78 | 2,4,6-$(CH_3)_3$ | | |
| 79 | 3,4,5-$(CH_3)_3$ | | |
| 80 | 2,3,4,6-$(CH_3)_4$ | | |
| 81 | 2,3,5,6-$(CH_3)_4$ | | |
| 82 | 2,3,4,5,6-$(CH_3)_5$ | | |
| 83 | 2-$C_2H_5$ | | |
| 84 | 3-$C_2H_5$ | | |
| 85 | 4-$C_2H_5$ | | |
| 86 | 2,4-$(C_2H_5)_2$ | | |
| 87 | 2,6-$(C_2H_5)_2$ | | |
| 88 | 3,5-$(C_2H_5)_2$ | | |
| 89 | 2,4,6-$(C_2H_5)_3$ | | |
| 90 | 2-n-$C_3H_7$ | | |
| 91 | 3-n-$C_3H_7$ | | |
| 92 | 4-n-$C_3H_7$ | | |
| 93 | 2-i-$C_3H_7$ | | |
| 94 | 3-i-$C_3H_7$ | | |
| 95 | 4-i-$C_3H_7$ | | |
| 96 | 2,4-(i-$C_3H_7)_2$ | | |
| 97 | 2,6-(i-$C_3H_7)_2$ | | |
| 98 | 3,5-(i-$C_3H_7)_2$ | | |
| 99 | 2,4,6-(i-$C_3H_7)_3$ | | |
| 100 | 2-S—$C_4H_9$ | | |
| 101 | 3-S—$C_4H_9$ | | |
| 102 | 4-S—$C_4H_9$ | | |
| 103 | 2-t-$C_4H_9$ | | |
| 104 | 3-t-$C_4H_9$ | | |
| 105 | 4-t-$C_4H_9$ | | |
| 106 | 2,3-(t-$C_4H_9)_2$ | | |
| 107 | 2,4-(t-$C_4H_9)_2$ | | |
| 108 | 2,5-(t-$C_4H_9)_2$ | | |
| 109 | 2,6-(t-$C_4H_9)_2$ | | |
| 110 | 3,4-(t-$C_4H_9)_2$ | | |
| 111 | 2,4,6-(t-$C_4H_9)_3$ | | |
| 112 | 4-n-$C_9H_{19}$ | | |
| 113 | 4-n-$C_{12}H_{25}$ | | |
| 114 | 3-n-$C_{15}H_{31}$ | | |
| 115 | 4-(1,1,3,3-tetramethylbutyl) | | |
| 116 | 4-(2,4,4-trimethylpropyl | | |
| 117 | 2-t-$C_4H_9$, 4-$CH_3$ | | |
| 118 | 2-t-$C_4H_9$, 5-$CH_3$ | | |
| 119 | 2,6-(t-$C_4H_9$), 4-$CH_3$ | | |
| 120 | 2-$CH_3$, 4-t-$C_4H_9$ | | |
| 121 | 2-$CH_3$, 6-t-$C_4H_9$ | | |
| 122 | 2-$CH_3$, 4-i-$C_3H_7$ | | |
| 123 | 2-$CH_3$, 5-i-$C_3H_7$ | | |
| 124 | 3-$CH_3$, 4-i-$C_3H_7$ | | |
| 125 | 2-i-$C_3H_7$, 5 $CH_3$ | | |
| 126 | 2,4-(t-$C_4H_9$), 6-i-$C_3H_7$ | | |
| 127 | 2-allyl | | |
| 128 | 3-allyl | | |
| 129 | 4-allyl | | |
| 130 | 2-allyl, 6-$CH_3$ | | |
| 131 | 2-cyclo-$C_6H_{11}$ | | |
| 132 | 3-cyclo-$C_6H_{11}$ | | |
| 133 | 4-cyclo-$C_6H_{11}$ | | |
| 134 | 2,4-(cyclo-$C_6H_{11})_2$, 6-$CH_3$ | | |
| 135 | 2-$CH_3$, 4-cyclo-$C_6H_{11}$ | | |
| 136 | 2-$CH_2$—$C_6H_5$ | | |
| 137 | 3-$CH_2$—$C_6H_5$ | | |
| 138 | 4-$CH_2$—$C_6H_5$ | | |

TABLE 12-continued

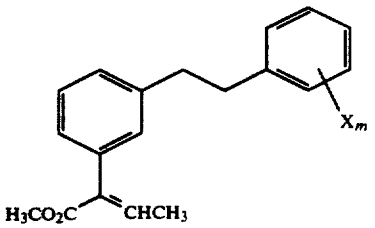

| No. | $X_m$ | mp | NMR: δ (ppm) |
|---|---|---|---|
| 139 | 2-$CH_2$—$C_6H_5$, 4-$CH_3$ | | |
| 140 | 2-$CH_3$, 4-$CH_2$—$C_6H_5$ | | |
| 141 | 2-$C_6H_5$ | | |
| 142 | 3-$C_6H_5$ | | |
| 143 | 4-$C_6H_5$ | | |
| 144 | 4-(2-i-$C_3H_7$—$C_6H_4$) | | |
| 145 | 4-$C_6H_5$, 2,6-$(CH_3)_2$ | | |
| 146 | 2-Cl, 4-$C_6H_5$ | | |
| 147 | 2-Br, 4-$C_6H_5$ | | |
| 148 | 2-$C_6H_5$, 4-Cl | | |
| 149 | 2-$C_6H_5$, 4-Br | | |
| 150 | 2-$CH_2C_6H_5$, 4-Cl | | |
| 151 | 2-$CH_2C_6H_5$, 4-Br | | |
| 152 | 2-Cl, 4-$CH_2C_6H_5$ | | |
| 153 | 2-Br, 4-$CH_2C_6H_5$ | | |
| 154 | 2-cyclo-$C_6H_{11}$, 4-Cl | | |
| 155 | 2-cyclo-$C_6H_{11}$, 4-Br | | |
| 156 | 2-Cl, 4-cyclo-$C_6H_{11}$ | | |
| 157 | 2-Br, 4-cyclo-$C_6H_{11}$ | | |
| 158 | 2-$OCH_3$ | | |
| 159 | 3-$OCH_3$ | | |
| 160 | 4-$OCH_3$ | | |
| 161 | 2-$OC_2H_5$ | | |
| 162 | 3-O—$C_2H_5$ | | |
| 163 | 4-O—$C_2H_5$ | | |
| 164 | 2-O-n-$C_3H_7$ | | |
| 165 | 3-O-n-$C_3H_7$ | | |
| 166 | 4-O-n-$C_3H_7$ | | |
| 167 | 2-O-i-$C_3H_7$ | | |
| 168 | 3-O-i-$C_3H_7$ | | |
| 169 | 4-O-i-$C_3H_7$ | | |
| 170 | 2-O-n-$C_6H_{13}$ | | |
| 171 | 3-O-n-$C_6H_{13}$ | | |
| 172 | 4-O-n-$C_6H_{13}$ | | |
| 173 | 2-O-n-$C_8H_{17}$ | | |
| 174 | 3-O-n-$C_8H_{17}$ | | |
| 175 | 4-O-n-$C_8H_{17}$ | | |
| 176 | 2-O—$CH_2C_6H_5$ | | |
| 177 | 3-O—$CH_2C_6H_5$ | | |
| 178 | 4-O—$CH_2C_6H_5$ | | |
| 179 | 2-O—$(CH_2)_3C_6H_5$ | | |
| 180 | 3-O—$(CH_2)_3C_6H_5$ | | |
| 181 | 4-O—$(CH_2)_3C_6H_5$ | | |
| 182 | 2,4-$(OCH_3)_2$ | | |
| 183 | 2-$CF_3$ | | |
| 184 | 3-$CF_3$ | | |
| 185 | 4-$CF_3$ | | |
| 186 | 2-$OCF_3$ | | |
| 187 | 3-$OCF_3$ | | |
| 188 | 4-$OCF_3$ | | |
| 189 | 3-$OCH_2CHF_2$ | | |
| 190 | 2-$NO_2$ | | |
| 191 | 3-$NO_2$ | | |
| 192 | 4-$NO_2$ | | |
| 193 | 2-CN | | |
| 194 | 3-CN | | |
| 195 | 4-CN | | |
| 196 | 2-$CH_3$, 3-Cl | | |
| 197 | 2-$CH_3$, 4-Cl | | |
| 198 | 2-$CH_3$, 5-Cl | | |
| 199 | 2-$CH_3$, 6-Cl | | |
| 200 | 2-$CH_3$, 3-F | | |
| 201 | 2-$CH_3$, 4-F | | |
| 202 | 2-$CH_3$, 5-F | | |
| 203 | 2-$CH_3$, 6-F | | |
| 204 | 2-$CH_3$, 3-Br | | |
| 205 | 2-$CH_3$, 4-Br | | |
| 206 | 2-$CH_3$, 5-Br | | |
| 207 | 2-$CH_3$, 6-Br | | |

TABLE 12-continued

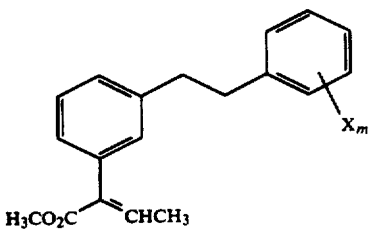

| No. | $X_m$ | mp | NMR: δ (ppm) |
|---|---|---|---|
| 208 | 2-Cl, 3-$CH_3$ | | |
| 209 | 2-Cl, 4-$CH_3$ | | |
| 210 | 2-Cl, 5-$CH_3$ | | |
| 211 | 2-F, 3-$CH_3$ | | |
| 212 | 2-F, 4-$CH_3$ | | |
| 213 | 2-F, 5-$CH_3$ | | |
| 214 | 2-Br, 3-$CH_3$ | | |
| 215 | 2-Br, 4-$CH_3$ | | |
| 216 | 2-Br, 5-$CH_3$ | | |
| 217 | 3-$CH_3$, 4-Cl | | |
| 218 | 3-$CH_3$, 5-Cl | | |
| 219 | 3-$CH_3$, 4-F | | |
| 220 | 3-$CH_3$, 4-Br | | |
| 221 | 3-$CH_3$, 4-Br | | |
| 222 | 3-$CH_3$, 5-Br | | |
| 223 | 3-F, 4-$CH_3$ | | |
| 224 | 3-Cl, 4-$CH_3$ | | |
| 225 | 3-Br, 4-$CH_3$ | | |
| 226 | 2-Cl, 4,5-$(CH_3)_2$ | | |
| 227 | 2-Br, 4,5-$(CH_3)_2$ | | |
| 228 | 2-Cl, 3,5-$(CH_3)_2$ | | |
| 229 | 2-Br, 3,5-$(CH_3)_2$ | | |
| 230 | 2,6-$Cl_2$, 4-$CH_3$ | | |
| 231 | 2,6-$F_2$, 4-$CH_3$ | | |
| 232 | 2,6-$Br_2$, 4-$CH_3$ | | |
| 233 | 2,4-$Cl_2$, 6-$CH_3$ | | |
| 234 | 2,4-$F_2$, 6-$CH_3$ | | |
| 235 | 2,4-$Br_2$, 6-$CH_3$ | | |
| 236 | 2,6-$(CH_3)_2$, 4-F | | |
| 237 | 2,6-$(CH_3)_2$, 4-Cl | | |
| 238 | 2,6-$(CH_3)_2$, 4-Br | | |
| 239 | 3,5-$(CH_3)_2$, 4-F | | |
| 240 | 3,5-$(CH_3)_2$, 4-Cl | | |
| 241 | 3,5-$(CH_3)_2$, 4-Br | | |
| 242 | 2,3,6-$(CH_3)_3$, 4-F | | |
| 243 | 2,3,6-$(CH_3)_3$, 4-Cl | | |
| 244 | 2,3,6-$(CH_3)_3$, 4-Br | | |
| 245 | 2,4-$(CH_3)_2$, 6-F | | |
| 246 | 2,4-$(CH_3)_2$, 6-Cl | | |
| 247 | 2,4-$(CH_3)_{62}$, 6-Br | | |
| 248 | 2-i-$C_3H_7$, 4-Cl, 5-$CH_3$ | | |
| 249 | 2-Cl, 4-$NO_2$ | | |
| 250 | 2-$NO_2$, 4-Cl | | |
| 251 | 2-$OCH_3$, 5-$NO_2$ | | |
| 252 | 2,4-$Cl_2$, 5-$NO_2$ | | |
| 253 | 2,4-$Cl_2$, 6-$NO_2$ | | |
| 254 | 2,6-$Cl_2$, 4-$NO_2$ | | |
| 255 | 2,6-$Br_2$, 4-$NO_2$ | | |
| 256 | 2,6-$I_2$, 4-$NO_2$ | | |
| 257 | 2-$CH_3$, 5-i-$C_3H_7$, 4-Cl | | |
| 258 | 2-$C_6H_5O$ | | |
| 259 | 3-$C_6H_5O$ | | |
| 260 | 4-$C_6H_5O$ | | |
| 261 | 2-$CHNOCH_3$ | | |
| 262 | 3-$CHNOCH_3$ | | |
| 263 | 4-$CHNOCH_3$ | | |
| 264 | 2-$CHNOC_2H_5$ | | |
| 265 | 3-$CHNOC_2H_5$ | | |
| 266 | 4-$CHNOC_2H_5$ | | |
| 267 | 2-CHNO(n-$C_3H_7$) | | |
| 268 | 3-CHNO(n-$C_3H_7$) | | |
| 269 | 4-CHNO(n-$C_3H_7$) | | |
| 270 | 2-CHNO(i-$C_3H_7$) | | |
| 271 | 3-CHNO(i-$C_3H_7$) | | |
| 272 | 4-CHNO(i-$C_3H_7$) | | |
| 273 | 2-CHNO(i-$C_6H_{13}$) | | |
| 274 | 3-CHNO(i-$C_6H_{13}$) | | |
| 275 | 4-CHNO(i-$C_6H_{13}$) | | |
| 276 | 2-CHNO(n-$C_8H_{17}$) | | |

TABLE 12-continued

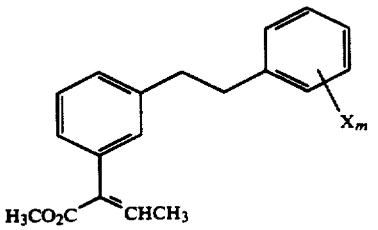

| No. | $X_m$ | mp | NMR: δ (ppm) |
|---|---|---|---|
| 277 | 3-CHNO(n-$C_8H_{17}$) | | |
| 278 | 4-CHNO(n-$C_8H_{17}$) | | |
| 279 | 2-$CHNOCH_2(C_6H_5)$ | | |
| 280 | 3-$CHNOCH_2(C_6H_5)$ | | |
| 281 | 4-$CHNOCH_2(C_6H_5)$ | | |
| 282 | 2-$CO_2CH_3$ | | |
| 283 | 3-$CO_2CH_3$ | | |
| 284 | 4-$CO_2CH_3$ | | |
| 285 | 2-$CO_2(C_2H_5)$ | | |
| 286 | 3-$CO_2(C_2H_5)$ | | |
| 287 | 4-$CO_2(C_2H_5)$ | | |
| 288 | 2-$CO_2$(n-$C_3H_7$) | | |
| 289 | 3-$CO_2$(n-$C_3H_7$) | | |
| 290 | 4-$CO_2$(n-$C_3H_7$) | | |
| 291 | 2-$CO_2$(i-$C_3H_7$) | | |
| 292 | 3-$CO_2$(i-$C_3H_7$) | | |
| 293 | 4-$CO_2$(i-$C_3H_7$) | | |
| 294 | 2-$CO_2$(i-$C_6H_{13}$) | | |
| 295 | 3-$CO_2$(i-$C_6H_{13}$) | | |
| 296 | 4-$CO_2$(i-$C_6H_{13}$) | | |
| 297 | 2-$CO_2$(n-$C_8H_{17}$) | | |
| 298 | 3-$CO_2$(n-$C_8H_{17}$) | | |
| 299 | 4-$CO_2$(n-$C_8H_{17}$) | | |
| 300 | 2-CHNO—$CH_2$—CH=$CH_2$ | | |
| 301 | 3-CHNO—$CH_2$—CH=$CH_2$ | | |
| 302 | 4-CHNO—$CH_2$—CH=$CH_2$ | | |
| 303 | 2-$CHNO(CH_2)_3(C_6H_5)$ | | |
| 304 | 3-$CHNO(CH_2)_3(C_6H_5)$ | | |
| 305 | 4-$CHNO(CH_2)_3(C_6H_5)$ | | |
| 306 | 2-$CH_2OCH_3$ | | |
| 307 | 3-$CH_2OCH_3$ | | |
| 308 | 4-$CH_2OCH_3$ | | |
| 309 | 2-$CH_2O(C_2H_5)$ | | |
| 310 | 3-$CH_2O(C_2H_5)$ | | |
| 311 | 4-$CH_2O(C_2H_5)$ | | |
| 312 | 2-$CH_2O$(n-$C_3H_7$) | | |
| 313 | 3-$CH_2O$(n-$C_3H_7$) | | |
| 314 | 4-$CH_2O$(n-$C_3H_7$) | | |
| 315 | 2-$CH_2O$(i-$C_3H_7$) | | |
| 316 | 3-$CH_2O$(i-$C_3H_7$) | | |
| 317 | 4-($CH_2O$(i-$C_3H_7$) | | |
| 318 | 2-$CH_2O$(n-$C_6H_{13}$) | | |
| 319 | 3-$CH_2O$(n-$C_6H_{13}$) | | |
| 320 | 4-$CH_2O$(n-$C_6H_{13}$) | | |
| 321 | 2-$CH_2O$(n-$C_8H_{17}$) | | |
| 322 | 3-$CH_2O$(n-$C_8H_{17}$) | | |
| 323 | 4-$CH_2O$(n-$C_8H_7$) | | |
| 324 | 2-$CH_2OCH_2(C_6H_5)$ | | |
| 325 | 3-$CH_2OCH_2(C_6H_5)$ | | |
| 326 | 4-$CH_2OCH_2(C_6H_5)$ | | |
| 327 | 2-$CH_2O(CH_2)_3$ | | |
| 328 | 3-$CH_2O(CH_2)_3(C_6H_5)$ | | |
| 329 | 4-$CH_2O(CH_2)_3(C_6H_5)$ | | |
| 330 | 2-CHO | | |
| 331 | 3-CHO | | |
| 332 | 4-CHO | | |

TABLE 13

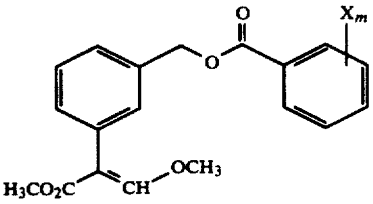

| No. | $X_m$ | mp | NMR: δ (ppm) |
|---|---|---|---|
| 1 | 2-F | | |
| 2 | 3-F | | |
| 3 | 4-F | | |
| 4 | 2,4-$F_2$ | | |
| 5 | 2,4,6-$F_3$ | | |
| 6 | 2,3,4,5,6-$F_5$ | | |
| 7 | 2,3-$F_2$ | | |
| 8 | 2-Cl | 83-85 | |
| 9 | 3-Cl | oil | 5.35(S, 2H); 7.6(S, 1H) |
| 10 | 4-Cl | oil | 5.35(S, 2H); 7.6(S, 1H) |
| 11 | 2,3-$Cl_2$ | | |
| 12 | 2,4-$Cl_2$ | | |
| 13 | 2,5-$Cl_2$ | | |
| 14 | 2,6-$Cl_2$ | | |
| 15 | 3,4-$Cl_2$ | | |
| 16 | 3,5-$Cl_2$ | | |
| 17 | 2,3,4-$Cl_3$ | | |
| 18 | 2,3,5-$Cl_3$ | | |
| 19 | 2,3,6-$Cl_3$ | | |
| 20 | 2,4,5-$Cl_3$ | | |
| 21 | 2,4,6-$Cl_3$ | | |
| 22 | 3,4,5-$Cl_3$ | | |
| 23 | 2,3,4,6-$Cl_4$ | | |
| 24 | 2,3,5,6-$Cl_4$ | | |
| 25 | 2,3,4,5,6-$Cl_5$ | | |
| 26 | 2-Br | | |
| 27 | 3-Br | | |
| 28 | 4-Br | | |
| 29 | 2,4-$Br_2$ | | |
| 30 | 2,5-$Br_5$ | | |
| 31 | 2,6-$Br_2$ | | |
| 32 | 2,4,6-$Br_3$ | | |
| 33 | 2,3,4,5,6-$Br_5$ | | |
| 34 | 2-I | | |
| 35 | 3-I | | |
| 36 | 4-I | | |
| 37 | 2,4-$I_2$ | | |
| 38 | 2-Cl, 3-F | | |
| 39 | 2-Cl, 4-F | | |
| 40 | 2-Cl, 5-F | | |
| 41 | 2-Cl, 6-F | | |
| 42 | 2-Cl, 3-Br | | |
| 43 | 2-Cl, 4-Br | | |
| 44 | 2-Cl, 6-Br | | |
| 45 | 2-Cl, 6-Br | | |
| 46 | 2-Br, 3-Cl | | |
| 47 | 2-Br, 4-Cl | | |
| 48 | 2-Br, 5-Cl | | |
| 49 | 2-Br, 3-F | | |
| 50 | 2-Br, 4-F | | |
| 51 | 2-Br, 5-F | | |
| 52 | 2-Br, 6-F | | |
| 53 | 2-F, 3-Cl | | |
| 54 | 2-F, 4-Cl | | |
| 55 | 2-F, 5-Cl | | |
| 56 | 3-Cl, 4-F | | |
| 57 | 3-Cl, 5-F | | |
| 58 | 3-Cl, 4-Br | | |
| 59 | 3-Cl, 5-Br | | |
| 60 | 3-F, 4-Cl | | |
| 61 | 3-F, 4-Br | | |
| 62 | 3-Br, 4-Cl | | |
| 63 | 3-Br, 4-F | | |
| 64 | 2,6-$Cl_2$, 4-Br | | |
| 65 | 2-$CH_3$ | 68-69 | |
| 66 | 3-$CH_3$ | oil | 5.35(S, 2H); 7.55(S, 1H) |
| 67 | 4-$CH_3$ | oil | 5.35(S, 2H); |

TABLE 13-continued

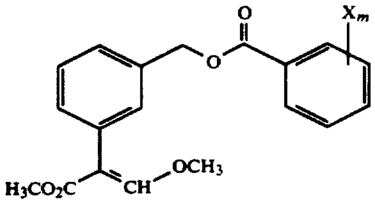

| No. | $X_m$ | mp | NMR: δ (ppm) |
|---|---|---|---|
| | | | 7.55(S, 1H) |
| 68 | 2,3-$(CH_3)_2$ | | |
| 69 | 2,4-$(CH_3)_2$ | | |
| 70 | 2,5-$(CH_3)_2$ | | |
| 71 | 2,6-$(CH_3)_2$ | | |
| 72 | 3,4-$(CH_3)_2$ | | |
| 73 | 3,5-$(CH_3)_2$ | | |
| 74 | 3,5-$(CH_3)_2$ | | |
| 75 | 2,3,4-$(CH_3)_3$ | | |
| 76 | 2,3,6-$(CH_3)_3$ | | |
| 77 | 2,4,5-$(CH_3)_3$ | | |
| 78 | 2,4,6-$(CH_3)_3$ | | |
| 79 | 3,4,5-$(CH_3)_3$ | | |
| 80 | 2,3,4,6-$(CH_3)_4$ | | |
| 81 | 2,3,5,6-$(CH_3)_4$ | | |
| 82 | 2,3,4,5,6-$(CH_3)_5$ | | |
| 83 | 2-$C_2H_5$ | | |
| 84 | 3-$C_2H_5$ | | |
| 85 | 4-$C_2H_5$ | | |
| 86 | 2,4-$(C_2H_5)_2$ | | |
| 87 | 2,6-$(C_2H_5)_2$ | | |
| 88 | 3,5-$(C_2H_5)_2$ | | |
| 89 | 2,4,6-$(C_2H_5)_3$ | | |
| 90 | 2-n-$C_3H_7$ | | |
| 91 | 3-n-$C_3H_7$ | | |
| 92 | 4-n-$C_3H_7$ | | |
| 93 | 2-i-$C_3H_7$ | | |
| 94 | 3-i-$C_3H_7$ | | |
| 95 | 4-i-$C_3H_7$ | | |
| 96 | 2,4-(i-$C_3H_7)_2$ | | |
| 97 | 2,6-(i-$C_3H_7)_2$ | | |
| 98 | 3,5-(i-$C_3H_7)_2$ | | |
| 99 | 2,4,6-(i-$C_3H_7)_3$ | | |
| 100 | 2-S—$C_4H_9$ | | |
| 101 | 3-S—$C_4H_9$ | | |
| 102 | 4-S—$C_4H_9$ | | |
| 103 | 2-t-$C_4H_9$ | | |
| 104 | 3-t-$C_4H_9$ | | |
| 105 | 4-t-$C_4H_9$ | | |
| 106 | 2,3-(t-$C_4H_9)_2$ | | |
| 107 | 2,4-(t-$C_4H_9)_2$ | | |
| 108 | 2,5-(t-$C_4H_9)_2$ | | |
| 109 | 2,6-(t-$C_4H_9)_2$ | | |
| 110 | 3,4-(t-$C_4H_9)_2$ | | |
| 111 | 2,4,6-(t-$C_4H_9)_3$ | | |
| 112 | 4-n-$C_9H_{19}$ | | |
| 113 | 4-n-$C_{12}H_{25}$ | | |
| 114 | 3-n-$C_{15}H_{31}$ | | |
| 115 | 4-(1,1,3,3-tetramethylbutyl) | | |
| 116 | 4-(2,4,4-trimethylpropyl | | |
| 117 | 2-t-$C_4H_9$, 4-$CH_3$ | | |
| 118 | 2-t-$C_4H_9$, 5-$CH_3$ | | |
| 119 | 2,6-(t-$C_4H_9$), 4-$CH_3$ | | |
| 120 | 2-$CH_3$, 4-t-$C_4H_9$ | | |
| 121 | 2-$CH_3$, 6-t-$C_4H_9$ | | |
| 122 | 2-$CH_3$, 4-i-$C_3H_7$ | | |
| 123 | 2-$CH_3$, 5-i-$C_3H_7$ | | |
| 124 | 3-$CH_3$, 4-i-$C_3H_7$ | | |
| 125 | 2-i-$C_3H_7$, 5 $CH_3$ | | |
| 126 | 2,4-(t-$C_4H_9$), 6-i-$C_3H_7$ | | |
| 127 | 2-allyl | | |
| 128 | 3-allyl | | |
| 129 | 4-allyl | | |
| 130 | 2-allyl, 6-$CH_3$ | | |
| 131 | 2-cyclo-$C_6H_{11}$ | | |
| 132 | 3-cyclo-$C_6H_{11}$ | | |
| 133 | 4-cyclo-$C_6H_{11}$ | | |
| 134 | 2,4-(cyclo-$C_6H_{11})_2$, 6-$CH_3$ | | |
| 135 | 2-$CH_3$, 4-cyclo-$C_6H_{11}$ | | |
| 136 | 2-$CH_2$—$C_6H_5$ | | |

TABLE 13-continued

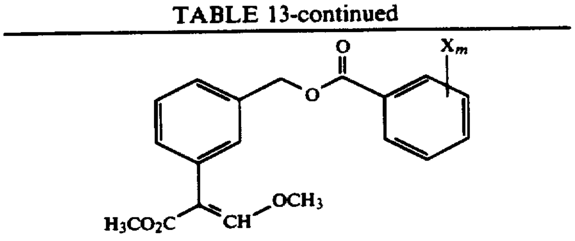

| No. | $X_m$ | mp | NMR: δ (ppm) |
|---|---|---|---|
| 137 | 3-$CH_2$—$C_6H_5$ | | |
| 138 | 4-$CH_2$—$C_6H_5$ | | |
| 139 | 2-$CH_2$—$C_6H_5$, 4-$CH_3$ | | |
| 140 | 2-$CH_3$, 4-$CH_2$—$C_6H_5$ | | |
| 141 | 2-$C_6H_5$ | | |
| 142 | 3-$C_6H_5$ | | |
| 143 | 4-$C_6H_5$ | | |
| 144 | 4-(2-i-$C_3H_7$—$C_6H_4$) | | |
| 145 | 4-$C_6H_5$, 2,6-$(CH_3)_2$ | | |
| 146 | 2-Cl, 4-$C_6H_5$ | | |
| 147 | 2-Br, 4-$C_6H_5$ | | |
| 148 | 2-$C_6H_5$, 4-Cl | | |
| 149 | 2-$C_6H_5$, 4-Br | | |
| 150 | 2-$CH_2C_6H_5$, 4-Cl | | |
| 151 | 2-$CH_2C_6H_5$, 4-Br | | |
| 152 | 2-Cl, 4-$CH_2C_6H_5$ | | |
| 153 | 2-Br, 4-$CH_2C_6H_5$ | | |
| 154 | 2-cyclo-$C_6H_{11}$, 4-Cl | | |
| 155 | 2-cyclo-$C_6H_{11}$, 4-Br | | |
| 156 | 2-Cl, 4-cyclo-$C_6H_{11}$ | | |
| 157 | 2-Br, 4-cyclo-$C_6H_{11}$ | | |
| 158 | 2-$OCH_3$ | 89-91 | |
| 159 | 3-$OCH_3$ | 72-73 | |
| 160 | 4-$OCH_3$ | oil | 5.35(S, 2H); 7.55(S, 1H) |
| 161 | 2-$OC_2H_5$ | | |
| 162 | 3-O—$C_2H_5$ | | |
| 163 | 4-O—$C_2H_5$ | | |
| 164 | 2-O-n-$C_3H_7$ | oil | 5.35(S, 2H); 7.55(S, 1H) |
| 165 | 3-O-n-$C_3H_7$ | oil | 5.35(S, 2H); 7.55(S, 1H) |
| 166 | 4-O-n-$C_3H_7$ | 73-74 | |
| 167 | 2-O-i-$C_3H_7$ | | |
| 168 | 3-O-i-$C_3H_7$ | | |
| 169 | 4-O-i-$C_3H_7$ | | |
| 170 | 2-O-n-$C_6H_{13}$ | oil | 5.35(S, 2H); 7.55(S, 1H) |
| 171 | 3-O-n-$C_6H_{13}$ | 43-45 | |
| 172 | 4-O-n-$C_6H_{13}$ | | |
| 173 | 2-O-n-$C_8H_{17}$ | | |
| 174 | 3-O-n-$C_8H_{17}$ | | |
| 175 | 4-O-n-$C_8H_{17}$ | | |
| 176 | 2-O—$CH_2C_6H_5$ | oil | 5.35(S, 2H); 7.55(S, 1H) |
| 177 | 3-O—$CH_2C_6H_5$ | oil | 5.35(S, 2H); 7.55(S, 1H) |
| 178 | 4-O—$CH_2C_6H_5$ | 103-106 | |
| 179 | 2-O—$(CH_2)_3C_6H_5$ | oil | 5.35(S, 2H); 7.55(S, 1H) |
| 180 | 3-O—$(CH_2)_3C_6H_5$ | oil | 5.35(S, 2H); 7.55(S, 1H) |
| 181 | 4-O—$(CH_2)_3C_6H_5$ | oil | 5.35(S, 2H); 7.55(S, 1H) |
| 182 | 2,4-$(OCH_3)_2$ | | |
| 183 | 2-$CF_3$ | | |
| 184 | 3-$CF_3$ | | |
| 185 | 4-$CF_3$ | | |
| 186 | 2-$OCF_3$ | | |
| 187 | 3-$OCF_3$ | | |
| 188 | 4-$OCF_3$ | | |
| 189 | 3-$OCH_2CHF_2$ | | |
| 190 | 2-$NO_2$ | | |
| 191 | 3-$NO_2$ | | |
| 192 | 4-$NO_2$ | | |
| 193 | 2-CN | | |
| 194 | 3-CN | | |
| 195 | 4-CN | | |
| 196 | 2-$CH_3$, 3-Cl | | |
| 197 | 2-$CH_3$, 4-Cl | | |

TABLE 13-continued

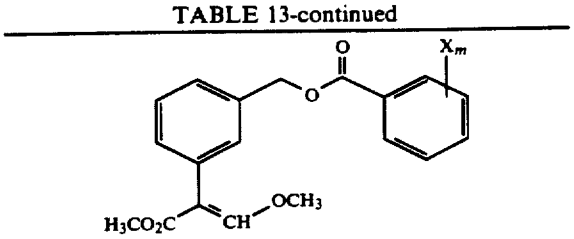

| No. | $X_m$ | mp | NMR: δ (ppm) |
|---|---|---|---|
| 198 | 2-$CH_3$, 5-Cl | | |
| 199 | 2-$CH_3$, 6-Cl | | |
| 200 | 2-$CH_3$, 3-F | | |
| 201 | 2-$CH_3$, 4-F | | |
| 202 | 2-$CH_3$, 5-F | | |
| 203 | 2-$CH_3$, 6-F | | |
| 204 | 2-$CH_3$, 3-Br | | |
| 205 | 2-$CH_3$, 4-Br | | |
| 206 | 2-$CH_3$, 5-Br | | |
| 207 | 2-$CH_3$, 6-Br | | |
| 208 | 2-Cl, 3-$CH_3$ | | |
| 209 | 2-Cl, 4-$CH_3$ | | |
| 210 | 2-Cl, 5-$CH_3$ | | |
| 211 | 2-F, 3-$CH_3$ | | |
| 212 | 2-F, 4-$CH_3$ | | |
| 213 | 2-F, 5-$CH_3$ | | |
| 214 | 2-Br, 3-$CH_3$ | | |
| 215 | 2-Br, 4-$CH_3$ | | |
| 216 | 2-Br, 5-$CH_3$ | | |
| 217 | 3-$CH_3$, 4-Cl | | |
| 218 | 3-$CH_3$, 5-Cl | | |
| 219 | 3-$CH_3$, 4-F | | |
| 220 | 3-$CH_3$, 4-Br | | |
| 221 | 3-$CH_3$, 4-Br | | |
| 222 | 3-$CH_3$, 5-Br | | |
| 223 | 3-F, 4-$CH_3$ | | |
| 224 | 3-Cl, 4-$CH_3$ | | |
| 225 | 3-Br, 4-$CH_3$ | | |
| 226 | 2-Cl, 4,5-$(CH_3)_2$ | | |
| 227 | 2-Br, 4,5-$(CH_3)_2$ | | |
| 228 | 2-Cl, 3,5-$(CH_3)_2$ | | |
| 229 | 2-Br, 3,5-$(CH_3)_2$ | | |
| 230 | 2,6-$Cl_2$, 4-$CH_3$ | | |
| 231 | 2,6-$F_2$, 4-$CH_3$ | | |
| 232 | 2,6-$Br_2$, 4-$CH_3$ | | |
| 233 | 2,4-$Cl_2$, 4-$CH_3$ | | |
| 234 | 2,4-$F_2$, 4-$CH_3$ | | |
| 235 | 2,4-$Br_2$, 4-$CH_3$ | | |
| 236 | 2,6-$(CH_3)_2$, 4-F | | |
| 237 | 2,6-$(CH_3)_2$, 4-Cl | | |
| 238 | 2,6-$(CH_3)_2$, 4-Br | | |
| 239 | 3,5-$(CH_3)_2$, 4-F | | |
| 240 | 3,5-$(CH_3)_2$, 4-Cl | | |
| 241 | 3,5-$(CH_3)_2$, 4-Br | | |
| 242 | 2,3,6-$(CH_3)_3$, 4-F | | |
| 243 | 2,3,6-$(CH_3)_3$, 4-Cl | | |
| 244 | 2,3,6-$(CH_3)_3$, 4-Br | | |
| 245 | 2,4-$(CH_3)_2$, 6-F | | |
| 246 | 2,4-$(CH_3)_2$, 6-Cl | | |
| 247 | 2,4-$(CH_3)_{62}$, 6-Br | | |
| 248 | 2-i-$C_3H_7$, 4-Cl, 5-$CH_3$ | | |
| 249 | 2-Cl, 4-$NO_2$ | | |
| 250 | 2-$NO_2$, 4-Cl | | |
| 251 | 2-$OCH_3$, 5-$NO_2$ | | |
| 252 | 2,4-$Cl_2$, 5-$NO_2$ | | |
| 253 | 2,4-$Cl_2$, 6-$NO_2$ | | |
| 254 | 2,6-$Cl_2$, 4-$NO_2$ | | |
| 255 | 2,6-$Br_2$, 4-$NO_2$ | | |
| 256 | 2,6-$I_2$, 4-$NO_2$ | | |
| 257 | 2-$CH_3$, 5-i-$C_3H_7$, 4-Cl | | |
| 258 | 2-$C_6H_5O$ | | |
| 259 | 3-$C_6H_5O$ | | |
| 260 | 4-$C_6H_5O$ | | |
| 261 | 2-$CHNOCH_3$ | | |
| 262 | 3-$CHNOCH_3$ | | |
| 263 | 4-$CHNOCH_3$ | | |
| 264 | 2-$CHNOC_2H_5$ | | |
| 265 | 3-$CHNOC_2H_5$ | | |
| 266 | 4-$CHNOC_2H_5$ | | |
| 267 | 2-CHNO(n-$C_3H_7$) | | |

TABLE 13-continued

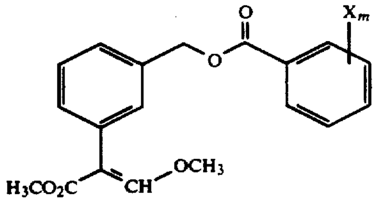

| No. | $X_m$ | mp | NMR: δ (ppm) |
|---|---|---|---|
| 268 | 3-CHNO(n-$C_3H_7$) | | |
| 269 | 4-CHNO(n-$C_3H_7$) | | |
| 270 | 2-CHNO(i-$C_3H_7$) | | |
| 271 | 3-CHNO(i-$C_3H_7$) | | |
| 272 | 4-CHNO(i-$C_3H_7$) | | |
| 273 | 2-CHNO(i-$C_6H_{13}$) | | |
| 274 | 3-CHNO(i-$C_6H_{13}$) | | |
| 275 | 4-CHNO(i-$C_6H_{13}$) | | |
| 276 | 2-CHNO(n-$C_8H_{17}$) | | |
| 277 | 3-CHNO(n-$C_8H_{17}$) | | |
| 278 | 4-CHNO(n-$C_8H_{17}$) | | |
| 279 | 2-$CHNOCH_2(C_6H_5)$ | | |
| 280 | 3-$CHNOCH_2(C_6H_5)$ | | |
| 281 | 4-$CHNOCH_2(C_6H_5)$ | | |
| 282 | 2-$CO_2CH_3$ | | |
| 283 | 3-$CO_2CH_3$ | | |
| 284 | 4-$CO_2CH_3$ | | |
| 285 | 2-$CO_2(C_2H_5)$ | | |
| 286 | 3-$CO_2(C_2H_5)$ | | |
| 287 | 4-$CO_2(C_2H_5)$ | | |
| 288 | 2-$CO_2$(n-$C_3H_7$) | | |
| 289 | 3-$CO_2$(n-$C_3H_7$) | | |
| 290 | 4-$CO_2$(n-$C_3H_7$) | | |
| 291 | 2-$CO_2$(i-$C_3H_7$) | | |
| 292 | 3-$CO_2$(i-$C_3H_7$) | | |
| 293 | 4-$CO_2$(i-$C_3H_7$) | | |
| 294 | 2-$CO_2$(i-$C_6H_{13}$) | | |
| 295 | 3-$CO_2$(i-$C_6H_{13}$) | | |
| 296 | 4-$CO_2$(i-$C_6H_{13}$) | | |
| 297 | 2-$CO_2$(n-$C_8H_{17}$) | | |
| 298 | 3-$CO_2$(n-$C_8H_{17}$) | | |
| 299 | 4-$CO_2$(n-$C_8H_{17}$) | | |
| 300 | 2-CHNO—$CH_2$—CH═$CH_2$ | | |
| 301 | 3-CHNO—$CH_2$—CH═$CH_2$ | | |
| 302 | 4-CHNO—$CH_2$—CH═$CH_2$ | | |
| 303 | 2-$CHNO(CH_2)_3(C_6H_5)$ | | |
| 304 | 3-$CHNO(CH_2)_3(C_6H_5)$ | | |
| 305 | 4-$CHNO(CH_2)_3(C_6H_5)$ | | |
| 306 | 2-$CH_2OCH_3$ | | |
| 307 | 3-$CH_2OCH_3$ | | |
| 308 | 4-$CH_2OCH_3$ | | |
| 309 | 2-$CH_2O(C_2H_5)$ | | |
| 310 | 3-$CH_2O(C_2H_5)$ | | |
| 311 | 4-$CH_2O(C_2H_5)$ | | |
| 312 | 2-$CH_2O$(n-$C_3H_7$) | | |
| 313 | 3-$CH_2O$(n-$C_3H_7$) | | |
| 314 | 4-$CH_2O$(n-$C_3H_7$) | | |
| 315 | 2-$CH_2O$(i-$C_3H_7$) | | |
| 316 | 3-$CH_2O$(i-$C_3H_7$) | | |
| 317 | 4-($CH_2O$(i-$C_3H_7$) | | |
| 318 | 2-$CH_2O$(n-$C_6H_{13}$) | | |
| 319 | 3-$CH_2O$(n-$C_6H_{13}$) | | |
| 320 | 4-$CH_2O$(n-$C_6H_{13}$) | | |
| 321 | 2-$CH_2O$(n-$C_8H_{17}$) | | |
| 322 | 3-$CH_2O$(n-$C_8H_{17}$) | | |
| 323 | 4-$CH_2O$(n-$C_8H_7$) | | |
| 324 | 2-$CH_2OCH_2(C_6H_5)$ | | |
| 325 | 3-$CH_2OCH_2(C_6H_5)$ | | |
| 326 | 4-$CH_2OCH_2(C_6H_5)$ | | |
| 327 | 2-$CH_2O(CH_2)_3$ | | |
| 328 | 3-$CH_2O(CH_2)_3(C_6H_5)$ | | |
| 329 | 4-$CH_2O(CH_2)_3(C_6H_5)$ | | |
| 330 | 2-CHO | | |
| 331 | 3-CHO | | |
| 332 | 4-CHO | | |

TABLE 14

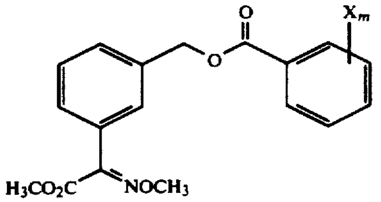

| No. | $X_m$ | mp | NMR: δ (ppm) |
|---|---|---|---|
| 1 | 2-F | | |
| 2 | 3-F | | |
| 3 | 4-F | | |
| 4 | 2,4-$F_2$ | | |
| 5 | 2,4,6-$F_3$ | | |
| 6 | 2,3,4,5,6-$F_5$ | | |
| 7 | 2,3-$F_2$ | | |
| 8 | 2-Cl | | |
| 9 | 3-Cl | | |
| 10 | 4-Cl | | |
| 11 | 2,3-$Cl_2$ | | |
| 12 | 2,4-$Cl_2$ | | |
| 13 | 2,5-$Cl_2$ | | |
| 14 | 2,6-$Cl_2$ | | |
| 15 | 3,4-$Cl_2$ | | |
| 16 | 3,5-$Cl_2$ | | |
| 17 | 2,3,4-$Cl_3$ | | |
| 18 | 2,3,5-$Cl_3$ | | |
| 19 | 2,3,6-$Cl_3$ | | |
| 20 | 2,4,5-$Cl_3$ | | |
| 21 | 2,4,6-$Cl_3$ | | |
| 22 | 3,4,5-$Cl_3$ | | |
| 23 | 2,3,4,6-$Cl_4$ | | |
| 24 | 2,3,5,6-$Cl_4$ | | |
| 25 | 2,3,4,5,6-$Cl_5$ | | |
| 26 | 2-Br | | |
| 27 | 3-Br | | |
| 28 | 4-Br | | |
| 29 | 2,4-$Br_2$ | | |
| 30 | 2,5-$Br_5$ | | |
| 31 | 2,6-$Br_2$ | | |
| 32 | 2,4,6-$Br_3$ | | |
| 33 | 2,3,4,5,6-$Br_5$ | | |
| 34 | 2-I | | |
| 35 | 3-I | | |
| 36 | 4-I | | |
| 37 | 2,4-$I_2$ | | |
| 38 | 2-Cl, 3-F | | |
| 39 | 2-Cl, 4-F | | |
| 40 | 2-Cl, 5-F | | |
| 41 | 2-Cl, 6-F | | |
| 42 | 2-Cl, 3-Br | | |
| 43 | 2-Cl, 4-Br | | |
| 44 | 2-Cl, 6-Br | | |
| 45 | 2-Cl, 6-Br | | |
| 46 | 2-Br, 3-Cl | | |
| 47 | 2-Br, 4-Cl | | |
| 48 | 2-Br, 5-Cl | | |
| 49 | 2-Br, 3-F | | |
| 50 | 2-Br, 4-F | | |
| 51 | 2-Br, 5-F | | |
| 52 | 2-Br, 6-F | | |
| 53 | 2-F, 3-Cl | | |
| 54 | 2-F, 4-Cl | | |
| 55 | 2-F, 5-Cl | | |
| 56 | 3-Cl, 4-F | | |
| 57 | 3-Cl, 5-F | | |
| 58 | 3-Cl, 4-Br | | |
| 59 | 3-Cl, 5-Br | | |
| 60 | 3-F, 4-Cl | | |
| 61 | 3-F, 4-Br | | |
| 62 | 3-Br, 4-Cl | | |
| 63 | 3-Br, 4-F | | |
| 64 | 2,6-$Cl_2$, 4-Br | | |
| 65 | 2-$CH_3$ | | |
| 66a) | 3-$CH_3$: non-polar isomer | oil | 3.9(S, 3H); 4.0(S, 3H); 5.15(S, 2H) |
| 66b) | 3-$CH_3$: polar isomer | 66–70 | |
| 67 | 4-$CH_3$ | | |
| 68 | 2,3-$(CH_3)_2$ | | |

TABLE 14-continued

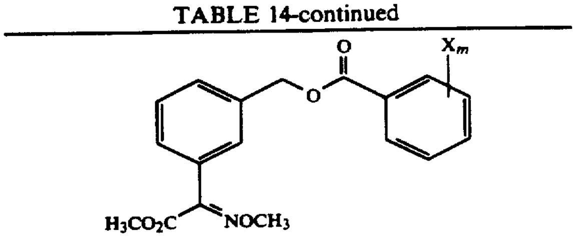

| No. | $X_m$ | mp | NMR: δ (ppm) |
|---|---|---|---|
| 69 | 2,4-$(CH_3)_2$ | | |
| 70 | 2,5-$(CH_3)_2$ | | |
| 71 | 2,6-$(CH_3)_2$ | | |
| 72 | 3,4-$(CH_3)_2$ | | |
| 73 | 3,5-$(CH_3)_2$ | | |
| 74 | 3,5-$(CH_3)_2$ | | |
| 75 | 2,3,4-$(CH_3)_3$ | | |
| 76 | 2,3,6-$(CH_3)_3$ | | |
| 77 | 2,4,5-$(CH_3)_3$ | | |
| 78 | 2,4,6-$(CH_3)_3$ | | |
| 79 | 3,4,5-$(CH_3)_3$ | | |
| 80 | 2,3,4,6-$(CH_3)_4$ | | |
| 81 | 2,3,5,6-$(CH_3)_4$ | | |
| 82 | 2,3,4,5,6-$(CH_3)_5$ | | |
| 83 | 2-$C_2H_5$ | | |
| 84 | 3-$C_2H_5$ | | |
| 85 | 4-$C_2H_5$ | | |
| 86 | 2,4-$(C_2H_5)_2$ | | |
| 87 | 2,6-$(C_2H_5)_2$ | | |
| 88 | 3,5-$(C_2H_5)_2$ | | |
| 89 | 2,4,6-$(C_2H_5)_3$ | | |
| 90 | 2-n-$C_3H_7$ | | |
| 91 | 3-n-$C_3H_7$ | | |
| 92 | 4-n-$C_3H_7$ | | |
| 93 | 2-i-$C_3H_7$ | | |
| 94 | 3-i-$C_3H_7$ | | |
| 95 | 4-i-$C_3H_7$ | | |
| 96 | 2,4-(i-$C_3H_7)_2$ | | |
| 97 | 2,6-(i-$C_3H_7)_2$ | | |
| 98 | 3,5-(i-$C_3H_7)_2$ | | |
| 99 | 2,4,6-(i-$C_3H_7)_3$ | | |
| 100 | 2-S—$C_4H_9$ | | |
| 101 | 3-S—$C_4H_9$ | | |
| 102 | 4-S—$C_4H_9$ | | |
| 103 | 2-t-$C_4H_9$ | | |
| 104 | 3-t-$C_4H_9$ | | |
| 105 | 4-t-$C_4H_9$ | | |
| 106 | 2,3-(t-$C_4H_9)_2$ | | |
| 107 | 2,4-(t-$C_4H_9)_2$ | | |
| 108 | 2,5-(t-$C_4H_9)_2$ | | |
| 109 | 2,6-(t-$C_4H_9)_2$ | | |
| 110 | 3,4-(t-$C_4H_9)_2$ | | |
| 111 | 2,4,6-(t-$C_4H_9)_3$ | | |
| 112 | 4-n-$C_9H_{19}$ | | |
| 113 | 4-n-$C_{12}H_{25}$ | | |
| 114 | 3-n-$C_{15}H_{31}$ | | |
| 115 | 4-(1,1,3,3-tetramethylbutyl) | | |
| 116 | 4-(2,4,4-trimethylpropyl | | |
| 117 | 2-t-$C_4H_9$, 4-$CH_3$ | | |
| 118 | 2-t-$C_4H_9$, 5-$CH_3$ | | |
| 119 | 2,6-(t-$C_4H_9$), 4-$CH_3$ | | |
| 120 | 2-$CH_3$, 4-t-$C_4H_9$ | | |
| 121 | 2-$CH_3$, 6-t-$C_4H_9$ | | |
| 122 | 2-$CH_3$, 4-i-$C_3H_7$ | | |
| 123 | 2-$CH_3$, 5-i-$C_3H_7$ | | |
| 124 | 3-$CH_3$, 4-i-$C_3H_7$ | | |
| 125 | 2-i-$C_3H_7$, 5 $CH_3$ | | |
| 126 | 2,4-(t-$C_4H_9$), 6-i-$C_3H_7$ | | |
| 127 | 2-allyl | | |
| 128 | 3-allyl | | |
| 129 | 4-allyl | | |
| 130 | 2-allyl, 6-$CH_3$ | | |
| 131 | 2-cyclo-$C_6H_{11}$ | | |
| 132 | 3-cyclo-$C_6H_{11}$ | | |
| 133 | 4-cyclo-$C_6H_{11}$ | | |
| 134 | 2,4-(cyclo-$C_6H_{11})_2$, 6-$CH_3$ | | |
| 135 | 2-$CH_3$, 4-cyclo-$C_6H_{11}$ | | |
| 136 | 2-$CH_2$—$C_6H_5$ | | |
| 137 | 3-$CH_2$—$C_6H_5$ | | |
| 138 | 4-$CH_2$—$C_2H_5$ | | |

TABLE 14-continued

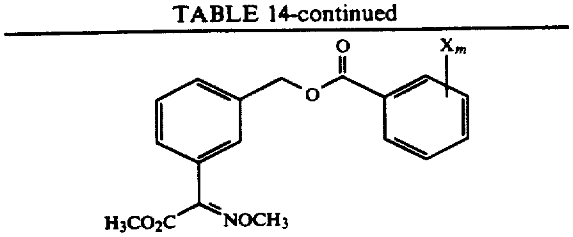

| No. | $X_m$ | mp | NMR: δ (ppm) |
|---|---|---|---|
| 139 | 2-$CH_2$—$C_6H_5$, 4-$CH_3$ | | |
| 140 | 2-$CH_3$, 4-$CH_2$—$C_6H_5$ | | |
| 141 | 2-$C_6H_5$ | | |
| 142 | 3-$C_6H_5$ | | |
| 143 | 4-$C_6H_5$ | | |
| 144 | 4-(2-i-$C_3H_7$—$C_6H_4$) | | |
| 145 | 4-$C_6H_5$, 2,6-$(CH_3)_2$ | | |
| 146 | 2-Cl, 4-$C_6H_5$ | | |
| 147 | 2-Br, 4-$C_6H_5$ | | |
| 148 | 2-$C_6H_5$, 4-Cl | | |
| 149 | 2-$C_6H_5$, 4-Br | | |
| 150 | 2-$CH_2C_6H_5$, 4-Cl | | |
| 151 | 2-$CH_2C_6H_5$, 4-Br | | |
| 152 | 2-Cl, 4-$CH_2C_6H_5$ | | |
| 153 | 2-Br, 4-$CH_2C_6H_5$ | | |
| 154 | 2-cyclo-$C_6H_{11}$, 4-Cl | | |
| 155 | 2-cyclo-$C_6H_{11}$, 4-Br | | |
| 156 | 2-Cl, 4-cyclo-$C_6H_{11}$ | | |
| 157 | 2-Br, 4-cyclo-$C_6H_{11}$ | | |
| 158 | 2-$OCH_3$ | | |
| 159 | 3-$OCH_3$ | | |
| 160 | 4-$OCH_3$ | | |
| 161 | 2-$OC_2H_5$ | | |
| 162 | 3-O—$C_2H_5$ | | |
| 163 | 4-O—$C_2H_5$ | | |
| 164 | 2-O-n-$C_3H_7$ | | |
| 165 | 3-O-n-$C_3H_7$ | | |
| 166 | 4-O-n-$C_3H_7$ | | |
| 167 | 2-O-i-$C_3H_7$ | | |
| 168 | 3-O-i-$C_3H_7$ | | |
| 169 | 4-O-i-$C_3H_7$ | | |
| 170 | 2-O-n-$C_6H_{13}$ | | |
| 171 | 3-O-n-$C_6H_{13}$ | | |
| 172 | 4-O-n-$C_6H_{13}$ | | |
| 173 | 2-O-n-$C_8H_{17}$ | | |
| 174 | 3-O-n-$C_8H_{17}$ | | |
| 175 | 4-O-n-$C_8H_{17}$ | | |
| 176 | 2-O—$CH_2C_6H_5$ | | |
| 177 | 3-O—$CH_2C_6H_5$ | | |
| 178 | 4-O—$CH_2C_6H_5$ | | |
| 179 | 2-O—$(CH_2)_3C_6H_5$ | | |
| 180 | 3-O—$(CH_2)_3C_6H_5$ | | |
| 181 | 4-O—$(CH_2)_3C_6H_5$ | | |
| 182 | 2,4-$(OCH_3)_2$ | | |
| 183 | 2-$CF_3$ | | |
| 184 | 3-$CF_3$ | | |
| 185 | 4-$CF_3$ | | |
| 186 | 2-$OCF_3$ | | |
| 187 | 3-$OCF_3$ | | |
| 188 | 4-$OCF_3$ | | |
| 189 | 3-$OCH_2CHF_2$ | | |
| 190 | 2-$NO_2$ | | |
| 191 | 3-$NO_2$ | | |
| 192 | 4-$NO_2$ | | |
| 193 | 2-CN | | |
| 194 | 3-CN | | |
| 195 | 4-CN | | |
| 196 | 2-$CH_3$, 3-Cl | | |
| 197 | 2-$CH_3$, 4-Cl | | |
| 198 | 2-$CH_3$, 5-Cl | | |
| 199 | 2-$CH_3$, 6-Cl | | |
| 200 | 2-$CH_3$, 3-F | | |
| 201 | 2-$CH_3$, 4-F | | |
| 202 | 2-$CH_3$, 5-F | | |
| 203 | 2-$CH_3$, 6-F | | |
| 204 | 2-$CH_3$, 3-Br | | |
| 205 | 2-$CH_3$, 4-Br | | |
| 206 | 2-$CH_3$, 5-Br | | |
| 207 | 2-$CH_3$, 6-Br | | |
| 208 | 2-Cl, 3-$CH_3$ | | |

TABLE 14-continued

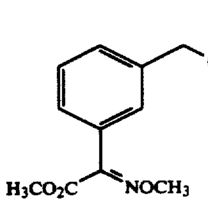

| No. | $X_m$ | mp | NMR: δ (ppm) |
|---|---|---|---|
| 209 | 2-Cl, 4-$CH_3$ | | |
| 210 | 2-Cl, 5-$CH_3$ | | |
| 211 | 2-F, 3-$CH_3$ | | |
| 212 | 2-F, 4-$CH_3$ | | |
| 213 | 2-F, 5-$CH_3$ | | |
| 214 | 2-Br, 3-$CH_3$ | | |
| 215 | 2-Br, 4-$CH_3$ | | |
| 216 | 2-Br, 5-$CH_3$ | | |
| 217 | 3-$CH_3$, 4-Cl | | |
| 218 | 3-$CH_3$, 5-Cl | | |
| 219 | 3-$CH_3$, 4-F | | |
| 220 | 3-$CH_3$, 4-Br | | |
| 221 | 3-$CH_3$, 4-Br | | |
| 222 | 3-$CH_3$, 5-Br | | |
| 223 | 3-F, 4-$CH_3$ | | |
| 224 | 3-Cl, 4-$CH_3$ | | |
| 225 | 3-Br, 4-$CH_3$ | | |
| 226 | 2-Cl, 4,5-$(CH_3)_2$ | | |
| 227 | 2-Br, 4,5-$(CH_3)_2$ | | |
| 228 | 2-Cl, 3,5-$(CH_3)_2$ | | |
| 229 | 2-Br, 3,5-$(CH_3)_2$ | | |
| 230 | 2,6-$Cl_2$, 4-$CH_3$ | | |
| 231 | 2,6-$F_2$, 4-$CH_3$ | | |
| 232 | 2,6-$Br_2$, 4-$CH_3$ | | |
| 233 | 2,4-$Cl_2$, 6-$CH_3$ | | |
| 234 | 2,4-$F_2$, 6-$CH_3$ | | |
| 235 | 2,4-$Br_2$, 6-$CH_3$ | | |
| 236 | 2,6-$(CH_3)_2$, 4-F | | |
| 237 | 2,6-$(CH_3)_2$, 4-Cl | | |
| 238 | 2,6-$(CH_3)_2$, 4-Br | | |
| 239 | 3,5-$(CH_3)_2$, 4-F | | |
| 240 | 3,5-$(CH_3)_2$, 4-Cl | | |
| 241 | 3,5-$(CH_3)_2$, 4-Br | | |
| 242 | 2,3,6-$(CH_3)_3$, 4-F | | |
| 243 | 2,3,6-$(CH_3)_3$, 4-Cl | | |
| 244 | 2,3,6-$(CH_3)_3$, 4-Br | | |
| 245 | 2,4-$(CH_3)_2$, 6-F | | |
| 246 | 2,4-$(CH_3)_2$, 6-Cl | | |
| 247 | 2,4-$(CH_3)_{62}$, 6-Br | | |
| 248 | 2-i-$C_3H_7$, 4-Cl, 5-$CH_3$ | | |
| 249 | 2-Cl, 4-$NO_2$ | | |
| 250 | 2-$NO_2$, 4-Cl | | |
| 251 | 2-$OCH_3$, 5-$NO_2$ | | |
| 252 | 2,4-$Cl_2$, 5-$NO_2$ | | |
| 253 | 2,4-$Cl_2$, 6-$NO_2$ | | |
| 254 | 2,6-$Cl_2$, 4-$NO_2$ | | |
| 255 | 2,6-$Br_2$, 4-$NO_2$ | | |
| 256 | 2,6-$I_2$, 4-$NO_2$ | | |
| 257 | 2-$CH_3$, 5-i-$C_3H_7$, 4-Cl | | |
| 258 | 2-$C_6H_5O$ | | |
| 259 | 3-$C_6H_5O$ | | |
| 260 | 4-$C_6H_5O$ | | |
| 261 | 2-$CHNOCH_3$ | | |
| 262 | 3-$CHNOCH_3$ | | |
| 263 | 4-$CHNOCH_3$ | | |
| 264 | 2-$CHNOC_2H_5$ | | |
| 265 | 3-$CHNOC_2H_5$ | | |
| 266 | 4-$CHNOC_2H_5$ | | |
| 267 | 2-CHNO(n-$C_3H_7$) | | |
| 268 | 3-CHNO(n-$C_3H_7$) | | |
| 269 | 4-CHNO(n-$C_3H_7$) | | |
| 270 | 2-CHNO(i-$C_3H_7$) | | |
| 271 | 3-CHNO(i-$C_3H_7$) | | |
| 272 | 4-CHNO(i-$C_3H_7$) | | |
| 273 | 2-CHNO(n-$C_6H_{13}$) | | |
| 274 | 3-CHNO(n-$C_6H_{13}$) | | |
| 275 | 4-CHNO(n-$C_6H_{13}$) | | |
| 276 | 2-CHNO(n-$C_8H_{17}$) | | |
| 277 | 3-CHNO(n-$C_8H_{17}$) | | |
| 278 | 4-CHNO(n-$C_8H_{17}$) | | |

TABLE 14-continued

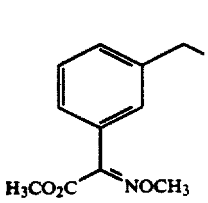

| No. | $X_m$ | mp | NMR: δ (ppm) |
|---|---|---|---|
| 279 | 2-$CHNOCH_2(C_6H_5)$ | | |
| 280 | 3-$CHNOCH_2(C_6H_5)$ | | |
| 281 | 4-$CHNOCH_2(C_6H_5)$ | | |
| 282 | 2-$CO_2CH_3$ | | |
| 283 | 3-$CO_2CH_3$ | | |
| 284 | 4-$CO_2CH_3$ | | |
| 285 | 2-$CO_2(C_2H_5)$ | | |
| 286 | 3-$CO_2(C_2H_5)$ | | |
| 287 | 4-$CO_2(C_2H_5)$ | | |
| 288 | 2-$CO_2$(n-$C_3H_7$) | | |
| 289 | 3-$CO_2$(n-$C_3H_7$) | | |
| 290 | 4-$CO_2$(n-$C_3H_7$) | | |
| 291 | 2-$CO_2$(i-$C_3H_7$) | | |
| 292 | 3-$CO_2$(i-$C_3H_7$) | | |
| 293 | 4-$CO_2$(i-$C_3H_7$) | | |
| 294 | 2-$CO_2$(n-$C_6H_{13}$) | | |
| 295 | 3-$CO_2$(n-$C_6H_{13}$) | | |
| 296 | 4-$CO_2$(n-$C_6H_{13}$) | | |
| 297 | 2-$CO_2$(n-$C_8H_{17}$) | | |
| 298 | 3-$CO_2$(n-$C_8H_{17}$) | | |
| 299 | 4-$CO_2$(n-$C_8H_{17}$) | | |
| 300 | 2-$CHNO{-}CH_2{-}CH{=}CH_2$ | | |
| 301 | 3-$CHNO{-}CH_2{-}CH{=}CH_2$ | | |
| 302 | 4-$CHNO{-}CH_2{-}CH{=}CH_2$ | | |
| 303 | 2-$CHNO(CH_2)_3(C_6H_5)$ | | |
| 304 | 3-$CHNO(CH_2)_3(C_6H_5)$ | | |
| 305 | 4-$CHNO(CH_2)_3(C_6H_5)$ | | |
| 306 | 2-$CH_2OCH_3$ | | |
| 307 | 3-$CH_2OCH_3$ | | |
| 308 | 4-$CH_2OCH_3$ | | |
| 309 | 2-$CH_2O(C_2H_5)$ | | |
| 310 | 3-$CH_2O(C_2H_5)$ | | |
| 311 | 4-$CH_2O(C_2H_5)$ | | |
| 312 | 2-$CH_2O$(n-$C_3H_7$) | | |
| 313 | 3-$CH_2O$(n-$C_3H_7$) | | |
| 314 | 4-$CH_2O$(n-$C_3H_7$) | | |
| 315 | 2-$CH_2O$(i-$C_3H_7$) | | |
| 316 | 3-$CH_2O$(i-$C_3H_7$) | | |
| 317 | 4-($CH_2O$(i-$C_3H_7$) | | |
| 318 | 2-$CH_2O$(n-$C_6H_{13}$) | | |
| 319 | 3-$CH_2O$(n-$C_6H_{13}$) | | |
| 320 | 4-$CH_2O$(n-$C_6H_{13}$) | | |
| 321 | 2-$CH_2O$(n-$C_8H_{17}$) | | |
| 322 | 3-$CH_2O$(n-$C_8H_{17}$) | | |
| 323 | 4-$CH_2O$(n-$C_8H_7$) | | |
| 324 | 2-$CH_2OCH_2(C_6H_5)$ | | |
| 325 | 3-$CH_2OCH_2(C_6H_5)$ | | |
| 326 | 4-$CH_2OCH_2(C_6H_5)$ | | |
| 327 | 2-$CH_2O(CH_2)_3$ | | |
| 328 | 3-$CH_2O(CH_2)_3(C_6H_5)$ | | |
| 329 | 4-$CH_2O(CH_2)_3(C_6H_5)$ | | |
| 330 | 2-CHO | | |
| 331 | 3-CHO | | |
| 332 | 4-CHO | | |

TABLE 15

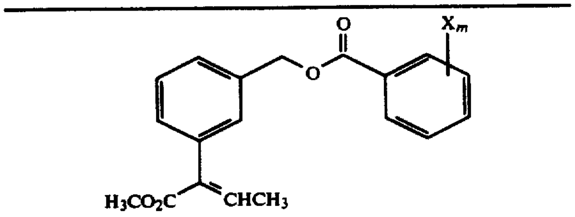

| No. | $X_m$ | mp | NMR: δ (ppm) |
|---|---|---|---|
| 1 | 2-F | | |
| 2 | 3-F | | |
| 3 | 4-F | | |
| 4 | 2,4-$F_2$ | | |
| 5 | 2,4,6-$F_3$ | | |
| 6 | 2,3,4,5,6-$F_5$ | | |
| 7 | 2,3-$F_2$ | | |
| 8 | 2-Cl | | |
| 9 | 3-Cl | | |
| 10 | 4-Cl | | |
| 11 | 2,3-$Cl_2$ | | |
| 12 | 2,4-$Cl_2$ | | |
| 13 | 2,5-$Cl_2$ | | |
| 14 | 2,6-$Cl_2$ | | |
| 15 | 3,4-$Cl_2$ | | |
| 16 | 3,5-$Cl_2$ | | |
| 17 | 2,3,4-$Cl_3$ | | |
| 18 | 2,3,5-$Cl_3$ | | |
| 19 | 2,3,6-$Cl_3$ | | |
| 20 | 2,4,5-$Cl_3$ | | |
| 21 | 2,4,6-$Cl_3$ | | |
| 22 | 3,4,5-$Cl_3$ | | |
| 23 | 2,3,4,6-$Cl_4$ | | |
| 24 | 2,3,5,6-$Cl_4$ | | |
| 25 | 2,3,4,5,6-$Cl_5$ | | |
| 26 | 2-Br | | |
| 27 | 3-Br | | |
| 28 | 4-Br | | |
| 29 | 2,4-$Br_2$ | | |
| 30 | 2,5-$Br_5$ | | |
| 31 | 2,6-$Br_2$ | | |
| 32 | 2,4,6-$Br_3$ | | |
| 33 | 2,3,4,5,6-$Br_5$ | | |
| 34 | 2-I | | |
| 35 | 3-I | | |
| 36 | 4-I | | |
| 37 | 2,4-$I_2$ | | |
| 38 | 2-Cl, 3-F | | |
| 39 | 2-Cl, 4-F | | |
| 40 | 2-Cl, 5-F | | |
| 41 | 2-Cl, 6-F | | |
| 42 | 2-Cl, 3-Br | | |
| 43 | 2-Cl, 4-Br | | |
| 44 | 2-Cl, 6-Br | | |
| 45 | 2-Cl, 6-Br | | |
| 46 | 2-Br, 3-Cl | | |
| 47 | 2-Br, 4-Cl | | |
| 48 | 2-Br, 5-Cl | | |
| 49 | 2-Br, 3-F | | |
| 50 | 2-Br, 4-F | | |
| 51 | 2-Br, 5-F | | |
| 52 | 2-Br, 6-F | | |
| 53 | 2-F, 3-Cl | | |
| 54 | 2-F, 4-Cl | | |
| 55 | 2-F, 5-Cl | | |
| 56 | 3-Cl, 4-F | | |
| 57 | 3-Cl, 5-F | | |
| 58 | 3-Cl, 4-Br | | |
| 59 | 3-Cl, 5-Br | | |
| 60 | 3-F, 4-Cl | | |
| 61 | 3-F, 4-Br | | |
| 62 | 3-Br, 4-Cl | | |
| 63 | 3-Br, 4-F | | |
| 64 | 2,6-$Cl_2$, 4-Br | | |
| 65 | 2-$CH_3$ | | |
| 66 | 3-$CH_3$ | | |
| 67 | 4-$CH_3$ | | |
| 68 | 2,3-$(CH_3)_2$ | | |
| 69 | 2,4-$(CH_3)_2$ | | |
| 70 | 2,5-$(CH_3)_2$ | | |

TABLE 15-continued

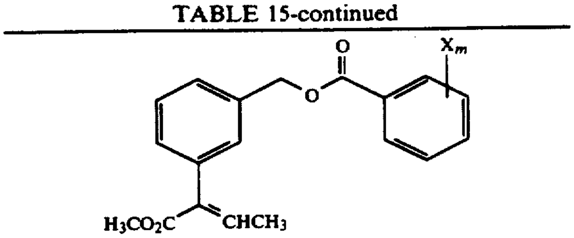

| No. | $X_m$ | mp | NMR: δ (ppm) |
|---|---|---|---|
| 71 | 2,6-$(CH_3)_2$ | | |
| 72 | 3,4-$(CH_3)_2$ | | |
| 73 | 3,5-$(CH_3)_2$ | | |
| 74 | 3,5-$(CH_3)_2$ | | |
| 75 | 2,3,4-$(CH_3)_3$ | | |
| 76 | 2,3,6-$(CH_3)_3$ | | |
| 77 | 2,4,5-$(CH_3)_3$ | | |
| 78 | 2,4,6-$(CH_3)_3$ | | |
| 79 | 3,4,5-$(CH_3)_3$ | | |
| 80 | 2,3,4,6-$(CH_3)_4$ | | |
| 81 | 2,3,5,6-$(CH_3)_4$ | | |
| 82 | 2,3,4,5,6-$(CH_3)_5$ | | |
| 83 | 2-$C_2H_5$ | | |
| 84 | 3-$C_2H_5$ | | |
| 85 | 4-$C_2H_5$ | | |
| 86 | 2,4-$(C_2H_5)_2$ | | |
| 87 | 2,6-$(C_2H_5)_2$ | | |
| 88 | 3,5-$(C_2H_5)_2$ | | |
| 89 | 2,4,6-$(C_2H_5)_3$ | | |
| 90 | 2-n-$C_3H_7$ | | |
| 91 | 3-n-$C_3H_7$ | | |
| 92 | 4-n-$C_3H_7$ | | |
| 93 | 2-i-$C_3H_7$ | | |
| 94 | 3-i-$C_3H_7$ | | |
| 95 | 4-i-$C_3H_7$ | | |
| 96 | 2,4-(i-$C_3H_7)_2$ | | |
| 97 | 2,6-(i-$C_3H_7)_2$ | | |
| 98 | 3,5-(i-$C_3H_7)_2$ | | |
| 99 | 2,4,6-(i-$C_3H_7)_3$ | | |
| 100 | 2-S-$C_4H_9$ | | |
| 101 | 3-S-$C_4H_9$ | | |
| 102 | 4-S-$C_4H_9$ | | |
| 103 | 2-t-$C_4H_9$ | | |
| 104 | 3-t-$C_4H_9$ | | |
| 105 | 4-t-$C_4H_9$ | | |
| 106 | 2,3-(t-$C_4H_9)_2$ | | |
| 107 | 2,4-(t-$C_4H_9)_2$ | | |
| 108 | 2,5-(t-$C_4H_9)_2$ | | |
| 109 | 2,6-(t-$C_4H_9)_2$ | | |
| 110 | 3,4-(t-$C_4H_9)_2$ | | |
| 111 | 2,4,6-(t-$C_4H_9)_3$ | | |
| 112 | 4-n-$C_9H_{19}$ | | |
| 113 | 4-n-$C_{12}H_{25}$ | | |
| 114 | 3-n-$C_{15}H_{31}$ | | |
| 115 | 4-(1,1,3,3-tetramethylbutyl) | | |
| 116 | 4-(2,4,4-trimethylpropyl | | |
| 117 | 2-t-$C_4H_9$, 4-$CH_3$ | | |
| 118 | 2-t-$C_4H_9$, 5-$CH_3$ | | |
| 119 | 2,6-(t-$C_4H_9$), 4-$CH_3$ | | |
| 120 | 2-$CH_3$, 4-t-$C_4H_9$ | | |
| 121 | 2-$CH_3$, 6-t-$C_4H_9$ | | |
| 122 | 2-$CH_3$, 4-i-$C_3H_7$ | | |
| 123 | 2-$CH_3$, 5-i-$C_3H_7$ | | |
| 124 | 3-$CH_3$, 4-i-$C_3H_7$ | | |
| 125 | 2-i-$C_3H_7$, 5 $CH_3$ | | |
| 126 | 2,4-(t-$C_4H_9$), 6-i-$C_3H_7$ | | |
| 127 | 2-allyl | | |
| 128 | 3-allyl | | |
| 129 | 4-allyl | | |
| 130 | 2-allyl, 6-$CH_3$ | | |
| 131 | 2-cyclo-$C_6H_{11}$ | | |
| 132 | 3-cyclo-$C_6H_{11}$ | | |
| 133 | 4-cyclo-$C_6H_{11}$ | | |
| 134 | 2,4-(cyclo-$C_6H_{11})_2$, 6-$CH_3$ | | |
| 135 | 2-$CH_3$, 4-cyclo-$C_6H_{11}$ | | |
| 136 | 2-$CH_2$—$C_6H_5$ | | |
| 137 | 3-$CH_2$—$C_6H_5$ | | |
| 138 | 4-$CH_2$—$C_2H_5$ | | |
| 139 | 2-$CH_2$—$C_6H_5$, 4-$CH_3$ | | |
| 140 | 2-$CH_3$, 4-$CH_2$—$C_6H_5$ | | |

TABLE 15-continued

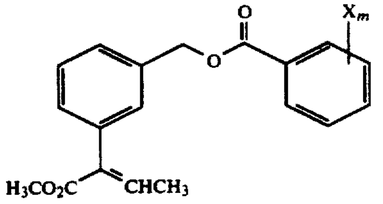

| No. | $X_m$ | mp | NMR: δ (ppm) |
|---|---|---|---|
| 141 | 2-$C_6H_5$ | | |
| 142 | 3-$C_6H_5$ | | |
| 143 | 4-$C_6H_5$ | | |
| 144 | 4-(2-i-$C_3H_7$—$C_6H_4$) | | |
| 145 | 4-$C_6H_5$, 2,6-$(CH_3)_2$ | | |
| 146 | 2-Cl, 4-$C_6H_5$ | | |
| 147 | 2-Br, 4-$C_6H_5$ | | |
| 148 | 2-$C_6H_5$, 4-Cl | | |
| 149 | 2-$C_6H_5$, 4-Br | | |
| 150 | 2-$CH_2C_6H_5$, 4-Cl | | |
| 151 | 2-$CH_2C_6H_5$, 4-Br | | |
| 152 | 2-Cl, 4-$CH_2C_6H_5$ | | |
| 153 | 2-Br, 4-$CH_2C_6H_5$ | | |
| 154 | 2-cyclo-$C_6H_{11}$, 4-Cl | | |
| 155 | 2-cyclo-$C_6H_{11}$, 4-Br | | |
| 156 | 2-Cl, 4-cyclo-$C_6H_{11}$ | | |
| 157 | 2-Br, 4-cyclo-$C_6H_{11}$ | | |
| 158 | 2-$OCH_3$ | | |
| 159 | 3-$OCH_3$ | | |
| 160 | 4-$OCH_3$ | | |
| 161 | 2-$OC_2H_5$ | | |
| 162 | 3-O-$C_2H_5$ | | |
| 163 | 4-O-$C_2H_5$ | | |
| 164 | 2-O-n-$C_3H_7$ | | |
| 165 | 3-O-n-$C_3H_7$ | | |
| 166 | 4-O-n-$C_3H_7$ | | |
| 167 | 2-O-i-$C_3H_7$ | | |
| 168 | 3-O-i-$C_3H_7$ | | |
| 169 | 4-O-i-$C_3H_7$ | | |
| 170 | 2-O-n-$C_6H_{13}$ | | |
| 171 | 3-O-n-$C_6H_{13}$ | | |
| 172 | 4-O-n-$C_6H_{13}$ | | |
| 173 | 2-O-n-$C_8H_{17}$ | | |
| 174 | 3-O-n-$C_8H_{17}$ | | |
| 175 | 4-O-n-$C_8H_{17}$ | | |
| 176 | 2-O-$CH_2C_6H_5$ | | |
| 177 | 3-O-$CH_2C_6H_5$ | | |
| 178 | 4-O-$CH_2C_6H_5$ | | |
| 179 | 2-O-$(CH_2)_3C_6H_5$ | | |
| 180 | 3-O-$(CH_2)_3C_6H_5$ | | |
| 181 | 4-O-$(CH_2)_3C_6H_5$ | | |
| 182 | 2,4-$(OCH_3)_2$ | | |
| 183 | 2-$CF_3$ | | |
| 184 | 3-$CF_3$ | | |
| 185 | 4-$CF_3$ | | |
| 186 | 2-$OCF_3$ | | |
| 187 | 3-$OCF_3$ | | |
| 188 | 4-$OCF_3$ | | |
| 189 | 3-$OCH_2CHF_2$ | | |
| 190 | 2-$NO_2$ | | |
| 191 | 3-$NO_2$ | | |
| 192 | 4-$NO_2$ | | |
| 193 | 2-CN | | |
| 194 | 3-CN | | |
| 195 | 4-CN | | |
| 196 | 2-$CH_3$, 3-Cl | | |
| 197 | 2-$CH_3$, 4-Cl | | |
| 198 | 2-$CH_3$, 5-Cl | | |
| 199 | 2-$CH_3$, 6-Cl | | |
| 200 | 2-$CH_3$, 3-F | | |
| 201 | 2-$CH_3$, 4-F | | |
| 202 | 2-$CH_3$, 5-F | | |
| 203 | 2-$CH_3$, 6-F | | |
| 204 | 2-$CH_3$, 3-Br | | |
| 205 | 2-$CH_3$, 4-Br | | |
| 206 | 2-$CH_3$, 5-Br | | |
| 207 | 2-$CH_3$, 6-Br | | |
| 208 | 2-Cl, 3-$CH_3$ | | |
| 209 | 2-Cl, 4-$CH_3$ | | |
| 210 | 2-Cl, 5-$CH_3$ | | |

TABLE 15-continued

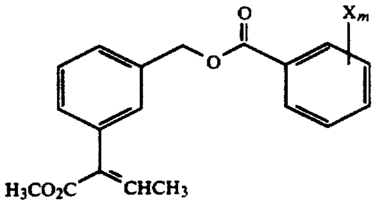

| No. | $X_m$ | mp | NMR: δ (ppm) |
|---|---|---|---|
| 211 | 2-F, 3-$CH_3$ | | |
| 212 | 2-F, 4-$CH_3$ | | |
| 213 | 2-F, 5-$CH_3$ | | |
| 214 | 2-Br, 3-$CH_3$ | | |
| 215 | 2-Br, 4-$CH_3$ | | |
| 216 | 2-Br, 5-$CH_3$ | | |
| 217 | 3-$CH_3$, 4-Cl | | |
| 218 | 3-$CH_3$, 5-Cl | | |
| 219 | 3-$CH_3$, 4-F | | |
| 220 | 3-$CH_3$, 4-Br | | |
| 221 | 3-$CH_3$, 4-Br | | |
| 222 | 3-$CH_3$, 5-Br | | |
| 223 | 3-F, 4-$CH_3$ | | |
| 224 | 3-Cl, 4-$CH_3$ | | |
| 225 | 3-Br, 4-$CH_3$ | | |
| 226 | 2-Cl, 4,5-$(CH_3)_2$ | | |
| 227 | 2-Br, 4,5-$(CH_3)_2$ | | |
| 228 | 2-Cl, 3,5-$(CH_3)_2$ | | |
| 229 | 2-Br, 3,5-$(CH_3)_2$ | | |
| 230 | 2,6-$Cl_2$, 4-$CH_3$ | | |
| 231 | 2,6-$F_2$, 4-$CH_3$ | | |
| 232 | 2,6-$Br_2$, 4-$CH_3$ | | |
| 233 | 2,4-$Cl_2$, 6-$CH_3$ | | |
| 234 | 2,4-$F_2$, 6-$CH_3$ | | |
| 235 | 2,4-$Br_2$, 6-$CH_3$ | | |
| 236 | 2,6-$(CH_3)_2$, 4-F | | |
| 237 | 2,6-$(CH_3)_2$, 4-Cl | | |
| 238 | 2,6-$(CH_3)_2$, 4-Br | | |
| 239 | 3,5-$(CH_3)_2$, 4-F | | |
| 240 | 3,5-$(CH_3)_2$, 4-Cl | | |
| 241 | 3,5-$(CH_3)_2$, 4-Br | | |
| 242 | 2,3,6-$(CH_3)_3$, 4-F | | |
| 243 | 2,3,6-$(CH_3)_3$, 4-Cl | | |
| 244 | 2,3,6-$(CH_3)_3$, 4-Br | | |
| 245 | 2,4-$(CH_3)_2$, 6-F | | |
| 246 | 2,4-$(CH_3)_2$, 6-Cl | | |
| 247 | 2,4-$(CH_3)_{62}$, 6-Br | | |
| 248 | 2-i-$C_3H_7$, 4-Cl, 5-$CH_3$ | | |
| 249 | 2-Cl, 4-$NO_2$ | | |
| 250 | 2-$NO_2$, 4-Cl | | |
| 251 | 2-$OCH_3$, 5-$NO_2$ | | |
| 252 | 2,4-$Cl_2$, 5-$NO_2$ | | |
| 253 | 2,4-$Cl_2$, 6-$NO_2$ | | |
| 254 | 2,6-$Cl_2$, 4-$NO_2$ | | |
| 255 | 2,6-$Br_2$, 4-$NO_2$ | | |
| 256 | 2,6-$I_2$, 4-$NO_2$ | | |
| 257 | 2-$CH_3$, 5-i-$C_3H_7$, 4-Cl | | |
| 258 | 2-$C_6H_5O$ | | |
| 259 | 3-$C_6H_5O$ | | |
| 260 | 4-$C_6H_5O$ | | |
| 261 | 2-$CHNOCH_3$ | | |
| 262 | 3-$CHNOCH_3$ | | |
| 263 | 4-$CHNOCH_3$ | | |
| 264 | 2-$CHNOC_2H_5$ | | |
| 265 | 3-$CHNOC_2H_5$ | | |
| 266 | 4-$CHNOC_2H_5$ | | |
| 267 | 2-CHNO(n-$C_3H_7$) | | |
| 268 | 3-CHNO(n-$C_3H_7$) | | |
| 269 | 4-CHNO(n-$C_3H_7$) | | |
| 270 | 2-CHNO(i-$C_3H_7$) | | |
| 271 | 3-CHNO(i-$C_3H_7$) | | |
| 272 | 4-CHNO(i-$C_3H_7$) | | |
| 273 | 2-CHNO(n-$C_6H_{13}$) | | |
| 274 | 3-CHNO(n-$C_6H_{13}$) | | |
| 275 | 4-CHNO(n-$C_6H_{13}$) | | |
| 276 | 2-CHNO(n-$C_8H_{17}$) | | |
| 277 | 3-CHNO(n-$C_8H_{17}$) | | |
| 278 | 4-CHNO(n-$C_8H_{17}$) | | |
| 279 | 2-$CHNOCH_2(C_6H_5)$ | | |
| 280 | 3-$CHNOCH_2(C_6H_5)$ | | |

TABLE 15-continued

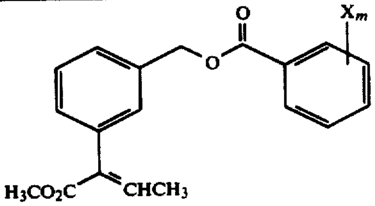

| No. | $X_m$ | mp | NMR: δ (ppm) |
|---|---|---|---|
| 281 | 4-$CHNOCH_2(C_6H_5)$ | | |
| 282 | 2-$CO_2CH_3$ | | |
| 283 | 3-$CO_2CH_3$ | | |
| 284 | 4-$CO_2CH_3$ | | |
| 285 | 2-$CO_2(C_2H_5)$ | | |
| 286 | 3-$CO_2(C_2H_5)$ | | |
| 287 | 4-$CO_2(C_2H_5)$ | | |
| 288 | 2-$CO_2$(n-$C_3H_7$) | | |
| 289 | 3-$CO_2$(n-$C_3H_7$) | | |
| 290 | 4-$CO_2$(n-$C_3H_7$) | | |
| 291 | 2-$CO_2$(i-$C_3H_7$) | | |
| 292 | 3-$CO_2$(i-$C_3H_7$) | | |
| 293 | 4-$CO_2$(i-$C_3H_7$) | | |
| 294 | 2-$CO_2$(n-$C_6H_{13}$) | | |
| 295 | 3-$CO_2$(n-$C_6H_{13}$) | | |
| 296 | 4-$CO_2$(n-$C_6H_{13}$) | | |
| 297 | 2-$CO_2$(n-$C_8H_{17}$) | | |
| 298 | 3-$CO_2$(n-$C_8H_{17}$) | | |
| 299 | 4-$CO_2$(n-$C_8H_{17}$) | | |
| 300 | 2-CHNO—$CH_2$—CH=$CH_2$ | | |
| 301 | 3-CHNO—$CH_2$—CH=$CH_2$ | | |
| 302 | 4-CHNO—$CH_2$—CH=$CH_2$ | | |
| 303 | 2-$CHNO(CH_2)_3(C_6H_5)$ | | |
| 304 | 3-$CHNO(CH_2)_3(C_6H_5)$ | | |
| 305 | 4-$CHNO(CH_2)_3(C_6H_5)$ | | |
| 306 | 2-$CH_2OCH_3$ | | |
| 307 | 3-$CH_2OCH_3$ | | |
| 308 | 4-$CH_2OCH_3$ | | |
| 309 | 2-$CH_2O(C_2H_5)$ | | |
| 310 | 3-$CH_2O(C_2H_5)$ | | |
| 311 | 4-$CH_2O(C_2H_5)$ | | |
| 312 | 2-$CH_2O$(n-$C_3H_7$) | | |
| 313 | 3-$CH_2O$(n-$C_3H_7$) | | |
| 314 | 4-$CH_2O$(n-$C_3H_7$) | | |
| 315 | 2-$CH_2O$(i-$C_3H_7$) | | |
| 316 | 3-$CH_2O$(i-$C_3H_7$) | | |
| 317 | 4-($CH_2O$(i-$C_3H_7$) | | |
| 318 | 2-$CH_2O$(n-$C_6H_{13}$) | | |
| 319 | 3-$CH_2O$(n-$C_6H_{13}$) | | |
| 320 | 4-$CH_2O$(n-$C_6H_{13}$) | | |
| 321 | 2-$CH_2O$(n-$C_8H_{17}$) | | |
| 322 | 3-$CH_2O$(n-$C_8H_{17}$) | | |
| 323 | 4-$CH_2O$(n-$C_8H_7$) | | |
| 324 | 2-$CH_2OCH_2(C_6H_5)$ | | |
| 325 | 3-$CH_2OCH_2(C_6H_5)$ | | |
| 326 | 4-$CH_2OCH_2(C_6H_5)$ | | |
| 327 | 2-$CH_2O(CH_2)_3$ | | |
| 328 | 3-$CH_2O(CH_2)_3(C_6H_5)$ | | |
| 329 | 4-$CH_2O(CH_2)_3(C_6H_5)$ | | |
| 330 | 2-CHO | | |
| 331 | 3-CHO | | |
| 332 | 4-CHO | | |

TABLE 16

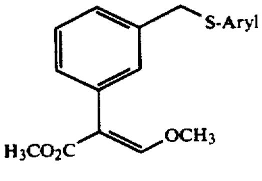

| No. | Aryl | mp | NMR: δ (ppm) |
|---|---|---|---|
| 1 | 1-naphthyl | | |
| 2 | 2-naphthyl | | |
| 3 | 3-phenanthrenyl | | |

TABLE 16-continued

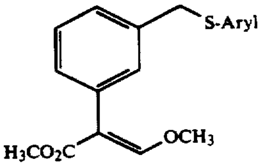

| No. | Aryl | mp | NMR: δ (ppm) |
|---|---|---|---|
| 4 | 2-chlorophenyl | | |
| 5 | 2-bromophenyl | | |
| 6 | 3-bromophenyl | | |
| 7 | 4-bromophenyl | | |
| 8 | 2-fluorophenyl | | |
| 9 | 3-fluorophenyl | | |
| 10 | 4-fluorophenyl | | |
| 11 | 2-ethyl-phenyl | | |
| 12 | 3-ethyl-phenyl | | |
| 13 | 4-ethyl-phenyl | | |
| 14 | 2-iso-propyl-phenyl | | |
| 15 | 3-iso-propyl-phenyl | | |
| 16 | 4-iso-propyl-phenyl | | |
| 17 | 2-tert-butyl-phenyl | | |
| 18 | 3-tert-butyl-phenyl | | |
| 19 | 4-tert-butyl-phenyl | | |
| 20 | 4-butyl-phenyl | | |
| 21 | 4-hexyl-phenyl | | |
| 22 | 4-nonyl-phenyl | | |
| 23 | 4-decyl-phenyl | | |
| 24 | 2-methoxy-phenyl | | |
| 25 | 3-methoxy-phenyl | | |
| 26 | 4-methoxy-phenyl | | |
| 27 | 2-trifluoromethyl-phenyl | | |
| 28 | 3-trifluoromethyl-phenyl | | |
| 29 | 4-trifluoromethyl-phenyl | | |
| 30 | 4-formyl-phenyl | | |
| 31 | 2-nitro-phenyl | | |
| 32 | 3-nitro-phenyl | | |
| 33 | 4-nitro-phenyl | | |
| 34 | 2,5-dichlorophenyl | | |
| 35 | 2,6-dichlorophenyl | | |
| 36 | 3,4-dichlorophenyl | | |
| 37 | 2,3-dichlorophenyl | | |
| 38 | 3,5-dichlorophenyl | | |
| 39 | 2,3,4-trichlorophenyl | | |
| 40 | 2,4,5-trichlorophenyl | | |
| 41 | 2,4,6-trichlorophenyl | | |
| 42 | 2,3,4,6-tetrachlorophenyl | | |
| 43 | 2,3,4,5,6-pentachlorophenyl | | |
| 44 | 2,3,4,5-tetrafluorophenyl | | |
| 45 | 2,3,5,6-tetrafluorophenyl | | |
| 46 | 2,3,4,5,6-pentafluorophenyl | | |
| 47 | 2-chloro, 4-fluorophenyl | | |
| 48 | 3-chloro, 4-fluorophenyl | | |
| 49 | 2-chloro, 6-methyl-phenyl | | |
| 50 | 4-chloro, 2-methyl-phenyl | | |
| 51 | 2,4-dichloro, 5-methyl-phenyl | | |
| 52 | 4-chloro, 2,5-dimethyl-phenyl | | |
| 53 | 3-bromo, 3-methyl-phenyl | | |
| 54 | 3,5-bistrifluoromethyl-phenyl | | |
| 55 | 2,5-dimethyl-phenyl | | |
| 56 | 2,4-dimethyl-phenyl | | |
| 57 | 2,5-dimethyl-phenyl | | |
| 58 | 2,6-dimethyl-phenyl | | |
| 59 | 3,4-dimethyl-phenyl | | |
| 60 | 3,5-dimethyl-phenyl | | |
| 61 | 2,4,5-trimethyl-phenyl | | |
| 62 | 2,6-diethyl-phenyl | | |
| 63 | 2,4-di-tert.-butyl-phenyl | | |
| 64 | 2,5-dimethoxy-phenyl | | |
| 65 | 3,4-dimethoxy-phenyl | | |
| 66 | 2-methyl, 4-tert.-butyl-phenyl | | |
| 67 | 2-methoxycarbonyl-phenyl | | |
| 68 | 2-ethoxycarbonyl-phenyl | | |
| 69 | 2-propoxycarbonyl-phenyl | | |
| 70 | 2-butoxycarbonyl-phenyl | | |
| 71 | 2-cyano-phenyl | | |
| 72 | 3-cyano-phenyl | | |
| 73 | 4-cyano-phenyl | | |

TABLE 17

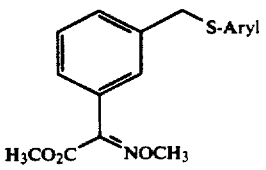

| No. | Aryl | mp | NMR: δ (ppm) |
|---|---|---|---|
| 1 | 1-naphthyl | | |
| 2 | 2-naphthyl | | |
| 3 | 3-phenanthrenyl | | |
| 4 | 2-chlorophenyl | | |
| 5 | 2-bromophenyl | | |
| 6 | 3-bromophenyl | | |
| 7 | 4-bromophenyl | | |
| 8 | 2-fluorophenyl | | |
| 9 | 3-fluorophenyl | | |
| 10 | 4-fluorophenyl | | |
| 11 | 2-ethyl-phenyl | | |
| 12 | 3-ethyl-phenyl | | |
| 13 | 4-ethyl-phenyl | | |
| 14 | 2-iso-propyl-phenyl | | |
| 15 | 3-iso-propyl-phenyl | | |
| 16 | 4-iso-propyl-phenyl | | |
| 17 | 2-tert-butyl-phenyl | | |
| 18 | 3-tert-butyl-phenyl | | |
| 19 | 4-tert-butyl-phenyl | | |
| 20 | 4-butyl-phenyl | | |
| 21 | 4-hexyl-phenyl | | |
| 22 | 4-nonyl-phenyl | | |
| 23 | 4-decyl-phenyl | | |
| 24 | 2-methoxy-phenyl | | |
| 25 | 3-methoxy-phenyl | | |
| 26 | 4-methoxy-phenyl | | |
| 27 | 2-trifluoromethyl-phenyl | | |
| 28 | 3-trifluoromethyl-phenyl | | |
| 29 | 4-trifluoromethyl-phenyl | | |
| 30 | 4-formyl-phenyl | | |
| 31 | 2-nitro-phenyl | | |
| 32 | 3-nitro-phenyl | | |
| 33 | 4-nitro-phenyl | | |
| 34 | 2,5-dichlorophenyl | | |
| 35 | 2,6-dichlorophenyl | | |
| 36 | 3,4-dichlorophenyl | | |
| 37 | 2,3-dichlorophenyl | | |
| 38 | 3,5-dichlorophenyl | | |
| 39 | 2,3,4-trichlorophenyl | | |
| 40 | 2,4,5-trichlorophenyl | | |
| 41 | 2,4,6-trichlorophenyl | | |
| 42 | 2,3,4,6-tetrachlorophenyl | | |
| 43 | 2,3,4,5,6-pentachlorophenyl | | |
| 44 | 2,3,4,5-tetrafluorophenyl | | |
| 45 | 2,3,5,6-tetrafluorophenyl | | |
| 46 | 2,3,4,5,6-pentafluorophenyl | | |
| 47 | 2-chloro, 4-fluorophenyl | | |
| 48 | 3-chloro, 4-fluorophenyl | | |
| 49 | 2-chloro, 6-methyl-phenyl | | |
| 50 | 4-chloro, 2-methyl-phenyl | | |
| 51 | 2,4-dichloro, 5-methyl-phenyl | | |
| 52 | 4-chloro, 2,5-dimethyl-phenyl | | |
| 53 | 3-bromo, 3-methyl-phenyl | | |
| 54 | 3,5-bistrifluoromethyl-phenyl | | |
| 55 | 2,5-dimethyl-phenyl | | |
| 56 | 2,4-dimethyl-phenyl | | |
| 57 | 2,5-dimethyl-phenyl | | |
| 58 | 2,6-dimethyl-phenyl | | |
| 59 | 3,4-dimethyl-phenyl | | |
| 60 | 3,5-dimethyl-phenyl | | |
| 61 | 2,4,5-trimethyl-phenyl | | |
| 62 | 2,6-diethyl-phenyl | | |
| 63 | 2,4-di-tert.-butyl-phenyl | | |
| 64 | 2,5-dimethoxy-phenyl | | |
| 65 | 3,4-dimethoxy-phenyl | | |
| 66 | 2-methyl, 4-tert.-butyl-phenyl | | |
| 67 | 2-methoxycarbonyl-phenyl | | |
| 68 | 2-ethoxycarbonyl-phenyl | | |
| 69 | 2-propoxycarbonyl-phenyl | | |
| 70 | 2-butoxycarbonyl-phenyl | | |
| 71 | 2-cyano-phenyl | | |
| 72 | 3-cyano-phenyl | | |

TABLE 17-continued

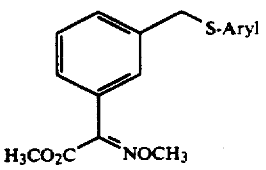

| No. | Aryl | mp | NMR: δ (ppm) |
|---|---|---|---|
| 73 | 4-cyano-phenyl | | |

TABLE 18

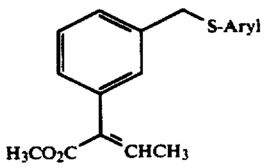

| No. | Aryl | mp | NMR: δ (ppm) |
|---|---|---|---|
| 1 | 1-naphthyl | | |
| 2 | 2-naphthyl | | |
| 3 | 3-phenanthrenyl | | |
| 4 | 2-chlorophenyl | | |
| 5 | 2-bromophenyl | | |
| 6 | 3-bromophenyl | | |
| 7 | 4-bromophenyl | | |
| 8 | 2-fluorophenyl | | |
| 9 | 3-fluorophenyl | | |
| 10 | 4-fluorophenyl | | |
| 11 | 2-ethyl-phenyl | | |
| 12 | 3-ethyl-phenyl | | |
| 13 | 4-ethyl-phenyl | | |
| 14 | 2-iso-propyl-phenyl | | |
| 15 | 3-iso-propyl-phenyl | | |
| 16 | 4-iso-propyl-phenyl | | |
| 17 | 2-tert-butyl-phenyl | | |
| 18 | 3-tert-butyl-phenyl | | |
| 19 | 4-tert-butyl-phenyl | | |
| 20 | 4-butyl-phenyl | | |
| 21 | 4-hexyl-phenyl | | |
| 22 | 4-nonyl-phenyl | | |
| 23 | 4-decyl-phenyl | | |
| 24 | 2-methoxy-phenyl | | |
| 25 | 3-methoxy-phenyl | | |
| 26 | 4-methoxy-phenyl | | |
| 27 | 2-trifluoromethyl-phenyl | | |
| 28 | 3-trifluoromethyl-phenyl | | |
| 29 | 4-trifluoromethyl-phenyl | | |
| 30 | 4-formyl-phenyl | | |
| 31 | 2-nitro-phenyl | | |
| 32 | 3-nitro-phenyl | | |
| 33 | 4-nitro-phenyl | | |
| 34 | 2,5-dichlorophenyl | | |
| 35 | 2,6-dichlorophenyl | | |
| 36 | 3,4-dichlorophenyl | | |
| 37 | 2,3-dichlorophenyl | | |
| 38 | 3,5-dichlorophenyl | | |
| 39 | 2,3,4-trichlorophenyl | | |
| 40 | 2,4,5-trichlorophenyl | | |
| 41 | 2,4,6-trichlorophenyl | | |
| 42 | 2,3,4,6-tetrachlorophenyl | | |
| 43 | 2,3,4,5,6-pentachlorophenyl | | |
| 44 | 2,3,4,5-tetrafluorophenyl | | |
| 45 | 2,3,5,6-tetrafluorophenyl | | |
| 46 | 2,3,4,5,6-pentafluorophenyl | | |
| 47 | 2-chloro, 4-fluorophenyl | | |
| 48 | 3-chloro, 4-fluorophenyl | | |
| 49 | 2-chloro, 6-methyl-phenyl | | |
| 50 | 4-chloro, 2-methyl-phenyl | | |
| 51 | 2,4-dichloro, 5-methyl-phenyl | | |
| 52 | 4-chloro, 2,5-dimethyl-phenyl | | |
| 53 | 3-bromo, 3-methyl-phenyl | | |
| 54 | 3,5-bistrifluoromethyl-phenyl | | |
| 55 | 2,5-dimethyl-phenyl | | |
| 56 | 2,4-dimethyl-phenyl | | |

TABLE 18-continued

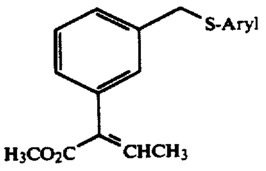

| No. | Aryl | mp | NMR: δ (ppm) |
|---|---|---|---|
| 57 | 2,5-dimethyl-phenyl | | |
| 58 | 2,6-dimethyl-phenyl | | |
| 59 | 3,4-dimethyl-phenyl | | |
| 60 | 3,5-dimethyl-phenyl | | |
| 61 | 2,4,5-trimethyl-phenyl | | |
| 62 | 2,6-diethyl-phenyl | | |
| 63 | 2,4-di-tert.-butyl-phenyl | | |
| 64 | 2,5-dimethoxy-phenyl | | |
| 65 | 3,4-dimethoxy-phenyl | | |

TABLE 18-continued

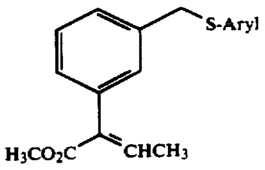

| No. | Aryl | mp | NMR: δ (ppm) |
|---|---|---|---|
| 66 | 2-methyl, 4-tert.-butyl-phenyl | | |
| 67 | 2-methoxycarbonyl-phenyl | | |
| 68 | 2-ethoxycarbonyl-phenyl | | |
| 69 | 2-propoxycarbonyl-phenyl | | |
| 70 | 2-butoxycarbonyl-phenyl | | |
| 71 | 2-cyano-phenyl | | |
| 72 | 3-cyano-phenyl | | |
| 73 | 4-cyano-phenyl | | |

TABLE 19

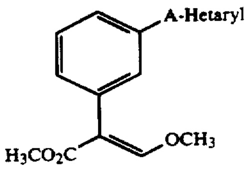

| No. | A | Hetaryl | mp | NMR: δ (ppm) |
|---|---|---|---|---|
| 1 | $CH_2-S$ | 4-pyridyl | 76–77 | |
| 2 | $CH_2-O$ | 6-methyl-2-pyridyl | 76–77 | |
| 3 | $CH_2-S$ | 6-methyl-2-pyridyl | | |
| 4 | $CH_2-O$ | 6-ethyl-2-pyridyl | | |
| 5 | $CH_2-S$ | 6-ethyl-2-pyridyl | | |
| 6 | $CH_2-O$ | 6-n-propyl-2-pyridyl | | |
| 7 | $CH_2-S$ | 6-n-propyl-2-pyridyl | | |
| 8 | $CH_2-O$ | 6-iso-propyl-2-pyridyl | | |
| 9 | $CH_2-S$ | 6-iso-propyl-2-pyridyl | | |
| 10 | $CH_2-O$ | 6-n-butyl-2-pyridyl | | |
| 11 | $CH_2-S$ | 6-n-butyl-2-pyridyl | | |
| 12 | $CH_2-O$ | 6-tert.-butyl-2-pyridyl | | |
| 13 | $CH_2-S$ | 6-tert.-butyl-2-pyridyl | | |
| 14 | $CH_2-O$ | 6-n-pentyl-2-pyridyl | | |
| 15 | $CH_2-S$ | 6-n-pentyl-2-pyridyl | | |
| 16 | $CH_2-O$ | 6-n-hexyl-2-pyridyl | | |
| 17 | $CH_2-S$ | 6-n-hexyl-2-pyridyl | | |
| 18 | $CH_2-O$ | 6-phenyl-2-pyridyl | | |
| 19 | $CH_2-S$ | 6-phenyl-2-pyridyl | | |
| 20 | $CH_2-O$ | 6-benzyl-2-pyridyl | | |
| 21 | $CH_2-S$ | 6-benzyl-2-pyridyl | | |
| 22 | $CH_2-S$ | 6-benzyl-2-pyridyl | | |
| 23 | $CH_2-S$ | 6-trifluoromethyl-2-pyridyl | | |
| 24 | $CH_2-O$ | 6-methoxy-2-pyridyl | | |
| 25 | $CH_2-S$ | 6-methoxy-2-pyridyl | | |
| 26 | $CH_2-O$ | 6-chloro-2-pyridyl | 72–73 | |
| 27 | $CH_2-S$ | 6-chloro-2-pyridyl | | |
| 28 | $CH_2-O$ | 3,6-dimethyl-2-pyridyl | | |
| 29 | $CH_2-S$ | 3,6-dimethyl-2-pyridyl | | |
| 30 | $CH_2-O$ | 3,6-diethyl-2-pyridyl | | |
| 31 | $CH_2-S$ | 3,6-diethyl-2-pyridyl | | |
| 32 | $CH_2-O$ | 4,6-dimethyl-2-pyridyl | | |
| 33 | $CH_2-S$ | 4,6-dimethyl-2-pyridyl | | |
| 34 | $CH_2-O$ | 5,6-dimethyl-2-pyridyl | | |
| 35 | $CH_2-S$ | 5,6-dimethyl-2-pyridyl | | |
| 36 | $CH_2-O$ | 4-phenyl-6-methyl-2-pyridyl | | |
| 37 | $CH_2-S$ | 4-phenyl-6-methyl-2-pyridyl | | |
| 38 | $CH_2-O$ | 4,6-diphenyl-2-pyridyl | | |
| 39 | $CH_2-S$ | 4,6-diphenyl-2-pyridyl | | |
| 40 | $CH_2-O$ | 3,4-dichloro-6-methyl-2-pyridyl | | |
| 41 | $CH_2-S$ | 3,4-dichloro-6-methyl-2-pyridyl | | |
| 42 | $CH_2-O$ | 3,4,5-trichloro-6-phenyl-2-pyridyl | | |
| 43 | $CH_2-S$ | 3,4,5-trichloro-6-phenyl-2-pyridyl | | |
| 44 | $CH_2-O$ | 4-trifluoromethyl-6-methyl-2-pyridyl | | |
| 45 | $CH_2-S$ | 4-trifluoromethyl-6-methyl-2-pyridyl | | |
| 46 | $CH_2-O$ | 3-acetyl-4,6-dimethyl-2-pyridyl | | |
| 47 | $CH_2-S$ | 3-acetyl-4,6-dimethyl-2-pyridyl | | |
| 48 | $CH_2-O$ | 3-cyano-6-methyl-2-pyridyl | | |
| 49 | $CH_2-S$ | 3-cyano-6-methyl-2-pyridyl | | |

TABLE 19-continued

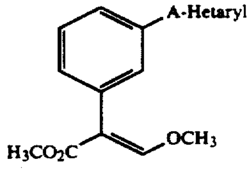

| No. | A | Hetaryl | mp | NMR: δ (ppm) |
|---|---|---|---|---|
| 50 | $CH_2$—O | 3-cyano-6-ethyl-2-pyridyl | | |
| 51 | $CH_2$—S | 3-cyano-6-ethyl-2-pyridyl | | |
| 52 | $CH_2$—O | 3-cyano-6-n-propyl-2-pyridyl | | |
| 53 | $CH_2$—S | 3-cyano-6-n-propyl-2-pyridyl | | |
| 54 | $CH_2$—O | 3-cyano-6-iso-propyl-2-pyridyl | | |
| 55 | $CH_2$—S | 3-cyano-6-iso-propyl-2-pyridyl | | |
| 56 | $CH_2$—O | 3-cyano-6-cyclo-propyl-2-pyridyl | | |
| 57 | $CH_2$—S | 3-cyano-6-cyclo-propyl-2-pyridyl | | |
| 58 | $CH_2$—O | 3-cyano-6-n-butyl-2-pyridyl | | |
| 59 | $CH_2$—S | 3-cyano-6-n-butyl-2-pyridyl | | |
| 60 | $CH_2$—O | 3-cyano-6-tert.-butyl-2-pyridyl | | |
| 61 | $CH_2$—S | 3-cyano-6-tert.-butyl-2-pyridyl | | |
| 62 | $CH_2$—O | 3-cyano-6-cyclo-hexyl-2-pyridyl | | |
| 63 | $CH_2$—S | 3-cyano-6-cyclo-hexyl-2-pyridyl | | |
| 64 | $CH_2$—O | 3-cyano-6-phenyl-2-pyridyl | | |
| 65 | $CH_2$—S | 3-cyano-6-phenyl-2-pyridyl | | |
| 66 | $CH_2$—O | 3-methyloxycarbonyl-6-iso-propyl-2-pyridyl | | |
| 67 | $CH_2$—S | 3-methyloxycarbonyl-6-iso-propyl-2-pyridyl | | |
| 68 | $CH_2$—O | 3-ethyloxycarbonyl-6-iso-propyl-2-pyridyl | | |
| 69 | $CH_2$—S | 3-ethyloxycarbonyl-6-iso-propyl-2-pyridyl | | |
| 70 | $CH_2$—O | 3-cyano-4,6-dimethyl-2-pyridyl | | |
| 71 | $CH_2$—S | 3-cyano-4,6-dimethyl-2-pyridyl | | |
| 72 | $CH_2$—O | 3,5,6-trichloro-2-pyridyl | | |
| 73 | $CH_2$—S | 3,5,6-trichloro-2-pyridyl | | |
| 74 | $CH_2$—O | 5-trifluoromethyl-2-pyridyl | | |
| 75 | $CH_2$—S | 5-trifluoromethyl-2-pyridyl | | |
| 76 | $CH_2$—O | 3-chloro-5-trifluoromethyl-2-pyridyl | | |
| 77 | $CH_2$—S | 3-chloro-5-trifluoromethyl-2-pyridyl | | |
| 78 | $CH_2$—O | 2-quinolyl | | |
| 79 | $CH_2$—S | 2-quinolyl | | |
| 80 | $CH_2$—O | 3-methyl-2-quinolyl | | |
| 81 | $CH_2$—S | 3-methyl-2-quinolyl | | |
| 82 | $CH_2$—O | 4-methyl-2-quinolyl | | |
| 83 | $CH_2$—S | 4-methyl-2-quinolyl | | |
| 84 | $CH_2$—O | 4-ethyl-2-quinolyl | | |
| 85 | $CH_2$—S | 4-ethyl-2-quinolyl | | |
| 86 | $CH_2$—O | 4-phenyl-2-quinolyl | | |
| 87 | $CH_2$—S | 4-phenyl-2-quinolyl | | |
| 88 | $CH_2$—O | 6-methyl-2-quinolyl | | |
| 89 | $CH_2$—S | 6-methyl-2-quinolyl | | |
| 90 | $CH_2$—O | 6-chloro-2-quinolyl | | |
| 91 | $Ch_2$—S | 6-chloro-2-quinolyl | | |
| 92 | $CH_2$—O | 8-methyl-2-quinolyl | | |
| 93 | $CH_2$—S | 8-methyl-2-quinolyl | | |
| 94 | $CH_2$—O | 8-chloro-2-quinolyl | | |
| 95 | $CH_2$—S | 8-chloro-2-quinolyl | | |
| 96 | $CH_2$—O | 4-Ethoxycarbonyl-2-quinolyl | | |
| 97 | $CH_2$—S | 4-Ethoxycarbonyl-2-quinolyl | | |
| 98 | $CH_2$—O | 3,4-dimethyl-2-quinolyl | | |
| 99 | $CH_2$—S | 3,4-dimethyl-2-quinolyl | | |
| 100 | $CH_2$—O | 4-methyl-8-methoxy-2-quinolyl | | |
| 101 | $CH_2$—S | 4-methyl-8-methoxy-2-quinolyl | | |
| 102 | $CH_2$—O | 4-phenyl-8-ethoxy-2-quinolyl | | |
| 103 | $CH_2$—S | 4-phenyl-8-ethoxy-2-quinolyl | | |
| 104 | $CH_2$—O | 4-methyl-8-chloro-2-quinolyl | | |
| 105 | $CH_2$—S | 4-methyl-8-chloro-2-quinolyl | | |
| 106 | $CH_2$—O | 4-methyl-8-fluoro-2-quinolyl | | |
| 107 | $CH_2$—S | 4-methyl-8-fluoro-2-quinolyl | | |
| 108 | $CH_2$—O | 4-quinolyl | | |
| 109 | $CH_2$—S | 4-quinolyl | | |
| 110 | $CH_2$—O | 2-methyl-4-quinolyl | | |
| 111 | $CH_2$—S | 2-methyl-4-quinolyl | | |
| 112 | $CH_2$—O | 2-trichloromethyl-4-quinolyl | | |
| 113 | $CH_2$—S | 2-trichloromethyl-4-quinolyl | | |
| 114 | $CH_2$—O | 2-trifluoromethyl-2-quinolyl | | |
| 115 | $CH_2$—S | 2-trifluoromethyl-2-quinolyl | | |
| 116 | $CH_2$—O | 2-iso-propyl-4-quinolyl | | |
| 117 | $CH_2$—S | 2-iso-propyl-4-quinolyl | | |
| 118 | $CH_2$—O | 2-n-pentyl-4-quinolyl | | |
| 119 | $CH_2$—S | 2-n-pentyl-4-quinolyl | | |
| 120 | $CH_2$—O | 2-phenyl-4-quinolyl | | |
| 121 | $CH_2$—S | 2-phenyl-4-quinolyl | | |

TABLE 19-continued

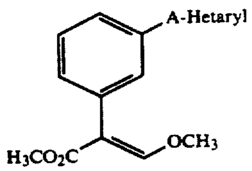

| No. | A | Hetaryl | mp | NMR: δ (ppm) |
|---|---|---|---|---|
| 122 | $CH_2$—O | 2-methoxycarbonyl-4-quinolyl | | |
| 123 | $CH_2$—S | 2-methoxycarbonyl-4-quinolyl | | |
| 124 | $CH_2$—O | 2,6-dimethyl-4-quinolyl | | |
| 125 | $CH_2$—S | 2,6-dimethyl-4-quinolyl | | |
| 126 | $CH_2$—O | 2-methyl-6-chloro-4-quinolyl | | |
| 127 | $CH_2$—S | 2-methyl-6-chloro-4-quinolyl | | |
| 128 | $CH_2$—O | 2-methyl-6-fluoro-4-quinolyl | | |
| 129 | $CH_2$—S | 2-methyl-6-fluoro-4-quinolyl | | |
| 130 | $CH_2$—O | 8-quinolyl | | |
| 131 | $CH_2$—S | 8-quinolyl | | |
| 132 | $CH_2$—O | 2-methyl-8-quinolyl | | |
| 133 | $CH_2$—S | 2-methyl-8-quinolyl | | |
| 134 | $CH_2$—O | 5,7-dichloro-8-quinolyl | | |
| 135 | $CH_2$—S | 5,7-dichloro-8-quinolyl | | |
| 136 | $CH_2$—O | 4,6-dimethyl-2-pyrimidinyl | | |
| 137 | $CH_2$—S | 4,6-dimethyl-2-pyrimidinyl | | |
| 138 | $CH_2$—O | 4-trifluoromethyl-2-pyrimidinyl | | |
| 139 | $CH_2$—S | 4-trifluoromethyl-2-pyrimidinyl | | |
| 140 | $CH_2$—O | 4,5,6-trimethyl-2-pyrimidinyl | | |
| 141 | $CH_2$—S | 4,5,6-trimethyl-2-pyrimidinyl | | |
| 142 | $CH_2$—O | 4-benzyl-6-methyl-2-pyrimidinyl | | |
| 143 | $CH_2$—S | 4-benzyl-6-methyl-2-pyrimidinyl | | |
| 144 | $CH_2$—O | 4-methyl-6-phenyl-2-pyrimidinyl | | |
| 145 | $CH_2$—S | 4-methyl-6-phenyl-2-pyrimidinyl | | |
| 146 | $CH_2$—O | 4,6-dimethyl-5-chloro-2-pyrimidinyl | | |
| 147 | $CH_2$—S | 4,6-dimethyl-5-chloro-2-pyrimidinyl | | |
| 148 | $CH_2$—O | 2,6-dimethyl-4-pyrimidinyl | | |
| 149 | $CH_2$—S | 2,6-dimethyl-4-pyrimidinyl | | |
| 150 | $CH_2$—O | 2,6-bis-(trifluoromethyl)-4-pyrimidinyl | | |
| 151 | $CH_2$—S | 2,6-bis-(trifluoromethyl)-4-pyrimidinyl | | |
| 152 | $CH_2$—O | 2-chloromethyl-6-methyl-4-pyrimidinyl | | |
| 153 | $CH_2$—S | 2-chloromethyl-6-methyl-4-pyrimidinyl | | |
| 154 | $CH_2$—O | 2-methyl-6-chloromethyl-4-pyrimidinyl | | |
| 155 | $CH_2$—S | 2-methyl-6-chloromethyl-4-pyrimidinyl | | |
| 156 | $CH_2$—O | 2-iso-propyl-6-methyl-4-pyrimidinyl | | |
| 157 | $CH_2$—S | 2-iso-propyl-6-methyl-4-pyrimidinyl | | |
| 158 | $CH_2$—O | 2-iso-propyl-6-chloromethyl-4-pyrimidinyl | | |
| 159 | $CH_2$—S | 2-iso-propyl-6-chloromethyl-4-pyrimidinyl | | |
| 160 | $CH_2$—O | 2-cyclo-propyl-6-chloromethyl-4-pyrimidinyl | | |
| 161 | $CH_2$—S | 2-cyclo-propyl-6-chloromethyl-4-pyrimidinyl | | |
| 162 | $CH_2$—O | 2-cyclo-propyl-6-methyl-4-pyrimidinyl | | |
| 163 | $CH_2$—S | 2-cyclo-propyl-6-methyl-4-pyrimidinyl | | |
| 164 | $CH_2$—O | 2-methyl-6-methoxymethyl-4-pyrimidinyl | | |
| 165 | $CH_2$—S | 2-methyl-6-methoxymethyl-4-pyrimidinyl | | |
| 166 | $CH_2$—O | 2-iso-propyl-6-methoxymethyl-4-pyrimidinyl | | |
| 167 | $CH_2$—S | 2-iso-propyl-6-methoxymethyl-4-pyrimidinyl | | |
| 168 | $CH_2$—O | 2-phenyl-4-pyrimidinyl | | |
| 169 | $CH_2$—S | 2-phenyl-4-pyrimidinyl | | |
| 170 | $CH_2$—O | 3,5-dimethyl-4-pyrimidinyl | | |
| 171 | $CH_2$—S | 3,5-dimethyl-4-pyrimidinyl | | |
| 172 | $CH_2$—O | 2-methylthio-6-trifluoromethyl-4-pyrimidinyl | | |
| 173 | $CH_2$—S | 2-methylthio-6-trifluoromethyl-4-pyrimidinyl | | |
| 174 | $CH_2$ —O | 2-methylthio-5-chloro-6-trifluoromethyl-4-pyrimidinyl | | |
| 175 | $CH_2$—S | 2-methylthio-5-chloro-6-trifluoromethyl-4-pyrimidinyl | | |
| 176 | $CH_2$—O | 2-methylthio-5-n-octyl-6-methyl-4-pyrimidinyl | | |
| 177 | $CH_2$—S | 2-methylthio-5-n-octyl-6-methyl-4-pyrimidinyl | | |
| 178 | $CH_2$—O | 2-methyl-6-trifluoromethyl-4-pyrimidinyl | | |
| 179 | $CH_2$—S | 2-methyl-6-trifluoromethyl-4-pyrimidinyl | | |
| 180 | $CH_2$—O | 2-n-propyl-6-trifluoromethyl-4-pyrimidinyl | | |
| 181 | $CH_2$—S | 2-n-propyl-6-trifluoromethyl-4-pyrimidinyl | | |
| 182 | $CH_2$—O | 2-iso-propyl-6-trifluoromethyl-4-pyrimidinyl | | |
| 183 | $CH_2$—S | 2-iso-propyl-6-trifluoromethyl-4-pyrimidinyl | | |
| 184 | $CH_2$—O | 2-tert.-butyl-6-trifluoromethyl-4-pyrimidinyl | | |
| 185 | $CH_2$—S | 2-tert.-butyl-6-trifluoromethyl-4-pyrimidinyl | | |
| 186 | $CH_2$—O | 2-methyl-5-chloro-6-trifluoromethyl-4-pyrimidinyl | | |
| 187 | $CH_2$—S | 2-methyl-5-chloro-6-trifluoromethyl-4-pyrimidinyl | | |
| 188 | $CH_2$—O | 2-n-propyl-5-chloro-6-trifluoromethyl-4-pyrimidinyl | | |
| 189 | $CH_2$—S | 2-n-propyl-5-chloro-6-trifluoromethyl-4-pyrimidinyl | | |
| 190 | $CH_2$—O | 2-iso-propyl-5-chloro-6-trifluoromethyl-4-pyrimidinyl | | |
| 191 | $CH_2$—S | 2-iso-propyl-5-chloro-6-trifluoromethyl-4-pyrimidinyl | | |
| 192 | $CH_2$—O | 2-tert.-butyl-5-chloro-6-trifluoromethyl-4-pyrimidininyl | | |
| 193 | $CH_2$—S | 2-tert.-butyl-5-chloro-6-trifluoromethyl-4-pyrimidininyl | | |

TABLE 19-continued

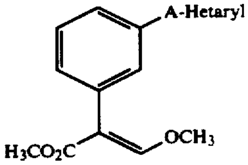

| No. | A | Hetaryl | mp | NMR: δ (ppm) |
|---|---|---|---|---|
| 194 | $CH_2$—S | 2-pyrimidinyl | 62–64 | |
| 195 | $CH_2$—O | 6-cyclopropyl-2-pyridyl | | |
| 196 | $CH_2$—S | 6-cyclopropyl-2-pyridyl | | |
| 197 | $CH_2$—O | 2-pyrazinyl | | |
| 198 | $CH_2$—S | 2-pyrazinyl | | |
| 199 | $CH_2$—O | 6-chloro-2-pyrazinyl | | |
| 200 | $CH_2$—S | 6-chloro-2-pyrazinyl | | |
| 201 | $CH_2$—O | 5-methyl-2-pyrazinyl | | |
| 202 | $CH_2$—S | 5-methyl-2-pyrazinyl | | |
| 203 | $CH_2$—O | 3-pyridazinyl | | |
| 204 | $CH_2$—S | 3-pyridazinyl | | |
| 205 | $CH_2$—O | 5-chloro-3-pyridazinyl | | |
| 206 | $CH_2$—S | 5-chloro-3-pyridazinyl | | |
| 207 | $CH_2$—O | 2-thienyl | | |
| 208 | $CH_2$—S | 2-thienyl | | |
| 209 | $CH_2$—O | 3-thienyl | | |
| 210 | $CH_2$—S | 3-thienyl | | |
| 211 | $CH_2$—O | 4-chloro-3-thienyl | | |
| 212 | $CH_2$—S | 4-chloro-3-thienyl | | |
| 213 | $CH_2$—O | 2-chloro-3-thienyl | | |
| 214 | $CH_2$—S | 2-chloro-3-thienyl | | |
| 215 | $CH_2$—O | 5-chloro-3-thienyl | | |
| 216 | $CH_2$—S | 5-chloro-3-thienyl | | |
| 217 | $CH_2$—O | 2-quinoxalinyl | | |
| 218 | $CH_2$—S | 2-quinoxalinyl | | |
| 219 | $CH_2$—O | 3-methyl-2-quinoxalinyl | | |
| 220 | $CH_2$—S | 3-methyl-2-quinoxalinyl | | |
| 221 | $CH_2$—O | 7,8-dimethyl-2-quinoxalinyl | | |
| 222 | $CH_2$—S | 7,8-dimethyl-2-quinoxalinyl | | |
| 223 | $CH_2$—O | 7,8-dichloro-2-quinoxalinyl | | |
| 224 | $CH_2$—S | 7,8-dichloro-2-quinoxalinyl | | |
| 225 | $CH_2$—O | 7-methyl-2-quinoxalinyl | | |
| 226 | $CH_2$—S | 7-methyl-2-quinoxalinyl | | |
| 227 | $CH_2$—O | 8-methyl-2-quinoxalinyl | | |
| 228 | $CH_2$—S | 8-methyl-2-quinoxalinyl | | |
| 229 | $CH_2$—O | 7-methoxy-2-qunioxalinyl | | |
| 230 | $CH_2$—S | 7-methoxy-2-quinoxalinyl | | |
| 231 | $CH_2$—O | 3-phenyl-5-isoxazolyl | | |
| 232 | $CH_2$—S | 3-phenyl-5-isoxazolyl | | |
| 233 | $CH_2$—O | 2-benzoxazolyl | | |
| 234 | $CH_2$—S | 2-benzoxazolyl | | |
| 235 | $CH_2$—O | 2-benzthiazolyl | | |
| 236 | $CH_2$—S | 2-benzthiazolyl | | |
| 237 | $CH_2$—S | 6-methyl-2-benzthiazolyl | 86–88 | |
| 238 | $CH_2$—S | 4-chloro-2-benzthiazolyl | oil | 4.6(S, 2H); 7, 55(S, 1H) |
| 239 | $CH_2$—S | 5-chloro-2-benzthiazolyl | 131–133 | |
| 240 | $CH_2$—S | 6-chloro-2-benzthiazolyl | 86–89 | |
| 241 | $CH_2$—S | 6-ethoxy-2-benzthiazolyl | | |
| 242 | $CH_2$—S | 5-trifluoromethyl-2-benzthiazolyl | oil | 4.6(S, 2H); 7.55(S, 1H) |
| 243 | $CH_2$—S | 4,8-dimethyl-2-quinolyl | | |
| 244 | $CH_2$—O | 4,8-dimethyl-2-quinolyl | | |
| 245 | $CH_2$—O | 6-iso-butyl-2-pyridyl | | |
| 246 | $CH_2$—O | 3-cyano-6-iso-butyl-2-pyridyl | | |

TABLE 20

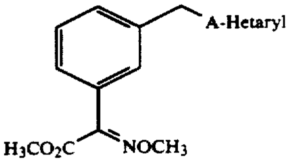

| No. | A | Hetaryl | mp | NMR: δ (ppm) |
|---|---|---|---|---|
| 1 | $CH_2$—S | 4-pyridyl | | |
| 2 | $CH_2$—O | 6-methyl-2-pyridyl | oil | 3.95(S, 3H); 4.05 (S, 3H); 5.35(S, 2H) |
| 3 | $CH_2$—S | 6-methyl-2-pyridyl | | |

TABLE 20-continued

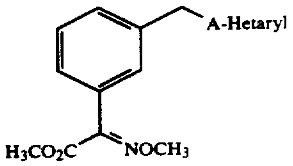

| No. | A | Hetaryl | mp | NMR: δ (ppm) |
|---|---|---|---|---|
| 4 | $CH_2$—O | 6-ethyl-2-pyridyl | | |
| 5 | $CH_2$—S | 6-ethyl-2-pyridyl | | |
| 6 | $CH_2$—O | 6-n-propyl-2-pyridyl | | |
| 7 | $CH_2$—S | 6-n-propyl-2-pyridyl | | |
| 8 | $CH_2$—O | 6-iso-propyl-2-pyridyl | | |
| 9 | $CH_2$—S | 6-iso-propyl-2-pyridyl | | |
| 10 | $CH_2$—O | 6-n-butyl-2-pyridyl | | |
| 11 | $CH_2$—S | 6-n-butyl-2-pyridyl | | |
| 12 | $CH_2$—O | 6-tert.-butyl-2-pyridyl | | |
| 13 | $CH_2$—S | 6-tert.-butyl-2-pyridyl | | |
| 14 | $CH_2$—O | 6-n-pentyl-2-pyridyl | | |
| 15 | $CH_2$—S | 6-n-pentyl-2-pyridyl | | |
| 16 | $CH_2$—O | 6-n-hexyl-2-pyridyl | | |
| 17 | $CH_2$—S | 6-n-hexyl-2-pyridyl | | |
| 18 | $CH_2$—O | 6-phenyl-2-pyridyl | | |
| 19 | $CH_2$—S | 6-phenyl-2-pyridyl | | |
| 20 | $CH_2$—O | 6-benzyl-2-pyridyl | | |
| 21 | $CH_2$—S | 6-benzyl-2-pyridyl | | |
| 22 | $CH_2$—S | 6-benzyl-2-pyridyl | | |
| 23 | $CH_2$—S | 6-trifluoromethyl-2-pyridyl | | |
| 24 | $CH_2$—O | 6-methoxy-2-pyridyl | | |
| 25 | $CH_2$—S | 6-methoxy-2-pyridyl | | |
| 26 | $CH_2$—O | 6-chloro-2-pyridyl | | |
| 27 | $CH_2$—S | 6-chloro-2-pyridyl | | |
| 28 | $CH_2$—O | 3,6-dimethyl-2-pyridyl | | |
| 29 | $CH_2$—S | 3,6-dimethyl-2-pyridyl | | |
| 30 | $CH_2$—O | 3,6-diethyl-2-pyridyl | | |
| 31 | $CH_2$—S | 3,6-diethyl-2-pyridyl | | |
| 32 | $CH_2$—O | 4,6-dimethyl-2-pyridyl | | |
| 33 | $CH_2$—S | 4,6-dimethyl-2-pyridyl | | |
| 34 | $CH_2$—O | 5,6-dimethyl-2-pyridyl | | |
| 35 | $CH_2$—S | 5,6-dimethyl-2-pyridyl | | |
| 36 | $CH_2$—O | 4-phenyl-6-methyl-2-pyridyl | | |
| 37 | $CH_2$—S | 4-phenyl-6-methyl-2-pyridyl | | |
| 38 | $CH_2$—O | 4,6-diphenyl-2-pyridyl | | |
| 39 | $CH_2$—S | 4,6-diphenyl-2-pyridyl | | |
| 40 | $CH_2$—O | 3,4-dichloro-6-methyl-2-pyridyl | | |
| 41 | $CH_2$—S | 3,4-dichloro-6-methyl-2-pyridyl | | |
| 42 | $CH_2$—O | 3,4,5-trichloro-6-phenyl-2-pyridyl | | |
| 43 | $CH_2$—S | 3,4,5-trichloro-6-phenyl-2-pyridyl | | |
| 44 | $CH_2$—O | 4-trifluoromethyl-6-methyl-2-pyridyl | | |
| 45 | $CH_2$—S | 4-trifluoromethyl-6-methyl-2-pyridyl | | |
| 46 | $CH_2$—O | 3-acetyl-4,6-dimethyl-2-pyridyl | | |
| 47 | $CH_2$—S | 3-acetyl-4,6-dimethyl-2-pyridyl | | |
| 48 | $CH_2$—O | 3-cyano-6-methyl-2-pyridyl | | |
| 49 | $CH_2$—S | 3-cyano-6-methyl-2-pyridyl | | |
| 50 | $CH_2$—O | 3-cyano-6-ethyl-2-pyridyl | | |
| 51 | $CH_2$—S | 3-cyano-6-ethyl-2-pyridyl | | |
| 52 | $CH_2$—O | 3-cyano-6-n-propyl-2-pyridyl | | |
| 53 | $CH_2$—S | 3-cyano-6-n-propyl-2-pyridyl | | |
| 54 | $CH_2$—O | 3-cyano-6-iso-propyl-2-pyridyl | | |
| 55 | $CH_2$—S | 3-cyano-6-iso-propyl-2-pyridyl | | |
| 56 | $CH_2$—O | 3-cyano-6-cyclo-propyl-2-pyridyl | | |
| 57 | $CH_2$—S | 3-cyano-6-cyclo-propyl-2-pyridyl | | |
| 58 | $CH_2$—O | 3-cyano-6-n-butyl-2-pyridyl | | |
| 59 | $CH_2$—S | 3-cyano-6-n-butyl-2-pyridyl | | |
| 60 | $CH_2$—O | 3-cyano-6-tert.-butyl-2-pyridyl | | |
| 61 | $CH_2$—S | 3-cyano-6-tert.-butyl-2-pyridyl | | |
| 62 | $CH_2$—O | 3-cyano-6-cyclo-hexyl-2-pyridyl | | |
| 63 | $CH_2$—S | 3-cyano-6-cyclo-hexyl-2-pyridyl | | |
| 64 | $CH_2$—O | 3-cyano-6-phenyl-2-pyridyl | | |
| 65 | $CH_2$—S | 3-cyano-6-phenyl-2-pyridyl | | |
| 66 | $CH_2$—O | 3-methyloxycarbonyl-6-iso-propyl-2-pyridyl | | |
| 67 | $CH_2$—S | 3-methyloxycarbonyl-6-iso-propyl-2-pyridyl | | |
| 68 | $CH_2$—O | 3-ethyloxycarbonyl-6-iso-propyl-2-pyridyl | | |
| 69 | $CH_2$—S | 3-ethyloxycarbonyl-6-iso-propyl-2-pyridyl | | |
| 70 | $CH_2$—O | 3-cyano-4,6-dimethyl-2-pyridyl | | |
| 71 | $CH_2$—S | 3-cyano-4,6-dimethyl-2-pyridyl | | |
| 72 | $CH_2$—O | 3,5,6-trichloro-2-pyridyl | | |
| 73 | $CH_2$—S | 3,5,6-trichloro-2-pyridyl | | |
| 74 | $CH_2$—O | 5-trifluoromethyl-2-pyridyl | | |
| 75 | $CH_2$—S | 5-trifluoromethyl-2-pyridyl | | |

TABLE 20-continued

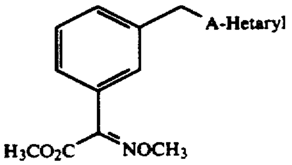

| No. | A | Hetaryl | mp | NMR: δ (ppm) |
|---|---|---|---|---|
| 76 | $CH_2$—O | 3-chloro-5-trifluoromethyl-2-pyridyl | | |
| 77 | $CH_2$—S | 3-chloro-5-trifluoromethyl-2-pyridyl | | |
| 78 | $CH_2$—O | 2-quinolyl | | |
| 79 | $CH_2$—S | 2-quinolyl | | |
| 80 | $CH_2$—O | 3-methyl-2-quinolyl | | |
| 81 | $CH_2$—S | 3-methyl-2-quinolyl | | |
| 82 | $CH_2$—O | 4-methyl-2-quinolyl | | |
| 83 | $CH_2$—S | 4-methyl-2-quinolyl | | |
| 84 | $CH_2$—O | 4-ethyl-2-quinolyl | | |
| 85 | $CH_2$—S | 4-ethyl-2-quinolyl | | |
| 86 | $CH_2$—O | 4-phenyl-2-quinolyl | | |
| 87 | $CH_2$—S | 4-phenyl-2-quinolyl | | |
| 88 | $CH_2$—O | 6-methyl-2-quinolyl | | |
| 89 | $CH_2$—S | 6-methyl-2-quinolyl | | |
| 90 | $CH_2$—O | 6-chloro-2-quinolyl | | |
| 91 | $CH_2$—S | 6-chloro-2-quinolyl | | |
| 92 | $CH_2$—O | 8-methyl-2-quinolyl | | |
| 93 | $CH_2$—S | 8-methyl-2-quinolyl | | |
| 94 | $CH_2$—O | 8-chloro-2-quinolyl | | |
| 95 | $CH_2$—S | 8-chloro-2-quinolyl | | |
| 96 | $CH_2$—O | 4-ethoxycarbonyl-2-quinolyl | | |
| 97 | $CH_2$—S | 4-ethoxycarbonyl-2-quinolyl | | |
| 98 | $CH_2$—O | 3,4-dimethyl-2-quinolyl | | |
| 99 | $CH_2$—S | 3,4-dimethyl-2-quinolyl | | |
| 100 | $CH_2$—O | 4-methyl-8-methoxy-2-quinolyl | | |
| 101 | $CH_2$—S | 4-methyl-8-methoxy-2-quinolyl | | |
| 102 | $CH_2$—O | 4-phenyl-8-ethoxy-2-quinolyl | | |
| 103 | $CH_2$—S | 4-phenyl-8-ethoxy-2-quinolyl | | |
| 104 | $CH_2$—O | 4-methyl-8-chloro-2-quinolyl | | |
| 105 | $CH_2$—S | 4-methyl-8-chloro-2-quinolyl | | |
| 106 | $CH_2$—O | 4-methyl-8-fluoro-2-quinolyl | | |
| 107 | $CH_2$—S | 4-methyl-8-fluoro-2-quinolyl | | |
| 108 | $CH_2$—O | 4-quinolyl | | |
| 109 | $CH_2$—S | 4-quinolyl | | |
| 110 | $CH_2$—O | 2-methyl-4-quinolyl | | |
| 111 | $CH_2$—S | 2-methyl-4-quinolyl | | |
| 112 | $CH_2$—O | 2-trichloromethyl-4-quinolyl | | |
| 113 | $CH_2$—S | 2-trichloromethyl-4-quinolyl | | |
| 114 | $CH_2$—O | 2-trichloromethyl-2-quinolyl | | |
| 115 | $CH_2$—S | 2-trichloromethyl-2-quinolyl | | |
| 116 | $CH_2$—O | 2-iso-propyl-4-quinolyl | | |
| 117 | $CH_2$—S | 2-iso-propyl-4-quinolyl | | |
| 118 | $CH_2$—O | 2-n-pentyl-4-quinolyl | | |
| 119 | $CH_2$—S | 2-n-pentyl-4-quinolyl | | |
| 120 | $CH_2$—O | 2-phenyl-4-quinolyl | | |
| 121 | $CH_2$—S | 2-phenyl-4-quinolyl | | |
| 122 | $CH_2$—O | 2-methoxycarbonyl-4-quinolyl | | |
| 123 | $CH_2$—S | 2-methoxycarbonyl-4-quinolyl | | |
| 124 | $CH_2$—O | 2,6-dimethyl-4-quinolyl | | |
| 125 | $CH_2$—S | 2,6-dimethyl-4-quinolyl | | |
| 126 | $CH_2$—O | 2-methyl-6-chloro-4-quinolyl | | |
| 127 | $CH_2$—S | 2-methyl-6-chloro-4-quinolyl | | |
| 128 | $CH_2$—O | 2-methyl-6-fluoro-4-quinolyl | | |
| 129 | $CH_2$—S | 2-methyl-6-fluoro-4-quinolyl | | |
| 130 | $CH_2$—O | 8-quinolyl | | |
| 131 | $CH_2$—S | 8-quinolyl | | |
| 132 | $CH_2$—O | 2-methyl-8-quinolyl | | |
| 133 | $CH_2$—S | 2-methyl-8-quinolyl | | |
| 134 | $CH_2$—O | 5,7-dichloro-8-quinolyl | | |
| 135 | $CH_2$—S | 5,7-dichloro-8-quinolyl | | |
| 136 | $CH_2$—O | 4,6-dimethyl-2-pyrimidinyl | | |
| 137 | $CH_2$—S | 4,6-dimethyl-2-pyrimidinyl | | |
| 138 | $CH_2$—O | 4-trifluoromethyl-2-pyrimidinyl | | |
| 139 | $CH_2$—S | 4-trifluoromethyl-2-pyrimidinyl | | |
| 140 | $CH_2$—O | 4,5,6-trimethyl-2-pyrimidinyl | | |
| 141 | $CH_2$—S | 4,5,6-trimethyl-2-pyrimidinyl | | |
| 142 | $CH_2$—O | 4-benzyl-6-methyl-2-pyrimidinyl | | |
| 143 | $CH_2$—S | 4-benzyl-6-methyl-2-pyrimidinyl | | |
| 144 | $CH_2$—O | 4-methyl-6-phenyl-2-pyrimidinyl | | |
| 145 | $CH_2$—S | 4-methyl-6-phenyl-2-pyrimidinyl | | |
| 146 | $CH_2$—O | 4,5-dimethyl-5-chloro-2-pyrimidinyl | | |
| 147 | $CH_2$—S | 4,5-dimethyl-5-chloro-2-pyrimidinyl | | |

TABLE 20-continued

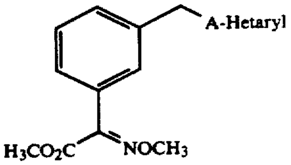

| No. | A | Hetaryl | mp | NMR: δ (ppm) |
|---|---|---|---|---|
| 148 | $CH_2$—O | 2,6-dimethyl-4-pyrimidinyl | | |
| 149 | $CH_2$—S | 2,6-dimethyl-4-pyrimidinyl | | |
| 150 | $CH_2$—O | 2,6-bis-(trifluoromethyl)-4-pyrimidinyl | | |
| 151 | $CH_2$—S | 2,6-bis-(trifluoromethyl)-4-pyrimidinyl | | |
| 152 | $CH_2$—O | 2-chloromethyl-6-methyl-4-pyrimidinyl | | |
| 153 | $CH_2$—S | 2-chloromethyl-6-methyl-4-pyrimidinyl | | |
| 154 | $CH_2$—O | 2-methyl-6-chloromethyl-4-pyrimidinyl | | |
| 155 | $CH_2$—S | 2-methyl-6-chloromethyl-4-pyrimidinyl | | |
| 156 | $CH_2$—O | 2-iso-propyl-6-methyl-4-pyrimidinyl | | |
| 157 | $CH_2$—S | 2-iso-propyl-6-methyl-4-pyrimidinyl | | |
| 158 | $CH_2$—O | 2-iso-propyl-6-chloromethyl-4-pyrimidinyl | | |
| 159 | $CH_2$—S | 2-iso-propyl-6-chloromethyl-4-pyrimidinyl | | |
| 160 | $CH_2$—O | 2-cyclo-propyl-6-chloromethyl-4-pyrimidinyl | | |
| 161 | $CH_2$—S | 2-cyclo-propyl-6-chloromethyl-4-pyrimidinyl | | |
| 162 | $CH_2$—O | 2-cyclo-propyl-6-methyl-4-pyrimidinyl | | |
| 163 | $CH_2$—S | 2-cyclo-propyl-6-methyl-4-pyrimidinyl | | |
| 164 | $CH_2$—O | 2-methyl-6-methoxymethyl-4-pyrimidinyl | | |
| 165 | $CH_2$—S | 2-methyl-6-methoxymethyl-4-pyrimidinyl | | |
| 166 | $CH_2$—O | 2-iso-propyl-6-methoxymethyl-4-pyrimidinyl | | |
| 167 | $CH_2$—S | 2-iso-propyl-6-methoxymethyl-4-pyrimidinyl | | |
| 168 | $CH_2$—O | 2-phenyl-4-pyrimidinyl | | |
| 169 | $CH_2$—S | 2-phenyl-4-pyrimidinyl | | |
| 170 | $CH_2$—O | 3,5-dimethyl-4-pyrimidinyl | | |
| 171 | $CH_2$—S | 3,5-dimethyl-4-pyrimidinyl | | |
| 172 | $CH_2$—O | 2-methylthio-6-trifluoromethyl-4-pyrimidinyl | | |
| 173 | $CH_2$—S | 2-methylthio-6-trifluoromethyl-4-pyrimidinyl | | |
| 174 | $CH_2$—O | 2-methylthio-5-chloro-6-trifluoromethyl-4-pyrimidinyl | | |
| 175 | $CH_2$—S | 2-methylthio-5-chloro-6-trifluoromethyl-4-pyrimidinyl | | |
| 176 | $CH_2$—O | 2-methylthio-5-n-octyl-6-trifluoromethyl-4-pyrimidinyl | | |
| 177 | $CH_2$—S | 2-methylthio-5-n-octyl-6-trifluoromethyl-4-pyrimidinyl | | |
| 178 | $CH_2$—O | 2-methyl-6-trifluoromethyl-4-pyrimidinyl | | |
| 179 | $CH_2$—S | 2-methyl-6-trifluoromethyl-4-pyrimidinyl | | |
| 180 | $CH_2$—O | 2-n-propyl-6-trifluoromethyl-4-pyrimidinyl | | |
| 181 | $CH_2$—S | 2-n-propyl-6-trifluoromethyl-4-pyrimidinyl | | |
| 182 | $CH_2$—O | 2-iso-propyl-6-trifluoromethyl-4-pyrimidinyl | | |
| 183 | $CH_2$—S | 2-iso-propyl-6-trifluoromethyl-4-pyrimidinyl | | |
| 184 | $CH_2$—O | 2-tert.-butyl-6-trifluoromethyl-4-pyrimidinyl | | |
| 185 | $CH_2$—S | 2-tert.-butyl-6-trifluoromethyl-4-pyrimidinyl | | |
| 186 | $CH_2$—O | 2-methyl-5-chloro-6-trifluoromethyl-4-pyrimidinyl | | |
| 187 | $CH_2$—S | 2-methyl-5-chloro-6-trifluoromethyl-4-pyrimidinyl | | |
| 188 | $CH_2$—O | 2-n-propyl-5-chloro-6-trifluoromethyl-4-pyrimidinyl | | |
| 189 | $CH_2$—S | 2-n-propyl-5-chloro-6-trifluoromethyl-4-pyrimidinyl | | |
| 190 | $CH_2$—O | 2-iso-propyl-5-chloro-6-trifluoromethyl-4-pyrimidinyl | | |
| 191 | $CH_2$—S | 2-iso-propyl-5-chloro-6-trifluoromethyl-4-pyrimidinyl | | |
| 192 | $CH_2$—O | 2-tert.-butyl-5-chloro-6-trifluoromethyl-4-pyrimidinyl | | |
| 193 | $CH_2$—S | 2-tert.-butyl-5-chloro-6-trifluoromethyl-4-pyrimidinyl | | |
| 194 | $CH_2$—S | 2-pyrimidinyl | | |
| 195 | $CH_2$—O | 6-cyclopropyl-2-pyridyl | | |
| 196 | $CH_2$—S | 6-cyclopropyl-2-pyridyl | | |
| 197 | $CH_2$—O | 2-pyrazinyl | | |
| 198 | $CH_2$—S | 2-pyrazinyl | | |
| 199 | $CH_2$—O | 6-chloro-2-pyrazinyl | | |
| 200 | $CH_2$—S | 6-chloro-2-pyrazinyl | | |
| 201 | $CH_2$—O | 5-methyl-2-pyrazinyl | | |
| 202 | $CH_2$—S | 5-methyl-2-pyrazinyl | | |
| 203 | $CH_2$—O | 3-pyridazinyl | | |
| 204 | $CH_2$—S | 3-pyridazinyl | | |
| 205 | $CH_2$—O | 5-chloro-3-pyridazinyl | | |
| 206 | $CH_2$—S | 5-chloro-3-pyridazinyl | | |
| 207 | $CH_2$—O | 2-thienyl | | |
| 208 | $CH_2$—S | 2-thienyl | | |
| 209 | $CH_2$—O | 3-thienyl | | |
| 210 | $CH_2$—S | 3-thienyl | | |
| 211 | $CH_2$—O | 4-chloro-3-thienyl | | |
| 212 | $CH_2$—S | 4-chloro-3-thienyl | | |
| 213 | $CH_2$—O | 2-chloro-3-thienyl | | |
| 214 | $CH_2$—S | 2-chloro-3-thienyl | | |
| 215 | $CH_2$—O | 5-chloro-3-thienyl | | |
| 216 | $CH_2$—S | 5-chloro-3-thienyl | | |
| 217 | $CH_2$—O | 2-quinoxalinyl | | |
| 218 | $CH_2$—S | 2-quinoxalinyl | | |
| 219 | $CH_2$—O | 3-methyl-2-quinoxalinyl | | |

TABLE 20-continued

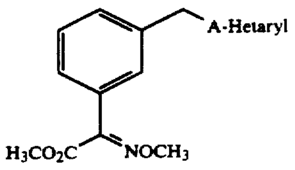

| No. | A | Hetaryl | mp | NMR: δ (ppm) |
|---|---|---|---|---|
| 220 | $CH_2$—S | 3-methyl-2-quinoxalinyl | | |
| 221 | $CH_2$—O | 7,8-dimethyl-2-quinoxalinyl | | |
| 222 | $CH_2$—S | 7,8-dimethyl-2-quinoxalinyl | | |
| 223 | $CH_2$—O | 7,8-dichloro-2-quinoxalinyl | | |
| 224 | $CH_2$—S | 7,8-dichloro-2-quinoxalinyl | | |
| 225 | $CH_2$—O | 7-methyl-2-quinoxalinyl | | |
| 226 | $CH_2$—S | 7-methyl-2-quinoxalinyl | | |
| 227 | $CH_2$—O | 8-methyl-2-quinoxalinyl | | |
| 228 | $CH_2$—S | 8-methyl-2-quinoxalinyl | | |
| 229 | $CH_2$—O | 7-methoxy-2-quinoxalinyl | | |
| 230 | $CH_2$—S | 7-methoxy-2-quinoxalinyl | | |
| 231 | $CH_2$—O | 3-phenyl-5-isoxazolyl | | |
| 232 | $CH_2$—S | 3-phenyl-5-isoxazolyl | | |
| 233 | $CH_2$—O | 2-benzoxazolyl | | |
| 234 | $CH_2$—S | 2-benzoxazolyl | | |
| 235 | $CH_2$—O | 2-benzthiazolyl | | |
| 236 | $CH_2$—S | 2-benzthiazolyl | | |
| 237 | $CH_2$—S | 6-methyl-2-benzthiazolyl (non-polar isomer) | oil | 3.9(S, 3H); 4.0(S, 3H); 4.55(S, 2H) |
| 238 | $CH_2$—S | 4-chloro-2-benzthiazolyl | | |
| 239 | $CH_2$—S | 5-chloro-2-benzthiazolyl | | |
| 240 | $CH_2$—S | 6-chloro-2-benzthiazolyl | | |
| 241 | $CH_2$—S | 6-ethoxy-2-benzthiazolyl | | |
| 242 | $CH_2$—S | 5-trifluoromethyl-2-benzthiazolyl | | |
| 243 | $CH_2$—S | 4,8-dimethyl-2-quinolyl | | |
| 244 | $CH_2$—O | 4,8-dimethyl-2-quinolyl | | |
| 245 | $CH_2$—O | 6-iso-butyl-2-pyridyl | | |
| 246 | $CH_2$—O | 3-cyano-6-iso-butyl-2-pyridyl | | |

TABLE 21

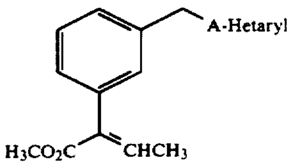

| No. | A | Hetaryl | mp | NMR: δ (ppm) |
|---|---|---|---|---|
| 1 | $CH_2$—S | 4-pyridyl | | |
| 2 | $CH_2$—O | 6-methyl-2-pyridyl | oil | 3.95(S, 3H); 4.05 (S, 3H); 5.35(S, 2H) |
| 3 | $CH_2$—S | 6-methy-2-pyridyl | | |
| 4 | $CH_2$—O | 6-ethyl-2-pyridyl | | |
| 5 | $CH_2$—S | 6-ethyl-2-pyridyl | | |
| 6 | $CH_2$—O | 6-n-propyl-2-pyridyl | | |
| 7 | $CH_2$—S | 6-n-propyl-2-pyridyl | | |
| 8 | $CH_2$—O | 6-iso-propyl-2-pyridyl | | |
| 9 | $CH_2$—S | 6-iso-propyl-2-pyridyl | | |
| 10 | $CH_2$—O | 6-n-butyl-2-pyridyl | | |
| 11 | $Ch_2$—S | 6-n-butyl-2-pyridyl | | |
| 12 | $CH_2$—O | 6-tert.-butyl-2-pyridyl | | |
| 13 | $CH_2$—S | 6-tert.-butyl-2-pyridyl | | |
| 14 | $CH_2$—O | 6-n-pentyl-2-pyridyl | | |
| 15 | $CH_2$—S | 6-n-pentyl-2-pyridyl | | |
| 16 | $CH_2$—O | 6-n-hexyl-2-pyridyl | | |
| 17 | $CH_2$—S | 6-n-hexyl-2-pyridyl | | |
| 18 | $CH_2$—O | 6-phenyl-2-pyridyl | | |
| 19 | $CH_2$—S | 6-phenyl-2-pyridyl | | |
| 20 | $CH_2$—O | 6-benzyl-2-pyridyl | | |
| 21 | $CH_2$—S | 6-benzyl-2-pyridyl | | |
| 22 | $CH_2$—S | 6-benzyl-2-pyridyl | | |
| 23 | $CH_2$—S | 6-trifluoromethyl-2-pyridyl | | |
| 24 | $CH_2$—O | 6-methoxy-2-pyridyl | | |
| 25 | $CH_2$—S | 6-methoxy-2-pyridyl | | |
| 26 | $CH_2$—O | 6-chloro-2-pyridyl | | |
| 27 | $CH_2$—S | 6-chloro-2-pyridyl | | |
| 28 | $CH_2$—O | 3,6-dimethyl-2-pyridyl | | |

TABLE 21-continued

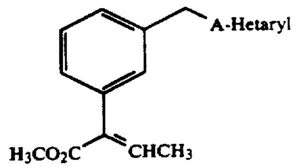

| No. | A | Hetaryl | mp | NMR: δ (ppm) |
|---|---|---|---|---|
| 29 | $CH_2—S$ | 3,6-dimethyl-2-pyridyl | | |
| 30 | $CH_2—O$ | 3,6-diethyl-2-pyridyl | | |
| 31 | $CH_2—S$ | 3,6-diethyl-2-pyridyl | | |
| 32 | $CH_2—O$ | 4,6-dimethyl-2-pyridyl | | |
| 33 | $CH_2—S$ | 4,6-dimethyl-2-pyridyl | | |
| 34 | $CH_2—O$ | 5,6-dimethyl-2-pyridyl | | |
| 35 | $CH_2—S$ | 5,6-dimethyl-2-pyridyl | | |
| 36 | $CH_2—O$ | 4-phenyl-6-methyl-2-pyridyl | | |
| 37 | $CH_2—S$ | 4-phenyl-6-methyl-2-pyridyl | | |
| 38 | $CH_2—O$ | 4,6-diphenyl-2-pyridyl | | |
| 39 | $CH_2—S$ | 4,6-diphenyl-2-pyridyl | | |
| 40 | $CH_2—O$ | 3,4-dichloro-6-methyl-2-pyridyl | | |
| 41 | $CH_2—S$ | 3,4-dichloro-6-methyl-2-pyridyl | | |
| 42 | $CH_2—O$ | 3,4,5-trichloro-6-phenyl-2-pyridyl | | |
| 43 | $CH_2—S$ | 3,4,5-trichloro-6-phenyl-2-pyridyl | | |
| 44 | $CH_2—O$ | 4-trifluoromethyl-6-methyl-2-pyridyl | | |
| 45 | $CH_2—S$ | 4-trifluoromethyl-6-methyl-2-pyridyl | | |
| 46 | $CH_2—O$ | 3-acetyl-4,6-dimethyl-2-pyridyl | | |
| 47 | $CH_2—S$ | 3-acetyl-4,6-dimethyl-2-pyridyl | | |
| 48 | $CH_2—O$ | 3-cyano-6-methyl-2-pyridyl | | |
| 49 | $CH_2—S$ | 3-cyano-6-methyl-2-pyridyl | | |
| 50 | $CH_2—O$ | 3-cyano-6-ethyl-2-pyridyl | | |
| 51 | $CH_2—S$ | 3-cyano-6-ethyl-2-pyridyl | | |
| 52 | $CH_2—O$ | 3-cyano-6-n-propyl-2-pyridyl | | |
| 53 | $CH_2—S$ | 3-cyano-6-n-propyl-2-pyridyl | | |
| 54 | $CH_2—O$ | 3-cyano-6-iso-propyl-2-pyridyl | | |
| 55 | $CH_2—S$ | 3-cyano-6-iso-propyl-2-pyridyl | | |
| 56 | $CH_2—O$ | 3-cyano-6-cyclo-propyl-2-pyridyl | | |
| 57 | $CH_2—S$ | 3-cyano-6-cyclo-propyl-2-pyridyl | | |
| 58 | $CH_2—O$ | 3-cyano-6-n-butyl-2-pyridyl | | |
| 59 | $CH_2—S$ | 3-cyano-6-n-butyl-2-pyridyl | | |
| 60 | $CH_2—O$ | 3-cyano-6-tert.-butyl-2-pyridyl | | |
| 61 | $CH_2—S$ | 3-cyano-6-tert.-butyl-2-pyridyl | | |
| 62 | $CH_2—O$ | 3-cyano-6-cyclo-hexyl-2-pyridyl | | |
| 63 | $CH_2—S$ | 3-cyano-6-cyclo-hexyl-2-pyridyl | | |
| 64 | $CH_2—O$ | 3-cyano-6-phenyl-2-pyridyl | | |
| 65 | $CH_2—S$ | 3-cyano-6-phenyl-2-pyridyl | | |
| 66 | $CH_2—O$ | 3-methyloxycarbonyl-6-iso-propyl-2-pyridyl | | |
| 67 | $CH_2—S$ | 3-methyloxycarbonyl-6-iso-propyl-2-pyridyl | | |
| 68 | $CH_2—O$ | 3-ethyloxycarbonyl-6-iso-propyl-2-pyridyl | | |
| 69 | $CH_2—S$ | 3-ethyloxycarbonyl-6-iso-propyl-2-pyridyl | | |
| 70 | $CH_2—O$ | 3-cyano-4,6-dimethyl-2-pyridyl | | |
| 71 | $CH_2—S$ | 3-cyano-4,6-dimethyl-2-pyridyl | | |
| 72 | $CH_2—O$ | 3,5,6-trichloro-2-pyridyl | | |
| 73 | $CH_2—S$ | 3,5,6-trichloro-2-pyridyl | | |
| 74 | $CH_2—O$ | 5-trifluoromethyl-2-pyridyl | | |
| 75 | $CH_2—S$ | 5-trifluoromethyl-2-pyridyl | | |
| 76 | $CH_2—O$ | 3-chloro-5-trifluoromethyl-2-pyridyl | | |
| 77 | $CH_2—S$ | 3-chloro-5-trifluoromethyl-2-pyridyl | | |
| 78 | $CH_2—O$ | 2-quinolyl | | |
| 79 | $CH_2—S$ | 2-quinolyl | | |
| 80 | $CH_2—O$ | 3-methyl-2-quinolyl | | |
| 81 | $CH_2—S$ | 3-methyl-2-quinolyl | | |
| 82 | $CH_2—O$ | 4-methyl-2-quinolyl | | |
| 83 | $CH_2—S$ | 4-methyl-2-quinolyl | | |
| 84 | $CH_2—O$ | 4-ethyl-2-quinolyl | | |
| 85 | $CH_2—S$ | 4-ethyl-2-quinolyl | | |
| 86 | $CH_2—O$ | 4-phenyl-2-quinolyl | | |
| 87 | $CH_2—S$ | 4-phenyl-2-quinolyl | | |
| 88 | $CH_2—O$ | 6-methyl-2-quinolyl | | |
| 89 | $CH_2—S$ | 6-methyl-2-quinolyl | | |
| 90 | $CH_2—O$ | 6-chloro-2-quinolyl | | |
| 91 | $CH_2—S$ | 6-chloro-2-quinolyl | | |
| 92 | $CH_2—O$ | 8-methyl-2-quinolyl | | |
| 93 | $CH_2—S$ | 8-methyl-2-quinolyl | | |
| 94 | $CH_2—O$ | 8-chloro-2-quinolyl | | |
| 95 | $CH_2—S$ | 8-chloro-2-quinolyl | | |
| 96 | $CH_2—O$ | 4-Ethoxycarbonyl-2-quinolyl | | |
| 97 | $CH_2—S$ | 4-Ethoxycarbonyl-2-quinolyl | | |
| 98 | $CH_2—O$ | 3,4-dimethyl-2-quinolyl | | |
| 99 | $CH_2—S$ | 3,4-dimethyl-2-quinolyl | | |
| 100 | $CH_2—O$ | 4-methyl-8-methoxy-2-quinolyl | | |

TABLE 21-continued

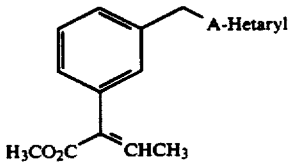

| No. | A | Hetaryl | mp | NMR: δ (ppm) |
|---|---|---|---|---|
| 101 | $CH_2$—S | 4-methyl-8-methoxy-2-quinolyl | | |
| 102 | $CH_2$—O | 4-phenyl-8-ethoxy-2-quinolyl | | |
| 103 | $CH_2$—S | 4-phenyl-8-ethoxy-2-quinolyl | | |
| 104 | $CH_2$—O | 4-methyl-8-chloro-2-quinolyl | | |
| 105 | $CH_2$—S | 4-methyl-8-chloro-2-quinolyl | | |
| 106 | $CH_2$—O | 4-methyl-8-fluoro-2-quinolyl | | |
| 107 | $CH_2$—S | 4-methyl-8-fluoro-2-quinolyl | | |
| 108 | $CH_2$—O | 4-quinolyl | | |
| 109 | $CH_2$—S | 4-quinolyl | | |
| 110 | $CH_2$—O | 2-methyl-4-quinolyl | | |
| 111 | $CH_2$—S | 2-methyl-4-quinolyl | | |
| 112 | $CH_2$—O | 2-trichloromethyl-4-quinolyl | | |
| 113 | $CH_2$—S | 2-trichloromethyl-4-quinolyl | | |
| 114 | $CH_2$—O | 2-trifluoromethyl-2-quinolyl | | |
| 115 | $CH_2$—S | 2-trifluoromethyl-2-quinolyl | | |
| 116 | $CH_2$—O | 2-iso-propyl-4-quinolyl | | |
| 117 | $CH_2$—S | 2-iso-propyl-4-quinolyl | | |
| 118 | $CH_2$—O | 2-n-pentyl-4-quinolyl | | |
| 119 | $CH_2$—S | 2-n-pentyl-4-quinolyl | | |
| 120 | $CH_2$—O | 2-phenyl-4-quinolyl | | |
| 121 | $CH_2$—S | 2-phenyl-4-quinolyl | | |
| 122 | $CH_2$—O | 2-methoxycarbonyl-4-quinolyl | | |
| 123 | $CH_2$—S | 2-methoxycarbonyl-4-quinolyl | | |
| 124 | $CH_2$—O | 2,6-dimethyl-4-quinolyl | | |
| 125 | $CH_2$—S | 2,6-dimethyl-4-quinolyl | | |
| 126 | $CH_2$—O | 2-methyl-6-chloro-4-quinolyl | | |
| 127 | $CH_2$—S | 2-methyl-6-chloro-4-quinolyl | | |
| 128 | $CH_2$—O | 2-methyl-6-fluoro-4-quinolyl | | |
| 129 | $CH_2$—S | 2-methyl-6-fluoro-4-quinolyl | | |
| 130 | $CH_2$—O | 8-quinolyl | | |
| 131 | $CH_2$—S | 8-quinolyl | | |
| 132 | $CH_2$—O | 2-methyl-8-quinolyl | | |
| 133 | $CH_2$—S | 2-methyl-8-quinolyl | | |
| 134 | $CH_2$—O | 5,7-dichloro-8-quinolyl | | |
| 135 | $CH_2$—S | 5,7-dichloro-8-quinolyl | | |
| 136 | $CH_2$—O | 4,6-dimethyl-2-pyrimidinyl | | |
| 137 | $CH_2$—S | 4,6-dimethyl-2-pyrimidinyl | | |
| 138 | $CH_2$—O | 4-trifluoromethyl-2-pyrimidinyl | | |
| 139 | $CH_2$—S | 4-trifluoromethyl-2-pyrimidinyl | | |
| 140 | $CH_2$—O | 4,5,6-trimethyl-2-pyrimidinyl | | |
| 141 | $CH_2$—S | 4,5,6-trimethyl-2-pyrimidinyl | | |
| 142 | $CH_2$—O | 4-benzyl-6-methyl-2-pyrimidinyl | | |
| 143 | $CH_2$—S | 4-benzyl-6-methyl-2-pyrimidinyl | | |
| 144 | $CH_2$—O | 4-methyl-6-phenyl-2-pyrimidinyl | | |
| 145 | $CH_2$—S | 4-methyl-6-phenyl-2-pyrimidinyl | | |
| 146 | $CH_2$—O | 4,6-dimethyl-5-chloro-2-pyrimidinyl | | |
| 147 | $CH_2$—S | 4,6-dimethyl-5-chloro-2-pyrimidinyl | | |
| 148 | $CH_2$—O | 2,6-dimethyl-4-pyrimidinyl | | |
| 149 | $CH_2$—S | 2,6-dimethyl-4-pyrimidinyl | | |
| 150 | $CH_2$—O | 2,6-bis-(trifluoromethyl)-4-pyrimidinyl | | |
| 151 | $CH_2$—S | 2,6-bis-(trifluoromethyl)-4-pyrimidinyl | | |
| 152 | $CH_2$—O | 2-chloromethyl-6-methyl-4-pyrimidinyl | | |
| 153 | $CH_2$—S | 2-chloromethyl-6-methyl-4-pyrimidinyl | | |
| 154 | $CH_2$—O | 2-methyl-6-chloromethyl-4-pyrimidinyl | | |
| 155 | $CH_2$—S | 2-methyl-6-chloromethyl-4-pyrimidinyl | | |
| 156 | $CH_2$—O | 2-iso-propyl-6-methyl-4-pyrimidinyl | | |
| 157 | $CH_2$—S | 2-iso-propyl-6-methyl-4-pyrimidinyl | | |
| 158 | $CH_2$—O | 2-iso-propyl-6-chloromethyl-4-pyrimidinyl | | |
| 159 | $CH_2$—S | 2-iso-propyl-6-chloromethyl-4-pyrimidinyl | | |
| 160 | $CH_2$—O | 2-cyclo-propyl-6-chloromethyl-4-pyrimidinyl | | |
| 161 | $CH_2$—S | 2-cyclo-propyl-6-chloromethyl-4-pyrimidinyl | | |
| 162 | $CH_2$—O | 2-cyclo-propyl-6-methyl-4-pyrimidinyl | | |
| 163 | $CH_2$—S | 2-cyclo-propyl-6-methyl-4-pyrimidinyl | | |
| 164 | $CH_2$—O | 2-methyl-6-methoxymethyl-4-pyrimidinyl | | |
| 165 | $CH_2$—S | 2-methyl-6-methoxymethyl-4-pyrimidinyl | | |
| 166 | $CH_2$—O | 2-iso-propyl-6-methoxymethyl-4-pyrimidinyl | | |
| 167 | $CH_2$—S | 2-iso-propyl-6-methoxymethyl-4-pyrimidinyl | | |
| 168 | $CH_2$—O | 2-phenyl-4-pyrimidinyl | | |
| 169 | $CH_2$—S | 2-phenyl-4-pyrimidinyl | | |
| 170 | $CH_2$—O | 3,5-dimethyl-4-pyrimidinyl | | |
| 171 | $CH_2$—S | 3,5-dimethyl-4-pyrimidinyl | | |
| 172 | $CH_2$—O | 2-methylthio-6-trifluoromethyl-4-pyrimidinyl | | |

TABLE 21-continued

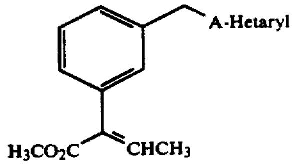

| No. | A | Hetaryl | mp | NMR: δ (ppm) |
|---|---|---|---|---|
| 173 | $CH_2$—S | 2-methylthio-6-trifluoromethyl-4-pyrimidinyl | | |
| 174 | $CH_2$—O | 2-methylthio-5-chloro-6-trifluoromethyl-4-pyrimidinyl | | |
| 175 | $CH_2$—S | 2-methylthio-5-chloro-6-trifluoromethyl-4-pyrimidinyl | | |
| 176 | $CH_2$—O | 2-methylthio-5-n-octyl-6-methyl-4-pyrimidinyl | | |
| 177 | $CH_2$—S | 2-methylthio-5-n-octyl-6-methyl-4-pyrimidinyl | | |
| 178 | $CH_2$—O | 2-methyl-6-trifluoromethyl-4-pyrimidinyl | | |
| 179 | $CH_2$—S | 2-methyl-6-trifluoromethyl-4-pyrimidinyl | | |
| 180 | $CH_2$—O | 2-n-propyl-6-trifluoromethyl-4-pyrimidinyl | | |
| 181 | $CH_2$—S | 2-n-propyl-6-trifluoromethyl-4-pyrimidinyl | | |
| 182 | $CH_2$—O | 2-iso-propyl-6-trifluoromethyl-4-pyrimidinyl | | |
| 183 | $CH_2$—S | 2-iso-propyl-6-trifluoromethyl-4-pyrimidinyl | | |
| 184 | $CH_2$—O | 2-tert.-butyl-6-trifluoromethyl-4-pyrimidinyl | | |
| 185 | $CH_2$—S | 2-tert.-butyl-6-trifluoromethyl-4-pyrimidinyl | | |
| 186 | $CH_2$—O | 2-methyl-5-chloro-6-trifluoromethyl-4-pyrimidinyl | | |
| 187 | $CH_2$—S | 2-methyl-5-chloro-6-trifluoromethyl-4-pyrimidinyl | | |
| 188 | $CH_2$—O | 2-n-propyl-5-chloro-6-trifluoromethyl-4-pyrimidinyl | | |
| 189 | $CH_2$—S | 2-n-propyl-5-chloro-6-trifluoromethyl-4-pyrimidinyl | | |
| 190 | $CH_2$—O | 2-iso-propyl-5-chloro-6-trifluoromethyl-4-pyrimidinyl | | |
| 191 | $CH_2$—S | 2-iso-propyl-5-chloro-6-trifluoromethyl-4-pyrimidinyl | | |
| 192 | $CH_2$—O | 2-tert.-butyl-5-chloro-6-trifluoromethyl-4-pyrimidininyl | | |
| 193 | $CH_2$—S | 2-tert.-butyl-5-chloro-6-trifluoromethyl-4-pyrimidininyl | | |
| 194 | $CH_2$—S | 2-pyrimidinyl | | |
| 195 | $CH_2$—O | 6-cyclopropyl-2-pyridyl | | |
| 196 | $CH_2$—S | 6-cyclopropyl-2-pyridyl | | |
| 197 | $CH_2$—O | 2-pyrizinyl | | |
| 198 | $CH_2$—S | 2-pyrazinyl | | |
| 199 | $CH_2$—O | 6-chloro-2-pyrazinyl | | |
| 200 | $CH_2$—S | 6-chloro-2-pyrazinyl | | |
| 201 | $CH_2$—O | 5-methyl-2-pyrazinyl | | |
| 202 | $CH_2$—S | 5-methyl-2-pyrazinyl | | |
| 203 | $CH_2$—O | 3-pyridazinyl | | |
| 204 | $CH_2$—S | 3-pyridazinyl | | |
| 205 | $CH_2$—O | 5-chloro-3-pyridazinyl | | |
| 206 | $CH_2$—S | 5-chloro-3-pyridazinyl | | |
| 207 | $CH_2$—O | 2-thienyl | | |
| 208 | $CH_2$—S | 2-thienyl | | |
| 209 | $CH_2$—O | 3-thienyl | | |
| 210 | $CH_2$—S | 3-thienyl | | |
| 211 | $CH_2$—O | 4-chloro-3-thienyl | | |
| 212 | $CH_2$—S | 4-chloro-3-thienyl | | |
| 213 | $CH_2$—O | 2-chloro-3-thienyl | | |
| 214 | $CH_2$—S | 2-chloro-3-thienyl | | |
| 215 | $CH_2$—O | 5-chloro-3-thienyl | | |
| 216 | $CH_2$—S | 5-chloro-3-thienyl | | |
| 217 | $CH_2$—O | 2-quinoxalinyl | | |
| 218 | $CH_2$—S | 2-quinoxalinyl | | |
| 219 | $CH_2$—O | 3-methyl-2-quinxalinyl | | |
| 220 | $CH_2$—S | 3-methyl-2-quinxalinyl | | |
| 221 | $CH_2$—O | 7,8-dimethyl-2-quinoxalinyl | | |
| 222 | $CH_2$—S | 7,8-dimethyl-2-quinoxalinyl | | |
| 223 | $CH_2$—O | 7,8-dichloro-2-quinoxalinyl | | |
| 224 | $CH_2$—S | 7,8-dichloro-2-quinoxalinyl | | |
| 225 | $CH_2$—O | 7-methyl-2-quinoxalinyl | | |
| 226 | $CH_2$—S | 7-methyl-2-quinoxalinyl | | |
| 227 | $CH_2$—O | 8-methyl-2-quinoxalinyl | | |
| 228 | $CH_2$—S | 8-methyl-2-quinoxalinyl | | |
| 229 | $CH_2$—O | 7-methoxy-2-quinoxalinyl | | |
| 230 | $CH_2$—S | 7-methoxy-2-quinoxalinyl | | |
| 231 | $CH_2$—O | 3-phenyl-5-isoxazolyl | | |
| 232 | $CH_2$—S | 3-phenyl-5-isoxazolyl | | |
| 233 | $CH_2$—O | 2-benzoxazolyl | | |
| 234 | $CH_2$—S | 2-benzoxazolyl | | |
| 235 | $CH_2$—O | 2-benzthiazolyl | | |
| 236 | $CH_2$—S | 2-benzthiazolyl | | |
| 237 | $CH_2$—S | 6-methyl-2-benzthiazolyl (non-polar isomer) | oil | 3.9(S, 3H); 4.0(S, 3H); 4, 55(S, 2H) |
| 238 | $CH_2$—S | 4-chloro-2-benzthiazolyl | | |
| 239 | $CH_2$—S | 5-chloro-2-benzthiazolyl | | |
| 240 | $CH_2$—S | 6-chloro-2-benzthiazolyl | | |
| 241 | $CH_2$—S | 6-Ethoxy-2-benzthiazolyl | | |
| 242 | $CH_2$—S | 5-trifluoromethyl-2-benzthiazolyl | | |
| 243 | $CH_2$—S | 4,8-dimethyl-2-quinolyl | | |

TABLE 21-continued

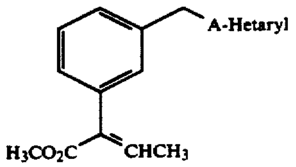

| No. | A | Hetaryl | mp | NMR: δ (ppm) |
|---|---|---|---|---|
| 244 | $CH_2$—O | 4,8-dimethyl-2-quinolyl | | |
| 245 | $CH_2$—O | 6-iso-butyl-2-pyridyl | | |
| 246 | $CH_2$—O | 3-cyano-6-iso-butyl-2-pyridyl | | |

TABLE 22

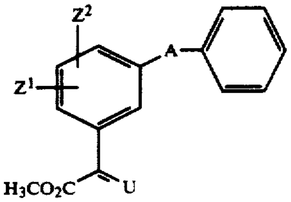

| No. | $Z^1$ | $Z^2$ | U | A | mp | NMR |
|---|---|---|---|---|---|---|
| 1 | 2-$OCH_3$ | H | $HCOCH_3$ | $CH_2$—$CH_2$ | | |
| 2 | 2-$OCH_3$ | H | $HCOCH_3$ | CH=CH | | |
| 3 | 2-$OCH_3$ | H | $HCOCH_3$ | $CH_2$—O | | |
| 4 | 2-$OCH_3$ | H | $HCOCH_3$ | $CH_2$—O—CO | | |
| 5 | 2-$OCH_3$ | H | $NOCH_3$ | $CH_2$—$CH_2$ | | |
| 6 | 2-$OCH_3$ | H | $NOCH_3$ | CH=CH | | |
| 7 | 2-$OCH_3$ | H | $NOCH_3$ | $CH_2$—O | | |
| 8 | 2-$OCH_3$ | H | $NOCH_3$ | $CH_2$—O—CO | | |
| 9 | 2-$OCH_3$ | H | $CHCH_3$ | $CH_2$—$CH_2$ | | |
| 10 | 2-$OCH_3$ | H | $CHCH_3$ | CH=CH | | |
| 11 | 2-$OCH_3$ | H | $CHCH_3$ | $CH_2$—O | | |
| 12 | 2-$OCH_3$ | H | $CHCH_3$ | $CH_2$—O—CO | | |
| 13 | 4-$OCH_3$ | H | $HCOCH_3$ | $CH_2$—$CH_2$ | | |
| 14 | 4-$OCH_3$ | H | $HCOCH_3$ | CH=CH | | |
| 15 | 4-$OCH_3$ | H | $HCOCH_3$ | $CH_2$—O | | |
| 16 | 4-$OCH_3$ | H | $HCOCH_3$ | $CH_2$—O—CO | | |
| 17 | 4-$OCH_3$ | H | $NOCH_3$ | $CH_2$—$CH_2$ | | |
| 18 | 4-$OCH_3$ | H | $NOCH_3$ | CH=CH | | |
| 19 | 4-$OCH_3$ | H | $NOCH_3$ | $CH_2$—O | | |
| 20 | 4-$OCH_3$ | H | $NOCH_3$ | $CH_2$—O—CO | | |
| 21 | 4-$OCH_3$ | H | $CHCH_3$ | $CH_2$—$CH_2$ | | |
| 22 | 4-$OCH_3$ | H | $CHCH_3$ | CH=CH | | |
| 23 | 4-$OCH_3$ | H | $CHCH_3$ | $CH_2$—O | | |
| 24 | 4-$OCH_3$ | H | $CHCH_3$ | $CH_2$—O—CO | | |
| 25 | 6-$N(CH_3)_2$ | H | $HCOCH_3$ | $CH_2$—$CH_2$ | | |
| 26 | 6-$N(CH_3)_2$ | H | $HCOCH_3$ | CH=CH | | |
| 27 | 6-$N(CH_3)_2$ | H | $HCOCH_3$ | $CH_2$—O | | |
| 28 | 6-$N(CH_3)_2$ | H | $HCOCH_3$ | $CH_2$—O—CO | | |
| 29 | 6-$N(CH_3)_2$ | H | $NOCH_3$ | $CH_2$—$CH_2$ | | |
| 30 | 6-$N(CH_3)_2$ | H | $NOCH_3$ | CH=CH | | |
| 31 | 6-$N(CH_3)_2$ | H | $NOCH_3$ | $CH_2$—O | | |
| 32 | 6-$N(CH_3)_2$ | H | $NOCH_3$ | $CH_2$—O | | |
| 33 | 6-$N(CH_3)_2$ | H | $CHCH_3$ | $CH_2$—$CH_2$ | | |
| 34 | 6-$N(CH_3)_2$ | H | $CHCH_3$ | CH=CH | | |
| 35 | 6-$N(CH_3)_2$ | H | $CHCH_3$ | $CH_2$—O | | |
| 36 | 6-$N(CH_3)_2$ | H | $CHCH_3$ | $CH_2$—O—CO | | |
| 37 | 5-$NO_2$ | 6-$OCH_3$ | $HCOCH_3$ | $CH_2$—$CH_2$ | | |
| 38 | 5-$NO_2$ | 6-$OCH_3$ | $HCOCH_3$ | CH=CH | | |
| 39 | 5-$NO_2$ | 6-$OCH_3$ | $HCOCH_3$ | $CH_2$—O | | |
| 40 | 5-$NO_2$ | 6-$OCH_3$ | $HCOCH_3$ | $CH_2$—O—CO | | |
| 41 | 5-$NO_2$ | 6-$OCH_3$ | $NOCH_3$ | $CH_2$—$CH_2$ | | |
| 42 | 5-$NO_2$ | 6-$OCH_3$ | $NOCH_3$ | CH=CH | | |
| 43 | 5-$NO_2$ | 6-$OCH_3$ | $NOCH_3$ | $CH_2$—O | | |
| 44 | 5-$NO_2$ | 6-$OCH_3$ | $NOCH_3$ | $CH_2$—O—CO | | |
| 45 | 5-$NO_2$ | 6-$OCH_3$ | $CHCH_3$ | $CH_2$—$CH_2$ | | |
| 46 | 5-$NO_2$ | 6-$OCH_3$ | $CHCH_3$ | CH=CH | | |
| 47 | 5-$NO_2$ | 6-$OCH_3$ | $CHCH_3$ | $CH_2$—O | | |
| 48 | 5-$NO_2$ | 6-$OCH_3$ | $CHCH_3$ | $CH_2$—O—CO | | |
| 49 | 5-$NO_2$ | H | $HCOCH_3$ | O—$CH_2$ | | |
| 50 | 5-$NO_2$ | H | $NOCH_3$ | O—$CH_2$ | | |
| 51 | 5-$NO_2$ | H | CH—$CH_3$ | O—$CH_2$ | | |
| 52 | 4-$NO_2$ | H | $HCOCH_3$ | O—$CH_2$ | | |

TABLE 22-continued

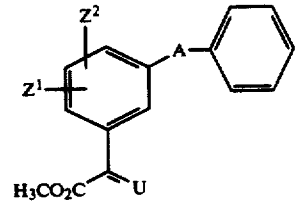

| No. | $Z^1$ | $Z^2$ | U | A | mp | NMR |
|---|---|---|---|---|---|---|
| 53 | 4-$NO_2$ | H | $NOCH_3$ | $O-CH_2$ | | |
| 54 | 4-$NO_2$ | H | $CHCH_3$ | $O-CH_2$ | | |
| 55 | 2-$CO_2CH_3$ | H | $HCOCH_3$ | $O-CH_2$ | | |
| 56 | 2-$CO_2CH_3$ | H | $NOCH_3$ | $O-CH_2$ | | |
| 57 | 2-$CO_2CH_3$ | H | $CH-CH_3$ | $O-CH_2$ | | |
| 58 | 4-$OCH_3$ | H | $HCOCH_3$ | $O-CH_2$ | | |
| 59 | 4-$OCH_3$ | H | $NOCH_3$ | $O-CH_2$ | | |
| 60 | 4-$OCH_3$ | H | $CHCH_3$ | $O-CH_2$ | | |
| 61 | 4-$OCH_3$ | 5-Br | $HCOCH_3$ | $O-CH_2$ | | |
| 62 | 4-$OCH_3$ | 5-Br | $NOCH_3$ | $O-CH_2$ | | |
| 63 | 4-$OCH_3$ | 5-Br | $CHCH_3$ | $O-CH_2$ | | |
| 64 | $CH_2-C_6H_5$ | H | $HCOCH_3$ | $O-CH_2$ | | |
| 65 | $CH_2-C_6H_5$ | H | $NOCH_3$ | $O-CH_2$ | | |
| 66 | $CH_2-C_6H_5$ | H | $CHCH_3$ | $O-CH_2$ | | |

In general terms, the novel compounds are extremely effective on a broad spectrum of phytopathogenic fungi, in particular those from the class consisting of the Ascomycetes and Basidiomycetes. Some of them have a systemic action and can be used as foliar and soil fungicides.

The fungicidal compounds are of particular interest for controlling a large number of fungi in various crops or their seeds, especially wheat, rye, barley, oats, rice, Indian corn, lawns, cotton, soybeans, coffee, sugar cane, fruit and ornamentals in horticulture and viticulture, and in vegetables such as cucumbers, beans and cucurbits.

The novel compounds are particularly useful for controlling the following plant diseases:

*Erysiphe graminis* in cereals,

*Erysiphe cichoracearum* and *Sphaerotheca fuliginea* in cucurbits,

*Podosphaera leucotricha* in apples,

*Uncinula necator* in vines,

Puccinia species in cereals,

*Rhizoctonia solani* in cotton,

Ustilago species in cereals and sugar cane,

*Venturia inaeualis* (scab) in apples,

Helminthosporium species in cereals,

*Septoria nodorum* in wheat,

*Botrytis cinerea* (gray mold) in strawberries and grapes,

*Cercospora arachidicola* in groundnuts,

*Pseudocercosporella herpotrichoides* in wheat and barley,

*Pyricularia oryzae* in rice,

*Phytophthora infestans* in potatoes and tomatoes,

Fusarium and Verticillium species in various plants,

*Plasmopara viticola* in grapes,

Alternaria species in fruit and vegetables.

The compounds are applied by spraying or dusting the plants with the active ingredients, or treating the seeds of the plants with the active ingredients. They may be applied before or after infection of the plants or seeds by the fungi. Either the fungi themselves, or the plants, seed, materials or the soil to be protected against fungus attack are treated with a fungicidally effective amount of the active ingredient.

The novel substances can be converted into conventional formulations such as solutions, emulsions, suspensions, dusts, powders, pastes and granules. The application forms depend entirely on the purposes for which they are intended; they should at all events ensure a fine and uniform distribution of the active ingredient. The formulations are produced in known manner, for example by extending the active ingredient with solvents and/or carriers, with or without the use of emulsifiers and dispersants; if water is used as solvent, it is also possible to employ other organic solvents as auxiliary solvents. Suitable auxiliaries for this purpose are solvents such as aromatics (e.g., xylene), chlorinated aromatics (e.g., chlorobenzenes), paraffins (e.g., crude oil fractions), alcohols (e.g., methanol, butanol), ketones (e.g., cyclohexanone), amines (e.g., ethanolamine, dimethylformamide), and water; carriers such as ground natural minerals (e.g., kaolins, aluminas, talc and chalk) and ground synthetic minerals (e.g., highly disperse silica and silicates); emulsifiers such as nonionic and anionic emulsifiers (e.g., polyoxyethylene fatty alcohol ethers, alkyl sulfonates and aryl sulfonates); and dispersants such as lignin, sulfite waste liquors and methylcellulose.

The fungicides generally contain from 0.1 to 95, and preferably from 0.5 to 90, wt % of active ingredient. The application rates are from 0.02 to 3 kg or more of active ingredient per hectare, depending on the type of effect desired. The novel compounds may also be used for protecting materials (timber), e.g., against *Paecilomyces variotii*. When the active ingredients are used for treating seed, rates of from 0.001 to 50, and preferably from 0.01 to 10, g per kg of seed are generally sufficient.

The agents and the ready-to-use formulations prepared from them, such as solutions, emulsions, suspensions, powders, dusts, pastes and granules, are applied in conventional manner, for example by spraying, atomizing, dusting, scattering, dressing or watering.

Examples of formulations are given below.

I. A solution of 90 parts by weight of compound no. 2/77 and 10 parts by weight of N-methyl-α-pyrrolidone, which is suitable for application in the form of very fine drops.

II. A mixture of 20 parts by weight of compound no. 4/65, 80 parts by weight of xylene, 10 parts by weight of the adduct of 8 to 10 moles of ethylene oxide and I mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By finely dispersing the mixture in water, an aqueous dispersion is obtained.

III. An aqueous dispersion of 20 parts by weight of compound no. 13/8, 40 parts by weight of cyclohexanone, 30 parts by weight of isobutanol, 20 parts by weight of the adduct of 40 moles of ethylene oxide and 1 mole of castor oil. By finely dispersing the mixture in water, an aqueous dispersion is obtained.

IV. An aqueous dispersion of 20 parts by weight of compound no. 19/2, 25 parts by weight of cyclohexanol, 65 parts by weight of a mineral oil fraction having a boiling point between 210° and 280° C., and 10 parts by weight of the adduct of 40 moles of ethylene oxide and 1 mole of castor oil. By finely dispersing the mixture in water, an aqueous dispersion is obtained.

V. A hammer-milled mixture of 80 parts by weight of compound no. 19/26, 3 parts by weight of the sodium salt of diisobutylnaphthalene-α-sulfonic acid, 10 parts by weight of the sodium salt of a lignin-sulfonic acid obtained from a sulfite waste liquor, and 7 parts by weight of powdered silica gel. By finely dispersing the mixture in water, a spray liquor is obtained.

VI. An intimate mixture of 3 parts by weight of compound no. 2111 and 97 parts by weight of particulate kaolin. The dust contains 3 wt % of the active ingredient.

VII. An intimate mixture of 30 parts by weight of compound no. 2/14, 92 parts by weight of powdered silica gel and 8 parts by weight of paraffin oil sprayed onto the surface of this silica gel. This formulation of the active ingredient exhibits good adherence.

VIII. A stable aqueous dispersion of 40 parts by weight of compound no. 2/24, 10 parts of the sodium salt of a phenolsulfonic acid-urea-formaldehyde condensate, 2 parts of silica gel and 48 parts of water, which dispersion can be further diluted.

IX. A stable oily dispersion of 20 parts by weight of compound no. 2/77, 2 parts by weight of the calcium salt of dodecylbenzenesulfonic acid, 8 parts by weight of a fatty alcohol polyglycol ether, 2 parts by weight of the sodium salt of a phenolsulfonic acid-urea-formaldehyde condensate and 68 parts by weight of a paraffinic mineral oil.

In these application forms, the agents according to the invention may also be present together with other active ingredients, for example herbicides, insecticides, growth regulators, and fungicides, and may furthermore be mixed and applied together with fertilizers. Admixture with other fungicides frequently results in a greater fungicidal action spectrum.

Methyloxime (B) disclosed in DE 36 23 921, and 2-phenyloxymethylenephenylglyoxylic acid-O-methyloxime (C) disclosed in DE 36 23 921 were used for comparison purposes.

USE EXAMPLE 1

Action on *Plasmopara viticola*

Leaves of potted vines of the Müller-Thurgau variety were sprayed with aqueous suspensions containing (dry basis) 80% of active ingredient and 20% of emulsifier. To assess the duration of action, the plants were set up, after the sprayed-on layer had dried, for 8 days in the greenhouse. Then the leaves were infected with a zoospore suspension of *Plasmopara viticola*. The plants were first placed for 48 hours in a water vapor-saturated chamber at 24° C. and then in a greenhouse for 5 days at from 20° to 30° C. To accelerate and intensify the sporangiophore discharge, the plants were then again placed in the moist chamber for 16 hours. The extent of fungus attack was then assessed on the undersides of the leaves. The results show that active ingredients 2/77, 4/65, 13/8, 19/2 and 19/26, applied as 0.006 wt % spray liquors, had a better fungicidal action (85%) than the prior art active ingredients A, B and C (60%).

USE EXAMPLE 2

Action on *Pyrenophora teres*

Barley seedlings of the "Igri" variety were sprayed to runoff at the 2-leaf stage with aqueous suspensions containing (dry basis) 80% of active ingredient and 20% emulsifier. After 24 hours the plants were inoculated with a spore suspension of the fungus *Pyrenophora teres* and placed for 48 hours in a high-humidity climatic cabinet kept at 18° C. The plants were then cultivated for a further 5 days in the greenhouse at 20°-22° C. and a relative humidity of 70%. The extent of fungus spread was then determined.

The results show that active ingredients 2/11, 2/14, 2/24, 2/77, 2/84, 2/456, 2/473, 2/474, 4/8, 4/65, 7/8, 7/66, 13/9, 13/10, 13/65, 13/66, 19/2, 19/26, 19/194, 19/237, 19/238, 19/239, 19/240 and 19/242, applied as 0.05% spray liquors, had a better fungicidal action (95%) than prior art active ingredients B (60%) and C (50%).

The novel compounds are also suitable for effectively combating pests such as insects, arachnids and nematodes. They may be used as pesticides in crop protection and in the hygiene, stores protection and veterinary sector.

Examples of injurious insects belonging to the Lepidoptera order are *Agrotis upsilon, Agrotis segetum, Alabama argillacea, Anticarsia gemmatalis, Argyresthia conjugella, Autographs gamma, Bupalus piniarius, Cacoecia murinana, Capua reticulana, Cheimatobia brumata, Choristoneura fumiferana, Choristoneura occidentalis, Cirphis unipuncta, Cydia pomonella, Dendrolimus pini, Diaphania nitidalis, Diatraea grandiosella, Earias insulana, Elasmopalpus lignosellus, Eupoecilia ambiguella, Evetria bouliana, Feltia subterranea, Galleria mellonella, Grapholita funebrana, Grapholita molests, Heliothis armigera, Heliothis virescens, Heliothis zea, Hellula undalis, Hibernia defoliaria, Hyphantria cunea, Hyponomeuta malinellus, Keifferia lycopersicella, Lambdina fiscellaria, Laphygma exigua, Leucoptera coffeella, Leucoptera scitella, Lithocolletis blancardella, Lobesia botrana, Loxostege sticticalis, Lymantria dispar, Lymantria monacha, Lyonetia clerkella, Malacosoma neustria, Mamestra brassicae, orgyia pseudotsugata, Ostrinia nubilalis, Panolis flamea, Pectinophora gossypiella, Peridroma saucia, Phalera bucephala, Phthorimaea operculella, Phyllocnistis citrella, Pieris brassicae, Plathypena scarbra, Plutella xylos-* tella, *Pseudoplusia includens, Phyacionia frustrana, Scrobipalpula absoluta, Sitotroga cerelella, Sparganothis pilleriana, Spodoptera frugiperda, Spodoptera littoralis, Spodoptera litura, Thaumatopoea pityocampa, Tortrix viridana, Trichoplusia ni* and *Zeiraphera canadensis.*

Examples from the Coleoptera order are *Agrilus sinuatus, Agriotes lineatus, Agriotes obscurus, Amphimallus solstitialis, Anisandrus dispar, Anthonomus grandis, Anthonomus pomorum, Atomaria linearis, Blastophagus piniperda, Blitophaga undata, Bruchus rufimanus, Bruchus pisorum, Bruchus lentis, Byctiscus betulae, Cassida nebulosa, Cerotoma trifurcata, Ceuthorrhynchus assimilis, Ceuthorrynchus napi, Chaetocnema tibialis, Conoderus vespertinus, Crioceris asparagi, Diabrotica longicornis, Diabrotica* 12-*punctata, Diabrotica virgifera, Epilachna varivestis, Epitrix hirtipennis, Eutinobothrus brasiliensis, Hylobius abietis, Hypera brunneipennis, Hypera postica, Ips typographus, Lema bilineata, Lema melanopus, Leptinotarsa decemlineata, Limonius californicus, Lissorhoptrus oryzophilus, Melanotus communis, Meligethes aeneus, melolontha hippocastani, Melolontha melolontha, Onlema oryzae, Ortiorrhynchus sulcatus, Ortiorrhynchus ovatus, Phaedon cochleariae, Phyllotreta chrysocephala,* Phyllophaga sp., *Phyllopertha horticola, Phyllotreta nemorum, Phyllotreta striolata, Popillia japonica, Sitona lineatus* and *Sitophilus granaria.*

Examples from the Diptera order are *Aedes aegypti, Aedes vexans, Anastrepha ludens, Anopheles maculipennis, Ceratitis capitata, Chrysomya bezziana, Chrysomya hominivorax, Chrysomya macellaria, Contarinia sorghicola, Cordylobia anthropophaga, Culex pipiens, Dacus cucurbitae, Dacus oleae, Dasineura brassicae, Fannia canicularis, Gasterophilus intestinalis, Glossia morsitans, Haematobia irritans, Haplodiplosis equestris, Hylemyia platura, Hypoderma lineata, Liriomyza sativae, Liriomyza trifolii, Lucilia caprina, Lucilia cuprina, Lucilia sericata, Lycoria pectoralis, Mayetiola destructor, Musca domestica, Muscina stabulans, Oestrus ovis, Oscinella frit, Pegomya hysocyami, Phorbia antiqua, Phorbia brassicae, Phorbia coarctata, Rhagoletis cerasi, Rhagoletis pomonella, Tabanus bovinus, Tipula oleracea* and *Tipula paludosa.*

Examples from the Thysanoptera order are *Frankliniella fusca, Frankliniella occidentalis, Frankliniella tritici, Scirtothrips citri, Thrips oryzae, Thrips palmi* and *Thrips tabaci.*

Examples from the Hymenoptera order are *Athalia rosae, Atta cephalotes, Atta sexdens, Atta texana, Hoplocampa minuta, Hoplocampa testundinea, Monomorium pharaonis, Solenopsis geminata* and *Solenopsis invicta.*

Examples from the Heteroptera order are *Acrosternum hilare, Blissus leucopterus, Cyrtopeltis notatus, Dysdercus cingulatus, Dysdercus intermedius, Eurygaster integriceps, Euchistus impictiventris, Leptoglossus phyllopus, Lygus lineolaris, Lygus pratensis, Nezara viridula, Piesma quadrata, Solubea insularis* and *Thyanta perditor.*

Examples from the nematodes class are root-knot nematodes, e.g., *Meloidogyne hapla, Meloidocivne incognita* and *Meloidogyne javanica,* cyst-forming nematodes, e.g., *Globodera rostochiensis, Heterodera avenae, Hetrodera glycinae, Heterodera schachtii* and *Heterodera trifolii,* and stem and leaf eelworms, e.g., *Belolaimus longicaudatus, Ditylenchus destructor, Ditylenchus dipsaci, Heliocotylenchus multicinctus, Longidorus elongatus, Radopholus similis, Rotylenchus robustus, Trichodorus primitivus, Tylenchorhynchus claytoni, Tylenchorhynchus dubius, Pratylenchus neglectus, Pratylenchus penetrans, Pratylenchus curvitatus* and *Pratylenchus goodeyi.*

When the active ingredients are used for combating pests, the concentration of the active ingredients in the finished formulations may vary over a wide range. Generally, they are from 0.0001 to 10, and preferably from 0.001 to 0.1, %.

The active ingredients may also successfully be used in the ultra-low-volume (ULV) method, where it is possible to apply formulations containing more than 95 wt % of active ingredient, or even the active ingredient without additives.

In the open, the amount of active ingredient applied is for example from 0.01 to 10, particularly from 0.01 to 1.0, kg/ha.

We claim:

1. A compound of the formula

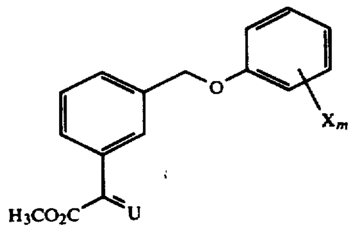

wherein U is $=CH_2$, $=CHCH_3$, or $=CHCH_2CH_3$; X is methyl; and m is 0, 1, or 2.

2. A fungicidal composition containing a fungicidally effective amount of a compound according to claim 1 and an inert carrier therefor.

3. A process for combatting fungi comprising applying to the fungi, or to the plants, materials, seeds, or soil threatened by fungus attack, a fungicidally effective amount of a compound according to claim 1.

4. A compound according to claim 1 wherein U is $=CHCH_3$ and m is 0.

5. A compound according to claim 1 wherein U is $=CHCH_3$ and $X_m$ is 2-methyl.

6. A compound according to claim 1, wherein U is $=CHCH_3$ and $X_m$ is 2,5-dimethyl.

* * * * *